US009522225B2

(12) United States Patent
Chong et al.

(10) Patent No.: US 9,522,225 B2
(45) Date of Patent: Dec. 20, 2016

(54) ADHESIVE PATCH SYSTEMS AND METHODS

(75) Inventors: Colin A. Chong, Burbank, CA (US); Christopher G. Griffin, Sylmar, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 0 days.

(21) Appl. No.: 12/411,236

(22) Filed: Mar. 25, 2009

(65) Prior Publication Data

US 2009/0198215 A1    Aug. 6, 2009

Related U.S. Application Data

(62) Division of application No. 12/027,963, filed on Feb. 7, 2008, now Pat. No. 8,323,250.
(Continued)

(51) Int. Cl.
*A61M 5/142* (2006.01)
*A61M 5/165* (2006.01)
(Continued)

(52) U.S. Cl.
CPC ....... *A61M 5/14248* (2013.01); *A61M 5/1413* (2013.01); *A61M 5/165* (2013.01);
(Continued)

(58) Field of Classification Search
CPC A61M 5/14248; A61M 5/1413; A61M 5/165; A61M 5/36; A61M 2005/14268; A61M 2005/31516; A61M 2005/341; A61M 2209/045
(Continued)

(56) References Cited

U.S. PATENT DOCUMENTS

| 1,948,982 A | 2/1934 | Cutter |
| 2,064,815 A | 12/1936 | Armstrong |

(Continued)

FOREIGN PATENT DOCUMENTS

| DE | 10 2004 055 870 A1 | 5/2006 |
| DE | 10 2004 055 870 U1 | 5/2006 |

(Continued)

OTHER PUBLICATIONS

PCT search report dated May 15, 2008 for PCT application No. PCT/US2007/076679.
(Continued)

*Primary Examiner* — Emily Schmidt
*Assistant Examiner* — Lauren M Peng
(74) *Attorney, Agent, or Firm* — Foley & Lardner LLP

(57) ABSTRACT

Various embodiments of the present invention are directed to patches for medical devices. In various embodiments, an adhesive patch of a medical device may have selective areas with adhesive material of varying adhesion strengths. In other embodiments, an adhesive patch of a medical device may include adhesive material that may be activated by a catalyst to increase or decrease the adhesion strength of the adhesive material. In further embodiments, a medical device may include a pierceable membrane containing an agent, the pierceable membrane positioned to be pierced by a needle and to cause some of the agent to be carried to the user-patient.

30 Claims, 97 Drawing Sheets

Related U.S. Application Data

(60) Provisional application No. 60/927,032, filed on Apr. 30, 2007.

(51) Int. Cl.
| | |
|---|---|
| *A61M 5/14* | (2006.01) |
| *A61M 5/36* | (2006.01) |
| *A61M 5/34* | (2006.01) |
| *A61M 5/315* | (2006.01) |

(52) U.S. Cl.
CPC ..... *A61M 5/36* (2013.01); *A61M 2005/14268* (2013.01); *A61M 2005/31516* (2013.01); *A61M 2005/341* (2013.01); *A61M 2209/045* (2013.01)

(58) Field of Classification Search
USPC .............. 604/21, 86–88, 111, 173, 200–205, 500, 604/507
See application file for complete search history.

(56) References Cited

U.S. PATENT DOCUMENTS

| | | | |
|---|---|---|---|
| 2,570,625 A | 10/1951 | Zimmerman et al. | |
| 2,627,857 A | 2/1953 | Marcelli | |
| 2,644,450 A | 7/1953 | Krewson | |
| 2,734,504 A | 2/1956 | Crescas et al. | |
| RE24,918 E | 1/1961 | Mills | |
| 2,973,758 A | 3/1961 | Murrish | |
| 3,085,454 A | 4/1963 | Federighi | |
| 3,223,289 A | 12/1965 | Bouet | |
| 3,342,180 A | 9/1967 | Ellsworth et al. | |
| 3,343,422 A | 9/1967 | McSmith | |
| 3,572,552 A | 3/1971 | Guinn | |
| 3,623,474 A | 11/1971 | Heilman et al. | |
| 3,650,093 A | 3/1972 | Rosenberg | |
| 3,662,753 A | 5/1972 | Tassell | |
| 3,729,032 A | 4/1973 | Tischlinger et al. | |
| 3,802,430 A | 4/1974 | Schwebel et al. | |
| 3,807,119 A | 4/1974 | Shields | |
| 3,923,058 A | 12/1975 | Weingarten | |
| 3,963,151 A | 6/1976 | North, Jr. | |
| 3,993,061 A | 11/1976 | O'Leary | |
| 4,064,879 A | 12/1977 | Leibinsohn | |
| 4,089,624 A | 5/1978 | Nichols et al. | |
| 4,093,108 A | 6/1978 | Hein et al. | |
| 4,117,841 A * | 10/1978 | Perrotta et al. | 604/304 |
| 4,215,701 A | 8/1980 | Raitto | |
| 4,219,055 A | 8/1980 | Wright | |
| 4,234,108 A | 11/1980 | Diamond | |
| 4,373,535 A | 2/1983 | Martell | |
| 4,392,850 A | 7/1983 | Elias et al. | |
| 4,411,662 A | 10/1983 | Pearson | |
| 4,434,820 A | 3/1984 | Glass | |
| 4,447,225 A | 5/1984 | Taff et al. | |
| 4,448,206 A | 5/1984 | Martell | |
| 4,493,704 A | 1/1985 | Beard et al. | |
| 4,508,532 A | 4/1985 | Drews et al. | |
| 4,568,336 A | 2/1986 | Cooper | |
| 4,572,210 A | 2/1986 | McKinnon | |
| 4,585,435 A | 4/1986 | Vaillancourt | |
| 4,684,365 A | 8/1987 | Reinicke | |
| 4,684,366 A | 8/1987 | Denny et al. | |
| 4,703,763 A | 11/1987 | McAlister et al. | |
| 4,743,249 A | 5/1988 | Loveland | |
| 4,744,955 A | 5/1988 | Shapiro | |
| 4,749,109 A | 6/1988 | Kamen | |
| 4,759,756 A | 7/1988 | Forman et al. | |
| 4,838,857 A | 6/1989 | Strowe et al. | |
| 4,865,592 A | 9/1989 | Rycroft | |
| 4,883,101 A | 11/1989 | Strong | |
| 4,913,703 A | 4/1990 | Pasqualucci et al. | |
| 4,936,841 A | 6/1990 | Aoki et al. | |
| 4,957,637 A | 9/1990 | Cornell | |
| 4,976,696 A | 12/1990 | Sanderson et al. | |
| 4,986,820 A | 1/1991 | Fischer | |
| 4,994,034 A | 2/1991 | Botich et al. | |
| 5,002,527 A | 3/1991 | Reller et al. | |
| 5,045,096 A | 9/1991 | Quang et al. | |
| 5,049,129 A | 9/1991 | Zdeb et al. | |
| 5,053,001 A | 10/1991 | Reller et al. | |
| 5,062,834 A | 11/1991 | Gross et al. | |
| 5,070,884 A | 12/1991 | Columbus et al. | |
| 5,090,963 A | 2/1992 | Gross et al. | |
| 5,115,948 A | 5/1992 | Johnson | |
| 5,156,591 A | 10/1992 | Gross et al. | |
| 5,176,502 A | 1/1993 | Sanderson et al. | |
| 5,186,805 A | 2/1993 | Gross et al. | |
| 5,190,522 A | 3/1993 | Wojcicki et al. | |
| 5,203,506 A | 4/1993 | Gross et al. | |
| 5,219,099 A | 6/1993 | Spence et al. | |
| 5,232,449 A | 8/1993 | Stern et al. | |
| 5,242,406 A | 9/1993 | Gross et al. | |
| 5,242,408 A | 9/1993 | Jhuboo et al. | |
| 5,246,147 A | 9/1993 | Gross | |
| 5,254,096 A | 10/1993 | Rondelet et al. | |
| 5,259,732 A | 11/1993 | Stern | |
| 5,261,884 A | 11/1993 | Stern et al. | |
| 5,275,582 A | 1/1994 | Wimmer | |
| 5,284,570 A | 2/1994 | Savage et al. | |
| 5,292,318 A | 3/1994 | Haber et al. | |
| 5,295,966 A | 3/1994 | Stern et al. | |
| 5,295,967 A | 3/1994 | Rondelet et al. | |
| 5,308,333 A | 5/1994 | Skakoon | |
| 5,312,364 A | 5/1994 | Jacobs | |
| 5,329,976 A | 7/1994 | Haber et al. | |
| 5,356,632 A | 10/1994 | Gross et al. | |
| 5,367,891 A | 11/1994 | Furuyama | |
| 5,385,559 A | 1/1995 | Mannix | |
| 5,387,450 A | 2/1995 | Stewart | |
| 5,407,434 A | 4/1995 | Gross | |
| 5,409,236 A | 4/1995 | Therrien | |
| 5,415,648 A | 5/1995 | Malay et al. | |
| 5,425,706 A | 6/1995 | Gross et al. | |
| 5,496,285 A | 3/1996 | Schumacher et al. | |
| 5,527,288 A | 6/1996 | Gross et al. | |
| 5,533,964 A | 7/1996 | Halperin et al. | |
| 5,647,851 A | 7/1997 | Pokras | |
| 5,651,373 A | 7/1997 | Mah | |
| 5,697,916 A | 12/1997 | Schraga | |
| 5,704,520 A | 1/1998 | Gross | |
| 5,800,420 A | 9/1998 | Gross et al. | |
| 5,807,375 A | 9/1998 | Gross et al. | |
| 5,814,020 A | 9/1998 | Gross | |
| 5,820,622 A * | 10/1998 | Gross et al. | 604/890.1 |
| 5,848,991 A | 12/1998 | Gross et al. | |
| 5,851,549 A | 12/1998 | Svec | |
| 5,858,001 A | 1/1999 | Tsals et al. | |
| 5,865,803 A | 2/1999 | Major | |
| 5,871,125 A | 2/1999 | Gross | |
| 5,873,859 A | 2/1999 | Muntz | |
| 5,887,752 A | 3/1999 | Strother | |
| 5,933,287 A | 8/1999 | Muller | |
| 5,951,523 A | 9/1999 | Osterlind et al. | |
| 5,954,697 A | 9/1999 | Srisathapat et al. | |
| 5,957,889 A | 9/1999 | Poulsen et al. | |
| 5,984,894 A | 11/1999 | Poulsen et al. | |
| 5,997,501 A | 12/1999 | Gross et al. | |
| 6,003,736 A | 12/1999 | Ljunggren | |
| 6,019,745 A | 2/2000 | Gray | |
| 6,033,377 A | 3/2000 | Rasmussen et al. | |
| 6,042,565 A | 3/2000 | Hirschman et al. | |
| 6,067,906 A | 5/2000 | Ryan et al. | |
| 6,077,252 A | 6/2000 | Siegel | |
| 6,088,608 A | 7/2000 | Schulman et al. | |
| 6,099,504 A | 8/2000 | Gross et al. | |
| 6,117,107 A | 9/2000 | Chen | |
| 6,119,028 A | 9/2000 | Schulman et al. | |
| 6,126,643 A | 10/2000 | Vaillancourt | |
| 6,186,982 B1 | 2/2001 | Gross et al. | |
| 6,229,584 B1 | 5/2001 | Chuo et al. | |
| 6,242,665 B1 | 6/2001 | Malowaniec | |
| 6,248,093 B1 | 6/2001 | Moberg | |

(56) References Cited

U.S. PATENT DOCUMENTS

| | | |
|---|---|---|
| 6,253,804 B1 | 7/2001 | Safabash |
| 6,261,272 B1 | 7/2001 | Gross et al. |
| 6,275,717 B1 | 8/2001 | Gross et al. |
| 6,277,095 B1 | 8/2001 | Kriesel et al. |
| 6,312,409 B1 | 11/2001 | Gross |
| 6,314,317 B1 | 11/2001 | Willis |
| 6,315,754 B1 | 11/2001 | Daoud et al. |
| 6,346,095 B1 | 2/2002 | Gross et al. |
| 6,364,865 B1 | 4/2002 | Lavi et al. |
| 6,364,866 B1 | 4/2002 | Furr et al. |
| 6,375,047 B1 | 4/2002 | Herda et al. |
| 6,406,455 B1 | 6/2002 | Willis et al. |
| 6,423,035 B1 | 7/2002 | Das et al. |
| 6,440,096 B1 | 8/2002 | Lastovich et al. |
| 6,450,993 B1 | 9/2002 | Lin |
| 6,453,956 B2 | 9/2002 | Safabash |
| 6,461,329 B1 | 10/2002 | Van Antwerp et al. |
| 6,474,219 B2 | 11/2002 | Klitmose et al. |
| 6,474,375 B2 | 11/2002 | Spero et al. |
| 6,478,771 B1 | 11/2002 | Lavi et al. |
| 6,479,587 B1 | 11/2002 | Stockinger et al. |
| 6,485,461 B1 | 11/2002 | Mason et al. |
| 6,485,465 B2 | 11/2002 | Moberg et al. |
| 6,490,483 B2 | 12/2002 | Willis |
| 6,503,225 B1 | 1/2003 | Kirsch et al. |
| 6,508,788 B2 | 1/2003 | Preuthun |
| 6,537,251 B2 | 3/2003 | Klitmose |
| 6,551,285 B1 | 4/2003 | Bierman |
| 6,572,600 B1 | 6/2003 | Roe et al. |
| 6,585,707 B2 | 7/2003 | Cabiri et al. |
| 6,589,229 B1 | 7/2003 | Connelly et al. |
| 6,591,876 B2 | 7/2003 | Safabash |
| 6,595,956 B1 | 7/2003 | Gross et al. |
| 6,607,509 B2 | 8/2003 | Bobroff et al. |
| 6,607,513 B1 | 8/2003 | Down et al. |
| 6,613,019 B2 | 9/2003 | Munk |
| 6,616,627 B2 | 9/2003 | Willis et al. |
| 6,626,874 B1 | 9/2003 | Duchamp |
| 6,641,565 B1 | 11/2003 | Lavi et al. |
| 6,641,566 B2 | 11/2003 | Douglas et al. |
| 6,645,181 B1 | 11/2003 | Lavi et al. |
| 6,656,147 B1 * | 12/2003 | Gertsek et al. ............... 604/28 |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,195 B2 | 4/2004 | Nolan, Jr. et al. |
| 6,719,734 B1 * | 4/2004 | Harkless ............ A61M 5/14248 433/90 |
| 6,723,068 B2 | 4/2004 | Lavi et al. |
| 6,723,072 B2 | 4/2004 | Flaherty et al. |
| 6,723,074 B1 | 4/2004 | Halseth |
| 6,740,059 B2 | 5/2004 | Flaherty |
| 6,740,072 B2 | 5/2004 | Starkweather et al. |
| 6,749,587 B2 | 6/2004 | Flaherty |
| 6,752,180 B2 | 6/2004 | Delay |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,796,965 B2 | 9/2004 | Dumaresq-Lucas et al. |
| 6,808,506 B2 | 10/2004 | Lastovich et al. |
| 6,827,702 B2 | 12/2004 | Lebel et al. |
| 6,830,558 B2 | 12/2004 | Flaherty et al. |
| 6,830,560 B1 | 12/2004 | Gross et al. |
| 6,886,724 B2 | 5/2005 | Hung |
| 6,899,699 B2 | 5/2005 | Enggaard |
| 6,915,147 B2 | 7/2005 | Lebel et al. |
| 6,918,887 B1 | 7/2005 | Gremel et al. |
| 6,936,006 B2 | 8/2005 | Sabra |
| 6,939,324 B2 | 9/2005 | Gonnelli et al. |
| 6,948,522 B2 | 9/2005 | Newbrough et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,041,082 B2 | 5/2006 | Blomquist et al. |
| 7,077,835 B2 | 7/2006 | Robinson et al. |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,220,245 B2 | 5/2007 | Kriesel |
| 7,220,889 B2 | 5/2007 | Sigjonsson et al. |
| 7,306,578 B2 | 12/2007 | Gray et al. |
| 7,318,816 B2 | 1/2008 | Bobroff et al. |
| 7,323,142 B2 | 1/2008 | Pendo et al. |
| 7,338,472 B2 | 3/2008 | Shearn |
| 7,361,156 B2 | 4/2008 | Joyce et al. |
| 7,390,294 B2 | 6/2008 | Hassler, Jr. |
| 7,399,484 B2 * | 7/2008 | Ellefson ............... A61F 13/02 424/448 |
| 7,507,221 B2 | 3/2009 | Neer |
| 7,540,863 B2 | 6/2009 | Haindl |
| 7,621,429 B2 | 11/2009 | Wu et al. |
| 7,637,891 B2 | 12/2009 | Wall |
| 7,686,787 B2 | 3/2010 | Moberg et al. |
| 7,708,717 B2 | 5/2010 | Estes et al. |
| 7,744,589 B2 | 6/2010 | Mounce et al. |
| 7,780,636 B2 | 8/2010 | Radmer et al. |
| 7,794,427 B2 | 9/2010 | Estes et al. |
| 7,828,765 B2 | 11/2010 | Hallahan et al. |
| 7,858,112 B2 * | 12/2010 | Hatanaka ............... A61K 9/703 424/449 |
| 7,955,305 B2 | 6/2011 | Moberg et al. |
| 7,963,954 B2 | 6/2011 | Kavazov |
| 7,981,085 B2 | 7/2011 | Ethelfeld |
| 8,034,026 B2 | 10/2011 | Grant et al. |
| 8,337,486 B2 | 12/2012 | Yodfat et al. |
| 8,360,114 B2 | 1/2013 | Clark |
| 8,409,143 B2 | 4/2013 | Lanigan et al. |
| 8,529,553 B2 | 9/2013 | Mounce et al. |
| 2001/0041869 A1 | 11/2001 | Causey et al. |
| 2002/0040208 A1 | 4/2002 | Flaherty et al. |
| 2002/0072733 A1 | 6/2002 | Flaherty |
| 2002/0104584 A1 | 8/2002 | Spero et al. |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0023206 A1 | 1/2003 | Bausmith et al. |
| 2003/0040714 A1 | 2/2003 | Coss |
| 2003/0050607 A1 | 3/2003 | Gagnieux et al. |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0104032 A1 | 6/2003 | Sawhney et al. |
| 2003/0125672 A1 | 7/2003 | Adair et al. |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0212364 A1 | 11/2003 | Mann et al. |
| 2003/0229310 A1 | 12/2003 | Flaherty et al. |
| 2003/0233069 A1 | 12/2003 | Gillespie et al. |
| 2004/0002682 A1 | 1/2004 | Kovelman et al. |
| 2004/0010207 A1 | 1/2004 | Flaherty et al. |
| 2004/0011866 A1 | 1/2004 | Saad |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |

(56) References Cited

U.S. PATENT DOCUMENTS

| | | |
|---|---|---|
| 2004/0073095 A1 | 4/2004 | Causey et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116847 A1 | 6/2004 | Wall |
| 2004/0116866 A1 | 6/2004 | Gorman et al. |
| 2004/0126413 A1 | 7/2004 | Sigurjonsson et al. |
| 2004/0140327 A1 | 7/2004 | Osborne et al. |
| 2004/0149349 A1 | 8/2004 | D'Antonio et al. |
| 2004/0158207 A1 | 8/2004 | Hunn et al. |
| 2004/0199140 A1 | 10/2004 | Rue et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0236201 A1 | 11/2004 | Lebel et al. |
| 2004/0260233 A1 | 12/2004 | Garibotto et al. |
| 2005/0022274 A1 | 1/2005 | Campbell et al. |
| 2005/0065760 A1 | 3/2005 | Murtfeldt et al. |
| 2005/0101920 A1 | 5/2005 | Keane et al. |
| 2005/0119618 A1 | 6/2005 | Gonnelli |
| 2005/0137530 A1 | 6/2005 | Campbell et al. |
| 2005/0240159 A1 | 10/2005 | Kito et al. |
| 2006/0106360 A1 | 5/2006 | Wong |
| 2006/0184103 A1 | 8/2006 | Paproski et al. |
| 2006/0184119 A1 | 8/2006 | Remde et al. |
| 2006/0200073 A1* | 9/2006 | Radmer ............ A61M 5/14244 604/93.01 |
| 2006/0253085 A1 | 11/2006 | Geismar et al. |
| 2006/0264835 A1 | 11/2006 | Nielsen et al. |
| 2006/0264894 A1 | 11/2006 | Moberg et al. |
| 2007/0062068 A1 | 3/2007 | Li |
| 2007/0066939 A1 | 3/2007 | Krulevich et al. |
| 2007/0073235 A1 | 3/2007 | Estes et al. |
| 2007/0079894 A1 | 4/2007 | Kraus et al. |
| 2007/0244444 A1 | 10/2007 | Guelker et al. |
| 2007/0293826 A1* | 12/2007 | Wall et al. .................... 604/200 |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0161772 A1 | 7/2008 | Nayak et al. |
| 2008/0172024 A1 | 7/2008 | Yow |
| 2008/0215030 A1 | 9/2008 | Ritsher |
| 2008/0249498 A1 | 10/2008 | Fangrow |
| 2008/0255521 A1 | 10/2008 | Kubo et al. |
| 2008/0257916 A1 | 10/2008 | Chang |
| 2008/0269682 A1 | 10/2008 | Kavazov et al. |
| 2008/0269687 A1 | 10/2008 | Chong et al. |
| 2009/0012497 A1 | 1/2009 | Uber et al. |
| 2009/0076453 A1 | 3/2009 | Mejlhede et al. |
| 2009/0206111 A1 | 8/2009 | Conrardy et al. |
| 2009/0221971 A1 | 9/2009 | Mejlhede et al. |
| 2009/0243283 A1 | 10/2009 | Schilp et al. |
| 2009/0326475 A1 | 12/2009 | Carlyon |
| 2010/0094241 A1 | 4/2010 | Remde et al. |
| 2010/0298768 A1 | 11/2010 | Halili et al. |
| 2011/0160654 A1 | 6/2011 | Hanson et al. |
| 2011/0282316 A1 | 11/2011 | Stepovich et al. |
| 2012/0004602 A1 | 1/2012 | Hanson et al. |
| 2012/0053520 A1 | 3/2012 | Kirkpatrick |
| 2015/0011971 A1 | 1/2015 | Lee |

FOREIGN PATENT DOCUMENTS

| | | |
|---|---|---|
| DE | 20 2007 006 363 U1 | 8/2007 |
| EP | 1 462 134 A1 | 9/2004 |
| EP | 1 527 792 A1 | 5/2005 |
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| EP | 2 077 128 B1 | 12/2010 |
| EP | 2301601 A1 | 3/2011 |
| EP | 2301602 A1 | 3/2011 |
| FR | 1.496.026 | 9/1967 |
| GB | 1 452 104 | 10/1976 |
| GB | 2 176 711 A | 1/1987 |
| GB | 2 207 652 A | 2/1989 |
| JP | 2004-524926 | 8/2004 |
| JP | 2005-503243 | 2/2005 |
| JP | 2006-520253 | 9/2006 |
| WO | WO 95/32015 | 11/1995 |
| WO | WO 96/26702 | 9/1996 |
| WO | WO 97/44078 | 11/1997 |
| WO | WO 97/46203 | 12/1997 |
| WO | WO 99/48546 | 9/1999 |
| WO | WO-99/59665 | 11/1999 |
| WO | WO-00/47254 | 8/2000 |
| WO | WO 00/69488 | 11/2000 |
| WO | WO 01/70307 A1 | 9/2001 |
| WO | WO-01/76684 A1 | 10/2001 |
| WO | WO 02/02165 A2 | 1/2002 |
| WO | WO-02/20073 A2 | 3/2002 |
| WO | WO-02/28454 A2 | 4/2002 |
| WO | WO-02/40083 A2 | 5/2002 |
| WO | WO-02/49509 A2 | 6/2002 |
| WO | WO-02/068015 A2 | 9/2002 |
| WO | WO-03/006090 A1 | 1/2003 |
| WO | WO-03/024504 A2 | 3/2003 |
| WO | WO 03/026728 A1 | 4/2003 |
| WO | WO-03/033051 A1 | 4/2003 |
| WO | WO-03/059372 A3 | 7/2003 |
| WO | WO 03/072172 A2 | 9/2003 |
| WO | WO-03/074121 A1 | 9/2003 |
| WO | WO-03/090509 A2 | 11/2003 |
| WO | WO-03/090819 A2 | 11/2003 |
| WO | WO-03/090838 A1 | 11/2003 |
| WO | WO-03/103758 A1 | 12/2003 |
| WO | WO-03/103763 A1 | 12/2003 |
| WO | WO 2004/006981 A2 | 1/2004 |
| WO | WO-2004/006982 A2 | 1/2004 |
| WO | WO 2004/030716 A2 | 4/2004 |
| WO | WO 2004/030717 A2 | 4/2004 |
| WO | WO-2004/047641 A2 | 6/2004 |
| WO | WO-2004/060436 A2 | 7/2004 |
| WO | WO-2004/082756 | 9/2004 |
| WO | WO-2004/093648 A2 | 11/2004 |
| WO | WO-2004/098390 A2 | 11/2004 |
| WO | WO-2004/098454 A2 | 11/2004 |
| WO | WO 2004/098683 A1 | 11/2004 |
| WO | WO 2004/110526 A1 | 12/2004 |
| WO | WO 2005/000382 A2 | 1/2005 |
| WO | WO-2005/072795 A0 | 8/2005 |
| WO | WO 2005/072795 A2 | 8/2005 |
| WO | WO-2005/094920 A1 | 10/2005 |
| WO | WO 2005/097237 A1 | 10/2005 |
| WO | WO-2006/015922 A1 | 2/2006 |
| WO | WO-2006/018425 A3 | 2/2006 |

(56) References Cited

FOREIGN PATENT DOCUMENTS

| WO | WO-2006/018447 A3 | 2/2006 |
|----|----|----|
| WO | WO-2006/024671 A1 | 3/2006 |
| WO | WO-2006/024672 A1 | 3/2006 |
| WO | WO-2006/032692 A1 | 3/2006 |
| WO | WO-2006/042811 A3 | 4/2006 |
| WO | WO 2006/058435 A2 | 6/2006 |
| WO | WO-2006/072416 A2 | 7/2006 |
| WO | WO-2006/075016 A1 | 7/2006 |
| WO | WO-2006/077262 A1 | 7/2006 |
| WO | WO-2006/077263 A1 | 7/2006 |
| WO | WO-2006/084464 A1 | 8/2006 |
| WO | WO-2006/086980 A1 | 8/2006 |
| WO | WO-2006/089547 A1 | 8/2006 |
| WO | WO-2006/089548 A1 | 8/2006 |
| WO | WO-2006/089965 A1 | 8/2006 |
| WO | WO-2006/096746 A1 | 9/2006 |
| WO | WO-2006/097453 A1 | 9/2006 |
| WO | WO-2006/104806 A2 | 10/2006 |
| WO | WO-2006/108775 A2 | 10/2006 |
| WO | WO-2006/108809 A1 | 10/2006 |
| WO | WO-2006/116997 A1 | 11/2006 |
| WO | WO-2006/120253 A2 | 11/2006 |
| WO | WO-2006/125692 A1 | 11/2006 |
| WO | WO-2007/000425 A2 | 1/2007 |
| WO | WO-2007/000426 A2 | 1/2007 |
| WO | WO-2007/000427 A1 | 1/2007 |
| WO | WO-2007/008511 | 1/2007 |
| WO | WO-2007/038091 A2 | 4/2007 |
| WO | WO 2007062068 A2 | 5/2007 |
| WO | 2007071258 A1 | 6/2007 |
| WO | WO-2007/071255 A1 | 6/2007 |
| WO | WO-2007/076641 A1 | 7/2007 |
| WO | WO-2007/087808 A1 | 8/2007 |
| WO | WO 2007/130809 A2 | 11/2007 |
| WO | WO 2008/024614 A2 | 2/2008 |
| WO | WO 2008/093063 A2 | 8/2008 |
| WO | WO-2008/136845 A1 | 11/2008 |
| WO | WO 2008/151241 A2 | 12/2008 |

OTHER PUBLICATIONS

PCT search report dated Feb. 3, 2009 from PCT Application No. PCT/US2008/082185.
Partial PCT search report (Invitation to Pay Additional Fees) dated Feb. 2, 2009 for related PCT application No. PCT/US2008/082186.
Partial PCT Search Report dated Mar. 5, 2009 from related PCT application No. PCT/US2008/082187.
PCT Search Report dated Apr. 28, 2009 from related PCT application No. PCT/US2008/082186.
Office Action dated Jan. 29, 2009 from related U.S. Appl. No. 11/604,172.
Office Action dated Apr. 10, 2009 from related U.S. Appl. No. 11/588,832.
Office Action dated Nov. 24, 2008 from related U.S. Appl. No. 11/759,725.
Office Action dated Apr. 13, 2009 from related U.S. Appl. No. 11/604,171.
Office Action dated Apr. 9, 2009 from related U.S. Appl. No. 11/515,225.
PCT Search Report Dated Jun. 5, 2009 from related PCT application No. PCT/US2008/082187.
Office Action dated Apr. 30, 2009 from related U.S. Appl. No. 12/027,963.
Office Action dated Jul. 8, 2009 from related U.S. Appl. No. 11/964,649.
Office Action dated Jul. 10, 2009 from related U.S. Appl. No. 12/411,236.
Office Action dated Aug. 4, 2009 from related U.S. Appl. No. 12/411,247.
Final Office Action dated Jan. 14, 2010 from related U.S. Appl. No. 12/411,247.
Final Office Action dated Sep. 24, 2009 for related U.S. Appl. No. 12/027,963.
Office Action dated Jan. 7, 2010 from related U.S. Appl. No. 11/964,649.
Office Action dated Mar. 4, 2010 from related U.S. Appl. No. 12/099,738.
US Office Action dated Nov. 10, 2009 from related U.S. Appl. No. 12/099,738.
US Office Action for U.S. Appl. No. 12/027,963 dated Sep. 24, 2009.
International Search Report and Written Opinion for PCT application No. PCT/US2008/082193 dated Jun. 29, 2010.
International Search Report and Written Opinion for related PCT Application No. PCT/US2007/076641 dated Feb. 27, 2008.
Office Action dated Jul. 21, 2010 from related U.S. Appl. No. 12/099,738.
Office Action dated Jun. 16, 2010 from related patent U.S. Appl. No. 12/027,963.
US Office Action dated Aug. 18, 2010 from related U.S. Appl. No. 12/107,580.
Office Action dated Dec. 22, 2010 from related U.S. Appl. No. 12/111,815.
Office Action dated Dec. 30, 2010 from related U.S. Appl. No. 12/107,580.
Office Action dated Dec. 9, 2010 from related U.S. Appl. No. 12/099,738.
US Office Action dated Oct. 15, 2010 from related U.S. Appl. No. 12/027,963.
US Office Action dated Oct. 1, 2010 U.S. Appl. No. 12/411,247.
U.S. Notice of Allowance dated Apr. 29, 2013 from related U.S. Appl. No. 12/497,345.
U.S. Notice of Allowance dated May 8, 2013 from related U.S. Appl. No. 11/515,225.
U.S. Notice of Allowance dated Jul. 30, 2013 from related U.S. Appl. No. 13/083,512.
U.S. Notice of Allowance dated Aug. 8, 2013 from related U.S. Appl. No. 13/163,548.
U.S. Notice of Allowance dated Aug. 21, 2013 from related U.S. Appl. No. 12/099,738.
US Notice of Allowance dated Mar. 3, 2011 from related U.S. Appl. No. 12/107,580.
US Office Action dated Mar. 29, 2011 from related U.S. Appl. No. 11/964,649.
US Office Action dated Mar. 8, 2011 from related U.S. Appl. No. 12/411,247.
U.S. Notice of Allowance from related U.S. Appl. No. 12/111,751, mailed Mar. 4, 2013.
Extended European Search Report (EESR) for EP Application No. 13191367.5 dated Dec. 17, 2013.
US Office Action from related U.S. Appl. No. 12/111,751, mailed Nov. 21, 2012, 13 pages.
US Office Action from related U.S. Appl. No. 12/099,738, mailed Dec. 20, 2012, 27 pages.
US Office Action from related U.S. Appl. No. 13/083,512, mailed Nov. 28, 2012, 18 pages.
US Notice of Allowance dated Jul. 27, 2011 from related U.S. Appl. No. 12/411,247.
U.S. Office Action dated May 7, 2015, from related U.S. Appl. No. 13/961,798.
U.S. Notice of Allowance dated May 22, 2015, from related U.S. Appl. No. 13/961,795.
U.S. Office Action dated Mar. 11, 2015, from related U.S. Appl. No. 13/971,771.
Canadian Examination Report dated Sep. 7, 2011, from related application No. 2685808.
Canadian Further Examination Report dated Jul. 12, 2012, from related Canadian patent application No. 2685808.
European Communication pursuant to Article 94(3) EPC dated Jan. 11, 2010 from related European patent application No. 07841183.2.
International Search Report and Written Opinion dated Feb. 29, 2008, from related international application No. PCT/US2007/076474.

(56) References Cited

OTHER PUBLICATIONS

Partial International Search Report dated Apr. 19, 2010, from related international application No. PCT/US2008/082193.
Partial International Search Report dated Feb. 18, 2008, from related international application No. PCT/US2007/076679.
US Notice of Allowance dated Apr. 29, 2011, from related U.S. Appl. No. 12/107,580.
US Office Action dated Aug. 10, 2010, from related U.S. Appl. No. 11/588,832.
US Office Action dated Feb. 23, 2011, from related U.S. Appl. No. 12/411,236.
US Office Action dated Jun. 17, 2009 from related U.S. Appl. No. 11/604,172.
US Office Action dated Jun. 7, 2012, from related U.S. Appl. No. 12/099,738.
US Office Action dated Sep. 28, 2010, from related U.S. Appl. No. 12/411,236.
US Notice of Allowance dated Apr. 1, 2013, from related U.S. Appl. No. 12/111,751.
US Notice of Allowance dated Apr. 20, 2011, from related U.S. Appl. No. 12/111,815.
US Notice of Allowance dated Apr. 26, 2010, from related U.S. Appl. No. 11/604,171.
US Notice of Allowance dated Aug. 12, 2015, on related U.S. Appl. No. 13/961,798.
US Notice of Allowance dated Aug. 9, 2012, from related U.S. Appl. No. 11/604,172.
US Notice of Allowance dated Feb. 16, 2012, from related U.S. Appl. No. 13/118,358.
US Notice of Allowance dated Jan. 19, 2010 from related U.S. Appl. No. 11/759,725.
US Notice of Allowance dated Jan. 26, 2011 from related U.S. Appl. No. 11/588,832.
US Notice of Allowance dated Jul. 28, 2015, from related U.S. Appl. No. 13/971,771.
US Notice of Allowance dated Jul. 3, 2012, from related U.S. Appl. No. 11/604,172.
US Notice of Allowance dated Jun. 23, 2009 from related U.S. Appl. No. 11/759,725.
US Notice of Allowance dated Mar. 21, 2013, from related U.S. Appl. No. 12/247,945.
US Notice of Allowance dated May 14, 2010 from related U.S. Appl. No. 11/759,725.
US Notice of Allowance dated Oct. 21, 2013, from related U.S. Appl. No. 13/163,548.
US Notice of Allowance dated Oct. 3, 2012, from related U.S. Appl. No. 12/027,963.
US Notice of Allowance dated Oct. 7, 2011, from related U.S. Appl. No. 11/964,649.
US Office Action dated Aug. 22, 2011, from related U.S. Appl. No. 12/247,945.
US Office Action dated Dec. 29, 2011, from related U.S. Appl. No. 12/111,751.
US Office Action dated Feb. 14, 2012, from related U.S. Appl. No. 12/247,945.
US Office Action dated Feb. 17, 2010, from related U.S. Appl. No. 11/604,172.
US Office Action dated Jun. 19, 2012, from related U.S. Appl. No. 12/111,751.
US Office Action dated Mar. 10, 2010, from related U.S. Appl. No. 11/515,225.
US Office Action dated Mar. 17, 2010, from related U.S. Appl. No. 11/604,171.
US Office Action dated Mar. 2, 2010 from related U.S. Appl. No. 11/588,832.
US Office Action dated May 24, 2013, from related U.S. Appl. No. 12/099,738.
US Office Action dated May 28, 2010, from related U.S. Appl. No. 11/604,172.
US Office Action dated May 29, 2013, from related U.S. Appl. No. 13/163,548.
US Office Action dated Nov. 19, 2008 from related U.S. Appl. No. 11/515,225.
US Office Action dated Nov. 21, 2008 from related U.S. Appl. No. 11/588,832.
US Office Action dated Nov. 21, 2008, from related U.S. Appl. No. 11/604,171.
US Office Action dated Nov. 21, 2012, from related U.S. Appl. No. 11/515,225.
US Office Action dated Nov. 26, 2012, from related U.S. Appl. No. 12/247,945.
US Office Action dated Oct. 10, 2012 from related U.S. Appl. No. 12/497,345.
US Office Action dated Oct. 19, 2009 from related U.S. Appl. No. 11/515,225.
US Office Action dated Oct. 24, 2011, from related U.S. Appl. No. 13/118,358.
US Office Action dated Oct. 9, 2009, from related U.S. Appl. No. 11/604,171.

\* cited by examiner

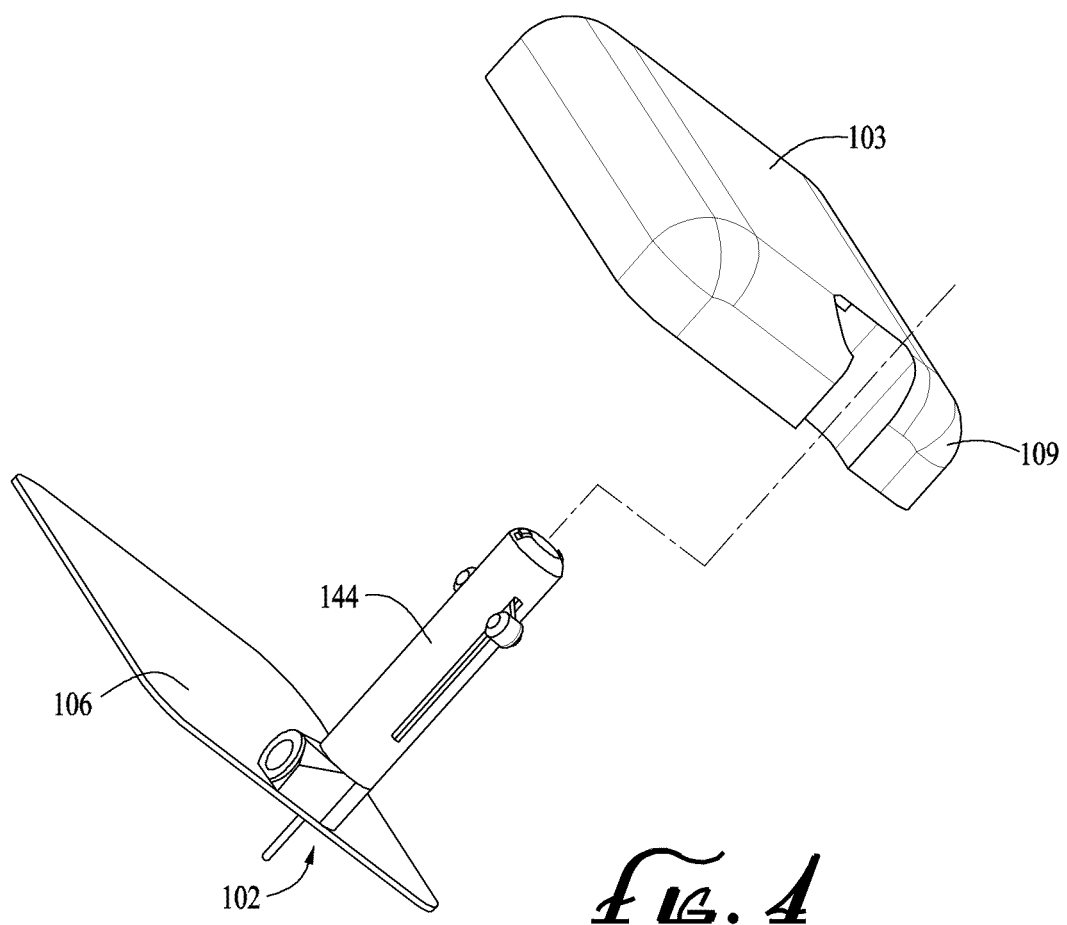

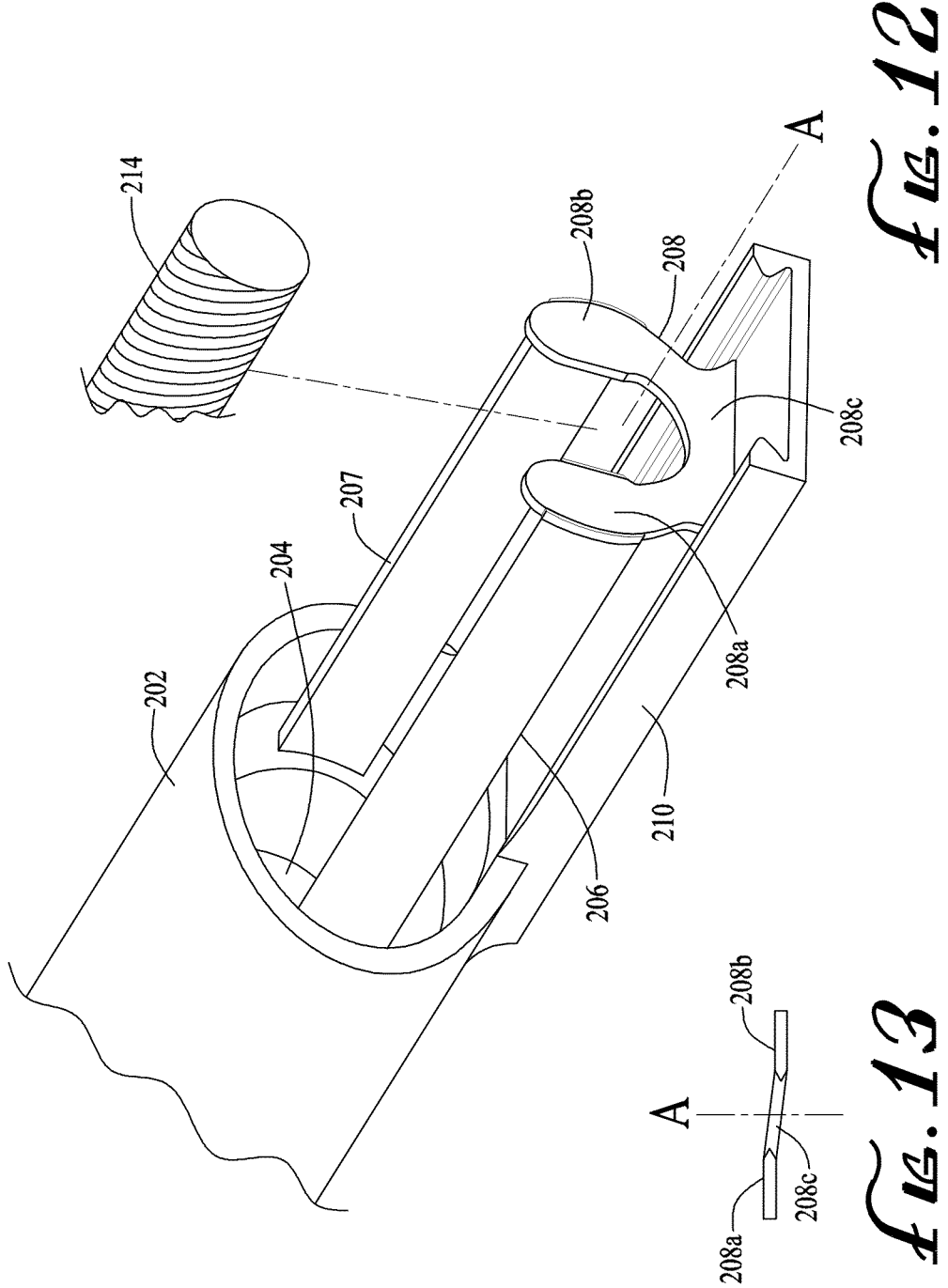

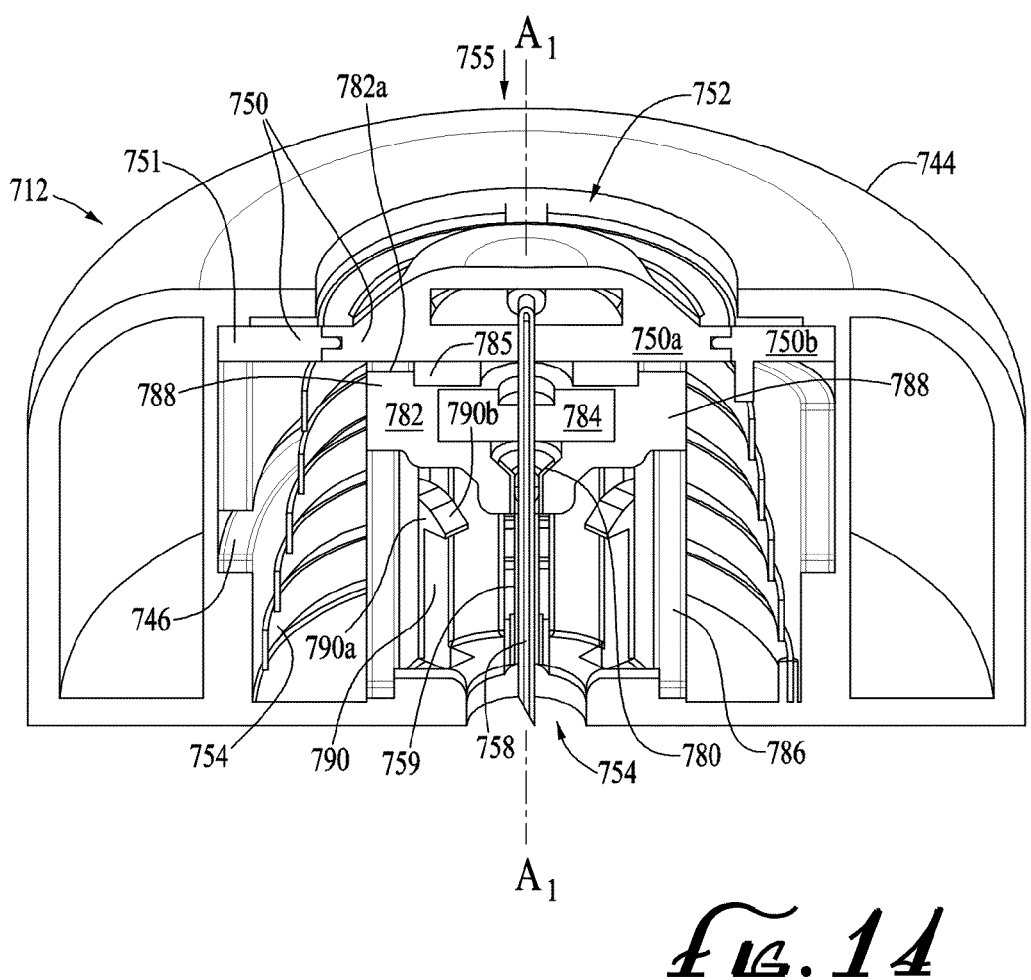

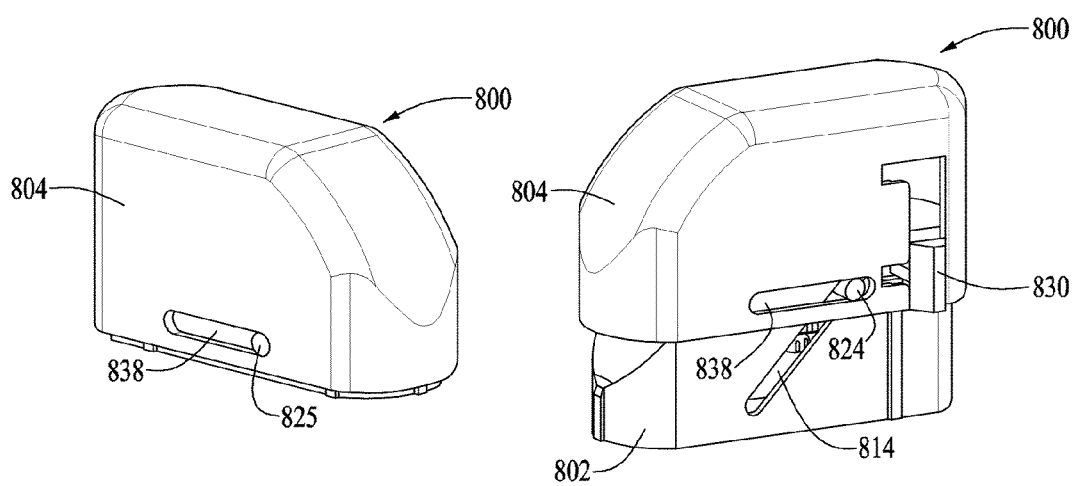

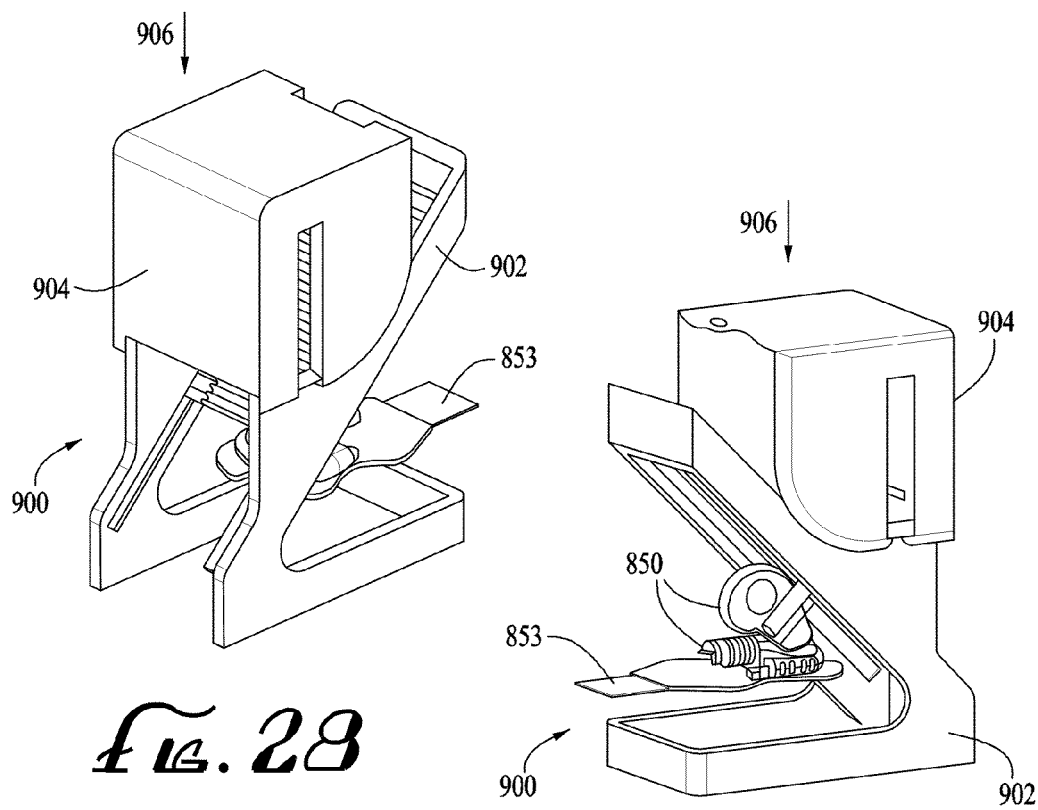
fig.28
fig.29
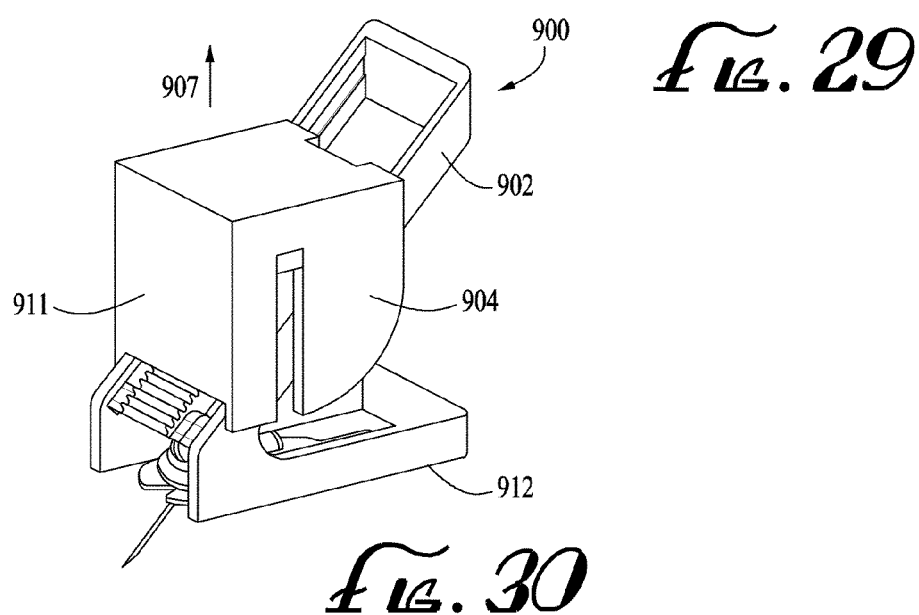
fig.30

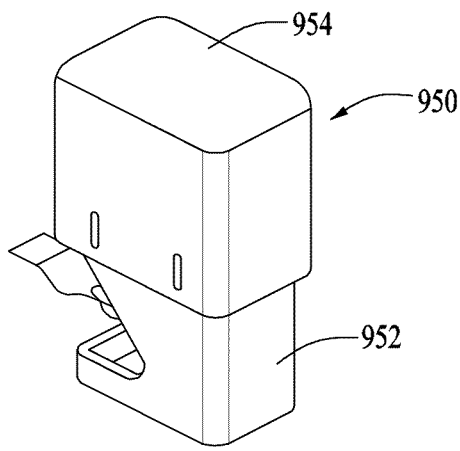
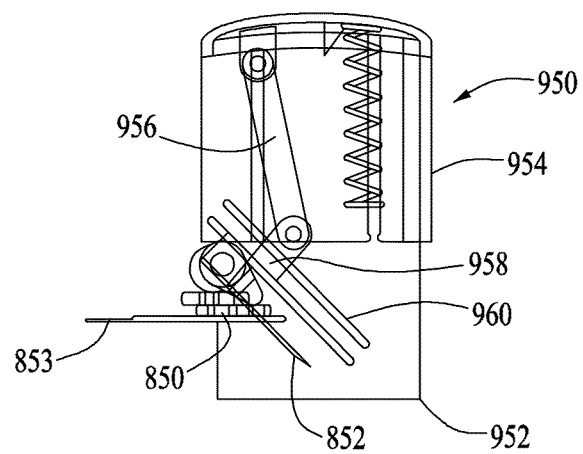
FIG. 35

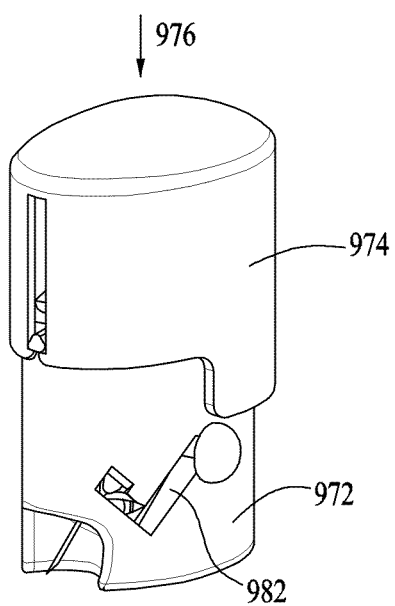
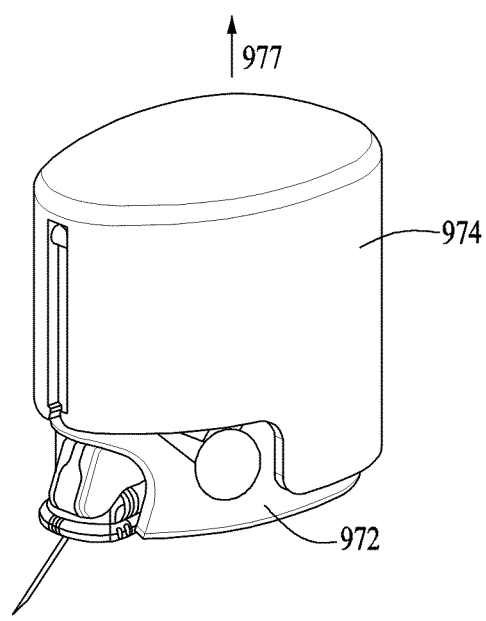

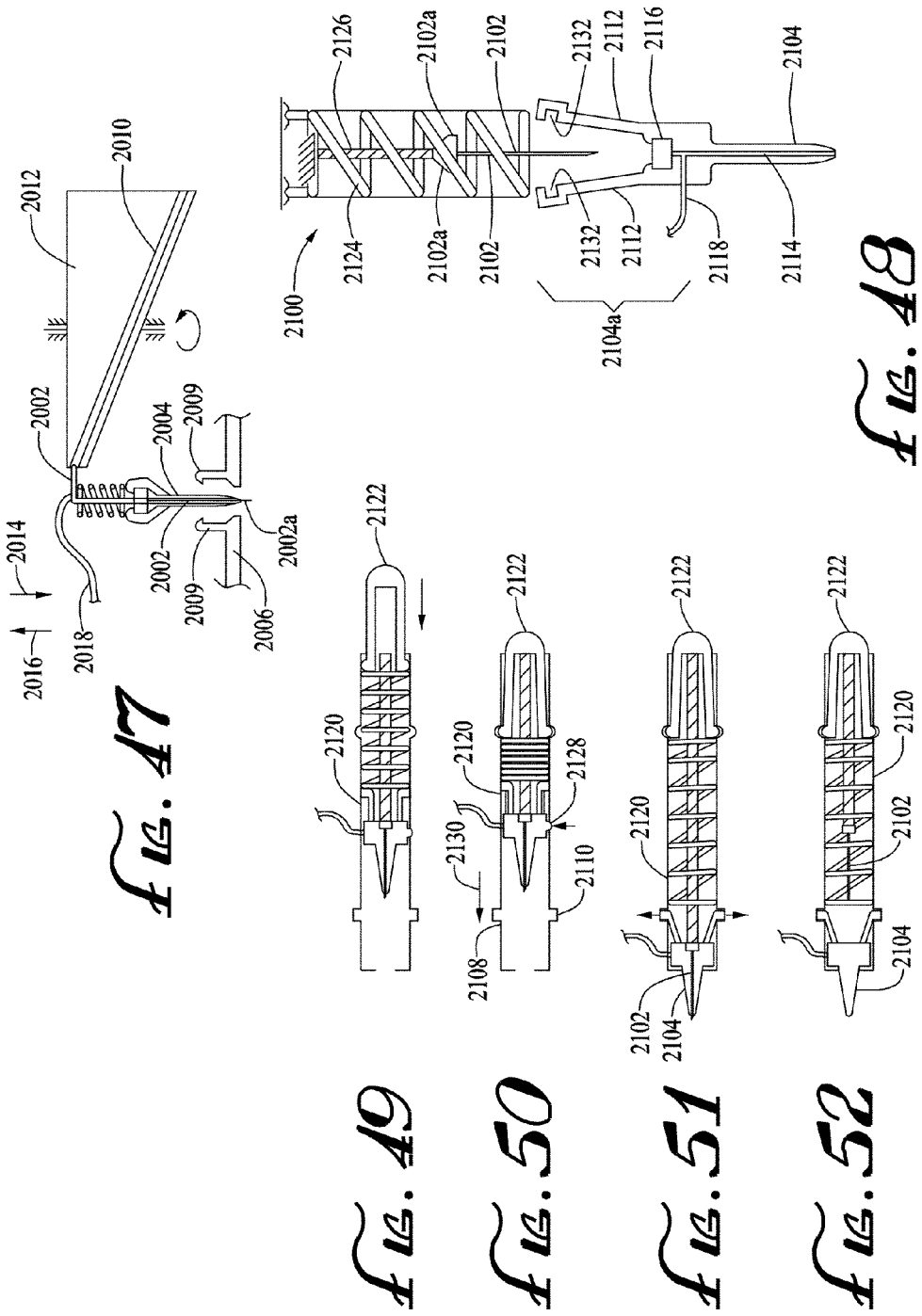

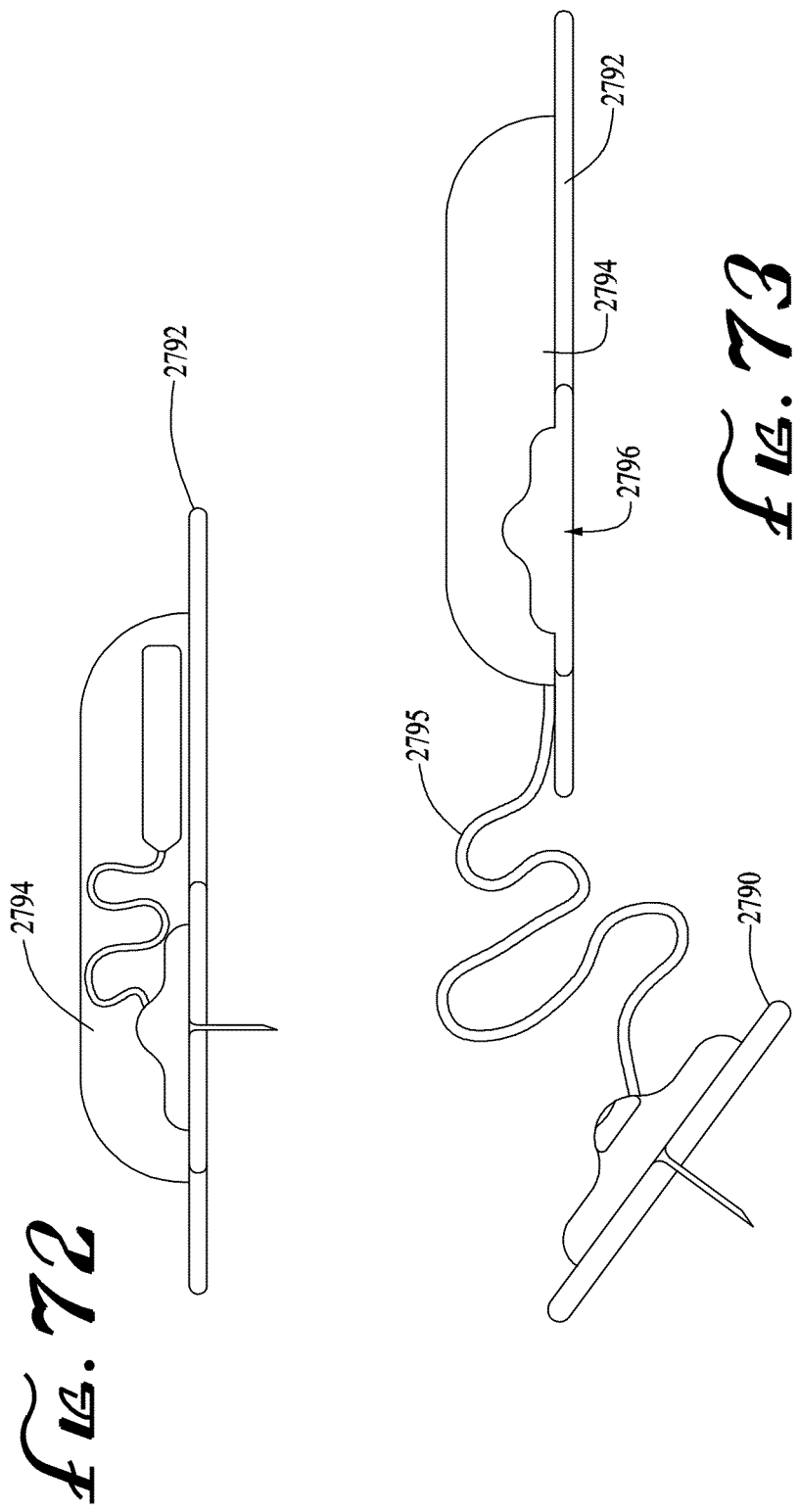

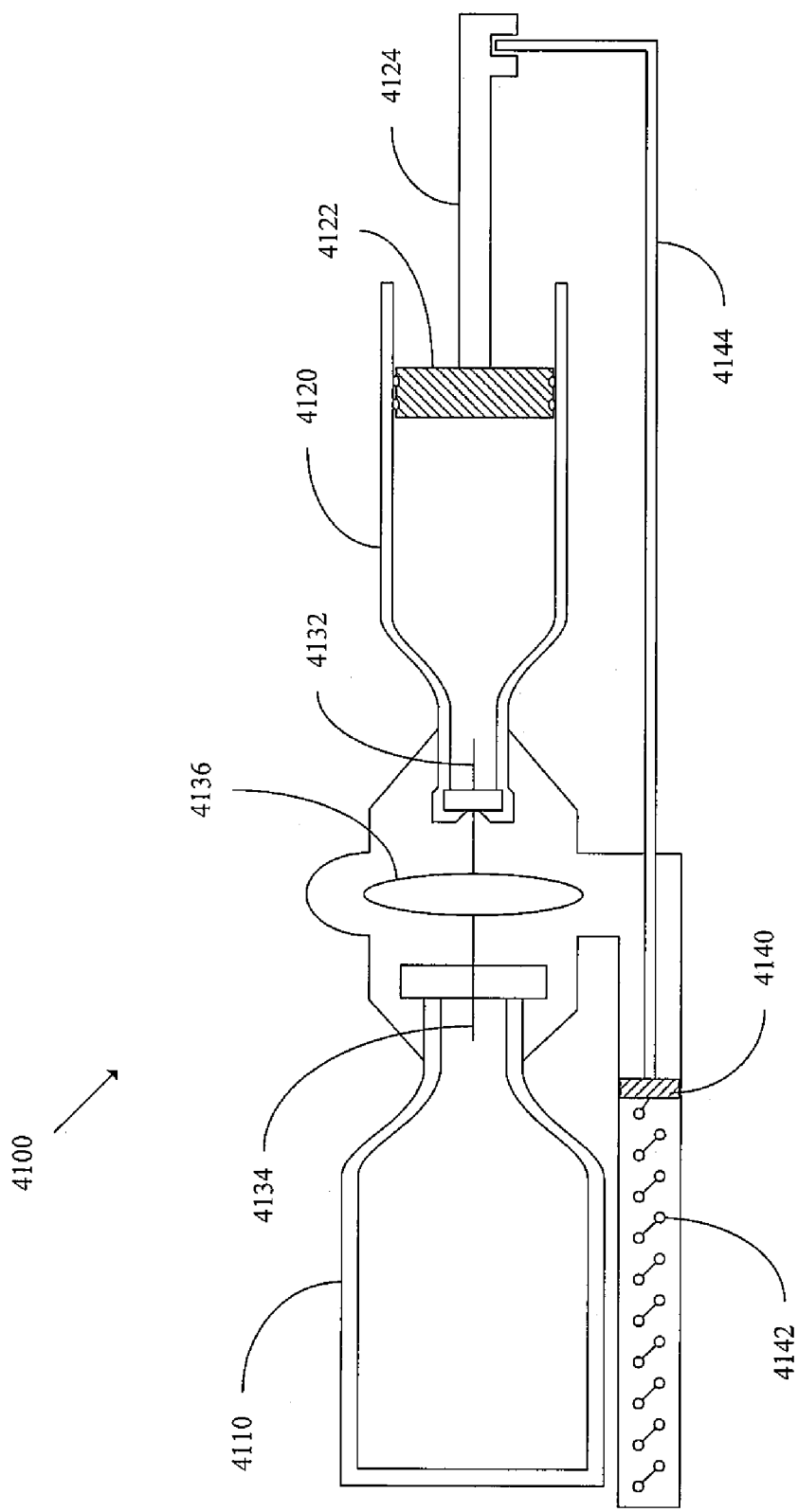

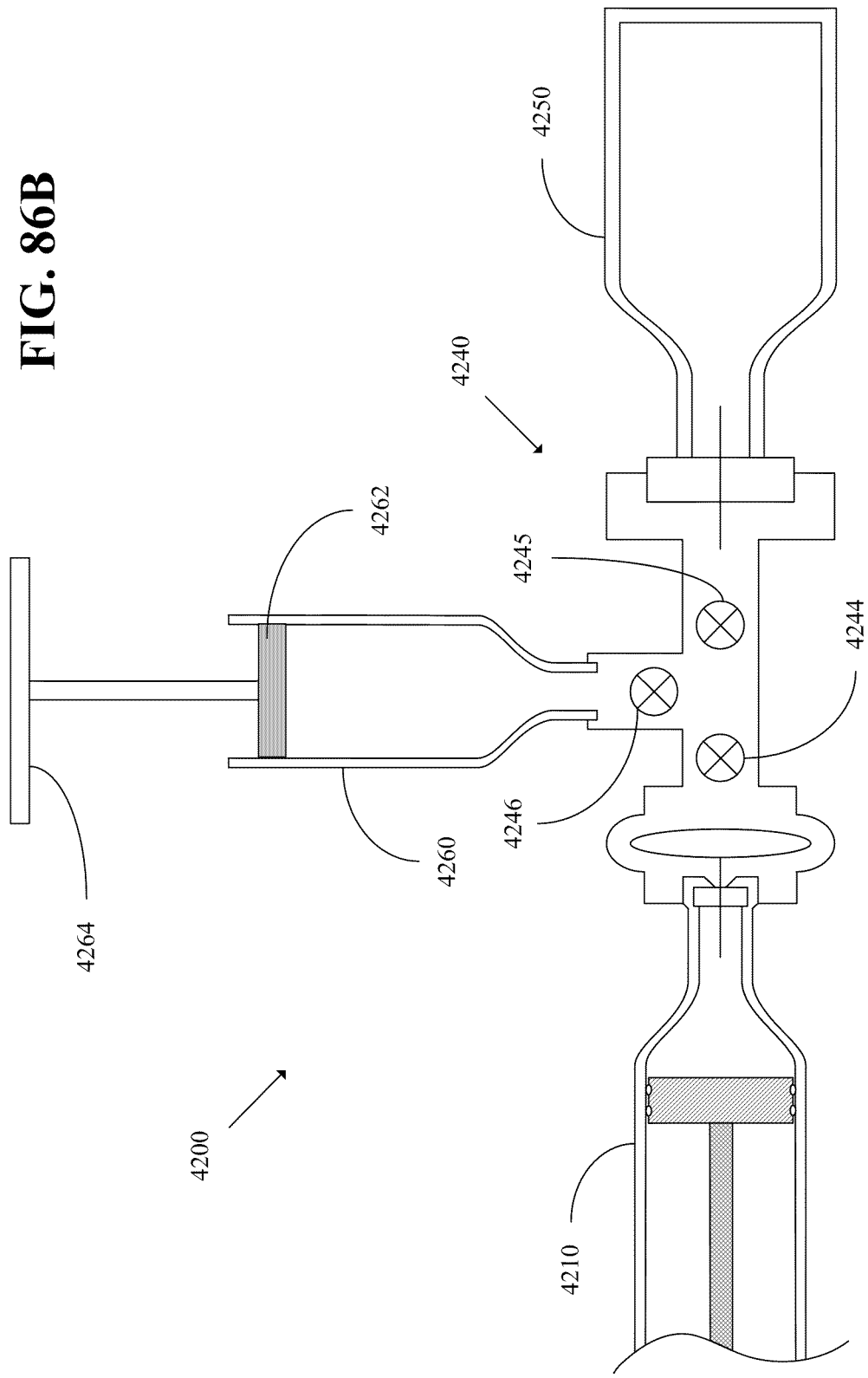

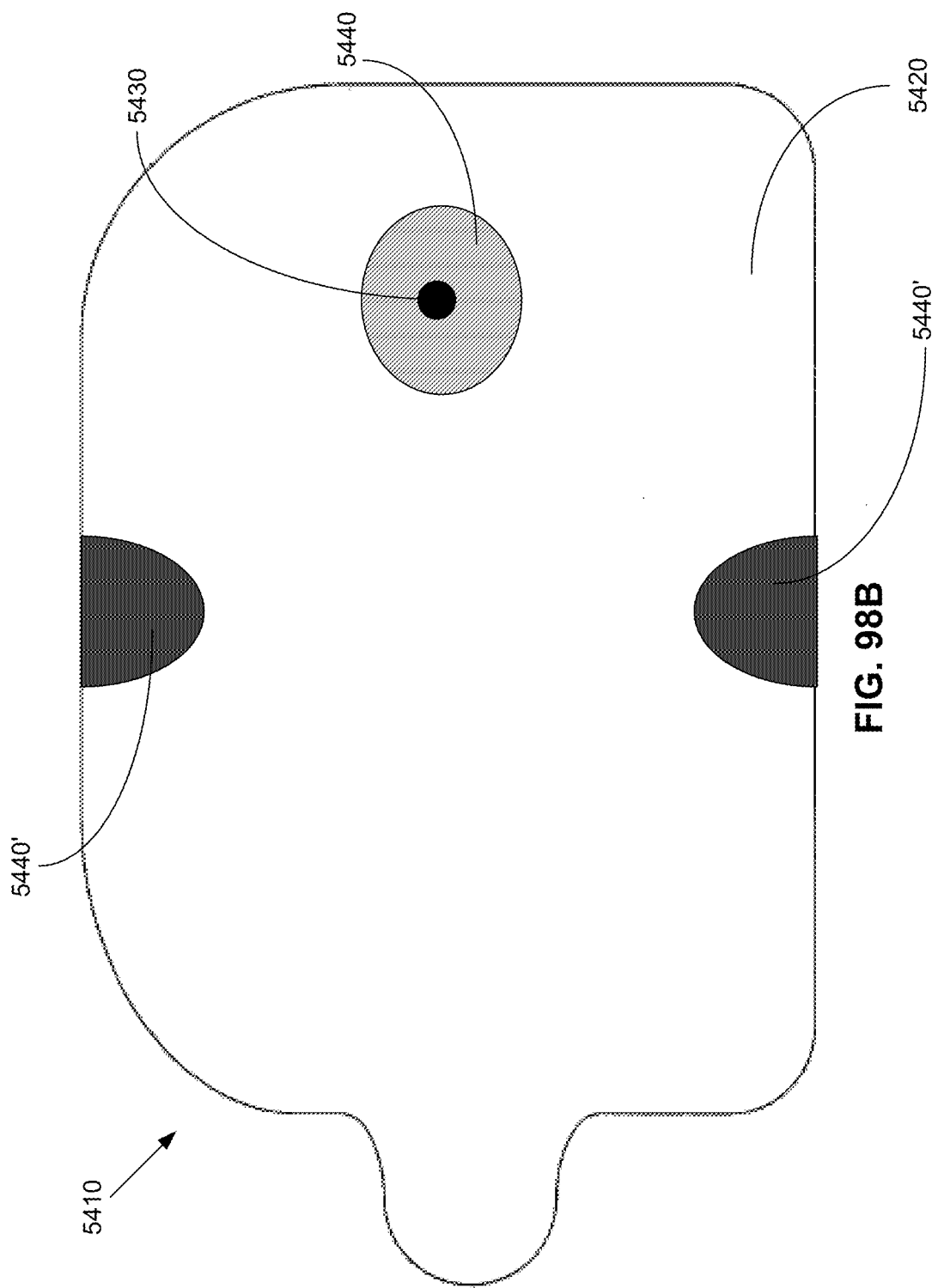

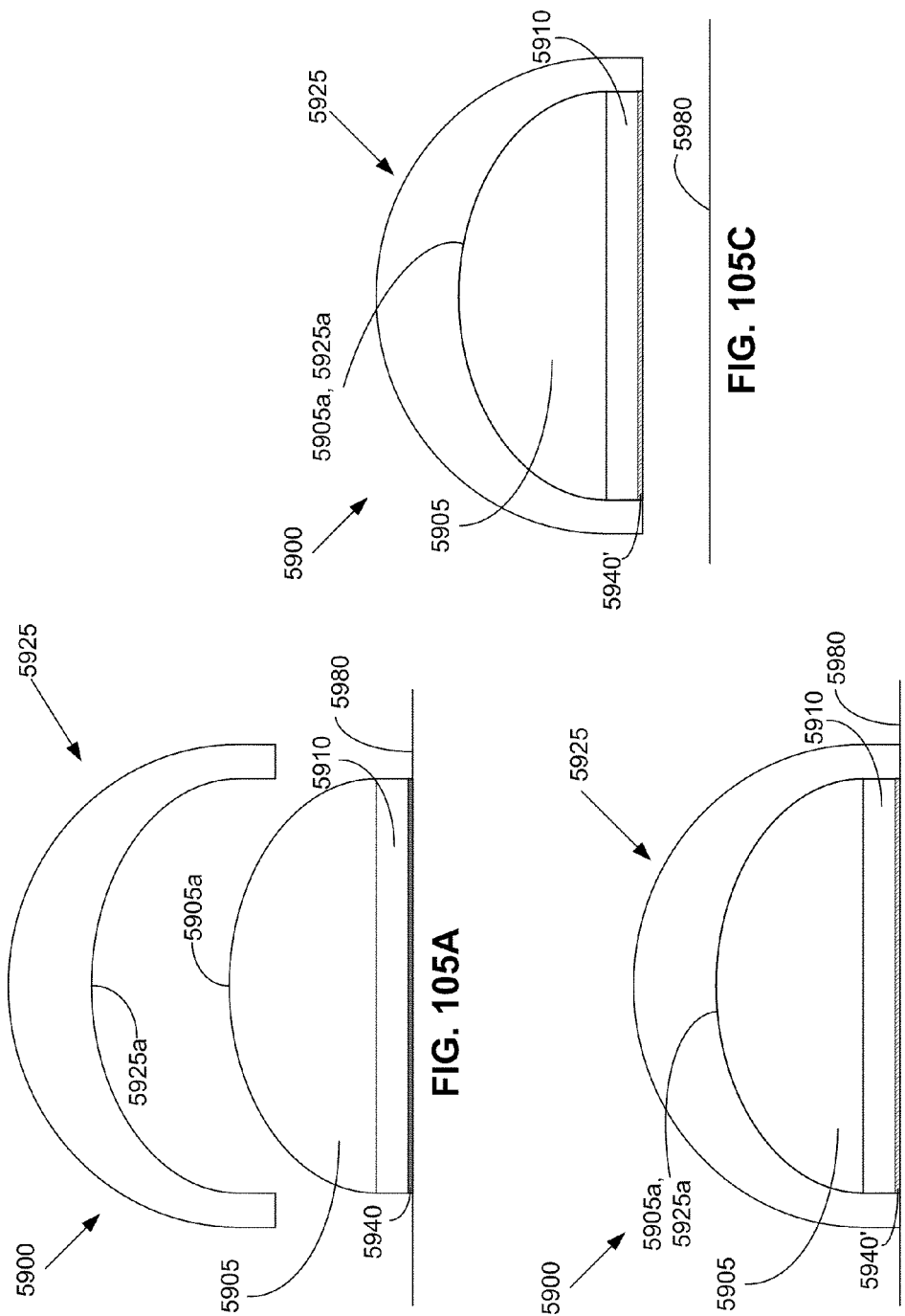

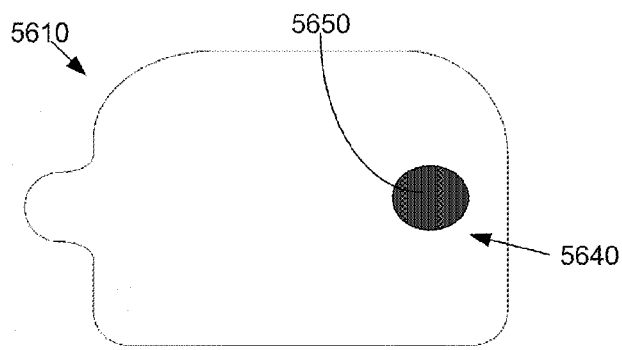
FIG. 106A
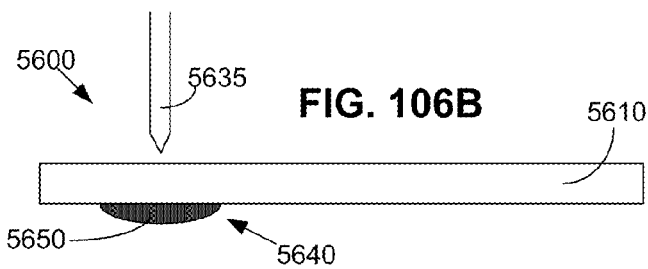
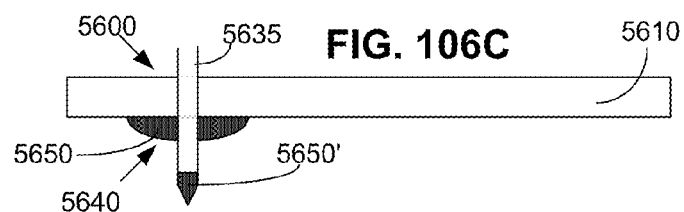
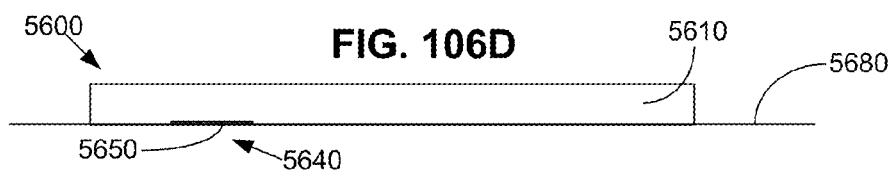
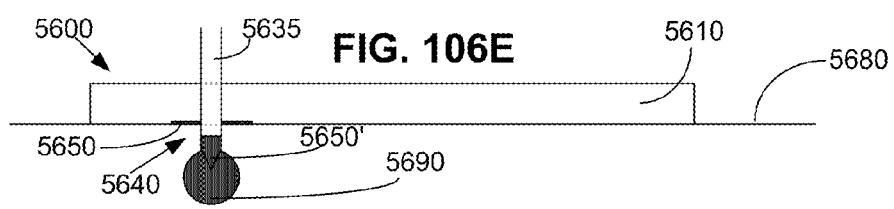

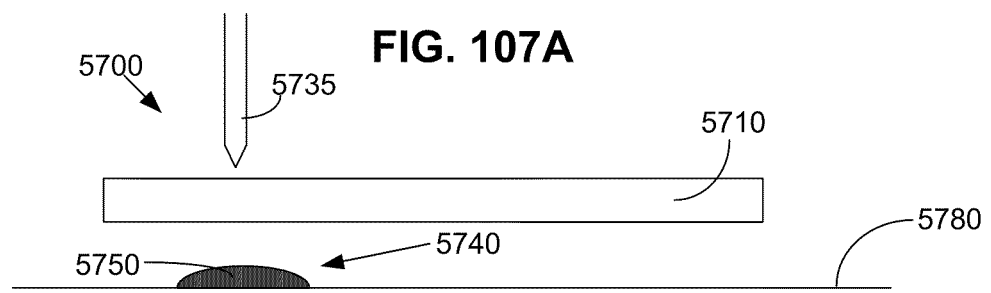
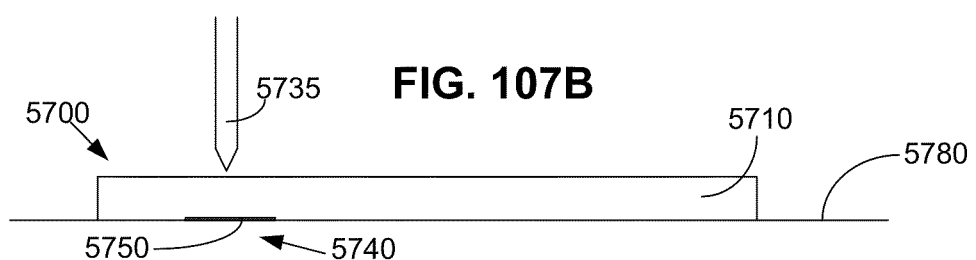
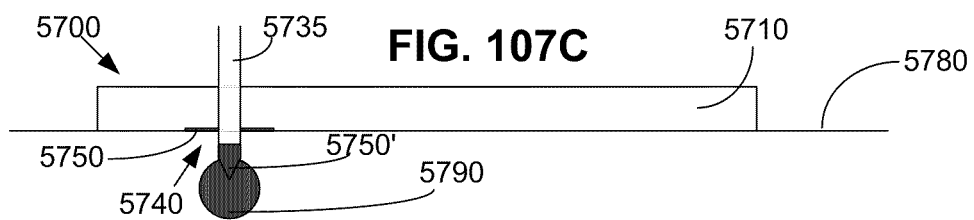

ADHESIVE PATCH SYSTEMS AND METHODS

CROSS-REFERENCE TO RELATED PATENT APPLICATIONS

This application is a Divisional of U.S. application Ser. No. 12/027,963, filed Feb. 7, 2008, incorporated herein by reference in its entirety, which claims priority from Provisional Application U.S. Application 60/927,032, filed Apr. 30, 2007, incorporated herein by reference in its entirety.

BACKGROUND OF THE INVENTION

Certain chronic diseases may be treated, according to modern medical techniques, by delivering a medication or other substance to a patient-user's body, either in a continuous manner or at particular times or time intervals within an overall time period. For example, diabetes is a chronic disease that is commonly treated by delivering defined amounts of insulin to the patient-user at appropriate times. Some common modes of providing an insulin therapy to a patient-user include delivery of insulin through manually operated syringes and insulin pens. Other modern systems employ programmable pumps to deliver controlled amounts of insulin to a patient-user.

Pump type delivery devices have been configured in external devices (that connect to a patient-user) or implantable devices (to be implanted inside of a patient-user's body). External pump type delivery devices include devices designed for use in a generally stationary location (for example, in a hospital or clinic), and further devices configured for ambulatory or portable use (to be carried by a patient-user). Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula or set of micro-needles.

In contexts in which the hollow tubing is connected to the patient-user through a hollow needle that pierces the patient-user's skin, a manual insertion of the needle into the patient-user can be somewhat traumatic to the patient-user. Accordingly, insertion mechanisms have been made to assist the insertion of a needle into the patient-user, whereby a needle is forced by a spring to quickly move from a retracted position into an extended position. As the needle is moved into the extended position, the needle is quickly forced through the patient-user's skin in a single, relatively abrupt motion that can be less traumatic to certain patient-users as compared to a slower, manual insertion of a needle. While a quick thrust of the needle into the patient-user's skin may be less traumatic to some patient's than a manual insertion, it is believed that, in some contexts, some patients may feel less trauma if the needle is moved a very slow, steady pace. Examples of insertion mechanisms that may be used with and may be built into a delivery device are described in: U.S. patent application Ser. No. 11/645,435, filed Dec. 26, 2006, titled "Infusion Medium Delivery system, Device And Method With Needle Inserter And Needle Inserter Device And Method,"; and U.S. patent application Ser. No. 11/211,095, filed Aug. 23, 2005, titled "Infusion Device And Method With Disposable Portion" (each of which is assigned to the assignee of the present invention), each of which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. Other examples of needle/cannula insertion tools that may be used (or modified for use) to insert a needle and/or cannula, are described in, for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

As compared to syringes and insulin pens, pump type delivery devices can be significantly more convenient to a patient-user, in that accurate doses of insulin may be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patient-users become more familiar with such devices, the popularity of external medical infusion pump treatment increases and is expected to increase substantially over the next decade.

SUMMARY OF THE INVENTION

Various embodiments of the present invention are directed to adhesive patches for medical devices. A medical device in accordance with an embodiment of the present invention may include, but is not limited to, a medical monitoring or treatment device, a base, and an adhesive material. The medical monitoring or treatment device may be configured to provide a monitoring or treatment operation on a user. The base may be adapted to be secured to the user during operation of the medical monitoring or treatment device. The base may have at least first and second areas that contact the user upon the base being secured to the user. The adhesive material may be provided on at least the first and second areas of the base for securing the base to the user. The adhesive material may have a different adhesion strength on the first area of the base than on the second area of the base. In some embodiments, the adhesive material may have a greater adhesion strength on the first area of the base than on the second area of the base. In other embodiments, the adhesive material may have a lesser adhesion strength on the first area of the base than on the second area of the base.

In various embodiments, the medical monitoring or treatment device may include at least one of a needle and a cannula for insertion into the skin of the user during operation of the medical monitoring or treatment device. The at least one of the needle and the cannula may be arranged in the first area of the base. In further embodiments, the base may have an opening through which the at least one of the needle and the cannula extend during operation of the medical monitoring or treatment device. The first area of the base may be adjacent to the opening in the base. In some embodiments, the first area of the base may be proximate to an edge of the base.

In various embodiments, the base may have at least a third area that contacts the user upon the base being secured to the user. The adhesive material may be provided on at least the third area of the base for securing the base to the user. The adhesive material may have a greater adhesion strength on the third area of the base than on the second area of the base. In some embodiments, the base may have an opening through which the at least one of the needle and the cannula extend during operation of the medical monitoring or treatment device. The third area of the base may be remotely located from the opening in the base. In some embodiments, the third area of the base may be proximate to an edge of the base. In some embodiments, the adhesive material may have an equal to or greater adhesion strength on the first area of the base than on the third area of the base.

In various embodiments, the base may have an opening through which the at least one of the needle and the cannula extend during operation of the medical monitoring or treatment device. The first area of the base may at least partially surround the opening in the base. In various embodiments, the base may be adapted to be secured to the skin of the user. The adhesive material may comprise a material that adheres to human skin. In various embodiments, a surface area of the second area of the base may be greater than a surface area of the first area of the base.

A method for securing a medical device may include, but is not limited to, supporting a medical monitoring or treatment device in a housing having a base, defining first and second areas of the base for contacting the user during operation of the medical monitoring or treatment device, and providing an adhesive material on at least the first and second areas of the base of the housing to allow the base to be secured to a user during operation of the medical monitoring or treatment device, including providing an adhesive material having a greater adhesion strength on the first area of the base than on the second area of the base.

A medical device in accordance with an embodiment of the present invention may include, but is not limited to, a medical monitoring or treatment device, a base, an adhesive material. The medical monitoring or treatment device may be configured to provide a monitoring or treatment operation on a user. The base may be adapted to be secured to the user during operation of the medical monitoring or treatment device. The base may have an area that contacts the user upon the base being secured to the user. The adhesive material may be provided on the area of the base for securing the base to the user. The adhesive material may be configured to react with a catalyst for activating the adhesive material.

In various embodiments, at least one of the catalyst and the adhesive material may be configured to activate upon the catalyst reacting with the adhesive material. In some embodiments, at least one of the catalyst and the adhesive material may be configured to activate a period of time after the catalyst reacts with the adhesive material. In various embodiments, at least one of the catalyst and the adhesive material configured to deactivate a period of time after activation of the adhesive material. In some embodiments, at least one of the catalyst and the adhesive material configured to react together to temporarily activate the adhesive material for a period of time. In various embodiments, the base may be adapted to be secured to the skin of the user. The adhesive material may comprise a material that adheres to human skin. In various embodiments, the adhesive material may have a greater adhesion strength upon activation of the adhesive material than before activation of the adhesive material.

In various embodiments, the adhesive material may have a different adhesion strength upon activation of the adhesive material than before activation of the adhesive material. In various embodiments, the catalyst may comprise at least one of a temperature source, a moisture source, a fluid source, a light source, an electromagnetic source, an infrared source, a frequency source, a vibration source, and a chemical agent.

In various embodiments, the medical monitoring or treatment device may be configured to operate with a delivery device for applying the catalyst to the adhesive material. In some embodiments, the medical monitoring or treatment device may be configured to operate with an inserter for at least one of the base and an infusion set having at least one of a cannula and an insertion needle for inserting into the skin of the user during operation of the medical monitoring or treatment device.

In various embodiments, the medical device may further include a delivery device for applying the catalyst to the adhesive material. The delivery device may be configured to operate with an inserter for at least one of the base and an infusion set having at least one of a cannula and an insertion needle for inserting into the skin of the user during operation of the medical monitoring or treatment device, such that the catalyst is applied to the adhesive material upon the at least one of the cannula and the insertion needle being inserted into the skin of the user.

In various embodiments, the delivery device may comprise a layer containing the catalyst. The layer may be applicable to a selective area of the adhesive material to activate the selective area of the adhesive material.

In various embodiments, the adhesive material may have a lesser adhesion strength upon activation of the adhesive material than before activation of the adhesive material. In various embodiments, the catalyst may comprise at least one of a temperature source, a moisture source, a fluid source, a light source, an electromagnetic source, an infrared source, a frequency source, a vibration source, a chemical agent, and air.

In various embodiments, the medical monitoring or treatment device may be configured to operate with a delivery device for applying the catalyst to the adhesive material. The medical monitoring or treatment device may be configured to operate with an inserter for at least one of the base and an infusion set having at least one of a cannula and an insertion needle for inserting into the skin of the user during operation of the medical monitoring or treatment device.

In various embodiments, the medical monitoring or treatment device may be configured to be operatively connectable to the delivery device. The medical monitoring or treatment device may be further configured to be removable by the delivery device in a case where the medical monitoring or treatment device is operatively connected to the delivery device and the adhesive material is activated. In various embodiments, the medical monitoring or treatment device may be configured to allow the delivery device to be inserted between the base of the medical monitoring or treatment device and the user to apply the catalyst to the adhesive material. In various embodiments, the delivery device may be configured to be inserted between the base of the medical monitoring or treatment device and the user to apply the catalyst to the adhesive material.

In various embodiments, the medical device may further include a delivery device for applying the catalyst to the adhesive material. The delivery device may be configured to operate with an inserter for at least one of the base and an infusion set having at least one of a cannula and an insertion needle for inserting into the skin of the user during operation of the medical monitoring or treatment device, such that the catalyst is applied to the adhesive material upon the at least one of the cannula and the insertion needle being inserted into the skin of the user.

A method for securing a medical device may include, but is not limited to, providing a medical monitoring or treatment device configured to provide a monitoring or treatment operation on a user, locating a base adapted to be secured to the user during operation of the medical monitoring or treatment device, the base having an area that contacts the user upon the base being secured to the user, and providing an adhesive material on the area of the base for securing the base to the user, the adhesive material configured to react with a catalyst for activating the adhesive material, the adhesive material having a different adhesion strength upon activation of the adhesive material than before activation of the adhesive material.

In various embodiments, the adhesive material may have a greater adhesion strength upon activation of the adhesive material than before activation of the adhesive material. In other embodiments, the adhesive material may have a lesser adhesion strength upon activation of the adhesive material than before activation of the adhesive material.

A medical device in accordance with an embodiment of the present invention may include, but is not limited to, a medical monitoring or treatment device and a pierceable membrane. The medical monitoring or treatment device may be configured to provide a monitoring or treatment operation on a user. The medical monitoring or treatment device may be operable with an insertion needle. The pierceable membrane may contain an agent. The pierceable membrane may be positioned to be pierced by the insertion needle during operation of the medical monitoring or treatment device and to allow the insertion needle to cause some of the agent to be carried from the pierceable membrane to the user.

In some embodiments, the insertion needle may carry some of the agent from the pierceable membrane to the user. In other embodiments, the insertion needle may pierce the pierceable membrane to allow at least some of the agent to flow from the pierceable membrane to the user.

In various embodiments, the base may be adapted to be secured to the user during operation of the medical monitoring or treatment device. The pierceable membrane may be positioned between the base and the user. In other embodiments, the base may be adapted to be secured to the user during operation of the medical monitoring or treatment device. The base may be positioned between the pierceable membrane and the user. In some embodiments, at least one of the pierceable membrane and the agent may be configured to allow the agent to react with the skin of the user before the pierceable membrane is pierced by the insertion needle.

In various embodiments, the agent may comprise at least one of an anti-inflammatory, an antiseptic, and an analgesic.

In various embodiments the medical device may further include a removable layer at least partially covering the pierceable membrane. At least one of the pierceable membrane and the agent may be configured to be reactable with air upon the removable layer being at least partially removed from the pierceable membrane.

A delivery method may include, but is not limited to, providing a medical monitoring or treatment device configured to provide a monitoring or treatment operation on a user, the medical monitoring or treatment device operable with an insertion needle, and positioning a pierceable membrane containing an agent to be pierced by the insertion needle during operation of the medical monitoring or treatment device and to allow the insertion needle to cause some of the agent to be carried from the pierceable membrane to the user.

BRIEF DESCRIPTION OF THE DRAWINGS

FIGS. 1-10 illustrate various aspects of a multiple-septum connections arrangement.

FIGS. 11-13 illustrate an example of an arrangement for connecting a drive shaft to a piston plunger in a pump device.

FIGS. 14-21 illustrate examples of a rotary needle inserting device.

FIGS. 22-70 illustrate further examples of needle inserting devices.

FIGS. 72 and 73 illustrate an infusion medium delivery system with a injection site module.

FIG. 85B illustrates a cross-sectional view of a system in accordance with an embodiment of the present invention;

FIG. 86B illustrates a cross-sectional view of a system in accordance with an embodiment of the present invention;

FIG. 98B illustrates an adhesive patch in accordance with an embodiment of the present invention;

FIGS. 105A-105C illustrate a medical device in accordance with an embodiment of the present invention;

FIGS. 106A and 106D illustrate a medical device in accordance with an embodiment of the present invention; and FIGS. 107A-107C illustrate a medical device in accordance with an embodiment of the present invention.

DETAILED DESCRIPTION OF THE PREFERRED EMBODIMENTS

Figure 1:
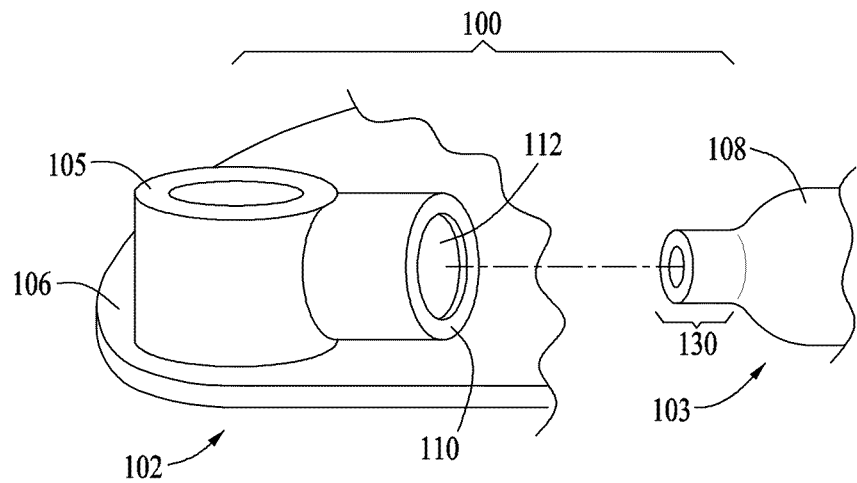

Aspects of the present invention relate, generally, to needle inserter or inserting devices and methods and medical devices, such as, but not limited to sensors, monitors and infusion medium delivery systems, devices and methods that include such needle inserting devices and methods. The needle inserting device and method may operate to insert a needle or cannula through a patient-user's skin, for example, to provide a fluid flow path for conveying an infusion medium through a hollow channel in the needle or cannula and into the patient-user and/or to convey a fluid from the patient-user to one or more sensor elements. Embodiments of the present invention may be configured, as described herein, to provide a reliable, cost effective and easy-to-use mechanism for inserting a needle or cannula to a specific depth into a patient-user with minimal traumatic effect.

In addition, embodiments may be configured to establish a contiguous fluid-flow passage for fluid transfer between a reservoir and the patient-user, when the hollow needle or cannula is inserted into the patient-user. Needle inserting devices according to embodiments of the present invention may be used with, connectable to and disconnectable from or incorporated in a portion of an infusion medium delivery system. For example, a needle inserting device may be connectable to a base structure of a pump type delivery device for insertion of a needle, after which the needle inserting device may be removed from the base structure, whereupon a further housing portion of the delivery device (containing components such as, but not limited to, a reservoir and pump or drive device) may be coupled to the base structure for operation. Alternatively, the needle inserting device may be incorporated into the further housing portion that contains other components as described above. In yet other embodiments, the needle inserting device may be connectable to (and releasable from) or incorporated within an injection site module or other housing that connects, for example, by flexible tubing, to other components of a medical device (such as, but not limited to an infusion medium delivery device). In yet other embodiments, needle inserter devices may be configured for use with systems other than infusion medium delivery systems, such as, but not limited to sensor and monitor systems, or the like.

Further aspects of the present invention relate to reservoir filling systems and processes and bubble management systems and processes for controlling bubbles during filling of a reservoir or operation of an infusion medium delivery device. Yet further aspects of the invention relate to connection structures for connecting devices in fluid-flow communication and tubing connectors that may be used for connecting fluid conduits used in infusion medium delivery devices or other systems involving fluid-flow.

A structure and method for connecting two members in fluid flow communication is described with reference to FIGS. 1-6.

The structure and method described with respect to FIGS. 1-6 may be employed in any suitable device or system in which two members that, at some period of time, are not connected in fluid flow communication, are to be connected together in a manner that allows fluid to flow from one member to the other. In one example embodiment, the structure and method is described with respect to a first member including a fluid reservoir for containing an infusion medium that is connectable to a second member including an injection site structure in which a hollow needle or cannula is or may be inserted into a patient-user, for conveying fluid media to the patient-user. However, connection structure according to embodiments of the present invention may be employed to connect any two (or more) members together, for fluid flow communication with each other.

In FIGS. 1-6, an example of a structure 100 and method for connecting two members in fluid flow communication is described with reference to a first member 102 and a second member 103. The first member 102 in the illustrated example includes a housing 104 on a base 106. The housing 104 may be formed integral with the base 106 or may be formed as a separate structure that is connected to the base 106 in a fixed relation to the base 106. The housing 104 and base 106 each may be made of any suitably rigid material, including, but not limited to plastic, metal, ceramic, composite material or the like.

The housing 104 in the illustrated example includes a section 105 that contains an injection site structure, in which a hollow needle or cannula may be inserted into a patient-user for conveying fluidic media to or from the patient-user. In other embodiments, instead of or in addition to an injection site, the housing 104 may contain, be part of or be operatively connected to any other suitable structure for conveying, containing and/or processing a fluidic medium.

The second member 103 also includes a housing 108, which, in the illustrated embodiment, is a housing of a reservoir for containing an infusion media. The second member 103 may be held within or otherwise covered by a further housing member 109 that is configured to attach to the base 106. The further housing 109 may connect to the base 106 of the first member 102 by any suitable connection structure. In particular embodiments, one or other of the housing 109 and the base 106 may include one or more flexible pawls, protrusions and/or indentations for engaging and receiving one or more corresponding pawls, protrusions and/or indentations on the other of the base 106 and the housing 109, to provide a suitable connection structure. Alternatively or in addition, the connection structure may include adhesive material or other suitable connectors.

In other embodiments, the housing 108 may be (or be connected to) a sensor housing that contains sensor components. In yet other embodiments, the housing 108 may contain, be part of or be operatively connected to any other suitable structure for conveying, containing and/or processing a fluidic medium. The housing 108 may be made of any suitably rigid material, including, but not limited to plastic, metal, ceramic, composite material or the like.

The housing 104 has or is connected to a receptacle structure 110. The receptacle structure has an opening 112 in the housing, that leads into a chamber 114 within the receptacle structure. In the illustrated embodiment, the receptacle structure 110 is part of the housing 104, adjacent the section of the housing that contains the injection site. In other embodiments, the receptacle structure 110 may include a further housing that is connected to the housing 104.

The receptacle structure 110 includes a first septum 116 located within the chamber 114 and moveable within the chamber 114, toward and away from the opening 112. The receptacle structure 110 also includes a bias mechanism 118, that applies a bias force on the septum 116, in the direction toward the opening 112. The bias mechanism 118 may force the septum 116 against the opening 112, wherein an annular protrusions (or one or more appropriately shaped or positioned protrusions) 120 adjacent the opening 112 may be provided to inhibit the septum 116 from being forced out of the chamber 114, through the opening 112. The septum 116 has a front surface 116a that is at least partially exposed through the opening 112, when the septum 116 is urged against the opening 112 by the bias mechanism 118. The septum 116 has a back surface 116b that faces toward the interior of the chamber 114. The septum 116 may be made of any suitable material that may be pierced by the needle 124, such as, but not limited to a natural or synthetic rubber material, silicon or the like. In particular embodiments, the septum 116 may be made of a self sealing material that is capable of sealing itself after a needle has pierced the septum and was subsequently withdrawn from the septum.

In the illustrated embodiment, the bias mechanism 118 is a coil spring located within the chamber 114, on the opposite side of the septum 116 with respect to the side of the septum that faces the opening 112. In other embodiments, the bias mechanism 118 may be provided by other suitable means for biasing the septum 116 toward the opening 112, including, but not limited to, other types of springs, pressurized fluid within the chamber 114, a collapsible skirt structure 122 extending from the septum 116 that has a natural or built-in spring force, chemical or substance that expands upon contact with another chemical or substance or upon application of energy from an energy source such as a heat, laser or other radiation source, or the like.

A hollow needle 124 is supported within the chamber 114, with a sharp end 124a of the needle 124 directed toward the back surface 116b of the septum 116. In the illustrated embodiment, the hollow needle 124 is supported within the coil spring bias mechanism 118, with its longitudinal axial dimension extending generally parallel to the longitudinal axial dimension of the coil spring. The hollow needle 124 may be supported by a supporting structure 126 located within the receptacle structure. In the illustrated embodiment, the supporting structure 126 is a wall that is integral with the housing of the receptacle structure 110 and is located on the opposite end of the chamber 114 relative to the end of the chamber 114 at which the opening 112 is located. However, in other embodiments, the supporting structure 126 may be any suitable structure that is generally fixed relative to the housing of the receptacle structure 110 and is able to support the needle 124 in a generally fixed relation to the housing of the receptacle structure 110.

The hollow needle 124 may be made of any suitably rigid material, including, but not limited to metal, plastic, ceramic, or the like, and has a hollow channel that extends in a lengthwise dimension of the needle. The hollow channel in the needle 124 is open on the sharp end 124 of the needle and is open at another location 124b along the length of the needle, such as, but not limited to, the needle end that is opposite to the sharp end 124a. The hollow channel in the needle 124 provides a fluid flow path between the sharp end 124a of the needle and the opening 124b of the needle. In the illustrated embodiment, the opening 124b of the hollow needle 124 is connected in fluid flow communication with a manifold 128 in a needle injector structure described below.

The housing 108 of the second member 103 includes a connection portion 130 that has a hollow interior chamber 132 and an opening 134 into the hollow interior. A second septum 136 is supported by the housing 108 to seal the opening 134. The septum 136 may be supported in a fixed relation to the housing 108, for example, within housing 108, at one end of the chamber 132.

Figure 2:
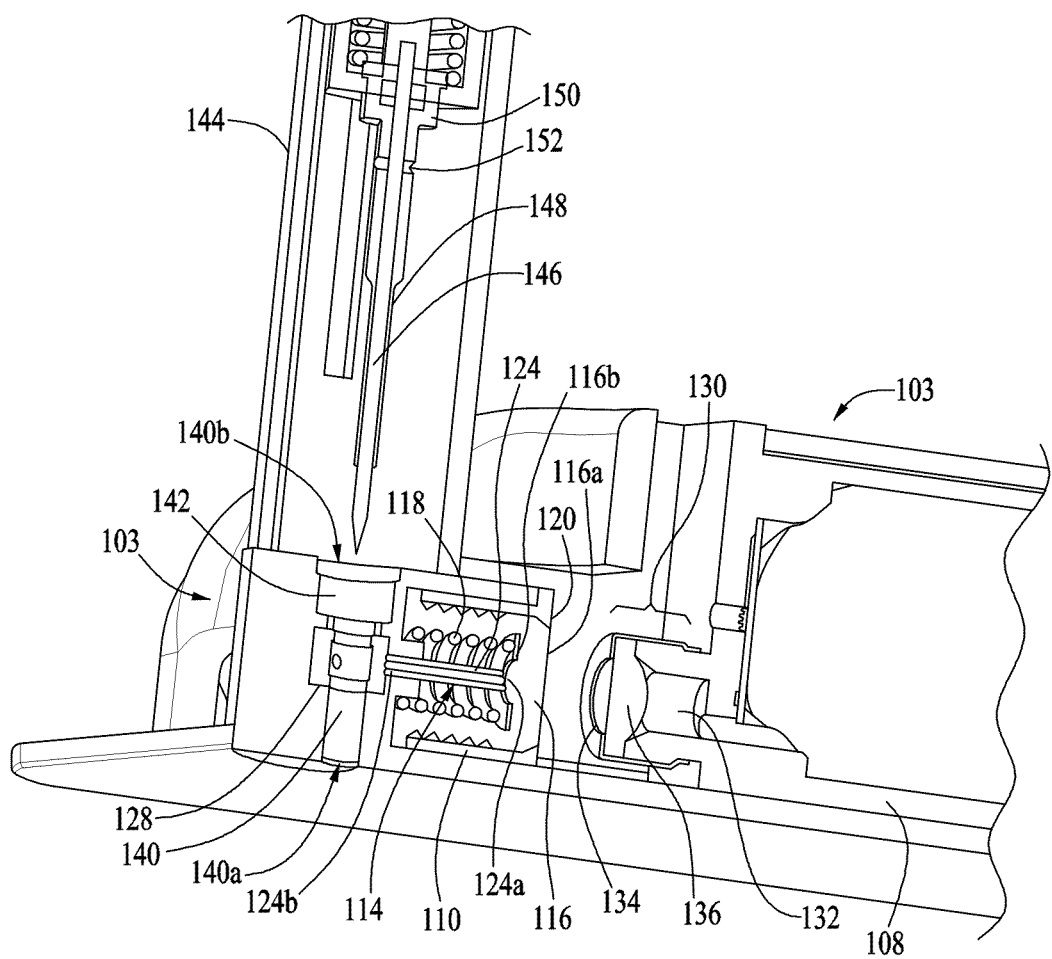
Figure 5:
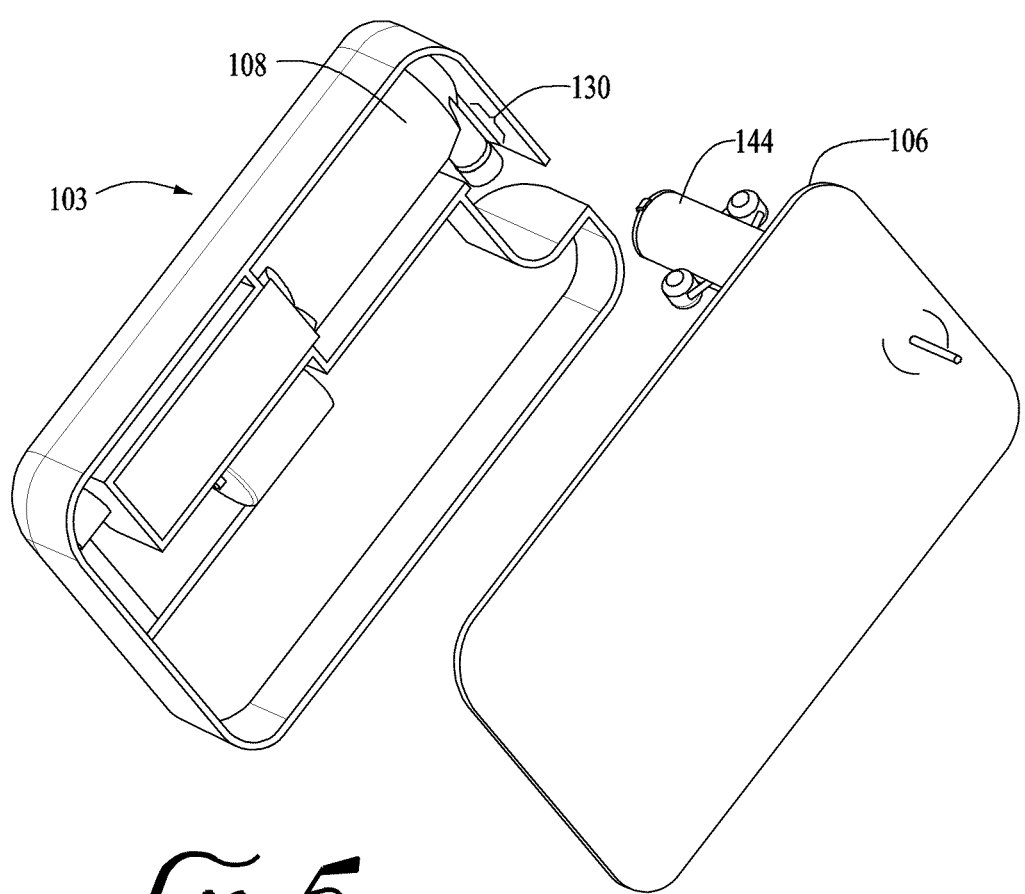
Figure 6:
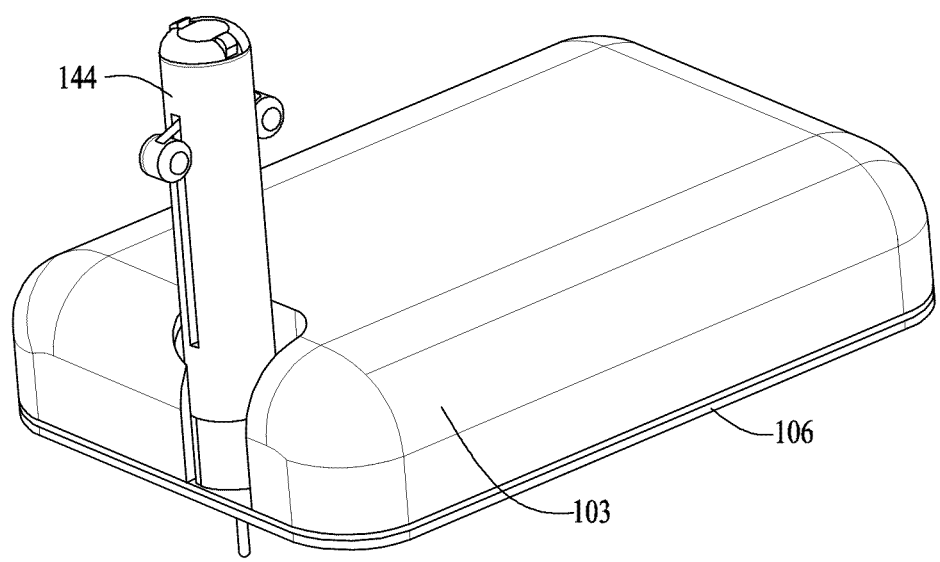

The connection portion 130 of the housing 108 has a suitable shape and size to fit at least partially within the opening 112 of the receptacle structure 110 in the first member 102, when the first and second members 102 and 103 are connected together. In the drawings of FIGS. 1 and 2, the first and second members 102 and 103 are shown in a separated, disconnected relation, wherein the connection portion 130 of the housing 108 is outside of the opening 112 of the receptacle structure 110. By moving the first and second members 102 and 103 together to insert the connection portion 130 into the opening 112 of the housing 108, an end surface 138 of the connection portion 130 is urged against the moveable septum 116 and causes the moveable septum 116 to move relative to the housing 108, against the force of the bias mechanism 118, toward the interior of the chamber 114. As the septum 116 is moved toward the interior of the housing 108, the sharp end 124a of the needle 124 pierces the septum 116. Continued relative movement of the first and second members 102 and 103 together causes the sharp end 124a of the needle 124 to pass through the septum 116 in the first member 102 and then pierce and pass through the septum 136 in the second member 103.

Figure 3:
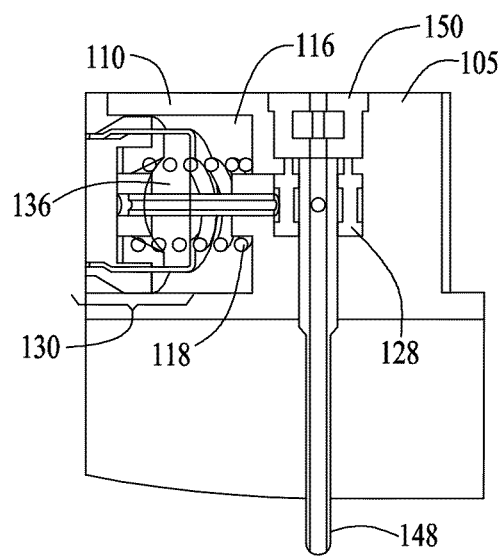

When the first and second members 102 and 103 are brought together as described above and as shown in FIG. 3, at least a portion of the connection portion 130 extends inside of the housing of the receptacle structure 110. In addition, the hollow needle pierces the first and second septa 116 and 136 to form a fluid flow path between the interior chamber 132 of the connection portion 130 and the manifold 128 (or other structure at the opening 124b of the needle 124). The receptacle structure 110 and the connection portion 130 may be provided with mating connectors that provide, for example, a snap or friction connection, upon the first and second members 102 and 103 being brought together as shown in FIG. 3. In one embodiment, the mating connectors may include a protrusion on one or the other of the receptacle structure 110 and the connection portion 130 and a groove or indentation in the other of the receptacle structure 110 and the connection portion 130, arranged to engage each other in a snap-fitting manner, upon the connection portion 130 being extending into the receptacle structure 110 a suitable distance.

As mentioned above, in the illustrated embodiment, the opening 124b of the needle 124 is connected in fluid flow communication with the manifold 128 in an injection site structure. The injection site structure is provided within the section 105 of the housing 104 (FIG. 1) and includes a channel 140 that extends through the housing 104 and the base 106. The channel 140 has an open end 140a on the bottom surface (relative to the orientation shown in FIG. 2) of the base 106. The channel 140 has another open end 140b at the upper surface (relative to the orientation shown in FIG. 2) of the section 105 of the housing 104. The manifold 128 is located along the length of the channel 140 and is in fluid flow communication with the channel 140. Accordingly, the hollow needle 124 is arranged in fluid flow communication with the interior of the channel 140, through the manifold 128. The channel 140 includes a channel section 142 that has a larger radial dimension relative to the rest of the channel 140 and has a suitable shape and size to receive a cannula head, as described below.

A needle inserting device 144 may be located adjacent the open end 140b of the channel 140 and arranged to selectively extend a needle and/or cannula into the open end 140b of the channel and at least partially through the channel 140 as described below. The needle inserting device 144 may be configured to be integral with or otherwise fixed to the section 105 of the housing 104 of the first member 102. Alternatively, the needle inserting device 144 may be a separate device (relative to the housing 104) and may be selectively connected to (in alignment with the channel 140 as shown in FIG. 2) and disconnected from the section 105 of the housing 104.

In embodiments in which the needle inserting device 144 is a separate structure that connects to and disconnects from the housing section 105, suitable connection structure may be provided on the needle inserting device 144 and the housing section 105 to provide a manually releasable connection between those components. Such connection structure may include, but not limited to a threaded extension on one or the other of the needle inserting device 144 and the housing section 105 and a corresponding threaded receptacle on the other of the housing section 105 and the needle inserting device 144, for receiving the threaded extension in threaded engagement. In other embodiments, other suitable connection structure may be employed, including, but not limited to flexible pawls or extensions on one or the other of the needle inserting device 144 and the housing section 105 and a corresponding aperture, stop surface or the like on the other of the other of the housing section 105 and the needle inserting device 144.

In the drawing of FIG. 2, the needle inserting device 144 is shown as connected to the housing section 105 and with a needle 146 and cannula 148 in a retracted state. The needle inserting device 144 operates to selectively move the needle 146 and cannula 148 from the retracted state (shown in FIG. 2) to an extended state (not shown) in which the needle and cannula are extended through the opening 140b of the channel 140 and at least partially through the channel 140, such that the sharp end of the needle 146 and at least a portion of the length of the cannula 148 extend out the opening 140a of the channel 140. Various examples of suitable structure for needle inserting devices are described in U.S. patent application Ser. No. 11/645,435, filed Dec. 26, 2006, titled "Infusion Medium Delivery system, Device And Method With Needle Inserter And Needle Inserter Device And Method," which is assigned to the assignee of the present invention and is incorporated herein by reference, in its entirety. Other examples of suitable structure for needle inserting devices are described herein.

The cannula 148 has a hollow central channel extending along its longitudinal length and open at one end (the cannula end adjacent the sharp end of the needle 146). The other end of the cannula 148 has a head 150 that has a larger radial dimension than the shaft portion of the cannula. The cannula head 150 has a suitable shape and size to fit into the section 142 of the channel 140, when the needle 146 and cannula 148 are moved to the extended state by the needle inserting device 144. In particular embodiments, the cannula head 150 may include one or more protrusions and/or indentations that engage with one or more corresponding indentations and/or protrusions in the channel section 142 of the housing section 105, to provide a friction fit, snap fit or the like, to lock or retain the cannula 148 in place within the housing section 105, upon the needle 146 and cannula 148 being moved to the extended state by the needle inserting device 144. In further embodiments, instead of or in addition to engaging protrusions and indentations, other mechanical structure may be employed to provide a suitable retaining function for retaining the cannula 148 in place within the housing section 105, upon the needle 146 and cannula 148 being moved to the extended state by the needle inserting device 144, including but not limited to friction fit structure, snap fit, or the like.

The cannula 148 also has a connection channel 152 that is provided in fluid flow communication with the central, longitudinal channel of the cannula. The connection channel 152 is provided, along the longitudinal length of the cannula, at a location at which the channel 152 aligns with the manifold 128 (in fluid flow communication with the interior of the manifold 128), when the needle 146 and cannula 148 have been moved to the extended state by the needle inserting device 144. In this manner, upon the cannula 148 being moved to the extended state, the central, longitudinal channel of the cannula is arranged in fluid flow communication with the hollow needle 124, through the manifold 128 and connection channel 152.

Accordingly, in operation, a first member 102 (which may include, for example, a housing 104 that has a receptacle 110 and a injection site section 105) is coupled together with a second member 103 (which may include, for example, a fluid reservoir housing 108), by inserting the connection portion 130 of the second member 103 into a receptacle 110 of the first member 102. Upon coupling the first and second members 102 and 103, fluid flow communication is provided between the interior of the second member 103 and the injection site structure in the first member 102.

In addition, the needle inserting device 144 is coupled to the section 105 of the housing 104 of the first member 102 (or is provided as part of a single, unitary structure with the section 105 of the housing 104). The base 106 of the first member 102 may be secured to a patient-user's skin (at a suitable injection location) with, for example, but not limited to, adhesive material as described in U.S. patent application Ser. No. 11/645,435, filed Dec. 26, 2006, titled "Infusion Medium Delivery system, Device And Method With Needle Inserter And Needle Inserter Device And Method," and/or as described herein. Alternatively or in addition, the base 106 may be secured to a patient-user by other suitable structure, including, but not limited to straps, or the like.

Once the base is suitably secured to the patient-user's skin at a suitable injection location, the inserting device 144 may be actuated to move the needle 146 and cannula 148 from a retracted state (shown in FIG. 2), to an extended state. In the extended state, the needle 146 and cannula 148 pierce the patient-user's skin adjacent the base 106. The cannula 148 may be locked into its extended state by engagement of the cannula head 150 and the channel section 142, as described above. With the cannula 148 locked in the extended state, the needle 146 may be retracted (for example, by automatic operation of the needle inserting device 144 and/or by manual removal of the needle inserting device 144 from the housing section 105). Once the needle 146 is removed, the cannula 148 is held in place by the housing section 105, with a portion of the cannula 148 extending into the patient-user, and with the cannula 148 connected in fluid-flow communication with the hollow needle 124. If the first and second members 102 and 103 are connected together, as described above, then a fluid-flow connection is provided from the reservoir 108 to the cannula 148, through the hollow needle 124 and the manifold 128.

The connection sequence (e.g., the sequence of connecting the needle inserting device 144 to the section 105 of the housing 104, connecting the receptacle 110 of the housing 104 to the connection portion 130 of the reservoir housing 108, and connecting the base 106 of the first member to a patient-user's skin) may be different for different embodiments. In one embodiment, a patient-user may be provided with a first member 102 that includes the base 106 and the housing 104 (including housing portion 105) in a pre-connected state with the needle inserting device 144. In this manner, the patient-user need not have to connect the needle inserting device 144 to the housing 104 (as those parts are supplied to the user in a pre-connected state, for example, from a manufacturing or assembly facility). In that embodiment, the patient-user (or a medical practitioner) may secure the base 106 of the first member 102 to his or her skin, at a suitable injection location. After securing the base 106 to the patient-user's skin, the patient-user (or a medical practitioner) may activate the needle inserting device 144 to cause the needle 146 and cannula 148 to be moved to the extended state and pierce the patient-user's skin.

After activation of the needle inserting device 144, the needle inserting device 144 may be removed from the housing section 105, leaving the cannula 148 in place within the housing section 105 and partially extended into the patient-user. With the base 106 of the first member 102 secured to the patient-user's skin and the cannula 148 inserted at least partially into the patient-user and arranged in fluid-flow communication with the hollow needle 124, the second member 103 may be connected to the first member 102. In particular, the connection portion 130 of the housing 108 of the second member 103 may be inserted into the receptacle 110 of the housing 104 of the first member 102, to provide a fluid-flow connection between the interior of the housing 108 and the hollow needle 124 and, thus, the cannula 148. Accordingly, the interior of the housing 108 (which may be a reservoir housing) may be coupled in fluid flow communication with a cannula 148 that has been extended into a patient-user, for delivering fluid from the reservoir, to the patient-user (or for conveying fluid from the patient-user to the reservoir).

While the connection sequence in the above embodiment involves securing the base 106 of the first member 102 to the patient-user, prior to connection of the second member 103 to the first member 102, in other embodiments, the second member 103 may be connected to the first member 102 (as described above) prior to securing the base 106 of the first member onto a patient-user's skin. In such other embodiments, the first and second members 102 and 103 may be connected together and, thereafter, the connected members 102 and 103 may be secured to a patient-user by adhering one or both of the first and second members 102 and 103 to the patient user's skin. Also, while the connection sequence in the above embodiment involves activating the needle inserting device prior to the connection of the second member 103 to the first member 102, in other embodiments, the second member 103 may be connected to the first member 102 (as described above) prior to activating the needle inserting device 144.

In the embodiment shown in FIGS. 1 and 2, the receptacle 110 is in the first member 102 and the connection portion 130 is in the second member 103. However, in other embodiments, the receptacle 110 may be in the second member 103 (for example, in or associated with a housing for a reservoir 108) and the connection portion 130 may be in the first member 102 (for example, in or associated with a housing that contains an injection site structure). Also, in the embodiment shown in FIGS. 1 and 2, the receptacle 110 is arranged to allow the connection portion 130 of the second member 103 to be inserted in a direction substantially parallel to the plane of the upper-facing (in the orientation of FIG. 2) surface of the base 106. In the orientation of FIG. 2, this direction of insertion is shown as a horizontal direction of relative motion between the first and second members 102 and 103. However, in other embodiments, the receptacle 110 may be arranged in other suitable orientations, including, but not limited to an orientation that allows an insertion direction (relative motion of the first and second members 102 and 103) to be substantially perpendicular to the plane of the upper-facing (in the orientation of FIG. 2) surface of the base 106. In yet other embodiments, the receptacle 110 may be arranged to allow any other suitable insertion direction at an angle transverse to the plane of the upper-facing (in the orientation of FIG. 2) surface of the base 106.

Figure 7:
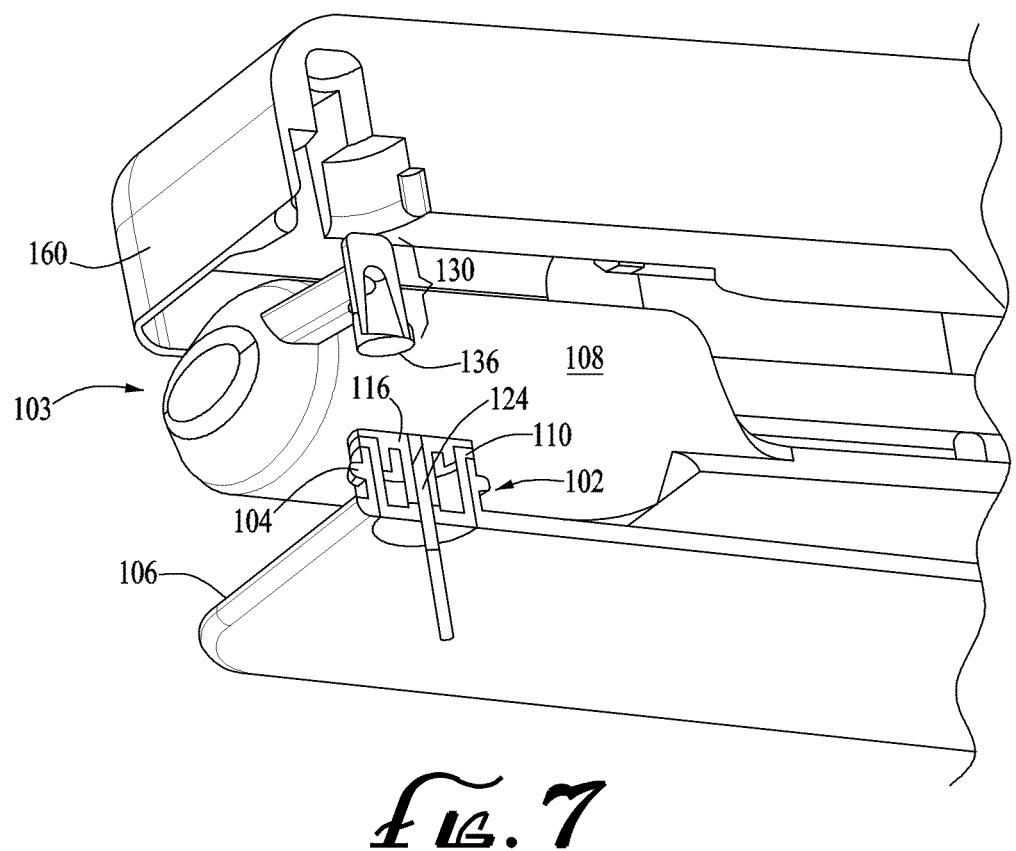
Figure 8:
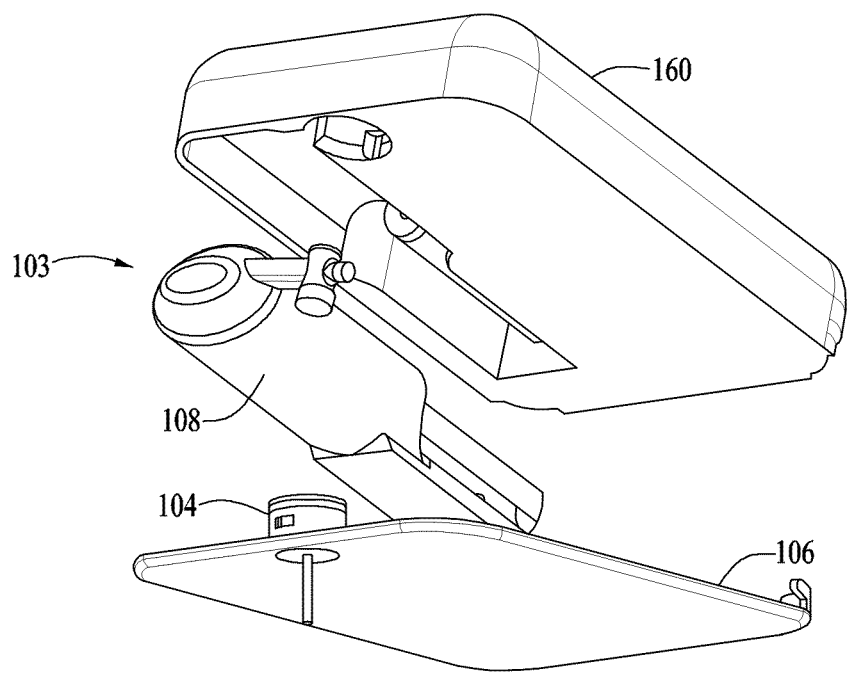

An example arrangement shown in FIGS. 7-10 provides an insertion direction (relative motion of the first and second members 102 and 103) that is substantially perpendicular to the plane of the upper-facing (in the orientation of FIG. 2) surface of the base 106. Components in FIGS. 7-10 are identified by reference numbers that are the same reference numbers used in FIGS. 1-6 for components having similar structure and function. In FIGS. 7 and 8, the injection site structure in the housing 104 is shown in a state after a needle inserting device has been operated to move a cannula 148 to the extended position.

Figure 9:
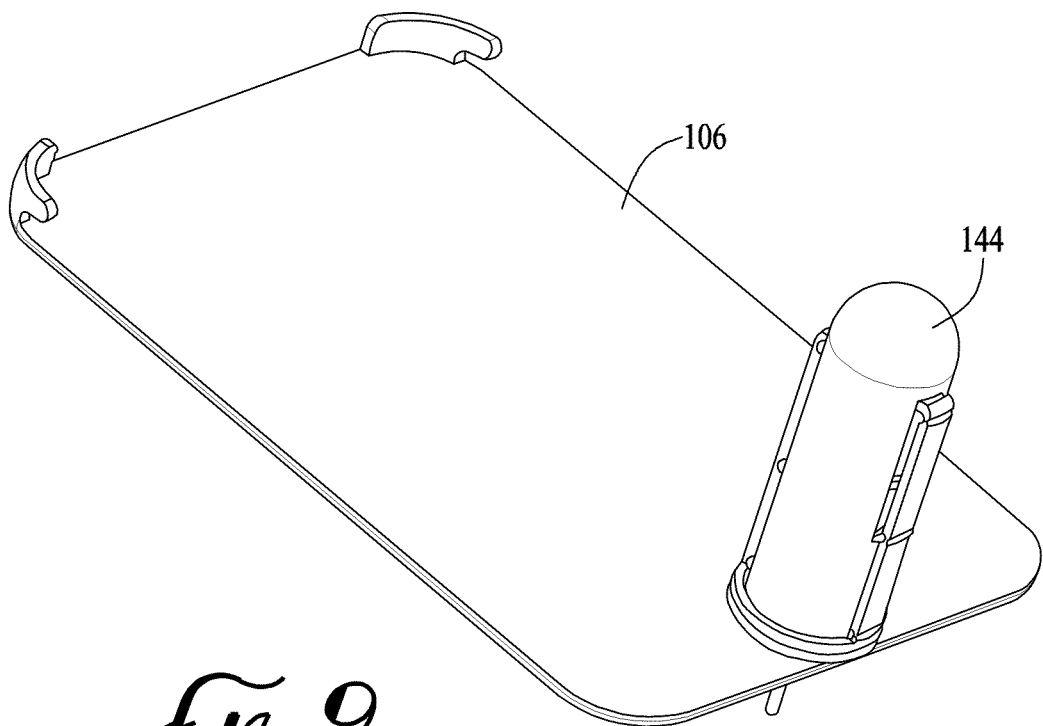
Figure 10:
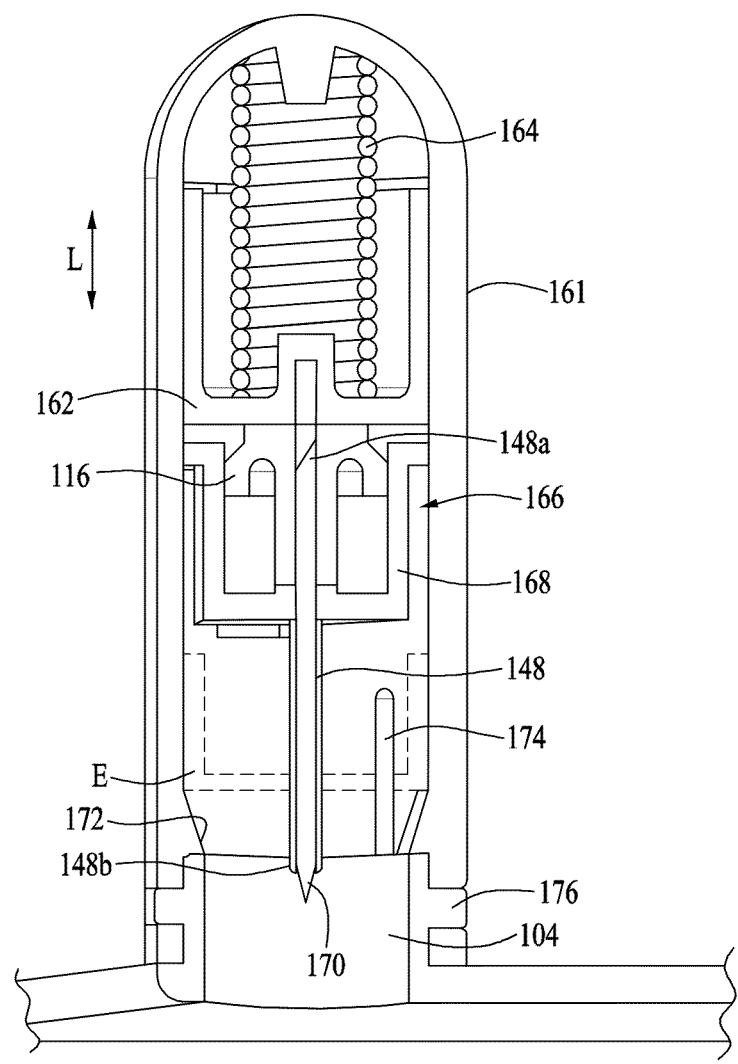

FIGS. 9 and 10 show the base 106 of the first member 102 (of the embodiment of FIGS. 7 and 8) with a needle inserting device 144 attached to the housing 104. The needle inserting device 144 in FIGS. 9 and 10 includes a housing 160 that is securable to the base 106 in any suitable manner, such as, but not limited to, the manners of connecting an inserting device 144 to the housing 105 discussed above with respect to the embodiment of FIGS. 1-6. As shown in FIG. 10, the housing 160 contains an internal chamber having a longitudinal dimension L and a moveable plunger 162 located within the housing 160 and moveable along the longitudinal dimension L, from a retracted position (shown in solid lines in FIG. 10) to an extended position (in which the plunger 162 is moved to a position E shown in broken lines in FIG. 10). A bias member 164, such as, but not limited to, a coil spring arranged within the housing 160, imparts a bias force on the plunger, when the plunger is in the retracted position, to urge the plunger 162 toward the extended position E. A locking mechanism (not shown) may be provided such as, but not limited to, a manually moveable projection, lever or slider that is connected to or extends through the housing 160 and engages the plunger 162 (or other structure holding the plunger) in a releasable manner, to selectively hold the plunger 162 in its retracted state, against the bias force of the bias member 164 and to allow a user to selectively release the plunger to move in the longitudinal direction L under the force of the bias member 164.

An insert structure 166 is arranged within the housing 160 for movement in the longitudinal direction L by action of movement of the moveable plunger 162. The insert structure 166 includes a cup-shaped body 168 that holds a first septum 116 (similar to the septum 116 described above with respect to the embodiment of FIGS. 1-6). A hollow cannula 148 (similar to the cannula 148 described above) has one open end 148a that may have a sharp tip positioned adjacent the septum 116 (or at least partially within the septum 116). The hollow cannula 148 extends through the cup-shaped body 168 and has a second open end 148b. The hollow cannula 148 may be fixed to the cup-shaped member 168, to move with movement of the cup-shaped member 168. A needle 170 is secured to the plunger 162 and extends through the septum 116 and cannula 148, when the plunger 162 is in the retracted position shown in FIG. 10.

In operation, a patient-user (or medical practitioner) may secure the base 106 to a patient-user's skin (as described above with respect to base 106 in FIGS. 1-6). Once the base 106 is secured to the patient-user's skin, the patient-user (or medical practitioner) may activate the needle inserting device 144 to cause the plunger 162 to move from its retracted state to its extended state and, as a result of such movement, to cause the insert structure 166 to be moved into the an opening into the interior of the housing 104. Upon movement of the insert structure 166 into the housing 104, the insert structure 166 may connect to the base housing 104 by any suitable connection structure. In particular embodiments, one or other of the cup-shaped member 168 of the insert structure 166 and the housing 104 may include one or more flexible pawls, protrusions and/or indentations for engaging and receiving one or more corresponding pawls, protrusions and/or indentations on the other of the housing 104 and the insert structure 166, to provide a suitable connection structure. Alternatively or in addition, the connection structure may include adhesive material or other suitable connectors. FIG. 7 shows the insert structure 166 in the extended position, and locked into the housing 104 (e.g., after insertion by the inserting device 144 and after removal of the inserting device 144 from the housing 104).

In particular embodiments, the housing 160 of the needle inserting device 144 may automatically release from the base 106, upon movement of the plunger 162 and the insert structure 166 from the retracted state (shown in FIG. 10) to an extended state. For example, the housing 160 of the needle inserting device 144 may be made of a material that has sufficient rigidity to operate as described herein, but also has a suitable flexibility (at least at the portion of the device 144 that connects to the housing 104) to bend away from and release from the housing 104, upon movement of the insert structure 166 to the extended state.

As shown in FIG. 10, a portion 172 of the internal surface of the housing 160 may include a ramped, wedge-shaped or angled (relative to an axial direction of the housing 144, cannula 148 and needle 170) cross-sectional shape that engages an outer peripheral surface of the insert structure 166 and/or the plunger 162, as the insert structure 166 and plunger 162 are moved toward the extended state. By engaging the angled, ramped or wedge-shaped portion 172 of the internal surface of the housing 160, the plunger 162 and/or insert structure 166 causes the wall(s) of the housing 160 to flex outward, as the plunger 162 and insert structure 166 are moved into the extended position. One or more slots, grooves or the like 174 may be formed in the housing 166 to enhance the ability of the wall(s) of the housing 160 to flex outward. One or more protrusions 176 and/or indentations may be provided on one or the other of the interior surface of the housing 166 and the exterior surface of the housing 104 for engaging one or more corresponding indentations 178 and/or protrusions in the other of the housing 104 and housing 166, when the plunger 162 and insert structure 166 are in the retracted state shown in FIG. 10.

The protrusions 176 and indentations 178, when engaged, lock the housing 160 of the needle inserting device 144 to the housing 104. The one or more protrusions and/or indentations disengage from each other, when the wall(s) of the housing 160 are flexed outward by the movement of the plunger 162 and insert structure 166 to the extended state. As a result, the housing 160 of the needle inserting device 144 may be automatically disengaged and released from the housing 104, upon movement of the plunger 162 and insert structure 166 to the extended state. After movement of the plunger 162 and insert structure 166 from the retracted state (shown in FIG. 10) to the extended state (at which the insert structure 166 will be locked into the housing 104, while the housing 166 of the needle inserting device is released from the housing 104), the bias member 164 (or a second bias member, not shown) may act on the needle 170 to move the needle 170 toward the retracted position and, thus, withdraw the needle 170 from the cannula 148. For example, a return motion of the coil spring after moving from the retracted state to the extended state may provide sufficient force to withdraw the needle 170 from the cannula 148.

Once the insert structure 166 has been locked into place within the housing 104 and the needle inserting device 144 removed from the housing 104, the cannula 148 may be connected in fluid flow communication with a connection portion 130 of a second member (such as, but not limited to a reservoir housing 108), in a manner similar to the manner in which the first and second members 102 and 103 are connectable in the embodiment of FIGS. 1-6. More specifically, the housing 104 forms a receptacle (similar to the receptacle 110 described above for FIGS. 1-6) and contains a septum 116 that functions as a first septum (similar to the first septum 116 of FIGS. 1-6).

Similar to the embodiment of FIGS. 1-6, the connection portion 130 in FIG. 7 also includes a second septum 136. In particular, the connection portion 130 may be inserted into the receptacle formed by the housing 104, to connect the interior of the reservoir housing 108 in fluid-flow communication with the cannula 148. The cannula 148 in FIG. 7 may include a sharp end 148a adjacent the septum 116. As the connection portion 130 is inserted into the housing 104, the connection portion will push the septum 116 against the sharp end 148a of the cannula 148, to cause the sharp end 148a of the cannula 148 to pierce the septum 116. Further insertion motion of the connection portion 130 into the housing 104 causes the sharp end 148a of the cannula 148 to pierce the septum 136 in the connection portion 130, to form a flow path from or to the connection portion 130, through the cannula 148.

Figure 11:
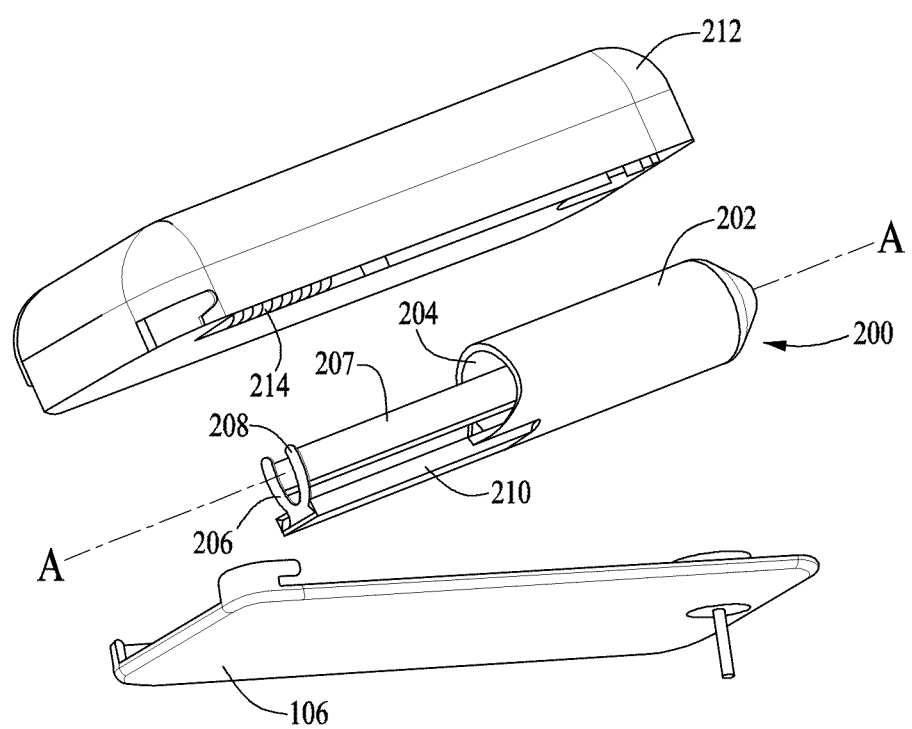

A further embodiment of a structure for connecting a drive mechanism to a reservoir plunger is described with reference to FIGS. 11-13. In FIG. 11, a reservoir 200 has a housing 202 with a hollow interior for containing a fluidic medium, as described above. A plunger head 204 is located within the reservoir housing 202 and is moveable in the axial direction A of the reservoir, to expand or contract the interior volume of the reservoir. A pair of rods 206 and 207 extend from the plunger head 204, outside of the reservoir housing 202. The rods 206 and 207 function to provide a rigid connection between a U-shaped nut 208 and the plunger 204. The U-shaped nut 208 may be supported by the rods 206 and 207. Alternatively or in addition, the U-shaped nut 208 may be supported by a guide rail 210 for movement in the axial direction A of the reservoir 200.

In FIG. 12, the U-shaped nut 208 has a pair of arms 208a and 208b that are connected by a span 208c and form a channel 210 there-between. In FIG. 11, the reservoir 200 is configured to be supported on the base 106, with the open side of the channel 210 of the U-shaped nut 208 oriented away from the base 106. A durable housing portion 212 is configured to secure to the base 106, over the reservoir 200. The durable housing portion 212 contains, among other components described above, a threaded drive shaft 214 that is operatively engaged with a drive device as described above. In FIG. 12, the drive shaft 214 is positioned within the durable housing portion 212 at a location at which it will fit within the channel 210 and engage the arms 208a and 208b, upon the durable housing portion 212 being arranged onto the base 106 for connection to the base 106. The channel 210 of the U-shaped nut 208 may have a sufficient depth to allow engagement of the drive shaft 214 with the arms 208a and 208b at any one of multiple locations of the drive shaft 214 in the dimension Z in FIG. 12, for ease of assembly and manufacturing tolerances. In particular embodiments, the placement of the durable housing portion 212 onto the base 106 in a position at which the durable housing portion 212 connects to the base 106 will also effect an alignment of the drive shaft 214 with the channel 210 of the U-shaped nut 208, so that no additional manipulation of the components are needed to operatively connect the drive shaft 214 to the nut 208.

In FIG. 12, the arms 208a and 208b of the U-shaped nut 208 may be offset in the axial direction A relative to each other and may be configured to engage threads on the drive shaft 214. As the drive shaft 214 is rotated while engaged with the U-shaped nut 208, the U-shaped nut 208 will be caused to move in the axial direction A. By abutting and/or connecting the U-shaped nut 208 against one or both of the rods 206 and 207, movement of the U-shaped nut 208 in the axial direction A is transferred to movement of the rods 206 and 207 and, thus, movement of the plunger head 204 in the axial direction A. Accordingly, when the drive shaft 214 is engaged with the U-shaped nut 208, movement of the reservoir plunger 204 may be selectively carried out and controlled by selectively driving the drive shaft 214.

Figure 24:
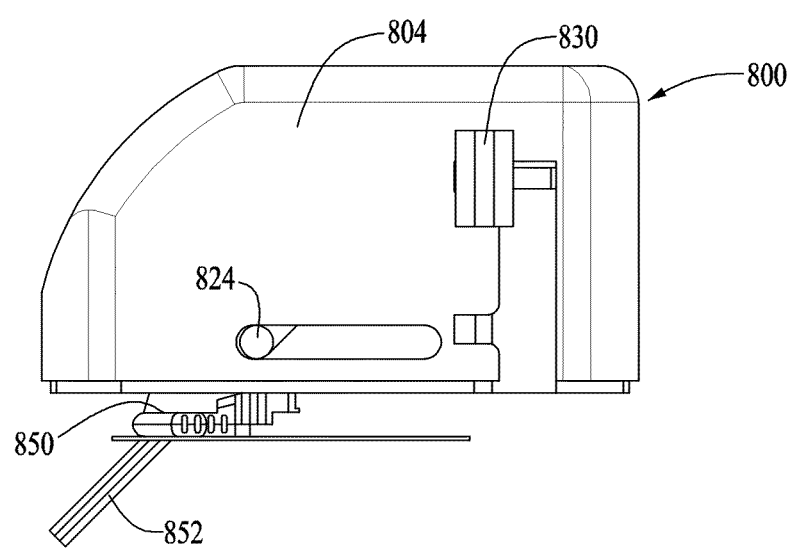
Figure 25:
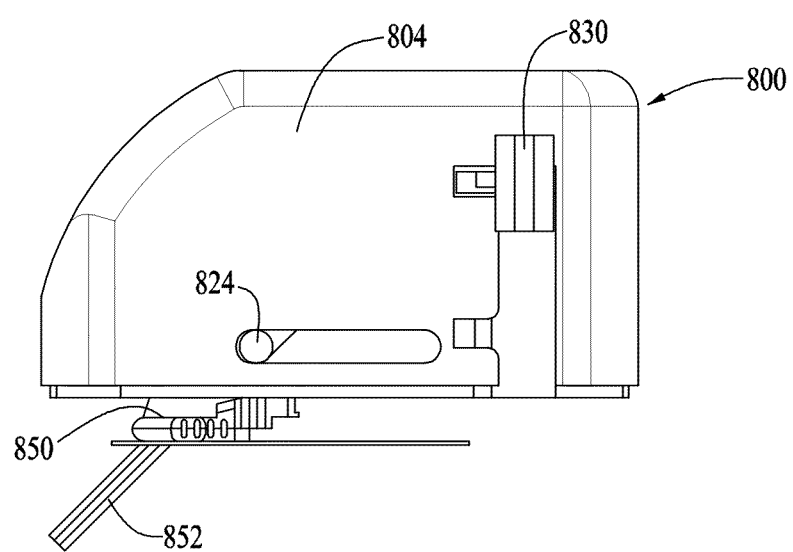

A further embodiment of a needle inserter device 712 is described with respect to FIGS. 24-25 in U.S. patent application Ser. No. 11/645,435, titled "Infusion Medium Delivery System Device And Method With Needle Inserter And Needle Inserter Device And Method" (assigned to the assignee of the present invention), which is incorporated herein by reference. Further aspects and variations of the needle inserter device 712 described in the above-referenced patent application are described herein with reference to FIGS. 14-21. Features and components of the structure shown in FIGS. 14-21 are identified by reference numbers that correspond to reference numbers used in the above-referenced U.S. patent application Ser. No. 11/645,435 for the same or similar features. A needle inserting device according to one embodiment of the invention is described with reference to FIGS. 14-16, while a needle inserting device according to a further embodiment of the invention is described with reference to FIGS. 17-21.

Figure 15:
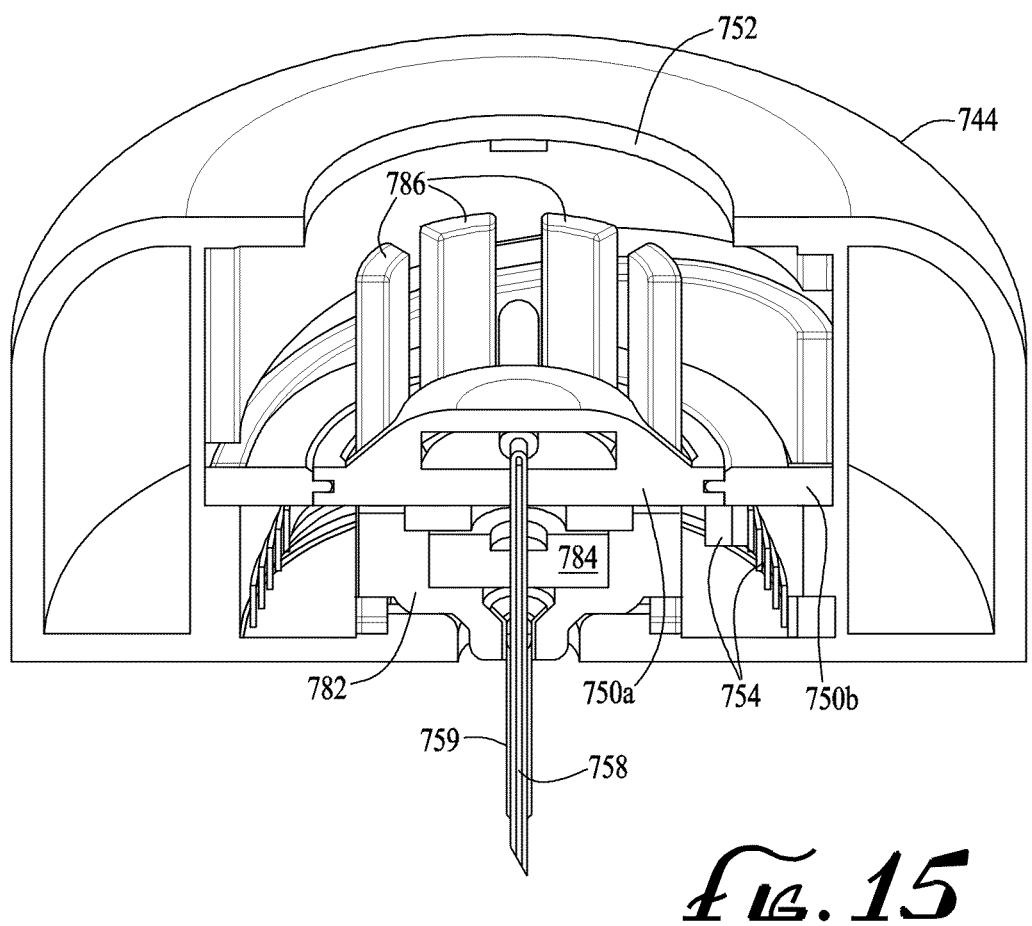

In FIG. 14, the needle inserter device 712 is in a starting position. In FIG. 15, the needle inserter device 712 is in an extended position. The needle inserter device 712 (shown in FIG. 14) includes a housing portion 744. The housing portion 744 may be part of or included within or connected to a further housing that contains other components of a system, such as, but not limited to, a reservoir, a drive device, linkage structure, and control electronics as described in the above-referenced U.S. patent application Ser. No. 11/645,435. In particular embodiments, the housing portion 744 may be part of or included within or connected to a disposable housing portion that connects to a durable housing portion as described in the above-referenced U.S. patent application Ser. No. 11/645,435.

In other embodiments, the needle inserter device 712 may be part of, located in or connected to the durable housing portion or an injection site module connected to the disposable housing portion or the durable housing portion, as described in the above-referenced U.S. patent application Ser. No. 11/645,435. Alternatively, the needle inserter device 712 may be included in other systems that operate by inserting a needle into a subject or object. The housing 744 may include a rigid, generally cylindrical or disc-shaped body, having a hollow, generally cylindrical interior and a longitudinal dimension along the axis $A_1$ of the generally cylindrical shape of the body. The interior surface of the housing 744 has a spiral groove 746 that starts near, but spaced from, the top of the housing 744 (relative to the orientation shown in FIG. 14) and extends around the inner peripheral wall of the housing 744, to a location near the base of the housing 744. A further, linear groove (not shown in FIG. 14, but shown at 748 in FIG. 24 of the above-referenced U.S. patent application Ser. No. 11/645,435) is provided at the base end of the spiral groove and extends toward the top end of the housing (relative to the orientation shown in FIG. 14). The linear groove connects the base end of the spiral groove 746 with the top end of the spiral groove 746 and extends a short distance above the top end of the spiral groove 746.

A cam member 750 is located within the interior of the housing 744 and has a projecting outer peripheral edge 751 that extends into the grooves 746. The housing 744 includes an opening 752 on one end (the top end in the orientation of FIG. 14), through which the cam member 750 may be operated by manual or automated force. A surface of the cam member 750 may be exposed through the opening 752. That exposed surface of the cam member 750 may include a convex-shape, that extends into or partially through the opening 752, when the cam member 750 is in a retracted position, as shown in FIG. 14. The housing 744 also includes a needle opening 754 through the base of the housing 744, through which a needle and cannula may be extended, as described below.

The cam member 750 is supported within the interior of the housing 744 by a coiled torsion spring 754. The spring 754 extends between the cam member 750 and the base of the housing 744 and has one end secured to (or adjacent to) the base portion of the housing 744 and another end secured to the cam member 750.

In the starting or retracted position of FIG. 14, the coil spring 754 is partially unwound against its natural wound state, such that the spring 754 imparts a force on the cam member 750, in the winding direction of the spring. However, because the projecting edge 751 of the cam member 750 is located within a section of the linear groove that is offset from the upper end of the spiral groove 746 (as shown in FIG. 24 of the above-referenced U.S. patent application Ser. No. 11/645,435), the spring 754 is held in the partially unwound state, against the natural winding force of the spring 754.

From the retracted position shown in FIG. 14, a manual or automated force may be applied to the cam member 750, through the opening 752 in the housing 744 (such as a downward directed force relative to the orientation in FIG. 14), to force the cam member to move in the axial direction $A_1$, along the direction of arrow 755 and partially compress the coil spring against the natural compression force of the spring, until the cam edge 751 moves along the linear groove (groove 748 in the above-referenced U.S. patent application Ser. No. 11/645,435), toward the base of the housing 744 to align with the top end (relative to the orientation of the drawings) of the spiral groove 746. Once the cam edge 751 is aligned with the spiral groove 746, the natural winding force of the spring 754 causes the cam member 750 to rotate and move toward the base of the housing 744, while the cam edge 751 follows the spiral groove 746, as the spring winds toward its natural, non-tensioned state of winding. However, as the cam member 750 moves toward the base of the housing 744, the cam member 750 compresses the spring 754 against its natural longitudinal dimension (in the dimension from the of the axis $A_1$).

As the cam member 750 moves toward the base of the housing 744, a needle 758 is moved through the opening 754 in the base of the housing 744, to the extended position (shown in FIG. 15). The needle 758 is secured to a surface of the cam member that faces the base, so as to move with the cam member from the start or retracted position of the cam member 750 and needle 758 (shown in FIG. 14) to the extended position of the cam member 750 and needle 758 (shown in FIG. 15).

A cannula 759 may be supported on the shaft of the needle 758, adjacent the sharp end of the needle. One end of the cannula 759 may be flared or attached to a head portion 780 that is secured to a moveable carriage 782. The carriage 782 is located within the housing 744, between the moveable cam member 750 and the base and needle opening 754 of the housing 744. The carriage 782 is supported within the housing 744 for movement in the axial direction $A_1$ with movement of the cam member 750 in the axial direction $A_1$.

The carriage 782 may include a body made of any suitably rigid material, such as, but not limited to plastic, metal, ceramic, composite material or the like. The body of the carriage 782 may include a central passage through which the needle 758 extends. A septum-like seal member 784 may be held within the body of the carriage 782. The needle 758 may extend through the seal member 784, and be slid through the seal member 784, while the seal member 784 forms a seal around the outer periphery of the needle 758. A retainer, such as, but not limited to, a generally rigid annular disk-shaped washer structure 785 may be arranged adjacent the seal member 784 to help retain the seal member 784 within the body of the carriage 782 and to provide additional rigidity to the seal member 784, while also providing a central passage through which the needle 758 may extend and move.

The carriage 782 has a surface 782a (the upper surface in the orientation shown in FIG. 14) that engages (or, at least, receives a force from) the cam member 750, as the cam member 750 is moved from the starting state of the cam member (shown FIG. 14) to the extended state of the cam member (shown in FIG. 15), to move the carriage 782 from its starting state (also shown in FIG. 14) to its extended state (also shown in FIG. 15). A guide structure 786 may be provided within the housing 744, for example, as an integral part of the housing 744 or, alternatively, as a separate structure that is secured to the base of the housing 744. The guide structure 786 may include one or more walls, rails or other suitable structure that engages one or more surfaces of the carriage 782 as the carriage is moved from its starting state (shown in FIG. 14) to its extended state (shown in FIG. 15). In one embodiment, as shown in FIG. 14, the guide structure 786 may include a tubular-shaped structure having a generally hollow cylindrical shape, with one or more slots or grooves extending in the axial dimension $A_1$ along the cylindrical wall of the guide structure to receive a corresponding one or more projections 788 extending from the carriage 782. The projection(s) 788 ride along the axial slots or grooves in the generally cylindrical wall of the guide structure 786, as the carriage 782 is moved in the axial dimension $A_1$.

Once the carriage 782 is moved from its start state (shown in FIG. 14) to its extended state (FIG. 15), the carriage 782 may be arranged in a location at which one or more locking mechanisms operate to lock the carriage 782 in place in its extended state position. In the illustrated embodiment one or more locking mechanisms may be provided by one or more flexible pawls 790. The flexible pawls 790 may be formed as part of the guide structure 786 or may be adjacent the guide structure 786. Each pawl 790 includes a flexible arm portion that extends along the axial direction $A_1$, from the base of the housing 744 toward the opening 752. Each pawl 790 also includes a head 790a that has a stop surface for engaging the carriage structure 782, to inhibit further movement of the carriage structure 782 in the axial direction $A_1$, once the carriage structure 782 has been moved to its extended state (shown in FIG. 15). In the illustrated embodiment, the pawls 790 are arranged to engage either or both the surface 782a of the carriage 782 or the retainer 785, when the carriage 782 is in the extended state (shown in FIG. 15). Each pawl 790 may have an angled surface 790b, for engaging the carriage 782 as the carriage is moved from its start state (FIG. 14) to its extended state (FIG. 15) and allow the carriage to push and flex the pawls radially outward (relative to the axis $A_1$) sufficient to allow the carriage 782 to pass the pawl heads 790 during the motion of the carriage toward its extended state.

Once the carriage 782 has been moved to its extended state (by the action of the movement of the cam member 750 to its extended state), the carriage 782 may be locked in place relative to the housing 744, by the pawls 790. Then, cam member 750 may be acted upon by the compression force of the spring 754 and may follow the linear groove (groove 748 in the above-referenced U.S. patent application Ser. No. 11/645,435) to move to its retracted state (shown in FIG. 16). As the cam member 750 moves to its retracted state, the cam member 750 moves the needle 758 in the axial direction $A_1$, to at least partially withdraw the needle 758 from the cannula 759 to open a fluid flow path into the cannula 759, through the cannula head 780.

Figure 16:
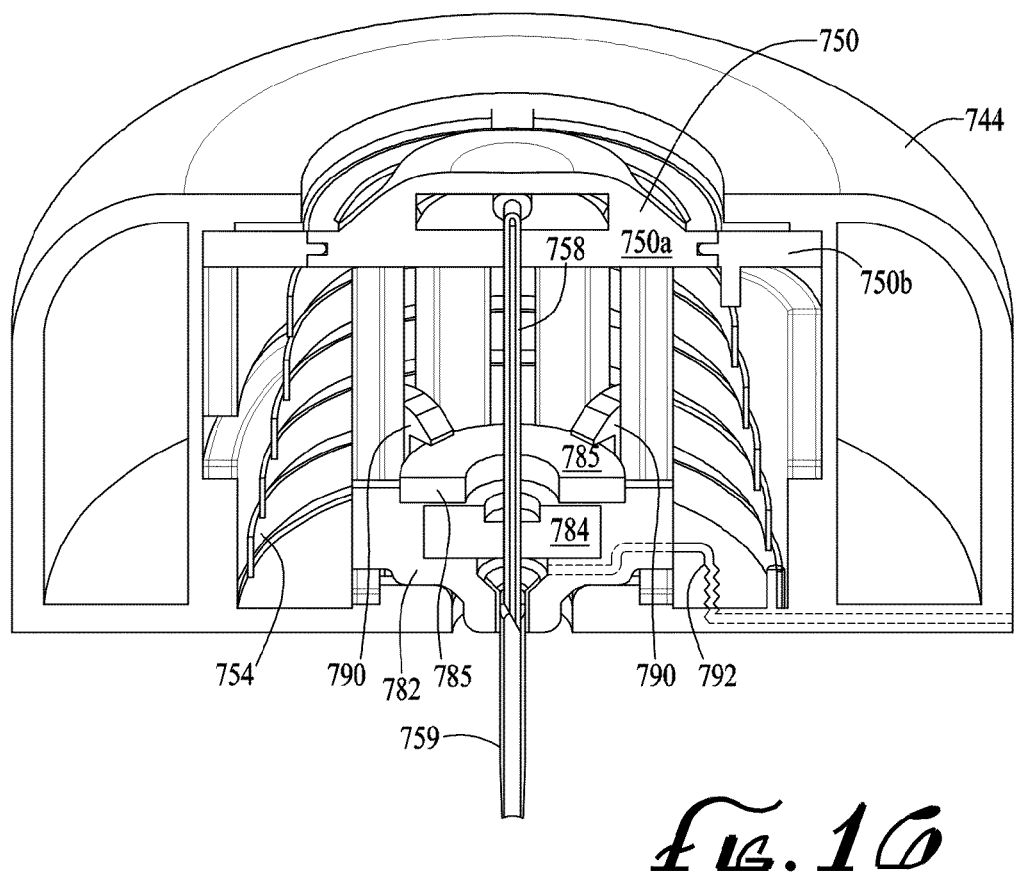

A fluid flow path to or from the cannula head 780 may be provided through the body of the carriage 782, and through a flexible conduit 792 attached to the carriage 782, as shown in FIG. 16. The conduit 792 may have sufficient flexibility and/or slack to allow the carriage 782 to move between its start state (shown in FIG. 14) and its extended state (shown in FIG. 15), while the conduit 792 remains attached to the carriage 782. The conduit 792 may extend and provide fluid flow communication to or from one or more of a reservoir, sensor structure, or other suitable fluid containing or processing mechanism (not shown in FIGS. 14-16).

Alternatively, the fluid flow passage through the body of the carriage 782 (shown in broken lines in FIG. 16) may be arranged to automatically align with a fluid flow path or conduit supported in the housing 744, when the carriage 782 reaches its extended state (shown in FIG. 15), to complete a fluid flow path to or from one or more of a reservoir, sensor structure, or other suitable fluid containing or processing mechanism (not shown in FIGS. 14-16). In yet further embodiments, the carriage 782 and the housing 744 may be provided with a needle and septum structure (similar to the needle 50 or 150 and septum 54 or 154 described in connection with the embodiments of FIGS. 4-8 of the above-referenced U.S. patent application Ser. No. 11/645, 435), which has been incorporated herein by reference, in its entirety, for connecting the cannula 759 in fluid-flow communication with a reservoir, sensor structure or other fluid containing or processing mechanism.

Thus, by supporting the base of the housing 744 at an injection site, the housing 744 may be arranged adjacent a patient-user's skin to allow the sharp end of the needle 758 to pierce the patient-user's skin and to allow the cannula around the needle shaft to be inserted at least partially into the patient-user's skin, when the needle is in the extended position of FIG. 15.

In the extended position (FIG. 15), the carriage 782 is locked in place, relative to the housing 744. Also, once the needle 758 and cannula 759 are in the extended position of FIG. 15, the cam projection 751 (which had followed the spiral path of the groove 746) is aligned with the linear groove (groove 748 in the above-referenced U.S. patent application No. 11/645,435). At that position, the spring 756 is extended in the longitudinal dimension of axis $A_1$ beyond its natural longitudinal state. Accordingly, the spring 756 provides a force on the cam member 750, to move the cam member 750 in the axial dimension $A_1$, in the direction opposite to the direction of arrow 755, while the projection 751 follows the linear groove (groove 748 in the above-referenced U.S. patent application Ser. No. 11/645,435), to the retracted position of FIG. 16.

As the cam member 750 is moved, under the compression force of the spring 754, to the retracted state, the needle 758 at least partially withdraws from the cannula 759 and opens a fluid flow path from the conduit 792 to the cannula 759, through a passage in the body of the carriage 782. Accordingly, the cannula may be inserted into a patient-user's skin and connected in fluid flow communication with the conduit 792 (and with a reservoir, sensor structure or other fluid containing or processing mechanism that is also connected in fluid flow communication with the conduit 792).

As described above, during movement of the cam member 750 in the axial direction $A_1$, from its start state (shown in FIG. 14) to its extended state (shown in FIG. 15), the cam member 750 is acted upon by the unwinding force of the spring 754 and follows a spiral groove 746 in the interior wall of the housing 744. As a result, the cam member 750 rotates around the axis $A_1$, during its movement from the start state to the extended state.

In particular embodiments, the cam member 750 may include an outer circumference portion 750a and an inner portion 750b, where the outer circumference portion 750a is connected to, but allowed to rotate (about the axis $A_1$) relative to the inner portion 750b of the cam member 750. A section of the spring 754 may be secured to the outer portion 750a of the cam member, such that an unwinding movement of the spring 754 will cause a rotational motion of the outer portion 750a of the cam member.

The outer portion 750a of the cam member may be connected to the inner portion 750b of the cam member by a tab and groove configuration, wherein one of the outer or inner portions 750a or 750b (the outer portion 750a in the illustrated embodiment) is provided with an annular tab that extends toward the other of the outer or inner portions 750a and 750b. The other of the outer and inner portions 750a and 750b (the inner portion 750b in the illustrated embodiment) is provided with an annular groove that aligns with and receives the annular tab. The annular tab and groove arrangement allows the outer and inner portions 750a and 750b of the cam member 750 to move together in the axial direction $A_1$, yet allows that outer portion 750a to rotate relative to the inner portion 750b around the axis $A_1$. Accordingly, the outer portion 750a of the cam member 750 may rotate under the unwinding action of the spring 754 and the direction of the spiral groove 746 as the cam member 750 moves in the axial direction $A_1$ from its start state (FIG. 14) to its extended state (FIG. 15). However, during such motion, the inner portion 750b of the cam member 750 need not rotate with the outer portion 750a. As a result, the needle 758 need not rotate about the axis $A_1$ as the cam member 750 moves from its start state to its extended state. In some contexts, user-patient comfort may be improved by inhibiting rotation of the needle 758, as the needle 758 and cannula 759 are inserted into the patient-user's skin.

In particular embodiments, the inner portion 750b of the cam member 750 may be held from rotating about the axis $A_1$ by retaining structure. For example, the inner portion 750b may engage one or more surfaces of the guide structure 786 as the cam member 750 moves in the axial direction $A_1$, to inhibit rotation of the inner portion 750b about the axis A₁. In the illustrated embodiment, the inner portion 750*b* of the cam member includes one or more slots or openings through which leg portions of the guide structure 786 extend. The engagement of the inner portion 750*b* with the one or more leg portions of the guide structure 786 inhibit rotation of the inner portion 750*b* about the axis A₁. In other embodiments, other suitable structural configurations may be employed to inhibit rotation of the inner portion 750*b* of the cam member 750 about the axis A₁.

In the embodiment in FIGS. 14-16, the needle 758 of the needle injecting structure remains in the housing 744 with the cannula 759, after the cannula has been inserted into the patient-user's skin and the needle 758 has been moved to its retracted position (shown in FIG. 16). In other embodiments, the needle injecting structure may be composed of multiple, separable parts that may be separated after the cannula has been moved into its extended state (and inserted into the patient-user), for removing the needle 758 (and other structure associated with the needle 758) from a base portion that holds the cannula in its extended state. An example of a multi-piece structure is shown in FIGS. 17-21. The structure and function of the embodiment in FIGS. 17-21 is similar to that of the embodiment described above for FIGS. 14-16, except that the housing 744 in FIGS. 17-21 has two parts including a base portion 744*a* and a nest portion 744*b* that is removable from the base portion 744*a*. Accordingly, corresponding reference numbers are used for corresponding components and reference is made to the above description of corresponding structure and function.

Figure 17:
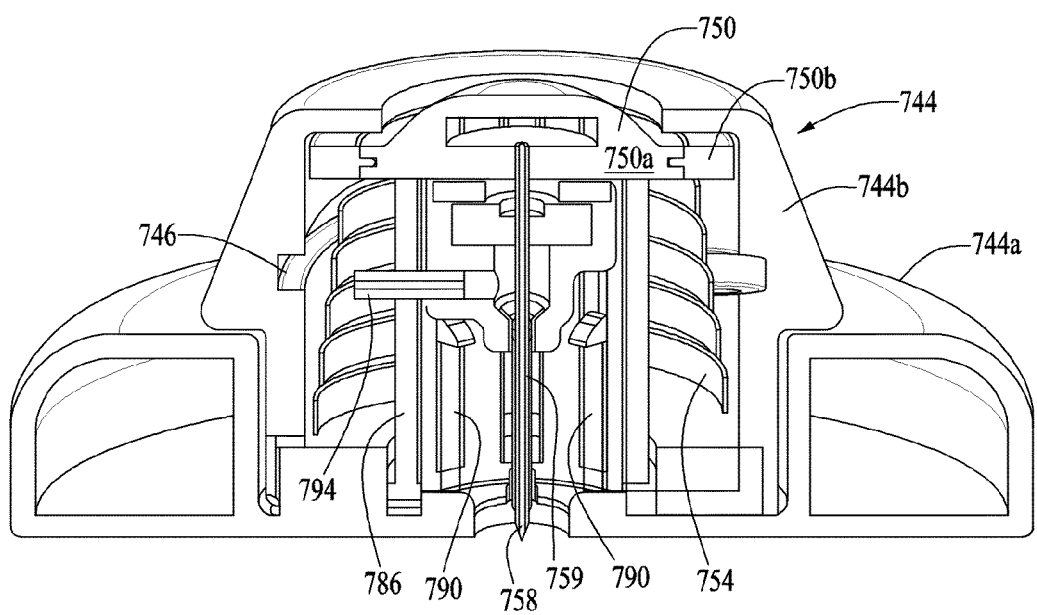
Figure 18:
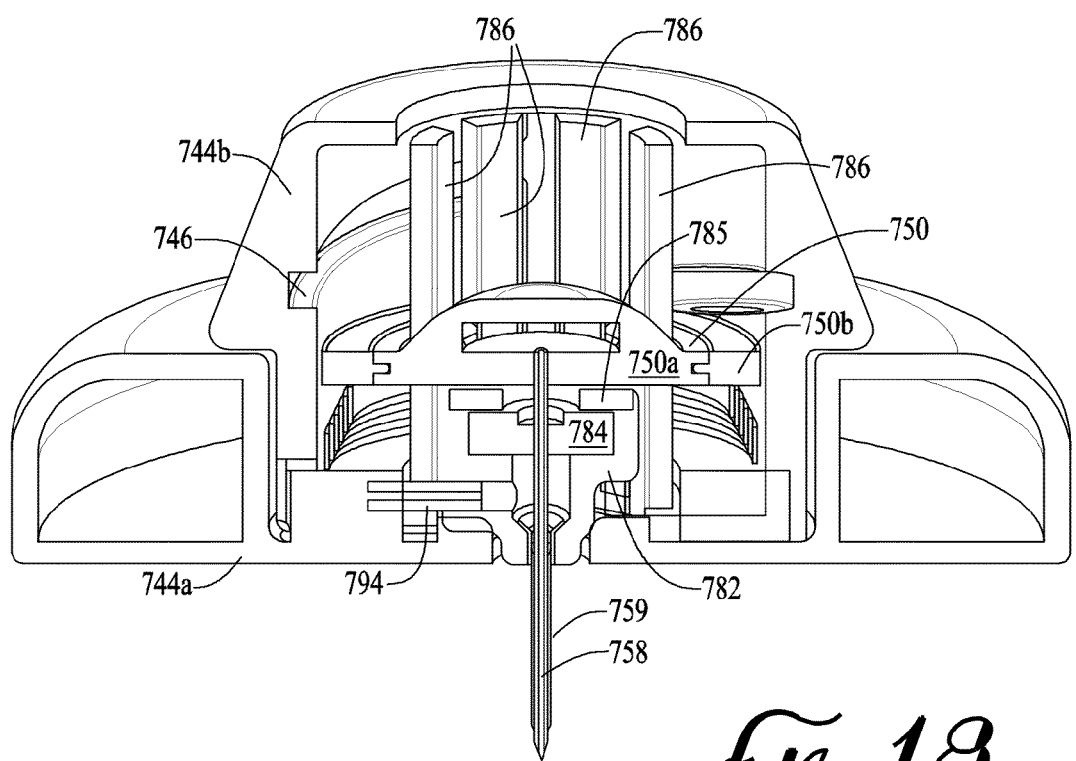
Figure 19:
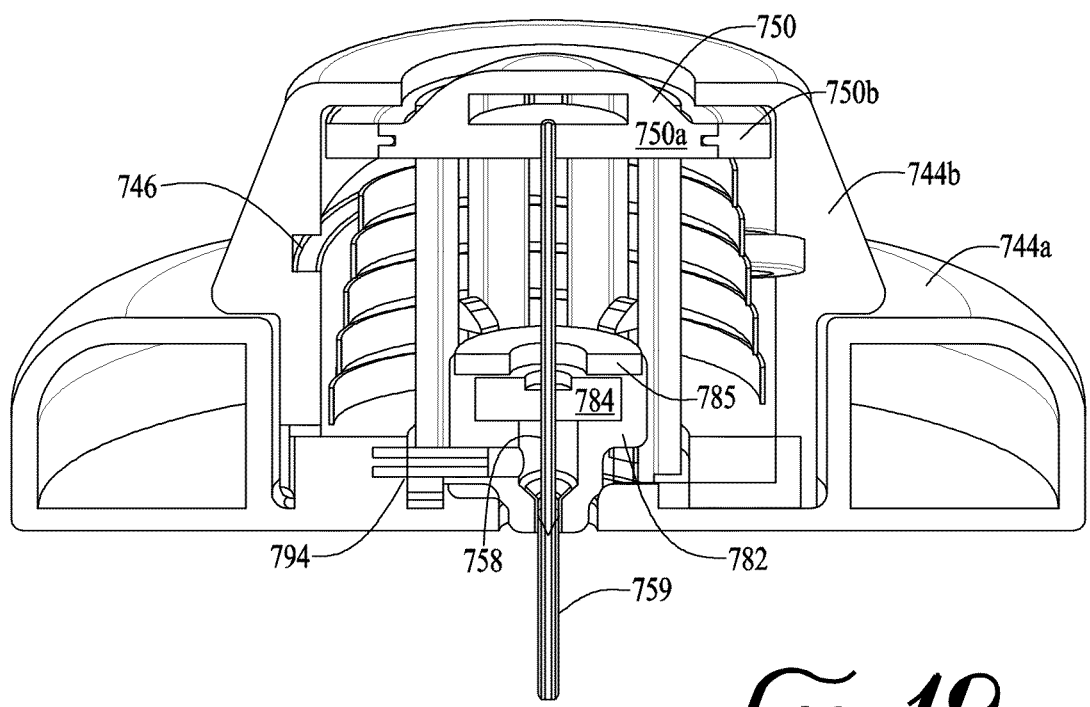
Figure 20:
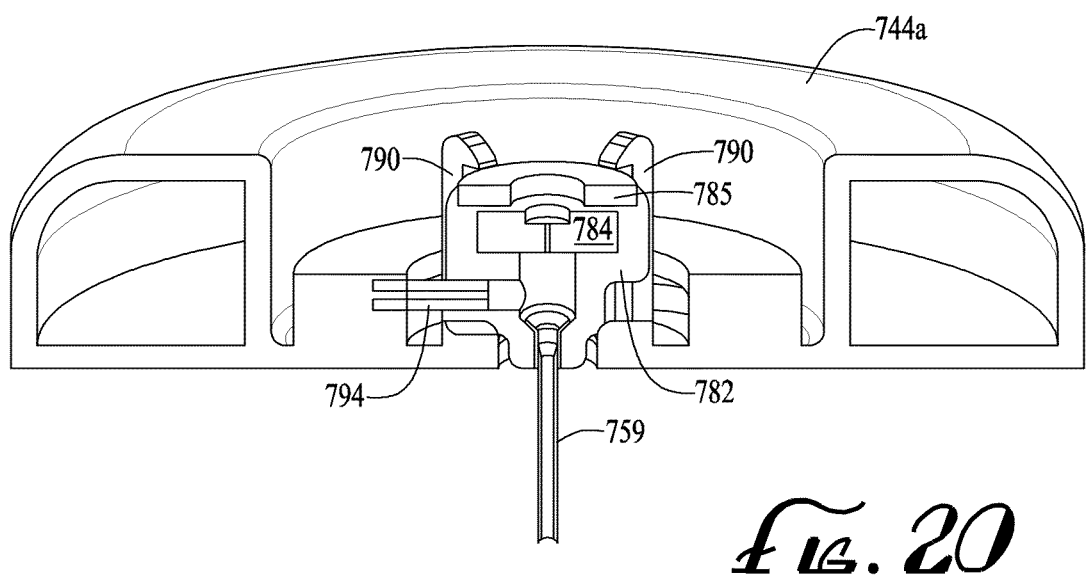
Figure 21:
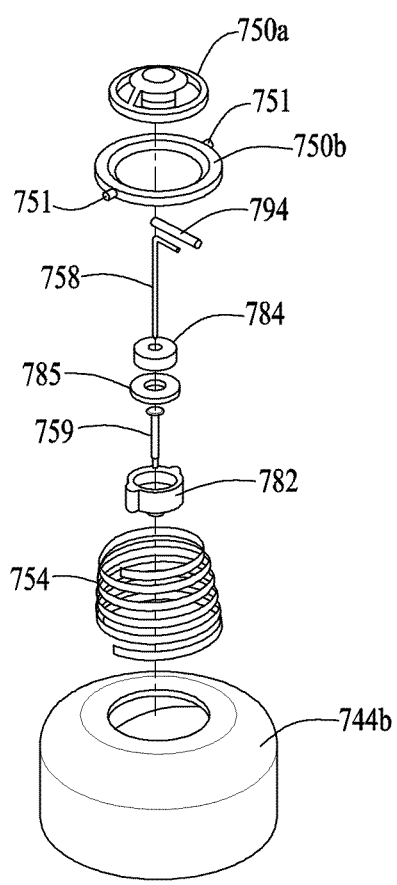

In FIG. 17, the multi-piece needle inserting device is shown in the start state, corresponding to the start state of the above-described embodiment shown in FIG. 14. In FIG. 18, the multi-piece needle inserting device is shown in the extended state, corresponding to the extended state of the above-described embodiment shown in FIG. 15. In FIG. 19, the multi-piece needle inserting device is shown in the retracted state, corresponding to the retracted state of the above-described embodiment shown in FIG. 16. In FIG. 20, various components of the example multi-piece needle inserting device are shown, in an exploded view.

In the embodiment of FIGS. 17-21, a fluid flow connection is provided to or from the cannula 759, through a tubing structure 794 that is extends through and/or is connected in fluid flow communication with a fluid passage through the body of the carriage 782. When the carriage 782 is moved to its extended state (shown in FIG. 18), the tubing structure 794 aligns with a fluid-flow passage formed in (or otherwise provided in) the base portion 744*a* of the housing 744. In particular embodiments, the tubing structure 794 may include a resiliently flexible tubing (made of a flexible material, such as, but not limited to, silicon, plastic, rubber or the like) that allows the tubing to bend and pass over a portion of the base structure as the carriage 782 moves to its extended state and then resiliently flex back to its natural shape to extend into an opening of a fluid flow passage in the base portion 744*a* of the housing 744 (as shown in FIGS. 18 and 19).

After the cam member 750 has moved to its retracted state (FIG. 19), the nest portion 744*b* of the housing 740 may be removed from the base portion 740*a* of the housing, as shown in FIG. 20. As a result, the base portion 744*b* of the housing may remain on the patient-user's skin, with the cannula 759 inserted into the patient-user, while the needle 758 (and other components, such as the spring 754 and cam member 750) may be removed by removing the nest portion 744*a* of the housing 744 from the base portion 744*b*. The base portion 744*b* may be integral with or connected to a disposable housing portion, a durable housing portion, a base of a disposable housing portion, a base of a durable housing portion or a separate injection site housing structure that may be connected to a durable housing portion, a disposable housing portion or the like. Examples of such various arrangements of needle inserting devices are described in the above-referenced U.S. patent application Ser. No. 11/645,435), which has been incorporated herein by reference, in its entirety.

FIGS. 22-27 illustrate an example embodiment of a needle inserting device 800 for inserting a needle and cannula or a hollow needle into a patient-user (or other subject) for fluid-flow connection to a further device, where the needle and/or cannula are inserted at an angle (a non-perpendicular angle relative to the patient-user's skin), such as, but not limited to, an angle within the range of 20° and 60° and, in particular embodiments, about 45° relative to the patient-user's skin (or insertion surface of another subject). In the illustrated embodiment, the further device is a sensor device, wherein insertion of a hollow needle or cannula into a patient-user (or other subject) provides a fluid flow connection between sensing material or electronics in the sensor device and the patient-user (or other subject). However, embodiments of the invention may be used for inserting a needle associated with other devices that require the insertion of a needle into a patient-user (or other subject), such as, but not limited to an infusion medium delivery device that has a reservoir for containing an infusion medium, wherein insertion of a hollow needle or cannula into a patient-user (or other subject) provides a fluid-flow connection between the reservoir and the patient-user (or other subject).

Figure 22A:
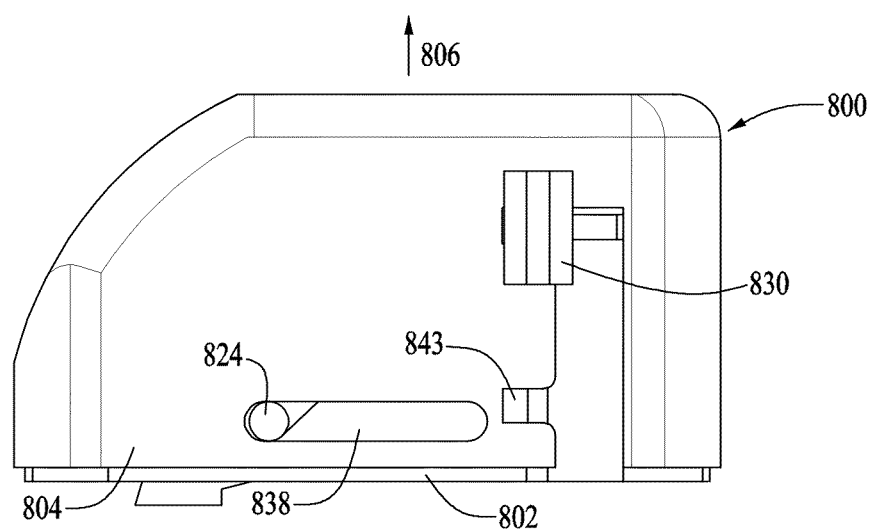
Figure 23A:
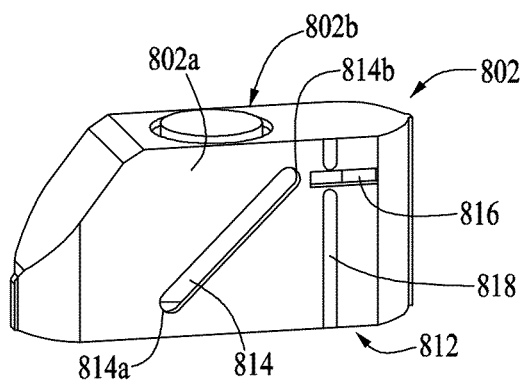
Figure 23B:
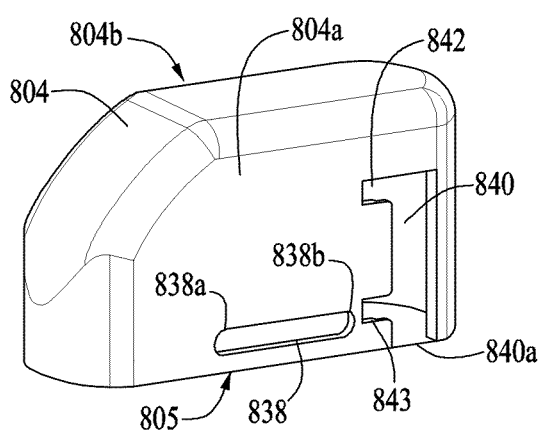
Figure 23C:
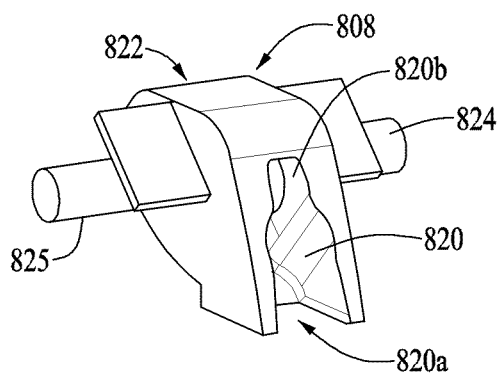
Figure 23D:
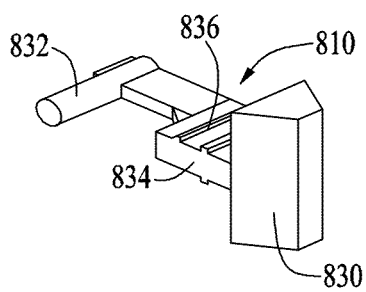

In FIGS. 22*a* and 22*b*, the needle inserting device 800 is shown in an assembled state, in initial position. In FIGS. 23*a*-23*b*, components of the needle inserting device 800 are shown, separate from each other. The needle inserting device 800 includes a base structure 802 (FIG. 23*a*), a cap structure 804 (FIG. 23*b*) that fits over the base structure (as shown in FIGS. 22*a* and 22*b*) and is moveable in a sliding motion in the direction of arrow 806 relative to the base structure 802. The needle inserting device 800 also includes a slide structure 808 (FIG. 23*c*) and an extractor structure 810 (FIG. 23*d*), each of which are located within the base structure 802 and moveable relative to the base structure 802. Each of the components 802, 803, 808 and 810 may be made of any suitably rigid material such as, but not limited to plastic, metal, ceramic, composite material, or the like. In particular embodiments, those components may be made of molded plastic material, for manufacturing efficiency and ease.

As shown in FIG. 23*a*, the base structure 802 has a generally rigid body with a hollow interior for containing the slide structure 808 and the extractor 810. The body of the base structure 802 has a pair of generally parallel walls 802*a* and 802*b*. The body of the base structure 802 also has a bottom surface 812 that is configured to be arranged adjacent a patient-user's skin (or surface of another subject) during a needle injection operation of the device 800.

The body of the base structure 802 has an angled slot 814 in each of the parallel walls 802*a* and 802*b* (where the wall 802*b* is facing into the page of FIG. 23*a* and, thus, hidden from view in that drawing). Each slot 814 has a longitudinal dimension extending between first and second ends 814*a* and 814*b* of the slot 814, where the first end 814*a* of the slot is closer to the bottom surface 812 of the base structure than the second end 814*b* of the slot. Accordingly, in operation, the first end 814a of the slot is closer to the patient-user's skin (or surface of other subject) than the second end 814b of the slot.

One of the walls 802a of the body of the base structure 802 has a second slot 816 that has a longitudinal dimension that is generally parallel to the bottom surface 812 of the base structure 802. The slot 816 is located adjacent the second end 814b of the slot 814. One or both of the walls 802a of the body of the base structure 802 has a groove (or a further slot) 818 that has a longitudinal dimension that is generally perpendicular to the bottom surface 812 of the base structure 802. Accordingly, in operation, the longitudinal dimension of the groove (or further slot) 818 is generally perpendicular to the patient-user's skin or surface of other subject to be injected).

The slide structure 808 (FIG. 23c) has a generally rigid body that forms a receptacle 820 for receiving and holding a device having a cannula (or hollow needle) assembly during operation. The device having a cannula (or hollow needle) assembly may be a sensor device, a needle set for connection to an infusion device or other device, or the like. The receptacle 820 in the illustrated embodiment includes a cup-shaped recess that is open on one side 820a and has a second side 820b that is open to a channel through the body of the slide structure 808. The channel (hidden from view in FIG. 23c) is also open on the rear side 822 (relative to the orientation shown in FIG. 23c) of the body of the slide structure 808. In other embodiments, the receptacle 820 may have any suitable configuration that is capable of holding and selectively releasing a device having a cannula (or hollow needle) assembly.

A pair of shafts or arms 824 and 825 protrude and extend from opposite sides of the body of the slide structure 808, generally perpendicular to the above-described channel through the body of the slide structure 808. When assembled with the base structure 802 (as shown in FIGS. 22a and 22b), the slide structure 808 is arranged inside the hollow interior of the base structure 802, with the arms 824 and 825 extended through the slots 814 in the sides 802a and 802b, respectively, of the base structure 802. The slide structure 808 is moveable within the interior of the base structure 802, as the arms 824 and 825 slide within the slots 814 in the respective sides 802a and 802b of the base structure. Accordingly, the angled direction of the slots 814 guide the motion of the slide structure 808 in an angled direction relative to the bottom surface 812 of the base structure 802 (and to the patient-user's skin or surface of other subject to be injected).

The extractor structure 810 (FIG. 23d) has a handle portion 830 that is located external to the base structure 802, when the extractor structure 810 is assembled inside of the interior of the base structure (as shown in FIG. 22a). The extractor structure 810 also has a shaft portion 832 that is configured to fit within at least a portion of the channel through the body of the slide structure 808, through the opening in the side 822 of the body of the slide structure 808. As described below, selective movement of the shaft portion 832 into the channel of the slide structure 808 may be carried out by manual operation of the handle portion 830, to selectively push a device having a cannula or hollow needle out of or in another release position relative to the receptacle 820 in the slide structure 808.

The extractor structure 810 has a connection portion 834, connecting the handle portion 830 to the shaft portion 832. The connection portion 834 is configured to extend through the slot 816 in the body of the base structure 802 and is moveable in the longitudinal direction of the slot, when the extractor structure 810 is assembled inside of the interior of the base structure (as shown in FIG. 22a). The connection portion 834 may be provided with a guide 836 for stabilizing and smoothing the motion of the extractor structure 810. The guide 836 may include one or more surfaces having a channel (formed between a pair of ribs in the illustrated embodiment) arranged generally parallel to the longitudinal dimension of the slot 816 (when the extractor structure 810 is assembled with the base structure 802). The channel has a width dimension that is greater than the thickness dimension of the wall 802a of the base structure 802, to allow the channel in the guide 836 to receive a portion of the wall 802a, when the extractor structure 810 is assembled with the base structure 802.

The cap structure 804 (FIG. 23b) has a generally rigid body that may be shaped similar to the shape of the body of the base structure 802, but slightly larger than the body of the base structure 802. The body of the cap structure 804 has a hollow interior and an open bottom side 805 (relative to the orientation shown in FIG. 23b), for receiving the base structure 802 when assembled in the manner shown in FIGS. 22a and 22b. The body of the cap structure 804 has a pair of generally parallel walls 804a and 804b, corresponding to the walls 802a and 802b, respectively, of the base structure 802.

One or more ribs or other projections (not in view in the drawings) may be provided on the interior-facing surface of one or both of the walls 804a and 804b in a location to align with and fit within the groove (or slot) 818 in one or both of the walls 802a and 802b, respectively, of the base structure 802, when the cap structure 804 and the base structure 802 are assembled as shown in FIGS. 22a and 22b. When the cap structure 804 is assembled with the base structure 802, the cap structure 804 is moveable in the direction of arrow 806 from an initial position (FIG. 22a) to a retracted position (FIG. 26a), and then in the direction opposite to the arrow 806 to an insertion position. The ribs or other projections on one or both of the walls 804a and 804b of the cap structure 804 ride along the groove (or slot) 818 on one or both of the walls 802a and 802b of the base structure 802 as the cap structure 804 is moved relative to the base structure 802 in the direction of (or opposite to) the arrow 806.

The body of the cap structure 804 has a slot 838 in each of the parallel walls 804a and 804b. Each slot 838 has a longitudinal dimension extending between first and second ends 838a and 838b of the slot 838, where the longitudinal dimension is generally parallel to the bottom surface 812 of the base structure 802 (when the cap structure 804 and the base structure 802 are assembled together) and, thus, during operation, generally parallel to the to the patient-user's skin or surface of other subject to be injected.

One of the walls 804a of the body of the cap structure 804 has a second slot 840 that has a longitudinal dimension that is generally perpendicular to the bottom surface 812 of the base structure 802 (when the cap structure 804 and the base structure 802 are assembled together). The slot 840 has a first end 840a that is open at the open bottom side 805 of the cap structure 804. The slot 840 has a second end 840b that is located at a distance from the open bottom side 805 corresponding to the longitudinal length of the slot 840. A first extension slot 842 extends laterally to one side of the slot 840, at the end 840a of the slot 840. The first extension slot 842 has a longitudinal dimension that is generally perpendicular to the longitudinal dimension of the slot 840. A second extension slot 843 extends laterally to one side of the slot 840, adjacent, but spaced from the open first end 840a of the slot 840. The second extension slot 843 also has a longitudinal dimension that is generally perpendicular to the longitudinal dimension of the slot 840. When the cap structure 804 is assembled with the base structure 802, slide structure 808 and extractor structure 810, the arms 824 and 825 of the slide structure 808 extend through the slots 838 in the body of the cap structure 804, and the connection portion 834 of the extractor structure 810 extends through the slot 840 and/or one of the extension slots 842 and 843 in the body of the cap structure 804, as shown in FIGS. 22*a* and 22*b*.

In operation, the needle inserting device 800 may come pre-assembled or may be assembled as shown in FIGS. 22*a* and 22*b*, with the slide structure and the extractor structure set in an initial position. In the initial position shown in FIGS. 22*a* and 22*b*, the cap structure 804 is arranged over the base structure 802 and is moved relative to the base structure 802 to the end of its full range of motion in the direction opposite to the direction of arrow 806. In the initial position, the bottom side 805 of the cap structure 804 is arranged adjacent to the bottom side 812 of the base structure 802. Also, in the initial position, the slide structure 808 is located such that the arms 824 and 825 are adjacent the end 814*a* of the slot 814 in the base structure 802 and adjacent the end 838*a* of the slot 838 in the cap structure 804.

Further, in the initial position of FIG. 22*a*, the extractor structure 810 is located in the first extension slot 842. The initial position of the extractor structure 810 inhibits relative movement between the cap structure 804 and the base structure 802 in the direction of arrow 806. The needle inserting device 800 may be shipped or stored in the initial position. Alternatively, the patient-user (or medical practitioner) may set the needle inserting device in the initial position, after retrieval from storage or shipping. In the initial position, the needle inserting device 800 may receive a device having a cannula or hollow needle for insertion into a patient-user (or other subject).

From the initial position of FIG. 22*a*, a patient-user (or a medical practitioner) may place a device having a cannula or hollow needle in the receptacle 820 of the slide structure 808, to place the needle inserter device in a loaded position. In FIG. 24, a needle inserter device 800 is shown with a sensor device 850 (having a needle and cannula structure 852) received within the receptacle of the slide structure 808, such that the needle inserter device 800 is in a sensor loaded position. In the loaded position, the needle and cannula structure 852 is arranged at an angle (a non-perpendicular angle) relative to the bottom surface 812 of the base structure 802 (and, thus, relative to the patient-user's skin or surface of subject to be injected, during an injection operation).

In further embodiments, the needle inserter device 800 may be shipped and/or stored in a loaded position, with a device (such as a sensor device 850) pre-loaded in the receptacle 820 of the slide structure 808, as shown in FIG. 24. In such pre-loaded embodiments, a removable cover (for removal prior to use of the device) may be provided over at least the portion of the device 800 holding the device 850, to protect the device 850 from damage and to inhibit accidental puncture from the sharp end of a needle or cannula extending from the device 850.

In the loaded position, the device 850 may be releasably locked in the receptacle 820 by any suitable releasable locking mechanism, including, but not limited to, a friction fit, a spring tab or the like. The locking mechanism may be configured to lock the device 850 in place and inhibit separation of the device from the receptacle 820 when the device 800 is placed in a loaded state, yet release the lock and allow the device 850 to be separated from the receptacle 820, by a releasing action of the extractor 810, as described below.

From the loaded position of FIG. 24, a patient-user (or medical practitioner) may set the extractor structure 810 of the device 800 into an unlock position shown in FIG. 25. The device 800 may be set to the unlock position by manually moving the handle portion 830 of the extractor structure 810 in the direction toward the slot 840, to align the connection portion 834 of the extractor structure 810 with the slot 840, as shown in FIG. 25.

Figure 26A:
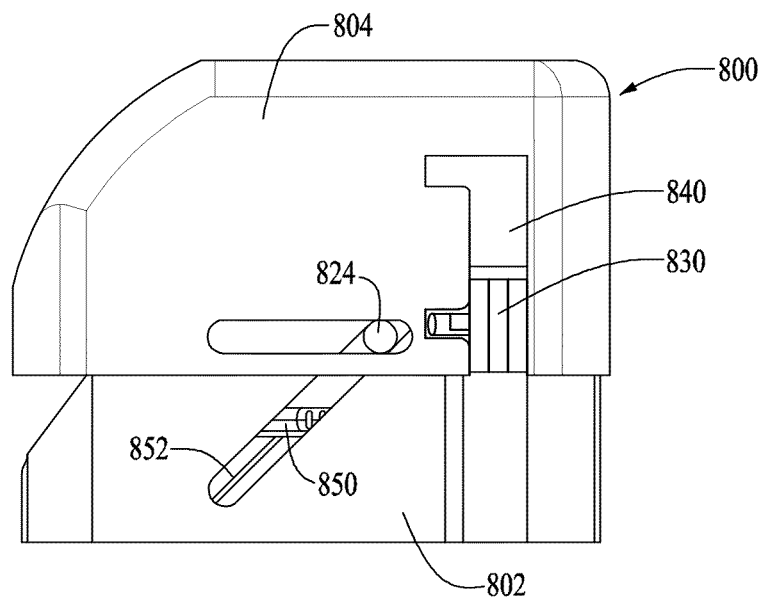

From the unlock position of FIG. 25, the patient-user (or medical practitioner) may set the device 800 into a retracted position as shown in FIGS. 26*a* and 26*c*, and in a cut-away view in 26*b*. The device 800 may be set to the retracted position by moving the cap structure 804 relative to the base structure 802, in the direction of arrow 806, to the position shown in FIGS. 26*a*, 26*b* and 26*c*. Movement of the cap structure 804 relative to the base structure 802 may be carried out manually, by gripping the cap structure 804 and/or the base structure 802 and drawing the two structures partially apart.

Figure 26B:
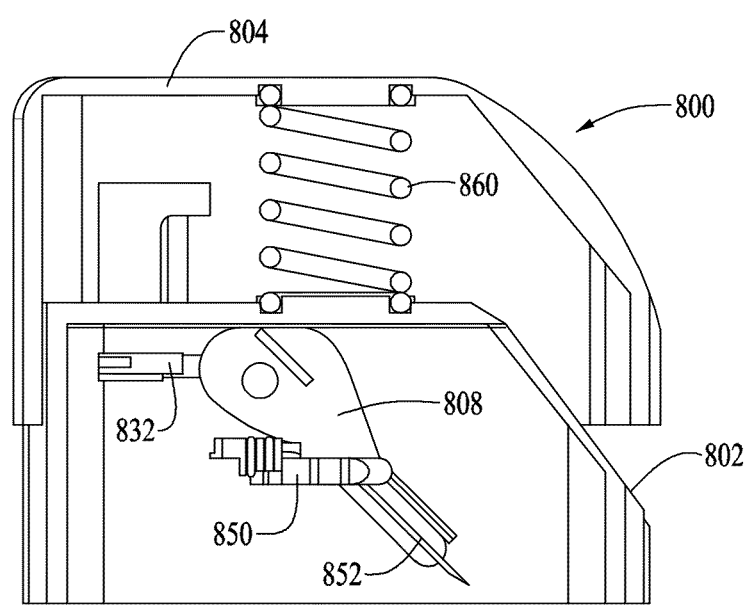

Alternatively or in addition, a bias mechanism, such as, but not limited to a coil spring or other spring structure, magnets or the like, may be provided within the device 800, to bias the cap structure 804 and base structure 802 toward the retracted position shown in FIG. 26*b*. For example, a coil spring 860 may be arranged between the cap structure 804 and the base structure 802, with one end of the coil coupled to the inside surface 862 of the upper wall of the cap structure 804 and the other end of the coil coupled to the outside surface 864 of the upper wall of the base structure 802 (relative to the orientation shown in FIG. 26*b*). The coil spring 860 may be configured to be in a compressed state (compressed against its natural length dimension) when the cap structure 804 and base structure 802 are in the initial, loaded and unlock positions of FIGS. 22*a*, 24 and 25, respectively, to impart a bias force directed toward separating the surface 862 of the cap structure 804 and surface 864 of the base structure 802. In other embodiments, a first magnet (such as a permanent magnet) may be arranged on or in the upper wall of the base structure 802 and a second magnet (such as a permanent magnet) may be arranged on or in the upper wall of the cap structure 804, with common poles of the two magnets facing each other to provide an opposing force directed toward separating the surface 862 of the cap structure 804 and surface 864 of the base structure 802.

By moving the base structure 802 and cap structure 804 to the retracted position (FIGS. 26*a*, 26*b* and 26*c*), the engagement of the arms 824 and 825 with the slots 838 in the side walls 804*a* and 804*b* of the cap structure 804 cause the slide structure 808 to move relative to the base structure 802 further into the interior of the base structure. As the slide structure 808 is moved further into the interior of the base structure, the arms 824 and 825 are guided by the angled slots 814 in the side walls 802*a* and 802*b* of the base structure 802, toward the second end 814*b* of the slots 814. By moving the slide structure 808 further into the interior of the base structure 802, the device 850 (including the needle or cannula portion 852 of the device 850) that is received in the receptacle 820 of the slide structure 808 is also drawn into the interior of the base structure 802.

In the retracted position, the device 800 may be arranged relative to a patient-user's skin (or surface of other subject to be injected) for injection of the needle or cannula portion 852 of the device 850. In particular, the bottom surface 812 of the base structure 802 may be arranged adjacent and generally parallel to the patient-user's skin (or surface of other subject to be injected) at a desired injection site.

In the retracted position (FIGS. 26a, 26b and 26c), the extractor structure 810 aligns with the second extension slot 843. From the retracted position of FIGS. 26a, 26b and 26c, the device may be set to the needle extract position shown in FIGS. 27a, 27b and 27c, by moving the handle 830 of the extractor structure 810 into the extension slot 843. As the handle 830 of the extractor structure 810 is moved into the extension slot 843, the shaft portion 832 of the extractor structure 810 is moved into (or further into) the channel in the body of the slide structure 808, through the opening in the surface 822 of the body of the slide structure 808, to release the device 850 from being locked within the. For example, the movement of the shaft portion 832 into (or further into) the channel in the body of the slide structure 808 may cause the free end of the shaft portion 832 to contact the device 850 and physically push the device 850 out of a friction fit with the receptacle 820. Alternatively, or in addition, such movement of the shaft portion 832 may cause the shaft portion 832 to engage and move a flexible tab, spring or other lock mechanism out of locking engagement with the device 850.

Once the device 800 is set in the needle extract position (FIGS. 27a, 27b and 27c), the device 800 may be operated to insert the needle or cannula 852 of the device 850 into the patient-user (or other subject). While the device 800 may have already be arranged relative to a patient-user's skin (or surface of other subject to be injected) for injection when the device was set in the retracted position, as described above, in other embodiments, the device 800 may not be arranged relative to the patient user's skin (or surface of other subject to be injected) until after the device 800 is set in the needle extract position.

The device 800 is operated to insert the needle or cannula 852 at an angle (a non-perpendicular angle) relative to the patient-user's skin (or surface of other subject to be injected). To insert the needle or cannula 852 into the patient-user's skin (or surface or other subject), a force in the direction opposite to the direction of arrow 806 is applied to move the cap structure 804 relative to the base structure 802, from the needle extract position (FIG. 27a) toward an insert position. The force is sufficient to overcome the bias mechanism 860, to move the cap structure 804 over the base structure 802 to a position similar to the relative positions of the cap structure 804 and base structure 802 shown in FIG. 25. The force may be applied manually, for example, by the patient-user (or medical technician) pressing downward (in the orientation of FIG. 27a) on the cap structure 804 at a desired velocity and timing. Alternatively, the force may be applied by an automated device, in response to an activation signal.

Figure 27A:
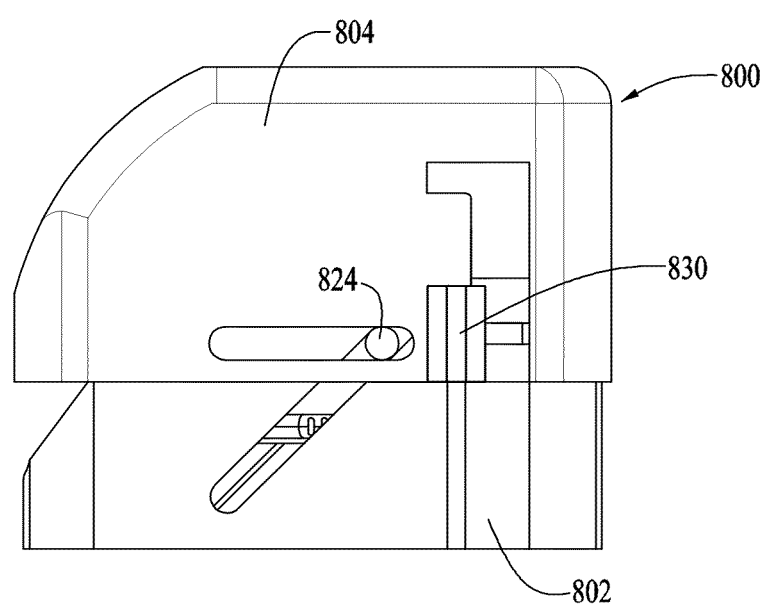
Figure 27B:
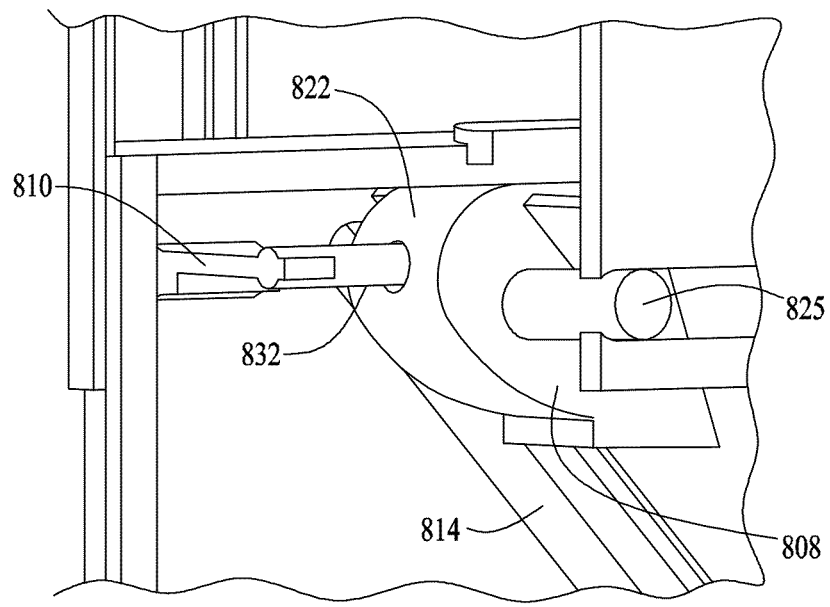
Figure 27C:
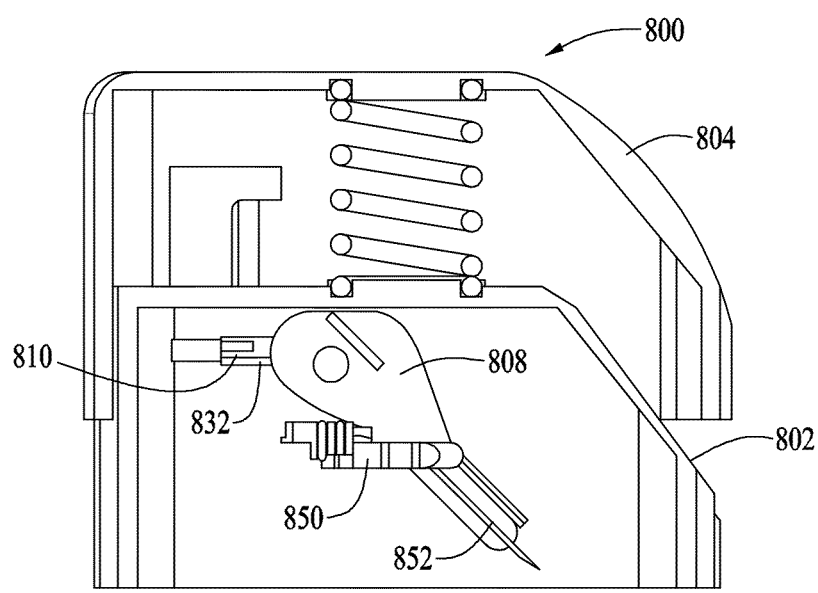

With the relative motion of the cap structure 804 and the base structure 802 from the needle extract position (FIG. 27a) toward the insert position, the arms 824 and 825 of the slide structure 808 are engaged by the slots 838 in the side surfaces 804a and 804b of the cap structure 804 and are moved downward (relative to the orientation of FIG. 27a). As the arms 824 and 825 move downward (relative to the orientation of FIG. 27a), the arms 824 and 825 are guided by the angled slots 814 in the base structure 802, to move the needle or cannula 852 at an angle relative to the bottom surface 812 of the base structure 802 (and, thus, at an angle relative to the patient-user's skin or the surface of other subject to be injected). The angled orientation of the needle or cannula 852 and the angled insertion direction provided by the angled slots 814, result in an insertion of the needle or cannula 852 at an angle (a non-perpendicular angle) relative to the patient-user's skin (or surface of other subject to be injected).

Accordingly, with the device 800, a force in a direction opposite to the arrow 806 and generally perpendicular to the patient-user's skin (or surface of other subject to be injected) results in an insertion of a needle or cannula 852 at an angle (a non-perpendicular angle) to the patient-user's skin (or surface of other subject). The angle of the slots 814 relative to the bottom surface 812 of the base structure 802 define the angle of insertion of the needle or cannula 852 relative to the bottom surface 812 of the base structure (and, thus, relative to the patient-user's skin or surface of other subject to be injected). That angle may be any suitable angle that is not perpendicular or parallel to the bottom surface 812 of the base structure (and, thus, relative to the patient-user's skin or surface of other subject to be injected). In one example embodiment, the angle is within the range of about 10° to about 80° (or 100° to 150°) and in a particular embodiment is about 45° (or 135°).

With the needle or cannula 852 inserted into the patient-user's skin (or surface of other subject), the device 850 (including the needle or cannula 852) may be withdrawn from the slide structure 808 and remain on the patient-user's skin (or surface of other subject). After the cap structure 804 and base structure 802 have been moved to the insert position and the device 850 has been withdrawn from the slide structure 808, the slide structure 808 may be withdrawn back into the interior of the base structure 802, toward the retracted position, for example, by returning the cap structure 804 and the base structure 802 to the retracted position (FIGS. 26a, 26b and 26c). In particular embodiments, a needle may be coupled to the slide structure 808 and retracted with the slide structure 808, leaving a hollow cannula (and other structure, such as a sensor structure) in place on the patient-user's skin (or surface of other subject). In other embodiments, the needle and cannula may be inserted as a set by the needle inserting device 800 and the needle may be removed from the cannula at a time after completion of the operation of the needle inserting device 800.

Another embodiment of a needle inserting device 900 is shown in FIGS. 28 to 33, for converting a force directed generally perpendicular to the patient-user's skin (or surface of other subject to be injected) into an angled insertion force for inserting a needle or cannula at an angle (a non-perpendicular angle) to the patient-user's skin (or surface of other subject). The device 900 is shown in a retracted position in FIGS. 28 and 29 and in an insert position in FIG. 30.

Figure 31:
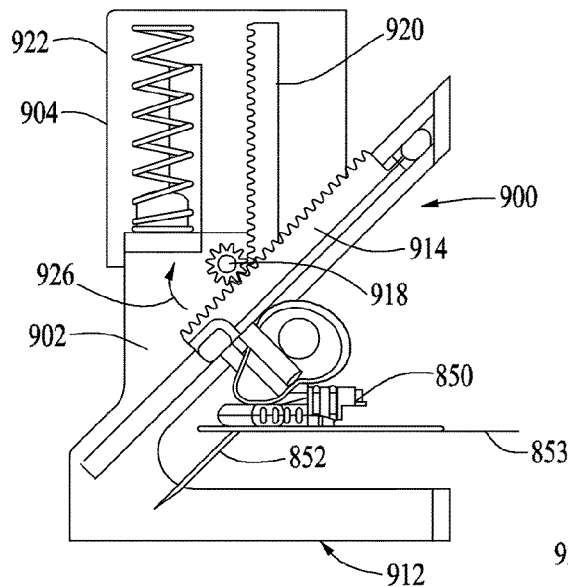
Figure 32:
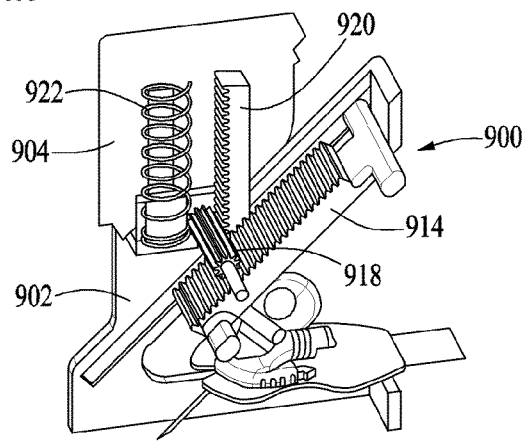
Figure 33:
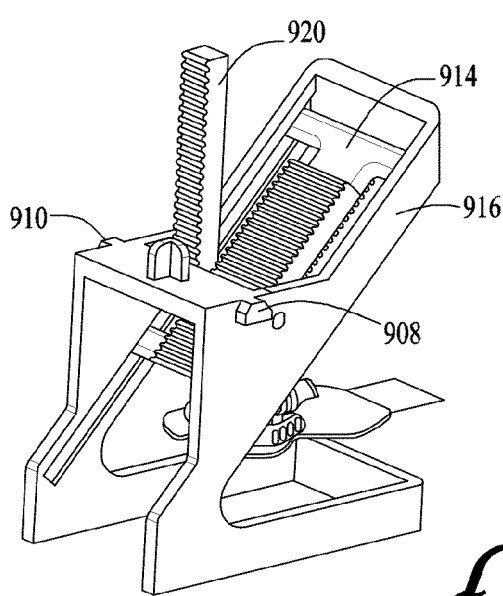

The device 900 includes a base structure 902 and a cap structure 904 that is supported by the base structure 902 for movement relative to the base structure 902 in the direction of arrows 906 and 907. Cross-section and partial views of the device 900 are shown in FIGS. 31-33, to illustrate an example of suitable structure of the device.

The base structure 902 and the cap structure, each has a generally rigid body made of any suitable material, including, but not limited to plastic, metal, ceramic, composite material or the like. The body of the base structure 902 has a pair of tabs 908 and 910 that extend in two opposite directions relative to each other. The tabs 908 and 910 engage a corresponding pair of slots 911 in two opposite side walls of the body of the cap structure 904. Each slot 911 has a longitudinal dimension, extending generally perpendicular to a bottom surface 912 of the base structure 902. The engagement of the tabs 908 and 910 with the slots 912 allow the cap structure 904 to move relative to the base structure 902 in a direction generally perpendicular to the bottom surface 912 of the base structure 902, from a retracted position (FIGS. 28, 29, 31 and 32) to an insert position (FIG. 30).

The base structure 902 supports a first linear gear 914 for movement at an angle (a non-perpendicular angle) relative to the bottom surface 912 of the base structure 902. In the illustrated embodiment, the base structure 902 includes a guide rail 916 on either side of the linear gear 914, having grooves for receiving projections extending from the linear gear. The grooves and projections guide the linear gear 914 in an angled direction of motion relative to the bottom surface 912 of the base structure 902, from a retracted position (shown in FIGS. 28, 29 and 31-33) to an insert position (FIG. 30).

The base structure also supports a rotary gear 918 in operative engagement with the linear gear 914. The rotary gear 918 is support for rotation and has a grooved portion of its length arranged in engagement with grooves on the linear gear 914. The rotary gear 918 has a further grooved portion of its length arranged in operative engagement with grooves on a second linear gear 920. The second linear gear 920 is fixed to the cap structure 904 and moves in a linear motion with the motion of the cap structure 904 (generally perpendicular to the bottom surface 912 of the base structure 902).

A bias mechanism, such as, but not limited to a coil spring or other spring structure, magnets or the like, may be provided within the device 900, to bias the cap structure 904 and base structure 902 toward the retracted position. For example, a coil spring 922 may be arranged between the cap structure 904 and the base structure 902, as described above with respect to the embodiment of FIGS. 300-27. Alternatively, or in addition, the bias mechanism may include a pair of magnets arranged as described above with respect to the embodiment of FIGS. 300-27.

Figure 34:
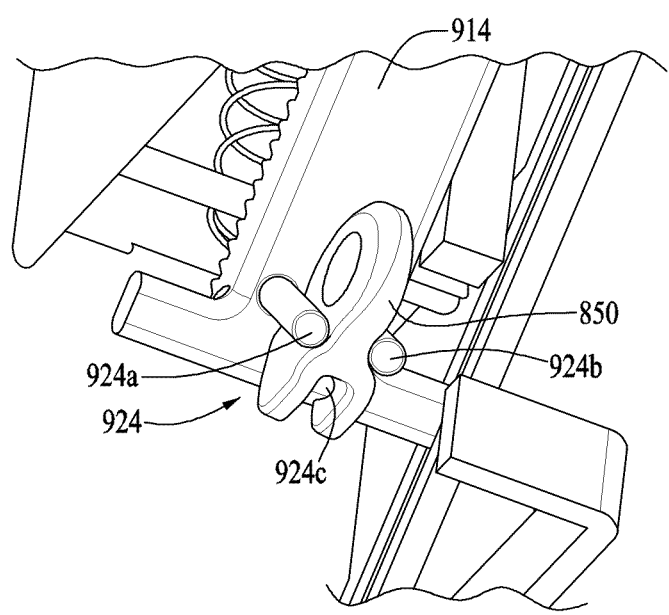

A receptacle structure 924 is connected in a fixed relation to the first linear gear 914. The receptacle structure 924 is configured to receive and retain a device 850 having a cannula or hollow needle 852, as described above. The receptacle structure 924 may have any suitable configuration that is capable of holding and selectively releasing a device having a cannula (or hollow needle) assembly. An example of a receptacle structure is described above with respect to receptacle 820 in FIG. 23c. A further example of a receptacle structure is shown in FIG. 34, wherein the receptacle structure 924 includes a set of three prongs 924a-c that extend from the first linear gear 914.

In operation, the needle inserting device 900 may come pre-assembled or may be assembled as shown in FIGS. 28 and 29. In a retracted position shown in FIGS. 28 and 29, the cap structure 904 is arranged over the base structure 902 and is arranged relative to the base structure 902 at the end of its full range of motion in the direction of arrow 907.

From the retracted position of FIGS. 28 and 29, a patient-user (or a medical practitioner) may place a device 850 in the receptacle 924 of the slide structure 808, to load the needle inserter device. In certain embodiments, the needle inserting device 900 may come from the manufacturer or assembler, pre-loaded and packaged with the device 850 in the receptacle 924, wherein the device 850 may be covered by a removable cover as described above.

In the retracted position, the device 900 may be arranged relative to a patient-user's skin (or surface of other subject to be injected) for injection of the needle or cannula portion 852 of the device 850. In particular, the bottom surface 912 of the base structure 902 may be arranged adjacent and generally parallel to the patient-user's skin (or surface of other subject to be injected) at a desired injection site.

The device 900 is operated to insert the needle or cannula 852 at an angle (a non-perpendicular angle) relative to the patient-user's skin (or surface of other subject to be injected). Prior to insertion of the needle or cannula 852, a peal-sheet 853 may be removed from the sensor structure 850 to expose an adhesive material that will allow the structure 850 to adhere to the patient-user's skin (or surface of other subject), when the structure is brought into contact therewith.

To insert the needle or cannula 852 into the patient-user's skin (or surface or other subject), a force in the direction of arrow 906 is applied to move the cap structure 904 relative to the base structure 902, from the retracted position (FIGS. 28 and 29) toward an insert position (FIG. 30). The force must be sufficient to move the cap structure 904 downward (in the orientation of FIG. 30) relative to the base structure 902, against the force of the bias mechanism 922. The force on the cap structure 904 is applied in a direction generally perpendicular to the bottom surface 912 of the base structure 902 and, thus, generally perpendicular to the patient-user's skin (or surface of other subject to be injected). The force may be applied manually, for example, by the patient-user (or medical technician) pressing downward (in the orientation of FIG. 30) on the cap structure 904 at a desired velocity and timing. Alternatively, the force may be applied by an automated device, in response to an activation signal.

With the relative motion of the cap structure 904 and the base structure 902 in the direction of arrow 906, from the retracted position (FIGS. 28, 29 and 31-33) toward the insert position (FIG. 30), the second linear gear 920 is moved with the cap structure 904 relative to the base structure 902 and rotates the rotary gear 918 about its axis of rotation in the direction of arrow 926. Rotation of the rotary gear 918 in the direction of arrow 926 causes the first linear gear 914 to move, linearly, in the direction of arrow 928. As the first linear gear 914 moves in the direction of arrow 928, the needle or cannula 952 is inserted into the patient-user's skin (or surface of other subject) at a non-perpendicular angle relative to the bottom surface 912 of the base structure 902 (and, thus, at a non-perpendicular angle relative to the patient-user's skin or surface of other subject to be injected). In addition, the exposed adhesive on the device 850 comes into contact with the patient-user's skin (or surface of other subject) and adheres the device 850 to the patient-user (or other subject).

Once the needle or cannula 852 is inserted into the patient-user's skin (or surface of other subject), the device 850 may be removed from the receptacle structure 924. In certain embodiments, the needle may be secured to the receptacle structure 924 and may be automatically withdrawn from a cannula by releasing the force on the cap structure 904 and allowing the bias mechanism 922 to return the cap structure 904 to the retracted position relative to the base structure 902 and, thus cause the linear gear 914 to move in the direction opposite to the direction of the arrow 928.

The angle of the first linear gear 914 (and the angle of the guide rails 914 and 916) relative to the bottom surface 912 of the base structure 902 defines the angle of insertion of the needle or cannula 852 relative to the bottom surface 912 of the base structure (and, thus, relative to the patient-user's skin or surface of other subject to be injected). That angle may be any suitable angle that is not perpendicular or parallel to the bottom surface 912 of the base structure (and, thus, to the patient-user's skin or surface of other subject to be injected). In one example embodiment, the angle is within the range of about 10° to about 80° (or 100° to 150°) and in a particular embodiment is about 45° (or 135°). Accordingly, with the device 900, a force in a direction of the arrow 906 and generally perpendicular to the patient-user's skin (or surface of other subject to be injected) results in an insertion of a needle or cannula 852 at an angle (a non-perpendicular angle) to the patient-user's skin (or surface of other subject).

In a further embodiment shown in FIG. 35, a needle inserting device 950 has a structure and operation similar to the device 900 in FIGS. 28-33. However, instead of a set of gears 914, 918 and 920 to transfer a generally perpendicular motion of the cap structure 954 relative to a base structure 952 into an angled insertion motion, the embodiment in FIG. 950 employs a pivoting link structure. In particular, at least one link rod 956 is connected at a first pivot point to the cap structure 954 and at a second pivot point to a slider 958. A receptacle for receiving and holding a device 850 with a needle or cannula 852, as described above, is provided on the slider 958.

The slider 958 engages and moves relative to the grooves one or more guide rails 960 (similar to guide rails 914 and 916 of the base structure 902 described above), to move a device 850 (including a needle or cannula 852) at an angle (defined by the angle of the guide rail 960) to an insert position. After insertion of the needle and cannula 852, the needle may be retracted, leaving the cannula and device 850 in place on the patient-user's skin (or surface of other subject), for example, by returning the cap structure 904 to its retracted position relative to the base structure 902. Upon retraction of the needle, the needle may be removed from the receptacle on the slider 958.

Figure 40:
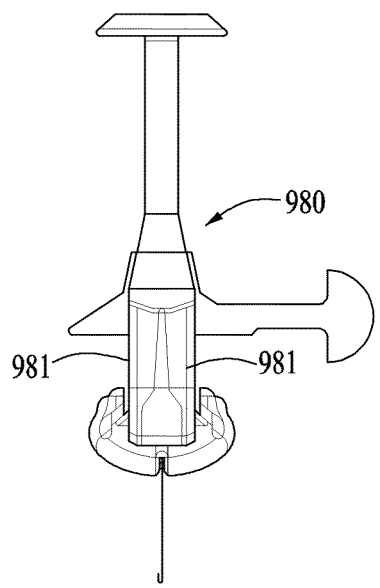
Figure 41:
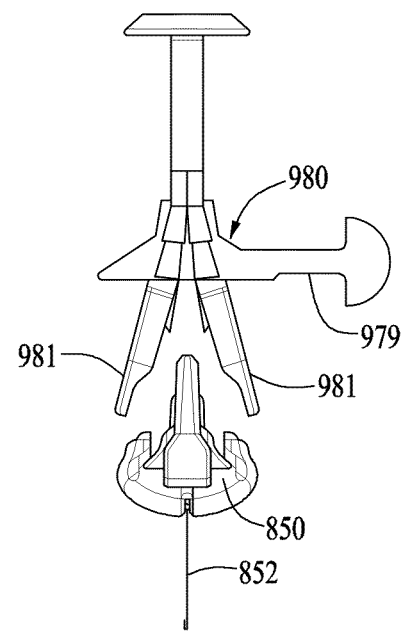

Further embodiments may employ other arrangements of angled slots, gears, pivoting links or the like to transfer a generally perpendicular motion of the cap structure relative to a base structure into an angled needle insertion motion. For example, another embodiment of a needle inserting device 970 is shown in FIGS. 36 to 41, for converting a force directed generally perpendicular to the patient-user's skin (or surface of other subject to be injected) into an angled insertion force for inserting a needle or cannula at an angle (a non-perpendicular angle) to the patient-user's skin (or surface of other subject). The device 970 is shown in a retracted position in FIGS. 36 and 37 and in an insert position in FIGS. 38 and 39. The receptacle of the device 970 is shown in FIG. 40 in a retracted position and is shown in FIG. 41 in an insert position.

Figures 37, 39:
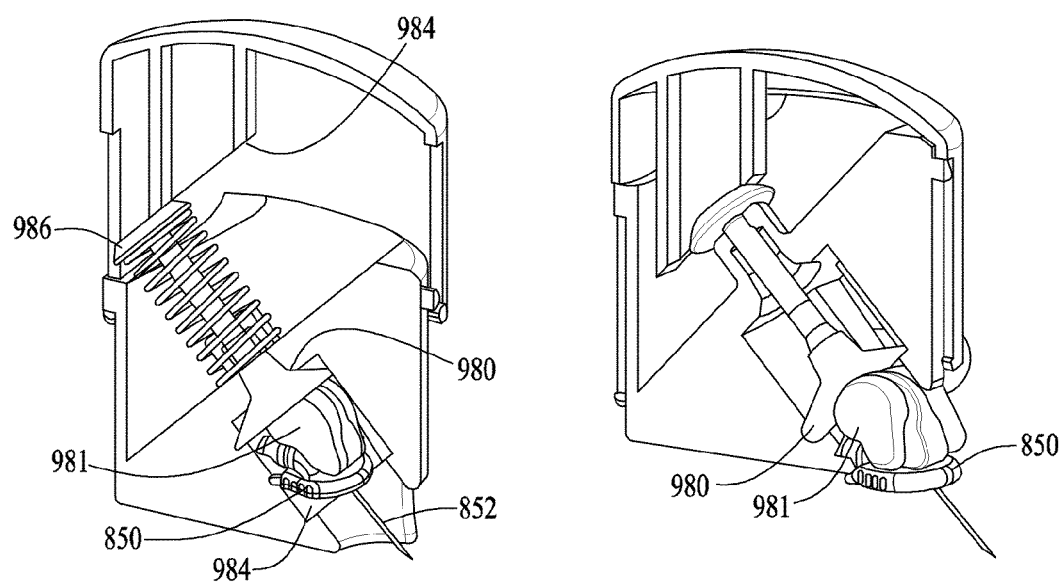

The device 970 includes a base structure 972 and a cap structure 974 that is supported by the base structure 972 for movement relative to the base structure 972 in the directions of arrows 976 and 977. The base structure 972 has a bottom surface 978 (relative to the orientation of FIGS. 36-39) that may be placed adjacent and generally parallel to a patient-user's skin (or surface of other subject to be injected), when the device 970 is in the retracted position (FIGS. 36 and 37). A force may be applied to the cap structure 974 in the direction of arrow 976, as described above, to move the cap structure 974 relative to the base structure 972, in the direction of arrow 976.

As the cap structure 974 moves in the direction of arrow 976 relative to the base structure 972, the cap structure 974 engage an arm 979 that extends from a needle device holder 980 located within the base structure 902. The base structure 902 includes an angled slot 982 through which the arm 979 extends. The base structure 902 also includes an angled channel 984 that provides a receptacle for receiving and holding a device 850 with a needle or cannula 852, as described above.

The needle device holder 980 includes two or more moveable jaws 981 at an end of shaft 982, where the jaws 981 may be moved together to clasp the device 850 between the jaws and may be moved apart to release the device 850. The jaws 981 may be biased toward an open direction by a natural spring force of the material that the holder 980 is made from and/or by bias springs or other bias structure included with the holder 980. The needle device holder 980 also includes a hood structure 982 that is slidable along the shaft to an extended position (FIG. 40) to selectively cover a portion of the jaws 981 and close the jaws 981 onto the device 850 or to a retracted position (FIG. 41) to withdraw from the jaws 981 and allow the jaws 981 to flex open. The hood structure 982 is connected to the arm 979.

Further movement of the cap structure 974 in the direction of arrow 976, after engagement with the arm 979 causes the arm 979 to move along the angled slot 982 and to draw the hood 982 over the jaws 981 to clamp the jaws 981 onto the device 850. As the cap structure 904 continues to move in the direction of arrow 976, the arm 979 continues to move along the angles slot 982 and to move with the holder 980 to the insert position (FIGS. 38 and 39). Also as the cap structure 974 continues to move in the direction of arrow 976, an angled surface 984 of or in the cap structure 974 contacts a plunger head 986 on one end of the shaft of the holder 980 and forces the shaft of the holder 980 toward the bottom surface 978 of the base structure 972, at a non-perpendicular angle relative to the bottom surface 978. In that manner, the needle or cannula 852 of the device 850 may be inserted into the patient-user's skin (or surface of other subject) at a non-perpendicular angle relative to the patient-user's skin (or surface of other subject). The angle of insertion is defined by the angle of orientation of the shaft of the holder 980 and the angle of the channel 984 in the base structure 972.

After insertion of the needle and cannula 852 of a device 850, the cap structure 974 may be returned to the retracted position (FIGS. 36 and 37), for example, by a bias mechanism 986. In the illustrated embodiment, the bias mechanism 986 is a coil spring arranged as described above. However, in other embodiments, other suitable bias mechanisms may be used, as described above, for biasing the cap structure 974 and base structure 972 toward the retracted state. As the cap structure 974 returns to the retracted state, the holder 980 also may be returned to the retracted state, wherein the hood 979 is withdrawn from the jaws 981 and allow the jaws to release the device 850 in its inserted state. The bias mechanism 986 may be arranged to impart a bias force on the plunger head 986 to urge the holder toward the retracted position.

Various embodiments of multi-piece infusion medium delivery devices are described in U.S. patent application Ser. No. 11/645,435, filed Dec. 26, 2006, titled "Infusion Medium Delivery system, Device And Method With Needle Inserter And Needle Inserter Device And Method," (assigned to the assignee of the present invention and incorporated herein by reference in its entirety). Such devices may include a first housing portion (which, in particular embodiments, may be a durable housing portion) for containing components that do not normally come into contact with the patient-user or infusion medium, during operation, such as, but not limited to control electronics, drive devices, power sources and the like. Such devices may also include a second housing portion (which, in particular embodiments, may be a disposable housing portion) for containing components that do normally come into contact with the patient-user or infusion medium during operation, such as, but not limited to, a reservoir.

Some of such multi-piece devices include a separate base member that may be adhered to a patient-user's skin (or surface of other subject to be injected) or otherwise carried by the patient-user, where the first and second housing portions are configured to connect together and to the base, for operation. Other of such multi-piece devices include a base portion that is part of the first or the second housing portion. Some of such multi-piece devices include injection site structure that is incorporated with the base and/or with one or the other of the first and second housing portions. Yet other of such multi-piece devices include an injection site module that contains injection site structure and is connected in fluid-flow communication with one or the other of the first and second housing portions or the base.

In any of those embodiments, a needle inserting device may be incorporated within or connectable to the injection site structure. Various examples of needle inserting devices that may be incorporated or connected to injection site structure is described in the present disclosure and in U.S. patent application Ser. No. 11/645,435, titled "Infusion Medium Delivery System Device And Method With Needle Inserter And Needle Inserter Device And Method" (assigned to the assignee of the present invention), which is incorporated herein by reference.

Figure 42:
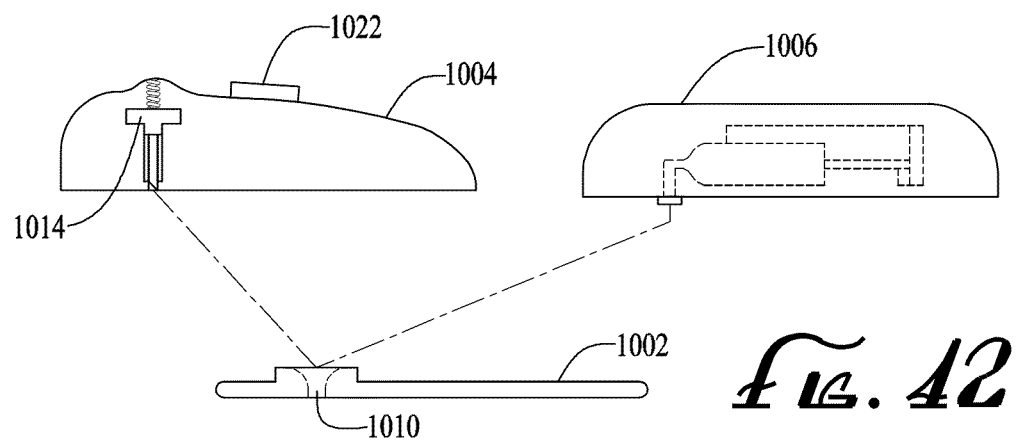
Figure 43:
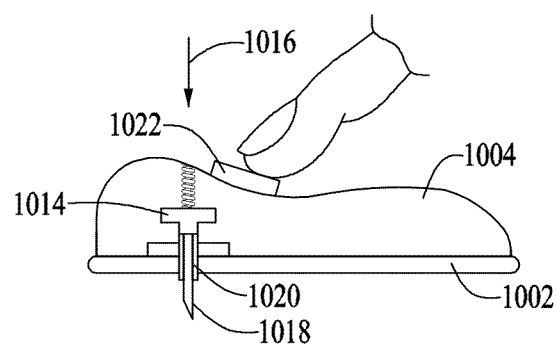
Figure 44:
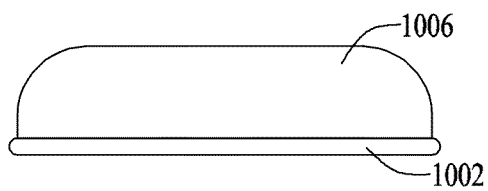

A further example of a multi-piece needle inserting device 1000 is describe with reference to FIGS. 42-44. Referring to FIG. 42, the multi-piece device 1000 includes a base structure 1002, an inserting device housing 1004 and a pump housing 1006. The base structure 1002, inserting device housing 1004 and pump housing 1006, each may be made of any suitably rigid material, including, but not limited to plastic, metal, ceramic, composite material or the like. The base structure 1002 is configured to be secured to a patient-user's skin (or surface of other subject to be injected) at a desired injection site. The inserting device housing 1004 may be secured to the base structure 1002 either before or after the base is adhered to the patient-user (or other subject), as shown in FIG. 43.

The inserting device housing 1004 includes a needle inserting device 1008, such as, but not limited to any suitable inserting device as described in the present disclosure or in U.S. patent application Ser. No. 11/645,435, titled "Infusion Medium Delivery System Device And Method With Needle Inserter And Needle Inserter Device And Method" (assigned to the assignee of the present invention), which is incorporated herein by reference. When the inserting device housing 1004 is secured to the base structure 1002, as shown in FIG. 43, the needle inserting device 1008 aligns with a needle insertion channel or opening 1010 in the base and may be operated to inject a needle or hollow cannula into the patient-user's skin (or surface of other subject to be injected).

Upon injecting a needle or cannula, a hollow needle or cannula is received and retained in a receptacle portion 1012 of the channel 1010 in the base structure 1002. After injecting the needle or cannula, the inserting device housing 1004 may be removed from the base structure 1002 and disposed of, stored or handled in some other manner, while the base structure 1002 and a hollow needle or cannula remains on the patient-user (or other subject).

After removal of the inserting device housing 1004 from the base structure 1002, the pump housing 1006 may be secured to the base structure 1002, for operation, as shown in FIG. 44. By securing the pump housing 1006 to the base structure 1002, a reservoir in the pump housing 1006 is connected in fluid flow communication with the hollow needle or cannula that has been inserted into the patient-user (or other subject).

In the embodiment of FIGS. 42-44, the inserting device 1008 has a moveable plunger 1014 that is supported for movement within the inserting device housing 1004 moveable in the direction of arrow 1016. A bias member 1017, such as, but not limited to a coil spring or other spring structure, is provided to impart a force on the plunger 1014 to draw the plunger into the inserting device housing 1004, as shown in FIG. 42. A needle 1018 having a sharp tip extends from an end of plunger 1014 and is aligned with the channel 1010 of the base structure 1002, when the inserting device housing 1004 is connected to the base 1002, as shown in FIG. 43. The needle 1018 is moveable in the direction of arrow 1016, with movement of the plunger 1014 in the direction of arrow 1016. A cannula 1020 with a cannula head as described herein may be supported on the needle 1018, for movement with the needle 1018.

The inserting device housing 1004 includes a button 1022 that may be manually operated by a patient-user (or medical technician) to cause the needle 1018 to be inserted into the patient-user's skin (or surface of other subject to be injected). In the illustrated embodiment, the inserting device housing 1004 is formed of a material that provides sufficient resiliency and flexibility to bend under the manual pressure from pressing the button 1022 and push the needle 1018 and cannula 1020 into and at least partially through the channel 1010. As the cannula 1022 is pushed into the channel 1010, the head of the cannula 1020 may engage and be retained by the receptacle 1012 of the channel 1010, for example, by friction fit, snap fit or other suitable retaining or connection arrangement.

Once the cannula 1020 has been received and retained by the receptacle 1012, the patient-user (or medical technician) may stop pressing the button 1022 and allow the inserting device housing 1004 to resiliently return to its original shape. In addition, the bias member 1017, such as, but not limited to a coil spring or other spring configuration, may be provided to draw the plunger 1014 back toward a retracted position (of FIG. 42) to draw the needle 1018 out of the cannula 1020 and into the housing 1004. The inserting device housing 1004 may then be removed from the base structure 1002, leaving the cannula 1020 in the patient-user (or other subject) to allow connection of the pump housing 1006 to the base structure 1002, as described above. Connection of the pump housing 1006 to the base structure 1002 also provides a connection of a reservoir in the pump housing 1006 to the cannula 1020, to provide a fluid-flow connection between the reservoir and the patient-user (or other subject). Various connectors for connecting a reservoir to a cannula may be employed, including connection structures as described in the present application. The multi-piece configuration of FIGS. 42-44 allow for a simplified injection and reservoir connection procedure.

While the needle inserting device 1008 of the embodiment in FIGS. 42-44 includes a manually movable plunger structure, other needle inserting devices may be used, including those describe in the present application and those described in U.S. patent application Ser. No. 11/645,435, titled "Infusion Medium Delivery System Device And Method With Needle Inserter And Needle Inserter Device And Method" (assigned to the assignee of the present invention), which is incorporated herein by reference. Other examples of needle inserting devices are described with reference to FIGS. 45-70.

Figures 45, 46:
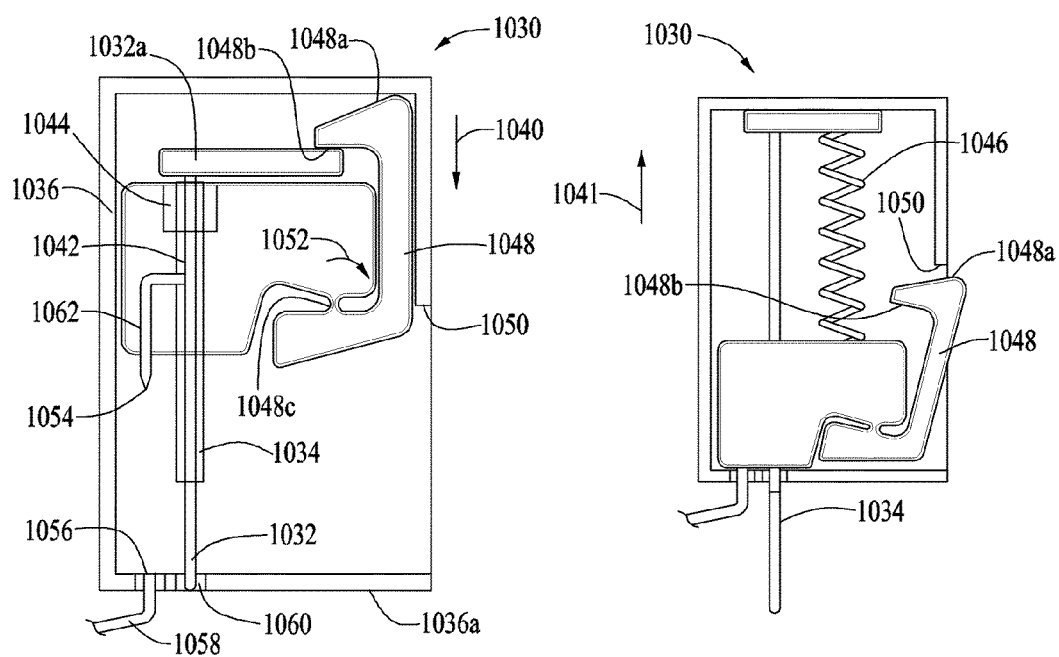

An example of a needle inserting device 1030 is described herein with reference to FIGS. 45 and 46. The needle inserting device 1030 is shown in a retracted position in FIG. 45, in which an introduction needle 1032 and cannula 1034 are located within a housing 1036. In FIG. 46, the needle 1032 and cannula 1034 are in an insert position to be inserted in a patient-user's skin (or surface of other subject to be injected).

The needle inserting device 1030 includes a carriage structure 1038 that is supported for movement by and relative to the housing 1036 in the direction of arrow 1040. The introduction needle 1032 is supported by the carriage structure 1038 and extends through a channel 1042 in the carriage structure 1038 in the direction of arrow 1040. One end of the cannula 1034 is attached to the carriage structure 1038, in fluid-flow communication with the channel 1042. The needle 1032 has a head portion 1032a and a shaft portion that extends from the head portion 1032a through the channel 1042 in the carriage structure 1038. A septum or other seal structure 1044 may be located within the channel 1042, to seal the channel 1042 around the needle 1032, yet allow motion of the needle 1032 in the direction of arrow 1041 relative to the carriage structure 1038.

A bias mechanism 1046 is provided to bias the needle head 1032a in the direction of arrow 1041, relative to the carriage structure 1038. In the illustrated embodiment, the bias mechanism is a coil spring. In other embodiments, the bias mechanism may be any suitable structure for providing a bias force on the needle 1032 in the direction of arrow 1041, including, but not limited to other types of spring configurations, magnet configurations as described herein, or the like.

The carriage structure 1038 has pivotal arm 1048 that has a stop surface 1048a arranged to engage a corresponding stop surface 1050 of or supported by the housing 1036, when the carriage structure 1038 is in the insert position (FIG. 46). The pivotal arm 1048 also stop surface 1048b that engages the needle head 1032a, when the carriage structure 1038 is in the retracted position (FIG. 45), yet disengages the needle head 1032a, when the carriage structure is in the insert position (FIG. 46). In the illustrated embodiment, the pivotal arm 1048 includes a flexible extension of the carriage structure 1038, for example, formed as single, molded unitary structure with the carriage structure 1038 and having a hinge connection portion 1048c that provides a natural spring-like force on the arm 1048 to urge the arm 1048 in the direction of arrow 1052. In other embodiments, a further spring or other bias mechanism may be included on the carriage structure 1038 to bias the arm 1048 in the direction of arrow 1052. In yet further embodiments, the pivotal arm 1048 may include a structure that is attached to the carriage structure 1038 for pivotal motion. In yet other embodiments, a resiliently deformable member may be employed, instead of or in addition to the pivotal arm 1048.

The carriage structure 1038 also has a connection needle 1054 that extends in the direction of arrow 1040 and is inserted through a septum 1056 in the housing 1036 for connection to a fluid-flow channel 1058, when the carriage structure 1038 is in the insert position (FIG. 46). The fluid-flow channel 1058 may be connected in fluid-flow communication with a reservoir, sensor structure, or other suitable fluid containing or processing structure, as described herein.

In operation, the needle inserting device 1030 is arranged in the retracted position (FIG. 45) and is placed with the bottom surface 1036a (relative to the orientation shown in FIG. 45) of the housing 1036 adjacent a patient-user's skin (or surface of other subject to be injected). The needle inserting device 1030 is then activated to cause the carriage structure 1038 to move in the direction of arrow 1040, to the insert position (FIG. 46), at which a portion of the length of the needle 1032 and cannula 1034 pass through an opening 1060 in the housing 1036 and are inserted into a patient-user's skin (or other subject). The carriage structure 1038 may be driven in the direction of arrow 1040, upon activation, by any suitable drive mechanism, including, but not limited to, spring drives, pressure drives, magnet drives motor drives, or the like, as described herein and in other applications incorporated by reference herein. Activation of the drive mechanism may be carried out by any suitable manual, mechanical, automatic, electronic or remote electronic mechanism.

As the carriage structure 1038 moves from the retracted position (FIG. 45) to the insert position (FIG. 46), the needle 1032 and cannula 1034 are inserted into the patient-user's skin (or surface of other subject). At the same time, the connection needle 1054 is inserted through the septum 1056, to make fluid flow connection with the channel 1058. The connection needle 1054 may be a hollow needle structure that is connected in fluid flow communication with the channel 1042, through a connection channel 1062 in the carriage structure 1038.

Once the carriage structure 1038 has reached the insert position (FIG. 46), the pivotal arm (or resiliently deformable structure) 1048 aligns with an opening, indentation, or other discontinuity 1062 in the housing 1036, to allow the flexible arm (or resiliently deformable structure) 1048 to flex outward (deform) to position the stop surface 1048a on the arm 1048 in alignment with the stop surface 1050 on the housing 1036. In that position, the arm 1048 inhibits the carriage 1038 from moving, relative to the housing 1036, in the direction of arrow 1041. In addition, in that position, the arm 1048 releases the needle head 1032a and allows the bias mechanism 1046 to move the needle 1032 in the direction of arrow 1041. As the needle 1032 moves in the direction of arrow 1041 by the action of the bias mechanism 1046, the needle is at least partially withdrawn from the cannula 1034 and a fluid flow connection is made between the cannula 1034 and the channel 1058, through the channel 1042, connection channel 1062 and connection needle 1054. The tension of the bias mechanism 1046 may be selected so as to impart a force on the carriage structure 1038, after the carriage structure 1038 reaches the insert position (FIG. 46), to help maintain the connection of the connection needle 1054 with the channel 1058.

In other embodiments, instead of a connection needle 1054 and septum 1056, a length of flexible conduit may be provided to connect the channels 1062 and 1058. The conduit may be stretchable and/or provided with sufficient slack to remain connected as the carriage structure 1038 moves between the retraced and insert positions.

An example of a needle inserting device 2000 is described herein with reference to FIG. 47. The needle inserting device 2000 operates to insert an introduction needle 2002 and a cannula 2004 into a patient-user's skin (or surface of other subject to be injected), then withdraw the needle 2002 and leave the cannula 2004 in place. The needle inserting device 2000 may be employed with a base structure 2006 (as described above), injection site module housing, or the like, that has a nest 2008 for receiving the head 2004a of the cannula 2004. The base structure 2006 may be placed adjacent a patient-user's skin (or surface of other subject to be injected) while the device 2000 is in a retracted state (as shown in FIG. 47). In that position, the device 2000 may be activated to move the needle 2002 and cannula 2004 to an insert position, in which at least a portion of the length of the needle 2002 and the cannula 2004 are moved through an opening in the base structure, to an insert position, to pierce the patient-user's skin (or surface of other subject). The nest 2008 may include one or more flexible pawls 2009 for retaining the cannula head 2004a in place, when the cannula 2004 is moved to an insert position.

The needle 2002 has a sharp end 2002a that is extended through the catheter 2004. The needle 2002 has a second end 2002b that is operatively connected to a rotary cam. In the illustrated embodiment, the second end 2002b forms a bend (about 90°) and is engaged with a groove 2010 in a rotary cam 2012. The cam 2012 is supported for rotation about a cam axis. The cam 2012 may include a disk-shaped member that has a peripheral edge that is thicker on one side of the axis than the other (when viewed in cross-section, as shown in FIG. 47. The groove 2010 extends along the peripheral edge of the disk-shaped member of the cam 2012, at a non-perpendicular angle relative to the rotation axis of the cam 2012.

The cam 2012 may be coupled to any suitable drive mechanism, for selectively driving the cam 2012 in a rotary motion about the axis of the cam. The drive mechanism may include a pre-wound spring (pre-wound to impart a rotational force on the cam 2012, in an unwinding or winding direction of the spring) coupled to the cam 2012. In other embodiments, other suitable drive mechanisms may be coupled to the cam 2012 for selectively driving the cam 2012, including, but not limited to other spring configurations, drive motors, magnetic drives, or the like.

As the cam 2012 is rotated, the needle end 2002b rides within the groove 2010 of the cam 2012 and translates the rotational motion of the cam 212 into a linear motion of the needle 2002 in the direction of arrow 2014 for insertion of at least a portion of the needle 2002 and the cannula 2004 into a patient-user's skin. Linear motion of the needle 2002 in the direction of arrow 2014 causes the cannula 2004 to move, with the needle 2002, in the direction of arrow 2014, to insert the needle and catheter into the patient-user (or other subject) until the cannula head 2004a engages and is retained within the nest 2008 of the base 2006.

Further rotation of the cam 2012 will result in the needle 2002 being withdrawn, at least partially, from the cannula 2004, leaving the cannula in the nest 2008 (and in the patient-user or other subject). A fluid-flow conduit 2018, such as, but not limited to a flexible tubing, may be connected in fluid-flow communication with the cannula. Accordingly, the device 2000 may be set such that a first part of a full rotation of the cam 2012 causes the needle 2002 and cannula 2004 to be inserted into the patient-user (or other subject) and the next part of the cam rotation causes the needle 2002 to withdraw (at least partially) from the cannula 2004.

An example of a needle inserting device 2100 is described herein with reference to FIGS. 48-52. The needle inserting device 2100 operates to insert an introduction needle 2102 and a cannula 2104 into a patient-user's skin (or surface of other subject to be injected), then withdraw the needle 2102 and leave the cannula 2104 in place. The needle inserting device 2100 is shown in a partial exploded view in FIG. 48, in an initial position in FIG. 49, in a loaded position in FIG. 50, in an insert position in FIG. 51 and in a retracted position in FIG. 52.

The needle inserting device 2100 may be employed with a base structure (as described above), injection site module housing, or the like, that has a nest 2108 for receiving the head 2104a of the cannula 2104. The base structure may be placed adjacent a patient-user's skin (or surface of other subject to be injected) while the device 2100 is in a loaded state (as shown in FIG. 50). In that position, the device 2100 may be activated to move the needle 2102 and cannula 2104 to an insert position, in which at least a portion of the length of the needle 2102 and the cannula 2104 are moved through an opening in the base structure, to an insert position, to pierce the patient-user's skin (or surface of other subject). The nest 2108 may include one or more indentations, openings, contours or the like 2110 for engaging one or more flexible arms 2112 on the cannula head 2104a and retaining the cannula 2104 in place, when the cannula 2104 is moved to an insert position (FIG. 51).

The cannula head 2104a has a central fluid-flow channel 2114 through which the needle 2104 may extend, and a septum 2116 arranged to seal the central channel 2114 around the needle 2104. A connection channel 2118 is connected in fluid-flow communication with the channel 2114 and may be further connected in fluid flow communication with a reservoir, sensor or other structure for holding or processing fluid.

The needle inserting device 2100 has a housing 2120 that has a generally cylindrical shape and a hollow interior. The housing 2120 is open on one end of the cylindrical shape to receive a portion of the length of a handle 2122. The housing 2120 is also open on the other end to receive the cannula 2104, with the flexible arms 2112 bent toward each other against their natural (or biased) shape (state) shown in FIG. 48. A compression spring 2124 is located within the housing 2120 and is arranged to impart a force on the cannula 2104, when the device 2100 is in the loaded position (FIG. 50). A retention spring 2126 is also located within the housing 2120 and is connected to a head or hub 2102a of the needle 2102, to retract the needle 2102, when the device 2100 is in the retracted position (FIG. 52). In the illustrated embodiments, the compression spring 2124 and the retention spring 2126 are coil springs. In other embodiments, other suitable spring or bias mechanisms may be used.

In operation, the needle inserting device 2100 may be arranged in an initial position, as shown in FIG. 49, with a cannula 2104 inserted at least partially into one end of the cylindrical housing 2120 and with the needle 2102 extending through the cannula 2104. In the initial position, the cannula may be releasably locked to the housing 2120, for example, by one or more flexible or deformable tabs, protrusions, arms or the like on the cannula 2104, that engage a corresponding opening, indentation, stop surface or the like in the housing 2120. Alternatively, or in addition, the tabs, protrusions, arms or the like may be on the housing 2120 and the opening, indentation, stop surface or the like may be on the cannula 2104. The cannula 2104 may be unlocked from a locked state with the housing 2120 by, for example, applying a suitable manual pressure on the housing (by squeezing the housing) at a release button location 2128 on the housing 2120. In other embodiments, the cannula 2104 may be locked to the housing 2120 in other suitable manners that allow for selective release of the lock, including, other mechanical locking structures and electronic or magnetically operated locks. In embodiments in which the sharp tip of the needle 2102 extends from the housing 2120 when the device 2100 is in the initial position, a removeable cover or cap may be provided over the needle tip and/or the needle end of the housing 2120.

From the initial position (FIG. 49), the device 2100 may be set to a loaded position (FIG. 50), by moving the handle 2122 further into the housing 2120. As the handle 2122 moves toward the loaded position, the compression spring 2124 compresses against its natural length and imparts a force on the cannula 2104 in the direction of arrow 2130. However, because the cannula 2104 is locked at 2128, the cannula 2104 remains inside of the housing 2120 in the loaded position.

The handle 2122 may be provided with by one or more flexible or deformable tabs, protrusions, arms or the like, that engage a corresponding opening, indentation, stop surface or the like in the housing 2120, when the handle 2122 is moved to the loaded position (FIG. 50). Alternatively, or in addition, the tabs, protrusions, arms or the like may be on the housing 2120 and the opening, indentation, stop surface or the like may be on the handle 2122. Accordingly, the handle 2122 may be locked relative to the housing 2120, when moved to the loaded position. In certain embodiments, a release mechanism, as described above for the cannula 2104, may be provided to selectively release the device 2100 from the loaded position. The handle 2122 may be moved to the loaded position, relative to the housing 2122, for example, by applying a manual pushing force onto the handle, until the tabs, protrusions, arms or the like engage with the opening, indentation, stop surface or the like.

Once the device is in the loaded position (FIG. 50), the device may be arranged with the needle end of the housing 2120 adjacent and aligned with the nest 2108. In that position, the cannula 2104 may be released from its locked state relative to the housing 2120, using any suitable release mechanism as described above. In one embodiment the release may be accomplished manually, by the patient-user (or medical technician). In other embodiments, the release may be accomplished electronically or electromechanically, from a remote device, on an automated basis, or the like.

Upon releasing the cannula 2104 from the loaded position of FIG. 50, the cannula is moved by the decompression action of the spring 2124 to the inserted position (FIG. 51) in which at least a portion of the length of the needle 2102 and the cannula 2104 is inserted into the patient-user's skin (or surface of other subject) and the cannula head 2104*a* is moved into the nest 2108. Upon the cannula head 2104*a* being received in the nest 2108, the arms 2112 of the cannula head 2104*a* are allowed to flex outward (under their natural or a biasing force) to engage and lock with a corresponding number of openings, indentations, stop surfaces or the like on the nest 2108. As the arms 2112 flex outward, the arms release the needle hub 2102*a* from a hub receptacle contour 2132 in the arms 2112.

From the inserted position (FIG. 51), the retaining spring 2126 is stretched beyond its natural length and applies a return force in the direction opposite to the arrow 2130 on the needle 2102. Upon release of the needle hub 2102*a* from the receptacle contours 2132 as the cannula arms 2112 flex outward, the retaining spring 2126 draws needle 2102 at least partially out of the cannula 2104. In particular embodiments, the retaining spring 2126 draws the needle 2102 fully into the housing 2120, to avoid inadvertent contact with the needle 2102, as shown in the retracted position of FIG. 52. Once the needle 2102 has been retracted, the housing 2120 may be separated from the nest 2108, while the cannula 2104 remains in place within the nest.

An example of a needle inserting device 2200 is described herein with reference to FIGS. 53-56. The needle inserting device 2200 has a structure and operation that is similar in many respects to the embodiment of FIGS. 1007-1011. Accordingly, like reference numbers are used for like elements in the two embodiments. However, instead of employing a compression spring 2124 to force the cannula toward the insert position (as described in the embodiment of FIGS. 1007-1011), the embodiment of FIGS. 53-55 employ pressurized fluid (such as pressurized air or other gas).

Figure 53:
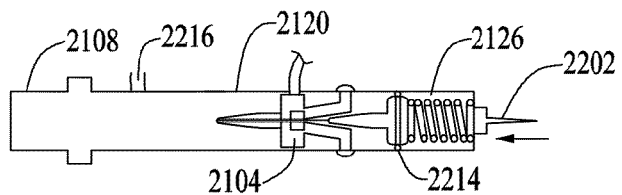
Figure 54:
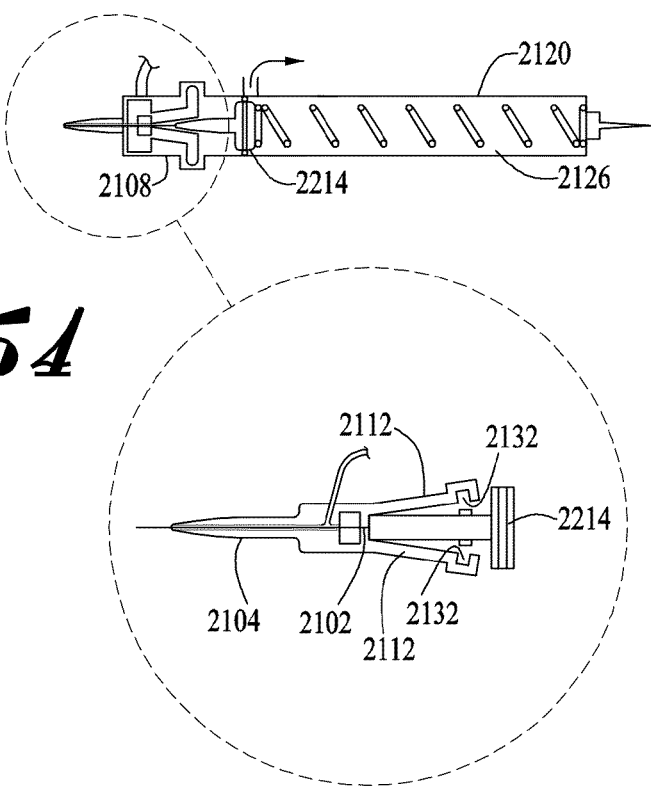
Figure 55:
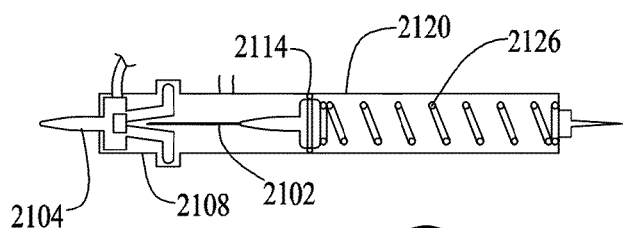
Figure 56:
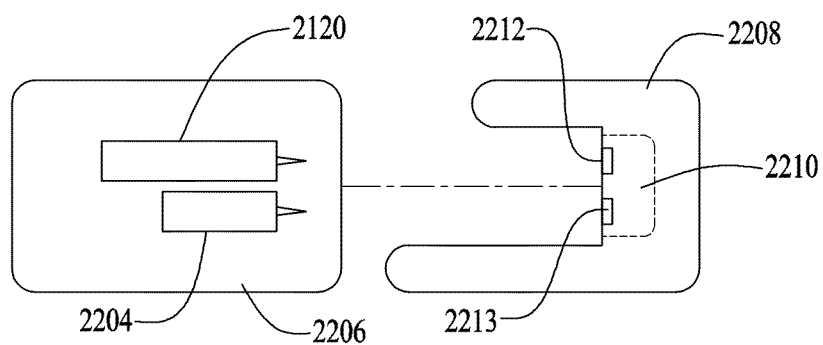

The device 2200 is shown in an initial position in FIG. 53. From the initial state, a source of pressurized fluid may be connected to a fluid inlet 2202 of the housing 2120 to set the device into a loaded position. A pressurized fluid source may be connected to the housing 2120 in any suitable manner. In one example as shown in FIGS. 56, a canister of pressurized fluid 2204 may be held on a support structure 2206 with the housing 2120 of the needle inserting device 2200. The support structure 2206 may be a housing and/or may be included as part of the packaging in which the device 2200 is provided to the patient-user. In the embodiment of FIG. 56, the canister 2204 is operatively connected to the inlet 2202 of the housing 2200 by connecting the support structure 2206 to a port structure 2208. The port structure 2208 includes a fluid flow volume 2210 that is sealed by a pair of septa 2212 and 2213. Upon connecting the support structure 2206 to the port structure 2208, a needle of the inlet 2202 and a similar needle for the outlet of the canister 2204 puncture and extend through the septa 2212 and 2213, respectively, to connect the interior of the canister 2204 in fluid flow communication with the interior of the housing 2120, through the volume 2210 in the port structure 2208.

Once the housing 2120 of the device 2200 has been pressurized, the pressure within the housing 2120 applies a force on a plunger head 2214 that is connected to the needle hub 2102*a* of the needle 2102. The plunger head 2214 has a seal structure for sealing against the interior surface of the housing 2120. The retaining spring 2126 may be connected to the plunger head 2214.

Once the device 2200 is in the loaded (pressurized) position, the device may be arranged with the needle end of the housing 2120 adjacent and aligned with the nest 2108 described in the embodiment of FIGS. 1007-1011. In that position, the cannula 2104 may be released from its locked state relative to the housing 2120, using any suitable release mechanism as described above. Upon releasing the cannula 2104 from the loaded position, the cannula is moved by the action of the pressurized gas on the plunger 2214 to the inserted position (FIG. 54) in which at least a portion of the length of the needle 2102 and the cannula 2104 is inserted into the patient-user's skin (or surface of other subject) and the cannula head 2104*a* is moved into the nest 2108.

Upon the cannula head 2104*a* being received in the nest 2108, the arms 2112 of the cannula head 2104*a* are allowed to flex outward (under their natural or a biasing force) to engage and lock with a corresponding number of openings, indentations, stop surfaces or the like on the nest 2108. As the arms 2112 flex outward, the arms release the needle hub 2102*a* from a hub receptacle contour 2132 in the arms 2112, as described above for the embodiment of FIGS. 1007-1011.

In addition, as the plunger head 2214 moves to the insert position (FIG. 54), the plunger head 2214 passes a fluid outlet 2216 in the housing 2120 and, as a result, the pressurized fluid within the housing 2120 is allowed to escape through the outlet 2216. Once sufficient pressurized fluid is released, the retaining spring 2126 draws the needle 2102 out of the cannula 2104.

In particular, when the device 2200 is in the inserted position (FIG. 54), the retaining spring 2126 is stretched beyond its natural length and applies a return force on the needle 2102. Upon release fluid pressure from the housing 2120 through the outlet 2216 and upon release of the needle hub 2102*a* from the cannula arms 2112, the retaining spring 2126 draws the needle 2102 at least partially out of the cannula 2104. In particular embodiments, the retaining spring 2126 draws the needle 2102 fully into the housing 2120, to avoid inadvertent contact with the needle 2102. Once the needle 2102 has been retracted (FIG. 55), the housing 2120 may be separated from the nest 2108, while the cannula 2104 remains in place within the nest.

Figure 57:
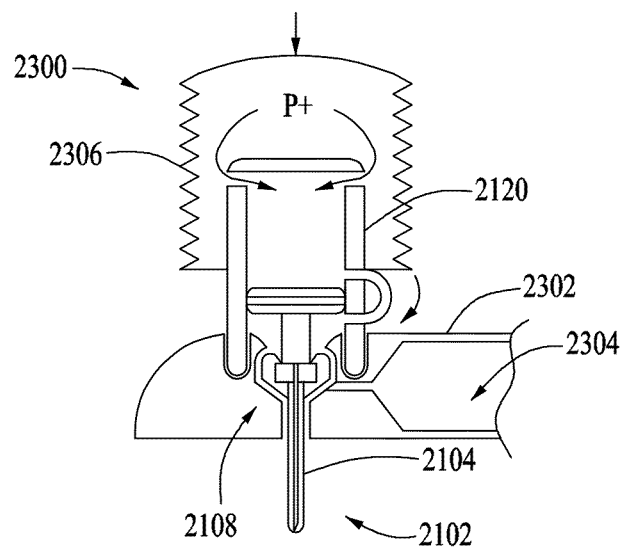

An example of a needle inserting device 2300 is described herein with reference to FIG. 57. The needle inserting device 2300 has a structure and operation that is similar in many respects to the embodiment of FIGS. 1012-1015. Accordingly, like reference numbers are used for like elements in the two embodiments. However, in the embodiment of FIG. 57, the source of pressurized fluid is a hand-operated bellows-like structure. The device 2300 is shown in FIG. 57, in an insert position, in which a needle 2102 and cannula 2104 are inserted into the nest 2108 of a base structure 2302. A fluid-flow channel 2118 connects the cannula 2104 in fluid-flow communication with a reservoir 2304.

The needle inserting device 2300 has a bellows-like structure 2306 (shown in a collapsed state in FIG. 57) that can be collapsed from an expanded state to force air (or other fluid that may be contained within the bellows structure) into one or more openings 2308 in the housing 2120. The bellows-like structure 2306 is connected to the housing 2120, over the openings 2308. The bellows-like structure 2306 may be any suitable flexible container structure that is capable of containing a fluid and flexibly compressing to pressurize the contained fluid. In particular embodiments, the bellows-like structure may be operated manually, by the patient-user (or medical technician), by pressing the bellows-like structure 2306 into a compressed state. In other embodiments, the bellows-like structure may be operated by automated mechanisms.

Compression of the bellows-like structure 2306 forces fluid into the housing 2120 to force the plunger head 2214 toward the insert position, to set the cannula 2104 into the nest 2108 and to release fluid pressure to allow retraction of the plunger head 2214 and needle 2102, similar to the operation of the device 2200 described above with respect to FIGS. 1012-1015. However, in embodiments of FIG. 57 that employ a manually operated bellows-like structure, the patient-user (or medical technician) can have a significant amount of control of the insertion rate and time.

Figure 58:
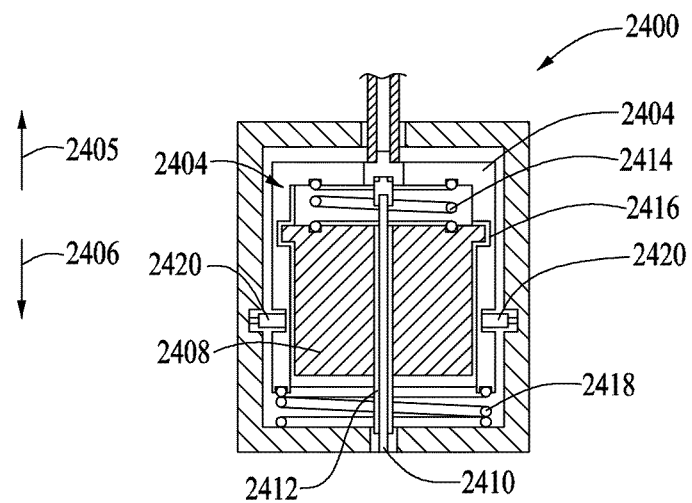

An example of a needle inserting device 2400 is described herein with reference to FIG. 58. The needle inserting device 2400 has a housing 2402 that contains and supports a needle carriage structure 2404 for movement in the directions of arrows 2405 and 2406 relative to the housing 2402. The housing 2402 also contains and supports a cannula carriage structure 2408 for movement in the direction of arrow 2406.

The needle carriage structure 2404 may have a cup-like shape and supports an introducer needle 2410 for movement with the needle carriage structure 2404. The cannula carriage structure 2408 is arranged within the cup-like shape of the needle carriage structure 2404 and supports a cannula 2412. A channel extends through the body of the cannula carriage structure 2408 and is aligned with the cannula 2412. The needle 2410 extends through the channel in the body of the cannula carriage structure 2408 and through the cannula 2412.

An insertion spring 2414 is arranged between the needle carriage structure 2404 and the cannula carriage structure 2408 to provide a rotary insertion force. The cannula carriage structure 2408 includes one or more protrusions that follow one or more spiral grooves 2416 in the needle support structure 2404, to guide the cannula carriage structure 2408 in a spiral insertion motion around the axis of the needle 2410 and cannula 2412. A retraction spring 2418 is provided between the needle support structure 2404 and the housing 2402, to retract the needle support structure 2404 and the needle 2410, after the needle 2410 and cannula 2412 have moved to the insert position.

The device 2400 is shown in FIG. 58 in a retracted state, in which the insertion spring 2414 is wound against its natural state of winding and imparts a rotational force on the cannula carriage structure 2408. In addition, the retraction spring 2418 is compressed against its natural length to impart a force on the needle carriage structure 2404 in the direction of arrow 2405, relative to the housing 2402. However, the needle carriage structure 2404 is locked in place with respect to the housing 2402 by one or more releasable lock mechanisms 2420. The cannula carriage structure 2408 may be locked in place by any suitable releasable locking mechanism (as described herein) and released by manual, automated or electronic operation.

Upon release of the cannula carriage structure 2408, the force of the spring 2414 causes the cannula carriage structure 2408 to rotate along the spiral groove 2416 and move in the direction of arrow 2406 with the spiral groove, to an insert position at which the needle and cannula are extended through an opening in the housing 2404. In the insert position, the spiral groove-following projections on the cannula carriage structure engage one or more lock mechanisms 2420 and unlock the needle carriage structure 2404 from the housing 2402. Once the needle carriage structure 2404 is unlocked from the housing 2402, the retraction spring 2418 is allowed to expand toward its natural length and move the needle carriage structure 2404 and needle 2410 in the direction of arrow 2405 to withdraw the needle 2410 at least partially from the cannula 2412, after insertion of the cannula 2412.

Various embodiments of needle inserting device configurations are described with respect to FIGS. 59-73. Such needle inserting devices may be employed in various suitable contexts described herein or in other applications of use.

Figure 59:
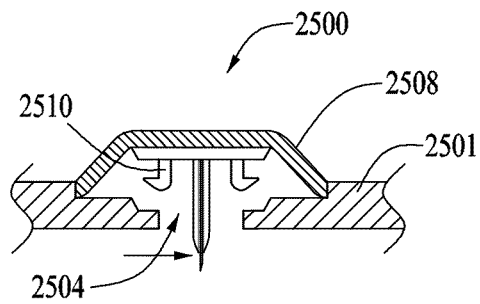
Figure 60:
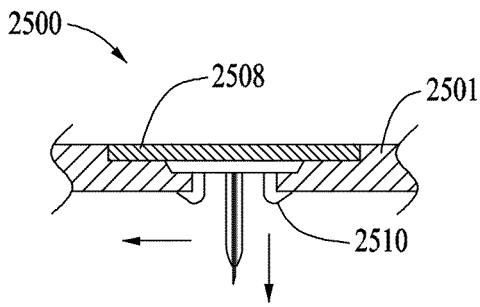

In the embodiment of FIGS. 59 and 60, a needle inserting device 2500 includes a sheet 2502 of rubber arranged over an opening 2504 in a housing or base structure 2501 and configured for placement adjacent an desired injection site on a patient-user's skin or other subject (as described herein). The rubber sheet 2502 is formed in a generally cup-shape configuration shown in FIG. 59, defining a convex surface on one side of the sheet (the side facing away from the opening 2504 and a concave surface on the other side of the sheet facing toward the opening 2504). The rubber sheet 2502 is resiliently flexible in that a force may be applied in the direction of arrow 2506 (for example, by manually pressing onto the upper surface of the sheet 2502) to deform the sheet to an insertion state at which the sheet takes the shape shown in FIG. 60. Upon release of the force on the sheet 2502, the sheet 2502 reverts to its cup-like shape shown in FIG. 59. While the sheet 2502 in FIGS. 59 and 60 is described as being made of rubber, other embodiments may employ any suitably flexible, resilient material, such as, but not limited to rubber, plastic, metal, composite material or the like, that is capable of flexing from a predefined shape and returning to the predefined shape under its own resiliency.

The needle inserting device 2500 also includes a cap structure 2508, attached to the concave surface of the sheet 2502. The cap 2506 includes a head portion 2508a that has a shape and size sufficient to cover the opening 2504, upon the sheet 2502 being forced to the insertion state shown in FIG. 60. The base 2501 may include a recess for receiving the head 2508a, when the sheet 2502 is in the insert state (FIG. 60). The cap structure 2508 also includes one or more pawls 2510 or other suitable locking mechanisms for locking the cap structure 2508 to the base 2501, upon the sheet 2502 being forced to the insert state (FIG. 60).

The cap structure 2508 also supports a hollow needle 2512 for movement between a retracted state (FIG. 59) and an insert state (FIG. 60). In the retracted state (FIG. 59), the needle 2512 is located at least partially within the cup-shaped configuration of the sheet 2502 and either does not extend through the opening 2504 or extends a small distance through the opening 2504. In the insert state (FIG. 60), the needle 2512 is more fully extended through the opening 2504. A suitable fluid-flow channel (not shown) may be connected in fluid-flow communication with the needle 2512, either prior to insertion or upon movement of the cap 2506 to the insert position (FIG. 60), for example, for connection of the needle 2519 to a reservoir, sensor or other device for holding or processing fluid.

While the embodiment of FIGS. 59 and 60 may be operated by manually pressing the sheet 2502, the device 2500 may be operated by mechanical, electrical or electromechanical mechanisms, as well. Indeed, various manners of applying a force onto a cap structure 2508 to insert a needle through a needle opening in a housing may be employed in other embodiments of the invention, in devices and systems as described above.

Figure 61:
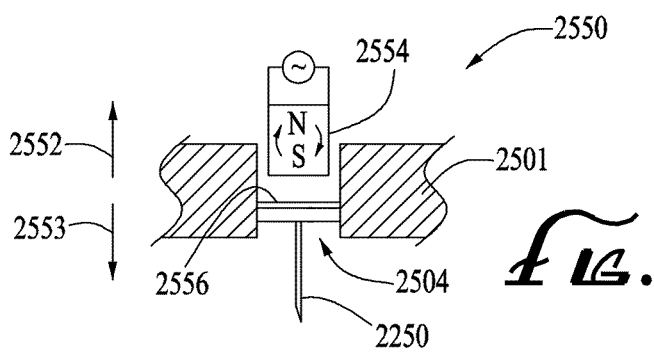

For example, in the embodiment of FIG. 61, a needle 2550 is moved in the direction of arrows 2552 and 2553 by selectively energizing an electromagnet 2554 arranged within proximity of the needle 2550. The speed and direction of motion of the needle 2250 may be controlled by controlling the level (strength of the magnetic field generated by the electromagnet) and direction of current supplied to the electromagnet (polarity of the electromagnet. The needle 2250 may be made of a magnetic material or such a material 2256 may be coated or otherwise attached to at least part of the needle 2250. When the electromagnet 2554 is energized in manner to provide a magnetic pole facing the needle 2250 that is the same as the magnetic polarity of the needle 2250, a force is imparted on the needle to move the needle in the direction of arrow 2552, away from the electromagnet 2554. When the electromagnet 2554 is energized in manner to provide a magnetic pole facing the needle 2250 that is the opposite to the magnetic polarity of the needle 2250, a force is imparted on the needle to move the needle in the direction of arrow 2553, toward the electromagnet 2554. Accordingly, the electromagnet 2554 may be operated to control the motion of the needle 2250 in an insert direction (and, in some embodiments, deposit a cannula into a nest as described above) and a withdraw direction.

Figure 62:
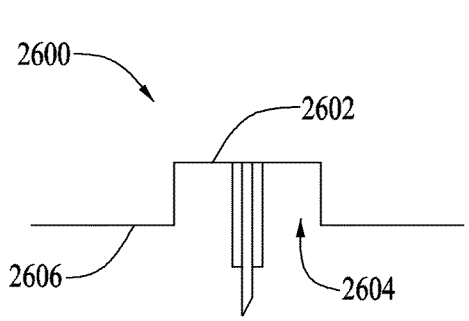
Figure 63:
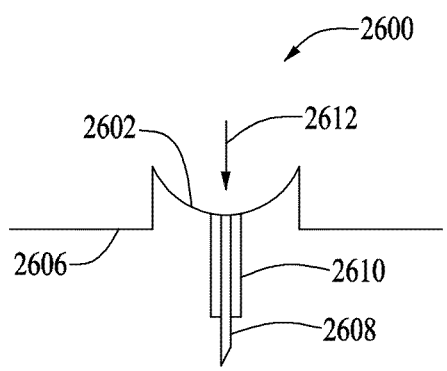

In the embodiment of FIGS. 62 and 63, a needle inserting device 2600 includes a sheet 2602 of piezoelectric material arranged over an opening 2604 in a housing or base structure 2606 and configured for placement adjacent an desired injection site on a patient-user's skin or other subject (as described herein). The piezoelectric material is a material that expands in at least one dimension, upon application of a suitable electrical signal. The sheet of piezoelectric material 2602 may be coupled to suitable control electronics for providing a suitable electrical signal to the material to cause the sheet 2602 to expand in at least one dimension. At least a portion of the sheet of piezoelectric material may be connected to the base structure 2606 or other suitable structure supported by the base structure 2606, to cause the sheet 2602 to buckle or bow as shown in FIG. 63, upon application of a suitable electrical signal to cause the sheet 2602 to expand. An needle 2608 may be supported by the sheet 2602 and a cannula 2610 may be supported on the needle 2608, for movement in the direction of arrow 2612 as the sheet 2602 is activated to expand and buckle as shown in FIG. 63 (and, in some embodiments, deposit a cannula into a nest as described above).

A similar configuration may employ a bistable spring, instead of a sheet of piezoelectric material. The bistable spring may be flat or first bowed (for example upward in the orientation of the drawing) at a start position, then pushed (for example by manual force) to a further bowed state (for example, bowed downward in the orientation of the drawing) to insert a needle and cannula. The bistable spring may be allowed to return to its flat or first bowed (e.g., bowed outward) state to withdraw the needle from a cannula, after insertion of a needle and cannula.

Figure 64:
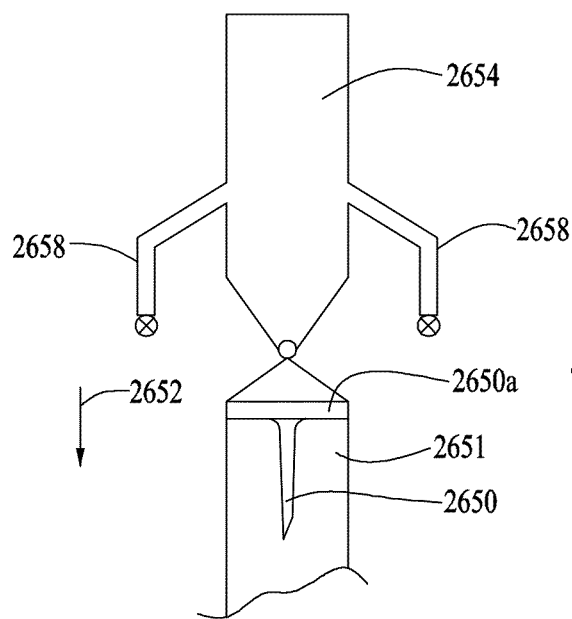

In the embodiment of FIG. 64, a needle 2650 is moveable within a channel 2651 in a housing or base structure configured for placement adjacent an desired injection site on a patient-user's skin or other subject (as described herein). The needle 2650 includes a needle head 2650a that provides a plunger function for converting a fluid pressure to a linear motion of the needle 2650 in the channel 2651 in the direction of arrow 2652. A source of pressurized fluid 2654 (such as, but not limited to, compressed air or other gas) is coupled to the chamber 2651, through a controllable valve 2656. One or more release vents having release valves 2658 are provided in fluid flow communication with the pressurized fluid source 2654. The needle 2650 may be moved toward in insert position, in the direction of arrow 2651, by opening the valve 2656. After the needle 2650 has moved to the insert position (and, in some embodiments, deposited a cannula into a nest as described above), the valves on the release vent valves 2658 may be opened to release pressure from the channel 2651. The needle may be biased (by a spring or other suitable bias mechanism, not shown) to retract in the direction opposite to the direction of arrow 2652, once the pressure has been released from the channel 2651.

Figure 65:
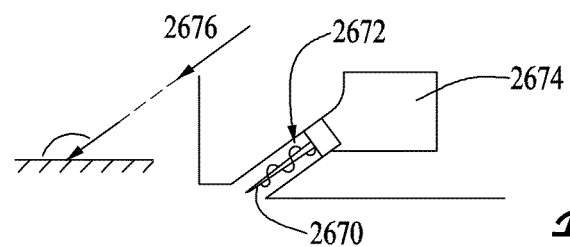

The embodiment of FIG. 65 is a variation of the embodiment of FIG. 64, wherein the insertion angle of a needle 2670 is arranged to be non-perpendicular to the bottom surface of the needle inserting device (and, thus, at a non-perpendicular angle to the skin of the patient-user or surface of other subject to be injected). Also, in the embodiment of FIG. 65, instead of controlling the activation of the needle motion with the opening of a control valve (as in the embodiment of FIG. 64), the needle motion is activated by releasing a releasable lock 2672 that, when locked, holds the needle 2670 from moving. Once the lock 2672 is released, pressurized fluid in the chamber 2674 causes the needle 2670 to move to the insert position in the direction of arrow 2676 (and, in some embodiments, deposited a cannula into a nest as described above). A return spring 2678 may be provided to retract the needle at least partially from the cannula, after insertion. Any or all of these features may be employed in the embodiment of FIG. 64

Figure 66:
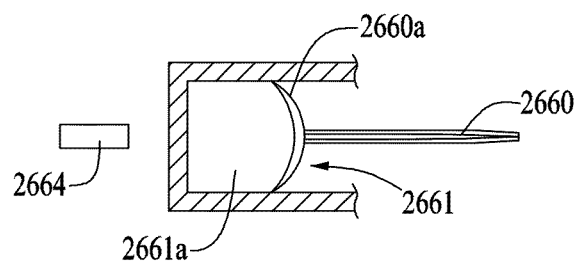

In the embodiment of FIG. 66, a needle 2660 is moveable within a channel 2661 in a housing or base structure configured for placement adjacent an desired injection site on a patient-user's skin or other subject (as described herein). The needle 2660 includes a needle head 2660a that provides a plunger function for converting a fluid pressure to a linear motion of the needle 2660 in the channel 2661 in the direction of arrow 2662. A portion 2661a of the channel 2661 behind the needle head 2660a may be sufficiently sealed and may contain an expandable gas or other material that expands (or forms an expandable gas) upon selective activation by one or more of a laser source, heat source, electrical source or other radiation source 2664. By imparting a laser, heat, electrical signal, or other radiation onto the material within the chamber portion 2661a the material expands (or forms an expanding gas) to produce a sufficient pressure within the chamber portion 2661a to move the needle 2660 toward an insert position, in the direction of arrow 2662 (and, in some embodiments, deposit a cannula into a nest as described above). The head 2660a of the needle 2660 may have a generally parabolic shape or other suitable shape for focusing or enhancing heat or other radiation into the chamber portion 2661a.

Figure 67:
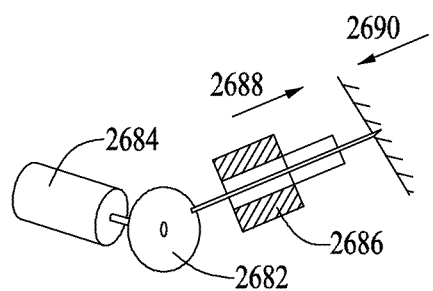

In the embodiment of FIG. 67, a needle 2680 is moveable by the rotary action of a rotary wheel or cam. In particular, the needle 2680 is connected at one end to a non-circular disk 2682. The non-circular disk 2682 is connected to a drive source 2684, to rotate about an axis of rotation. The drive source may be a drive motor, spring drive or any suitable mechanism for imparting a controllable rotary force on the disk 2682. The needle 2680 extends through a needle guide or holder 2686, such that, as the disk 2682 rotates, the rotary motion of the disk 2682 is converted into a linear motion of the needle in the insert direction of arrow 2688 (and, in some embodiments, deposit a cannula into a nest as described above) and, then a retract direction of arrow 2690. The insertion direction may be selected to be generally perpendicular or at a non-perpendicular angle relative to the patient-user's skin (or surface of other subject to be injected), by selecting the angle of orientation of the holder or guide 2686.

Figure 68:
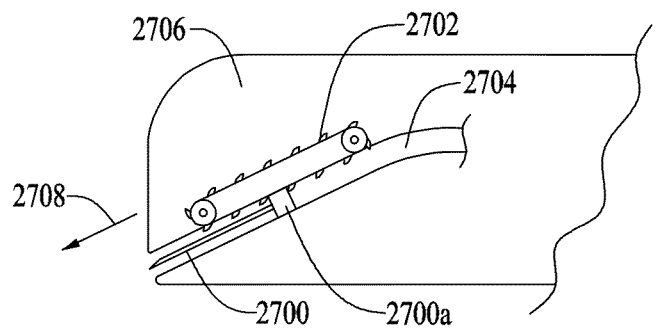

In the embodiment of FIG. 68, a needle 2700 is moveable by a drive force imparted on a needle head 2700a by a belt drive 2702. The needle head 2700 may be moveable within a channel 2704 in a housing or base structure 2706 configured for placement adjacent a desired injection site on a patient-user's skin or other subject (as described herein). The insertion direction may be selected to be generally perpendicular or at a non-perpendicular angle relative to the patient-user's skin (or surface of other subject to be injected), by selecting the angle of orientation of the channel 2705. The belt drive 2702 may include a belt extending around a pair of wheels, one of which may be coupled to a drive source (not shown), such as, but not limited to a drive motor, spring motor, magnetic drive or the like. The belt may have serrations, teeth or other discontinuities that are configured to engage a corresponding set of serrations, teeth or other discontinuities on the surface of the needle head 2700a. The belt may be driven in one direction for moving the needle 2700 toward an insert position, in the direction of arrow 2708 (and, in some embodiments, deposit a cannula into a nest as described above). The belt may be driven in the opposite direction, for withdrawing the needle, for example, and leaving the cannula in the inserted position. The belt speed and, thus, the needle insertion speed, may be controlled with relatively high precision.

Figure 69:
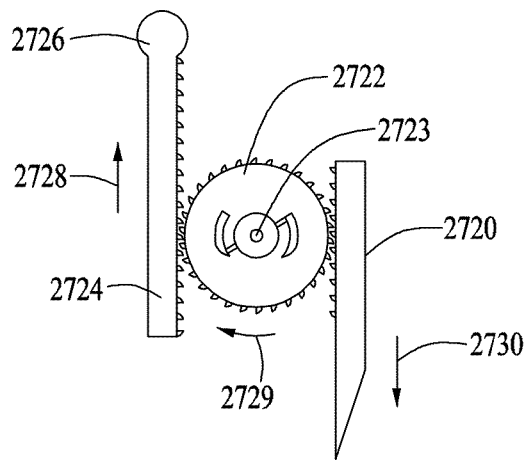

FIG. 69 shows a configuration for converting a linear force in one direction to a linear needle inserting force in an opposite direction. In FIG. 69, a needle 2720 has serrations, teeth or other discontinuities along a linear length of the needle and is supported with the serrations, teeth or other discontinuities in engagement with corresponding serrations, teeth or other discontinuities on a rotary wheel or gear 2722. The wheel 2722 is supported for rotation about an axis 2723. A linear shaft 2724 is provided with serrations, teeth or other discontinuities and is also arranged in engagement with corresponding serrations, teeth or other discontinuities on a rotary wheel or gear 2722. The linear shaft 2724 may include a handle 2726 for manual operation or may be connected to a linear drive source. By applying a force on the shaft 2724 in the direction of arrow 2728, the wheel 2722 is caused to rotate about the axis 2724 in the direction of arrow 2729. The rotational motion of the wheel 2722 is transferred to a linear motion of the needle 2720 in the direction of arrow 2730, toward an insert position (and, in some embodiments, to a position to deposit a cannula into a nest as described above). Movement of the shaft 2724 in the direction opposite to the direction of arrow 2728 will cause the needle 2720 to move in a direction opposite to the arrow 2730, to withdraw the needle, for example, at least partially from a cannula. A weight structure may be provided on the wheel 2722, to assist the rotational motion. A torsion spring may be provided on the wheel 2722, to wind as the wheel rotates toward an insert position and impart an force in the opposite direction to automatically withdraw the needle after insertion of a cannula.

Figure 70:
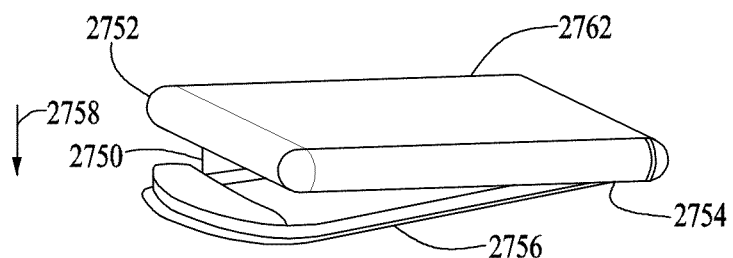

FIG. 70 shows a configuration in which a needle 2750 is moved to an insert position, by the pivotal motion of a pivotal arm 2752. The pivotal arm 2752 may be connected at a pivot point 2754 to a housing or base structure 2756 configured for placement adjacent a desired injection site on a patient-user's skin or other subject (as described herein). The pivotal arm 2752 may be biased toward an open position shown in FIG. 70 by any suitable bias mechanism, such as, but not limited to a coil spring, other spring configuration, magnet configuration, or the like. The pivotal arm 2752 may be moved by manual pressure against the force of the bias mechanism, to move the needle 2750 toward an insert position, in the direction of arrow 2758 (and, in some embodiments, to a position to deposit a cannula into a nest as described above). After insertion of the needle and cannula, the pressure on the arm 2752 may be released to allow the arm 2752 to move back to the retracted position (shown in FIG. 70) under the force of the bias mechanism, while the cannula may be left in place in a nest, as described above. In particular embodiments, the pivotal arm 2752 may include a durable housing portion of a multi-piece infusion device, as described in the above-cited patent applications that have been incorporated herein by reference, where the durable housing portion contains one or more of a reservoir, control electronics, a drive device for driving fluid from a reservoir, linkage structure for linking a drive device to a reservoir and a power source for the drive device.

In the above-described embodiments of needle inserting devices, various mechanisms may be employed for activating the device to insert a needle and cannula. In some contexts, a manual activation may be preferred, wherein a patient-user (or medical technician) manually operates a mechanism (pushes a button, moves a lever, compresses a bellows-like structure or the like). In other embodiments, activation may be accomplished by electronic actuators controlled by an electronic switch that may be manually operated, operated by a control program, or the like. Activation may be accomplished by a remote (wired or wireless) device, by a wireless proximity device or the like. In one example embodiment, a needle inserting device may include an electronic, magnetic or other suitable activator that responds to a transmitter located within a defined proximity of the needle inserting device. For example, the needle inserting device may be configured to include a receiver or other electronics, magnetic devices or the like, that respond to a particular hand-held transmitter, magnet or the like (that transmits a particular signal). The needle inserting device may be configured to respond to a detection of the proximity of the hand-held transmitter or magnet (or detection of the proximity over a period of time or a predefined number of detections of the proximity over a defined period of time, such as, but not limited to, three detections of the transmitter within a five second period).

Figure 71:
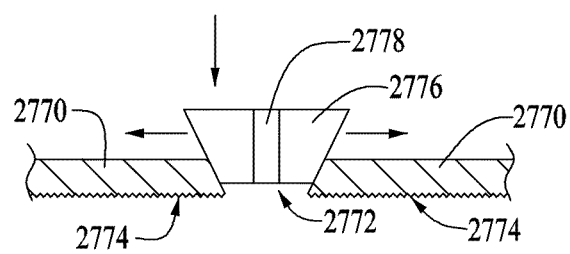
FIG. 71 illustrates a skin spreader arrangement.

In any of the above embodiments, a skin stretcher structure may be employed in the surface of the housing or base that contacts the patient-user's skin during an needle injecting operation. An example of a skin stretching configuration is shown in FIG. 71, wherein a portion of the housing or base 2770 adjacent a needle insertion opening 2772 is provided with a rough surface 2774 that is designed to frictionally grip the patient-user's skin, when pressed against the skin. The rough surface 2774 may be formed by serrations, grooves and ribs or any suitable pattern of discontinuities that can sufficiently enhance friction between the surface 2774 and the patient-user's skin. The rough surface 2774 may be formed directly on portions of the housing or base or may be provided on pads that are moveably secured to the housing or base.

In any of the above-described embodiments of needle inserting devices, the needle inserter device housing, the base structure and/or other housing structure that contacts the patent-user's skin adjacent a needle opening may be provided with one or more patches of an anesthesia substance to help numb the skin around the injection site. For example, one or more patches, having microneedles directed toward the patient-user's skin may be provided on the bottom surface of the needle inserter device, base structure or other housing that contacts the patient-user's skin adjacent the injection site.

As part of a needle insertion operation or prior to needle insertion, a wedge-shaped (or cone-shaped) member 2776 is inserted into the opening 2772. The width or diameter of the wedge-shaped member is selected, relative to the width or diameter of the opening 2772, so as to allow the wedge shaped member 2776 to engage the edge of the opening 2772 and impart a spreading force on the structure of the housing or base (or pads) 2770 around the opening 2772. The force imparted by the wedge-shaped member is sufficient to move the surface 2774 outward, relative to the center of the opening 2772 and spread or stretch the patient-user's skin at the location adjacent to the opening 2772. The wedge-shaped member 2776 may include a needle channel 2778, that allows the passage of a needle and/or cannula from a needle inserting device. The channel 2778 is arranged to align the needle and/or cannula with a stretched portion of the patient-user's skin adjacent the opening 2772. In this manner, the needle inserting device may operate to insert a needle and/or cannula through a stretched portion of the patient-user's skin, for improved user comfort.

Embodiments of the present invention may be employed in a multi-piece infusion delivery device as described in above-cited applications that have been incorporated by reference in the present application. Such embodiments may include one or more housing portions for containing a reservoir, a drive device, linkage structure, a power source and a needle inserting device. Some embodiments include a separate base structure to which the one or more housing portions may connect. Embodiments may include a needle inserting device that is part of the base structure. In other embodiments, a needle inserting device may be provided in a module that connects to the one or more housing portions and base, through a flexible tubing, to allow the needle inserting device (and, thus, the injection site) to be located apart from the one or more housing portions and base structure.

In the embodiment of FIGS. 72 and 73, an injection site module 2790 is connected to a base 2792 of a housing portion 2794, through a flexible tubing 2794. The base 2792 and housing 2794 include a receptacle region 2996 in which the injection site module 2790 may be stowed for use, storage or shipment. In the embodiment of FIGS. 72 and 73, the injection site module 2790 may be stowed in the receptacle region 2996 and used as an onboard needle inserting device. Alternatively, the injection site module 2790 may be removed from the receptacle region 2996 for use in a location spaced apart from the location at which the base 2792 and housing 2794 may be secured. Thus, the embodiment of FIGS. 72 and 73 provides a flexibility as to the location of the injection site and can be used in contexts in which it is desired to have an injection site at the same location as the base 2792 and housing 2794 or in contexts in which it is desired to space the injection site apart from the base 2792 and housing 2794.

Figure 74A:
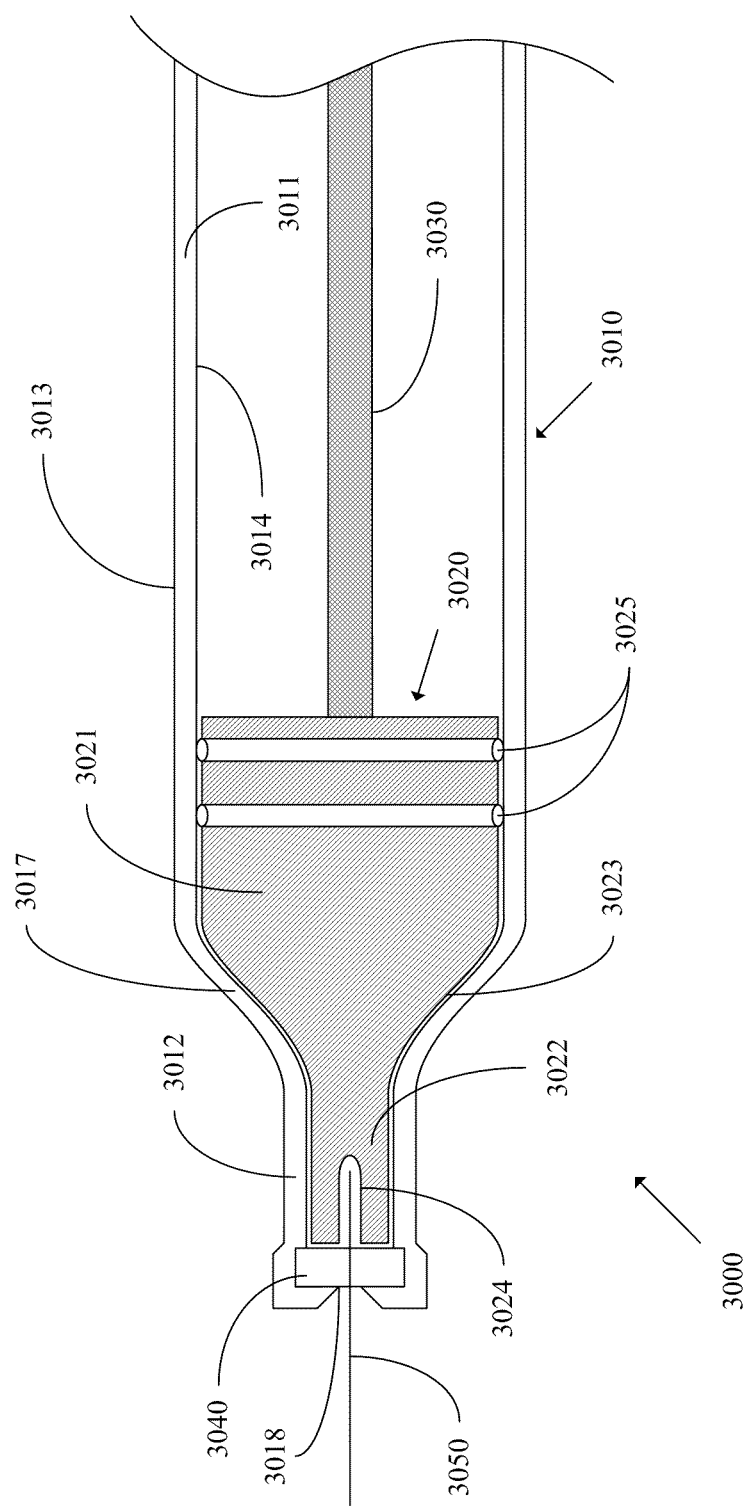
FIG. 74A illustrates a cross-sectional view of a system in accordance with an embodiment of the present invention.

FIG. 74A illustrates a cross-sectional view of a system 3000 in accordance with an embodiment of the present invention. The system 3000 includes a reservoir 3010, a plunger head 3020, a plunger arm 3030, and a septum 3040. In various embodiments, the system 3000 further includes a needle 3050. The reservoir 3010 includes a barrel portion 3011, a barrel headspace or neck portion 3012, and a curved or sloped portion 3017 that connects the barrel portion 3011 and the neck portion 3012. The reservoir 3010 has an outer surface 3013 and an inner surface 3014. The inner surface 3014 of the reservoir 3010 defines a hollow interior of the reservoir 3010, and the hollow interior of the reservoir 3010 is able to contain an infusion medium or fluidic medium. The reservoir 3010 further includes a port 3018 at an end of the neck portion 3012, through which the fluidic medium may be filled into or expelled from the hollow interior of the reservoir 3010.

The plunger head 3020 is located within the reservoir 3010, and is moveable in an axial direction of the reservoir 3010, to expand or contract an interior volume of the reservoir 3010 in which a fluidic medium may be contained. The plunger head 3020 is connected to the plunger arm 3030, such that movement of the plunger arm 3030 in the axial direction of the reservoir 3010 causes movement of the plunger head 3020 in the axial direction of the reservoir 3010. The plunger head 3020 includes a plunger barrel portion 3021, a plunger headspace or neck portion 3022, and a plunger curved or sloped portion 3023 that connects the plunger barrel portion 3021 and the plunger neck portion 3022. In various embodiments, the plunger head 3020 further includes one or more O-rings 3025 that surround a portion of the plunger barrel portion 3021.

The plunger barrel portion 3021 is shaped such that a contour of an outer surface of the plunger barrel portion 3021 substantially matches or is substantially the same as a contour of an inner surface of the barrel portion 3011 of the reservoir 3010. In various embodiments, the plunger barrel portion 3021 has a diameter that is slightly smaller than a diameter of the inner surface of the barrel portion 3011 of the reservoir 3010, such that the plunger head 3020 is able to slide within the reservoir 3010. In some embodiments, an O-ring 3025 on the plunger barrel portion 3021 is in contact with the inner surface of the barrel portion 3011 of the reservoir 3010 when the plunger head 3020 is within the reservoir 3010.

The plunger neck portion 3022 is shaped such that a contour of an outer surface of the plunger neck portion 3022 substantially matches or is substantially the same as a contour of an inner surface of the neck portion 3012 of the reservoir 3010. In various embodiments, the plunger neck portion 3022 has a diameter that is slightly smaller than a diameter of the inner surface of the neck portion 3012 of the reservoir 3010, such that the plunger neck portion 3022 is able to slide within the neck portion 3012 of the reservoir 3010. The plunger sloped portion 3023 is shaped such that a contour of an outer surface of the plunger sloped portion 3023 substantially matches or is substantially the same as a contour of an inner surface of the sloped portion 3017 of the reservoir 3010.

The septum 3040 is located at the port 3018 of the reservoir 3010. The neck portion 3012 has a certain length from an end of the sloped portion 3017 to the septum 3040. In various embodiments, the plunger neck portion 3022 has a length that is substantially the same as the certain length of the neck portion 3012 of the reservoir 3010. In some such embodiments, the plunger neck portion 3022 is able to extend substantially all of the way into the neck portion 3012 of the reservoir 3010 when the plunger head 3020 is fully depressed within the reservoir 3010. Thus, in some embodiments, an end of the plunger neck portion 3022 may be close to or in contact with the septum 3040 when the plunger head 3020 is fully depressed within the reservoir 3010.

The septum 3040 is able to be pierced by the needle 3050, such as to allow for a fluidic medium to be passed through the needle 3050 and into the hollow interior of the reservoir 3010. In various embodiments, the plunger neck portion 3022 includes a hole or a channel or a relief 3024 that is able to accommodate a portion of the needle 3050 when the plunger head 3020 is fully depressed within the reservoir 3010 and the septum 3040 is pierced by the needle 3050. In various embodiments, a diameter of the relief 3024 is larger than a diameter of the needle 3050, such that an end of the needle 3050 is able to fit within the relief 3024. In some embodiments, a length of the relief 3024 in the plunger neck portion 3022 in a direction from the septum 3040 toward the plunger barrel portion 3021 is greater than one-quarter of a length of the plunger neck portion 3022. Also, in some embodiments, the relief 3024 is positioned at a center of an end surface of the plunger neck portion 3022.

A method in accordance with an embodiment of the present invention allows for filling the reservoir 3010 with a fluidic medium and for expelling the fluidic medium from the reservoir 3010. In a first step of the method, the septum 3040 is pierced with the needle 3050, and the plunger arm 3030 is moved such that the plunger head 3020 is fully depressed within the reservoir 3010. When the plunger head 3020 is fully depressed within the reservoir 3010, a portion of the needle 3050 extends into the relief 3024 of the plunger neck portion 3022, which allows the plunger neck portion 3022 to extend substantially all the way to the septum 3040. As a consequence, a presence of air pockets between an end of the plunger head 3020 and the septum 3040 is able to be substantially limited or eliminated when the plunger head 3020 is fully depressed within the reservoir 3010. Reducing air pockets between the plunger head 3020 and the septum 3040 prior to filling the reservoir 3010 is beneficial, because it limits an amount of air bubble that subsequently enter the fluidic medium when the fluidic medium is drawn into the reservoir 3010.

Figure 74B:
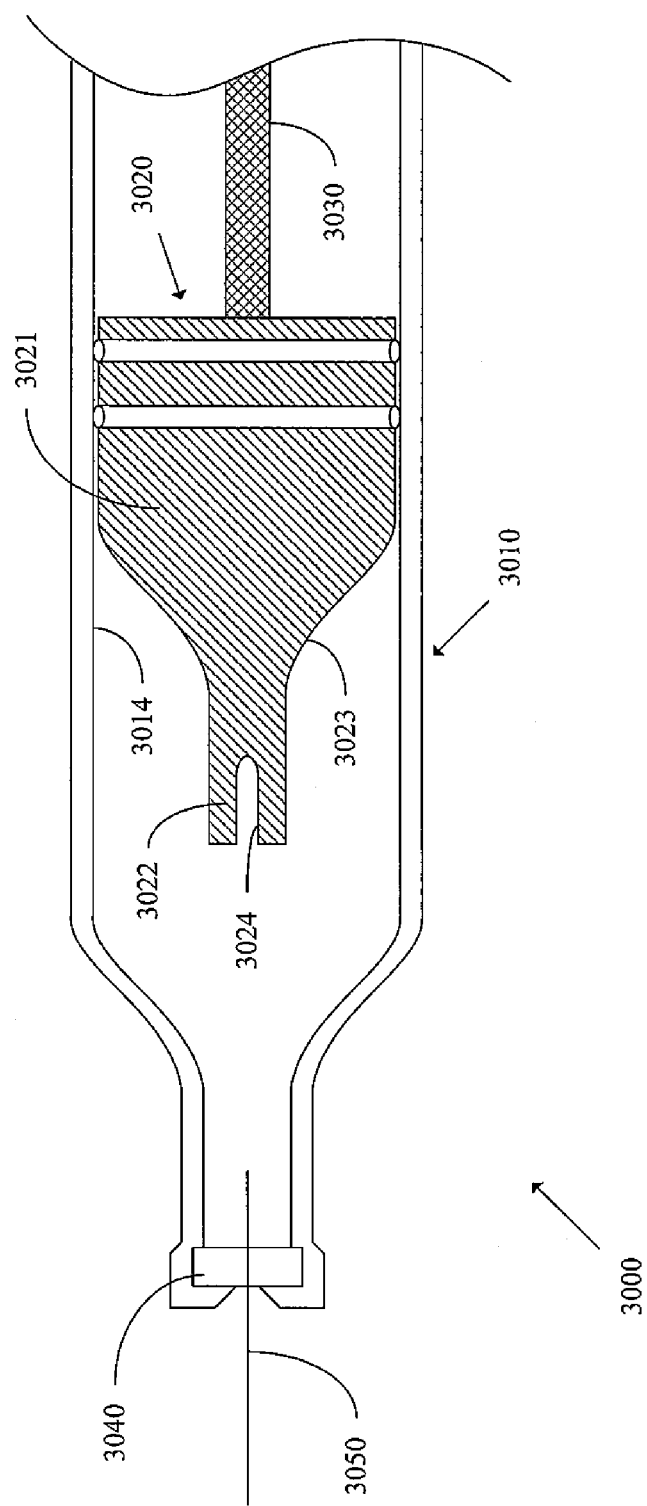
FIG. 74B illustrates a cross-sectional view of a system in accordance with an embodiment of the present invention.

In a second step of the method, the plunger arm 3030 is moved such that the plunger head 3020 is retracted within the reservoir 3010. FIG. 74B illustrates the system 3000 when the plunger head 3020 has been partially retracted within the reservoir 3010. By retracting the plunger head 3020 within the reservoir 3010, the fluidic medium is able to pass through the needle 3050 and into the hollow interior of the reservoir 3010. Because an amount of air in the reservoir 3010 was limited prior to filling the reservoir 3010, an amount of air bubbles in the fluidic medium is also limited when the fluidic medium is filled into the reservoir 3010. Limiting or reducing an amount of air bubbles in the fluidic medium is beneficial, because it limits an amount of air bubbles that are later expelled from the reservoir 3010 into a patient or user, and thus helps to improve a delivery accuracy when delivering a specified amount of the fluidic medium to a user.

In a third step of the method, the plunger arm 3030 is moved such that the plunger head 3020 is depressed within the reservoir 3010, so as to expel the fluidic medium from the reservoir 3010. FIG. 74A illustrates the system 3000 when the plunger head 3020 has been substantially fully depressed within the reservoir 3010. When the plunger head 3020 is depressed within the reservoir 3010, the close fitting contour of the plunger head 3020 to the interior surface of the reservoir 3010 limits or reduces a volume of wasted fluidic medium that remains in the reservoir 3010. Thus, by having a plunger head 3020 with a plunger neck portion 3022 that is shaped to very closely fit within the neck portion 3012 of the reservoir 3010 when the plunger head 3020 is fully depressed, a presence of air bubbles in a fluidic medium may be limited during filling of the reservoir 3010, and a volume of wasted fluidic medium may be reduced when the fluidic medium is expelled from the reservoir 3010.

Figure 74C:
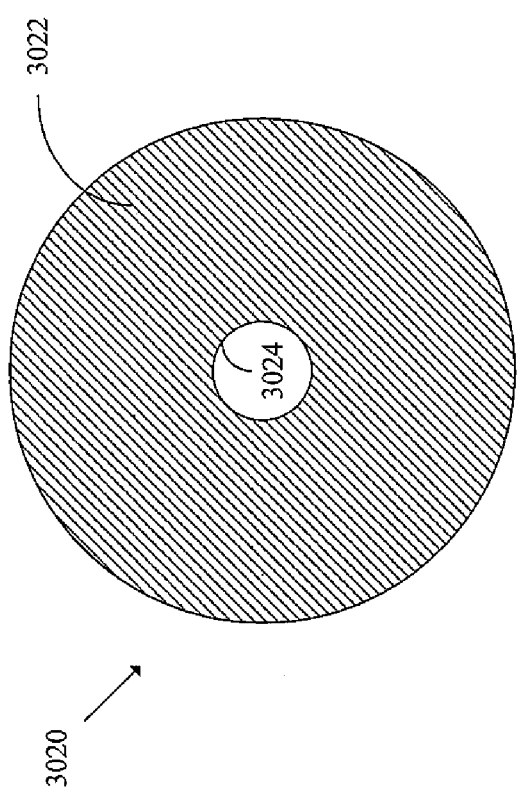
FIG. 74C illustrates a cross-sectional view of a plunger head in accordance with an embodiment of the present invention.
Figure 74D:
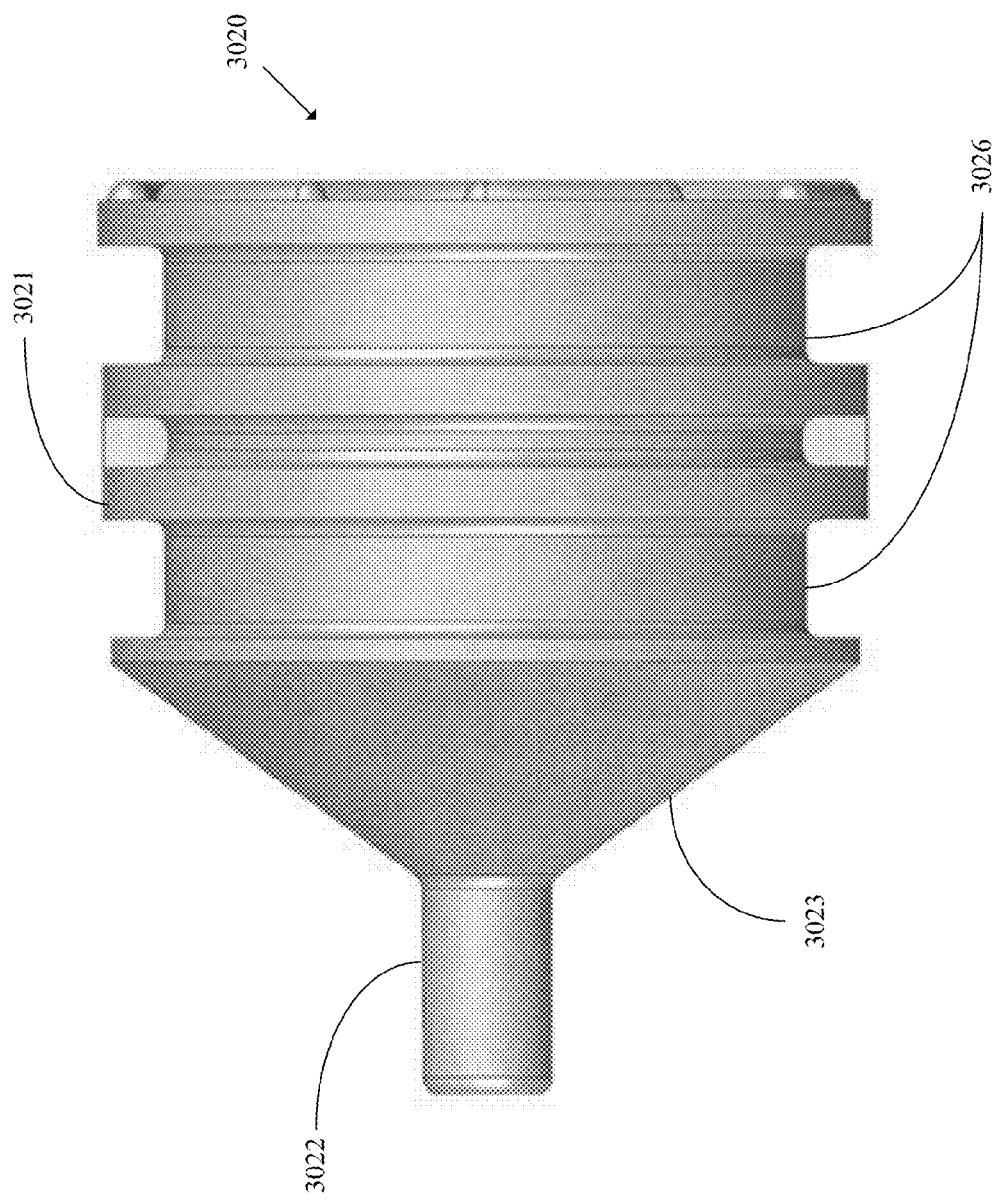
FIG. 74D illustrates a side view of a plunger head in accordance with an embodiment of the present invention.

FIG. 74C illustrates a cross-sectional view from a front direction of the plunger neck portion 3022 of the plunger head 3020 in accordance with an embodiment of the present invention. The plunger neck portion 3022 includes the relief 3024 for accommodating a needle. In various embodiments, the relief 3024 is positioned substantially near a center of a face of the plunger neck portion 3022. FIG. 74D illustrates a side view of the plunger head 3020 in accordance with an embodiment of the present invention. The plunger head 3020 includes the plunger barrel portion 3021, the plunger neck portion 3022, and the plunger sloped portion 3023. In various embodiments, the plunger barrel portion 3021 includes one or more depressions or cavities 3026 in which the one or more O-rings 3025 (refer to FIG. 74A) may be placed.

FIGS. 75, 76, 77, 78A, and 78B illustrate systems in accordance with various embodiments of the present invention that include reservoirs with geometries that allow for capturing air bubbles so as to reduce a number of air bubble that are delivered with a fluidic medium. Such systems allow for bubble management since they have bubble trapping shapes and, by reducing a number of air bubbles that are delivered with a fluidic medium, such systems are able to improve a delivery accuracy when attempting to deliver a specified volume of the fluidic medium. Thus, such systems provide reservoir geometries that allow for capturing a greater amount of air bubbles than with standard reservoir geometries, so that the captured air bubbles remain in the reservoir and are not dispended with the fluidic medium.

Figure 75:
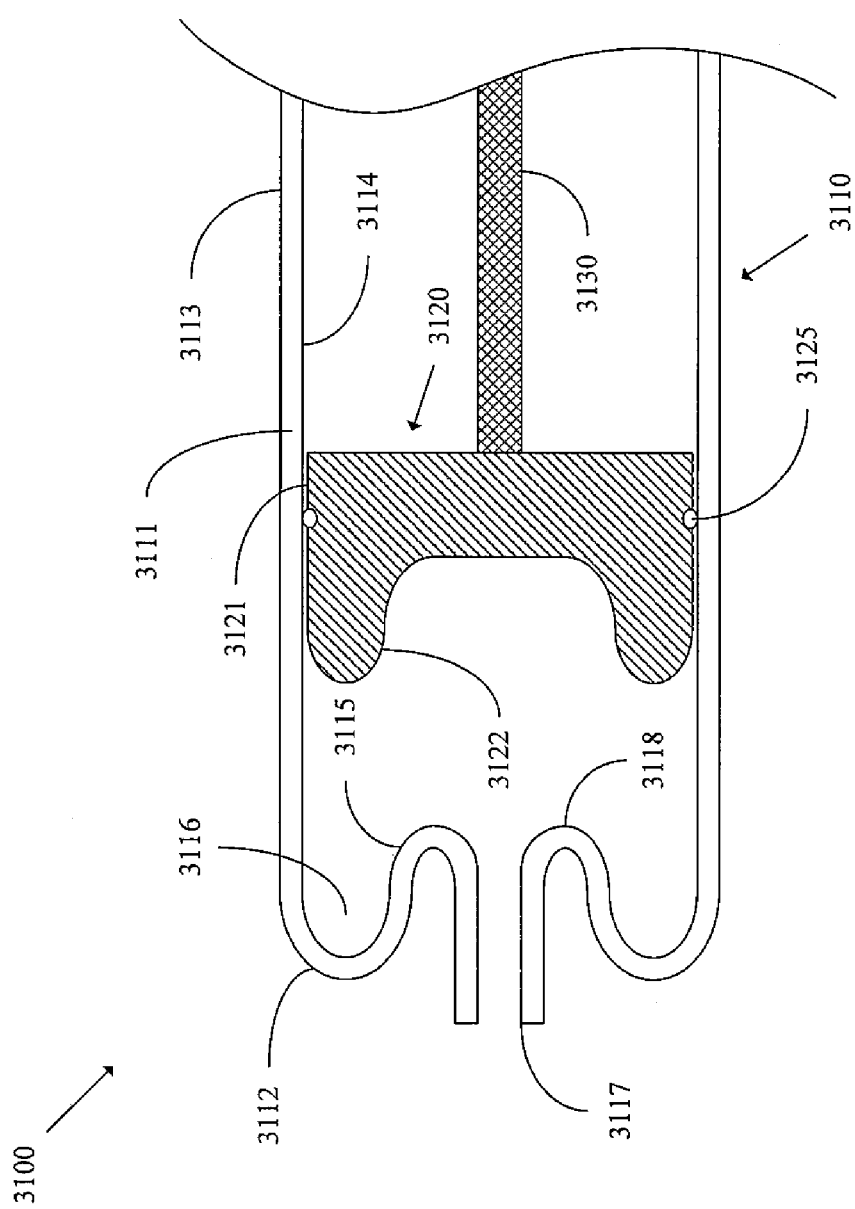
FIG. 75 illustrates a cross-sectional view of a system in accordance with an embodiment of the present invention.

FIG. 75 illustrates a cross-sectional view of a system 3100 in accordance with an embodiment of the present invention. The system 3100 includes a reservoir 3110, a plunger head 3120, and a plunger arm 3130. The reservoir 3110 includes a barrel portion 3111, a bubble trap portion 3112, and a port 3117. The reservoir 3110 has an outer surface 3113 and an inner surface 3114. The inner surface 3114 of the reservoir 3110 defines a hollow interior of the reservoir 3110, and the hollow interior of the reservoir 3110 is able to contain a fluidic medium. The port 3117 of the reservoir 3110 allows for the fluidic medium to be filled into or expelled from the hollow interior of the reservoir 3110.

The plunger head 3120 is located within the reservoir 3110, and is moveable in an axial direction of the reservoir 3110, to expand or contract an interior volume of the reservoir 3110 in which a fluidic medium may be contained. The plunger head 3120 is connected to the plunger arm 3130, such that movement of the plunger arm 3130 in the axial direction of the reservoir 3110 causes movement of the plunger head 3120 in the axial direction of the reservoir 3110. The plunger head 3120 includes a plunger barrel portion 3121 and a plunger protruding portion 3122. In various embodiments, the plunger head 3120 further includes one or more O-rings 3125 that surround a portion of the plunger barrel portion 3121.

The bubble trap portion 3112 of the reservoir 3110 is shaped so as to form a bubble trap region 3116 within an interior of the reservoir 3110, such that air bubbles in a fluidic medium may be trapped in the bubble trap region 3116 when the fluidic medium is expelled from the reservoir 3110 through the port 3117. In various embodiments, an interior surface of the bubble trap portion 3112 is curved or angled near the port 3117, so as to define the bubble trap region 3116. In some embodiments, the bubble trap portion 3112 extends from the barrel portion 3111 of the reservoir 3110 past a point 3118 of the reservoir 3110 where a fluidic medium from the barrel portion 3111 is able to move into an area of the reservoir 3110 that leads to the port 3117.

In various embodiments, the reservoir 3110 is shaped such that as the plunger head 3120 is depressed within the reservoir 3110, a fluidic medium is able to pass through the port 3117 while air bubbles in the reservoir 3110 collect in the bubble trap region 3116 defined by a curved or angled surface of the bubble trap portion 3112 of the reservoir 3110. Such a geometry of the reservoir 3110 allows for decreasing an amount of air bubbles that are delivered with a fluidic medium as compared with traditional reservoir geometries. In some embodiments, the bubble trap portion 3112 of the reservoir 3110 is curved outward from an interior region of the reservoir 3110 defined by the barrel portion 3111, and a fluidic medium is able to pass directly from the interior region of the reservoir 3110 defined by the barrel portion 3111 to the port 3117. In some embodiments, a surface 3115 of the bubble trap portion 3112 of the reservoir 3110 includes a surface finish or material such that air bubbles substantially do no stick to the surface 3115 and are shunted away from the port 3117 toward the bubble trap region 3116.

The plunger barrel portion 3121 is shaped such that a contour of an outer surface of the plunger barrel portion 3121 substantially matches or is substantially the same as a contour of an inner surface of the barrel portion 3111 of the reservoir 3110. In various embodiments, the plunger barrel portion 3121 has a diameter that is slightly smaller than a diameter of the inner surface of the barrel portion 3111 of the reservoir 3110, such that the plunger head 3120 is able to slide within the reservoir 3110. In some embodiments, an O-ring 3125 on the plunger barrel portion 3121 is in contact with the inner surface of the barrel portion 3111 of the reservoir 3110 when the plunger head 3120 is within the reservoir 3110.

In various embodiments, the plunger protruding portion 3122 is shaped such that a contour of an outer surface of the plunger protruding portion 3122 substantially matches or is substantially the same as a contour of an inner surface of the bubble trap portion 3112 of the reservoir 3110. In some embodiments, the plunger protruding portion 3122 is curved and protrudes from the plunger barrel portion 3121. In various embodiments, the plunger protruding portion 3122 has a size that is slightly smaller than a region defined by the inner surface of the bubble trap portion 3112 of the reservoir 3110, such that the plunger protruding portion 3122 is able to slide within the bubble trap region 3116 of the reservoir 3110, and such that a space for a dead volume of air is left when the plunger head 3120 is fully depressed within the reservoir 3110. Thus, in various embodiments, the geometry of the reservoir 3110 and the plunger head 3120 allow for capturing air bubbles in a bubble trap region 3116 of the reservoir 3110 when a fluidic medium is being expelled from the port 3117 of the reservoir 3110.

Figure 76:
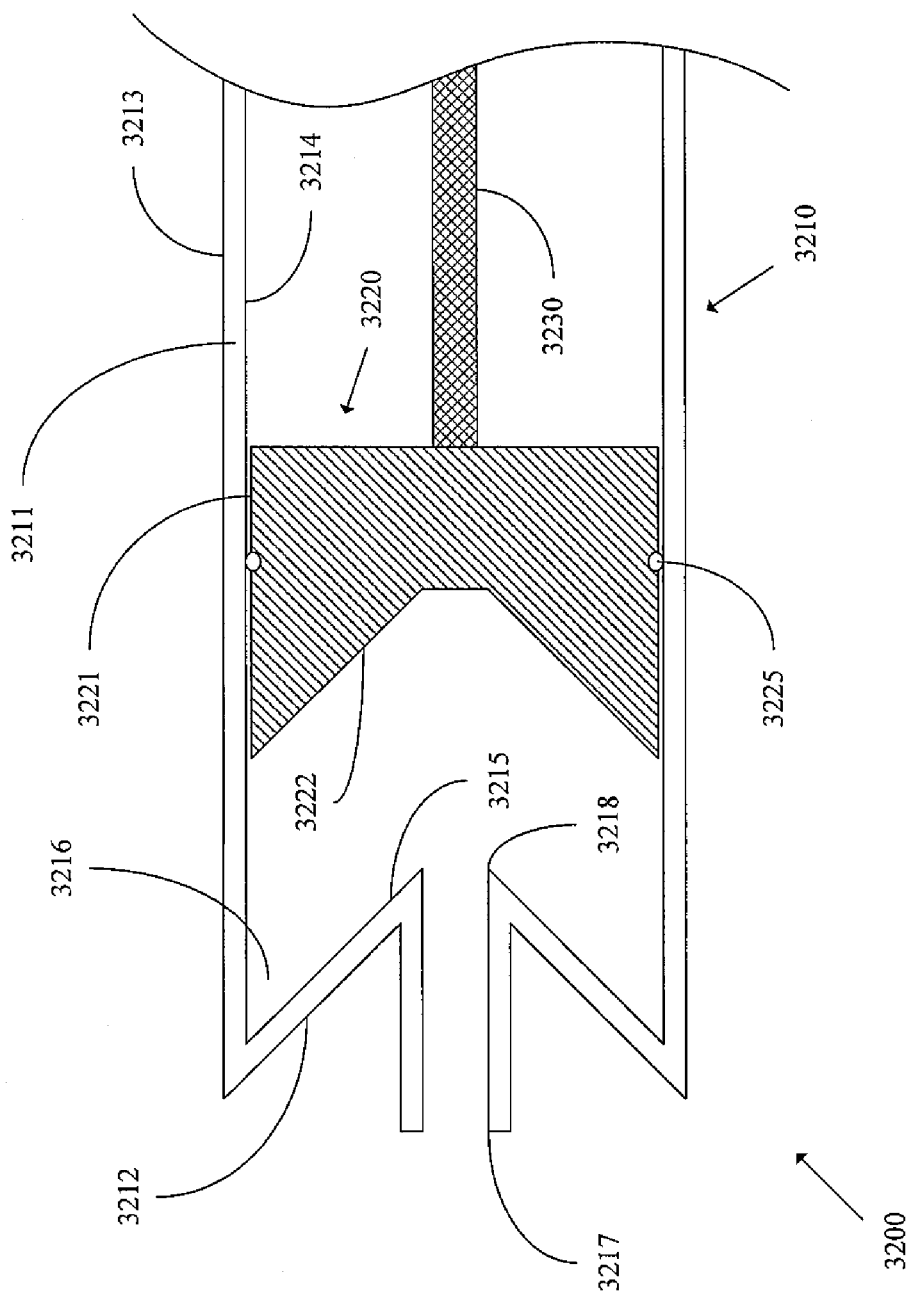
FIG. 76 illustrates a cross-sectional view of a system in accordance with an embodiment of the present invention.

FIG. 76 illustrates a cross-sectional view of a system 3200 in accordance with an embodiment of the present invention. The system 3200 includes a reservoir 3210, a plunger head 3220, and a plunger arm 3230. The reservoir 3210 includes a barrel portion 3211, a bubble trap portion 3212, and a port 3217. The reservoir 3210 has an outer surface 3213 and an inner surface 3214. The inner surface 3214 of the reservoir 3210 defines a hollow interior of the reservoir 3210, and the hollow interior of the reservoir 3210 is able to contain a fluidic medium. The port 3217 of the reservoir 3210 allows for the fluidic medium to be filled into or expelled from the hollow interior of the reservoir 3210.

The plunger head 3220 is located within the reservoir 3210, and is moveable in an axial direction of the reservoir 3210, to expand or contract an interior volume of the reservoir 3210 in which a fluidic medium may be contained. The plunger head 3220 is connected to the plunger arm 3230, such that movement of the plunger arm 3230 in the axial direction of the reservoir 3210 causes movement of the plunger head 3220 in the axial direction of the reservoir 3210. The plunger head 3220 includes a plunger barrel portion 3221 and a plunger protruding portion 3222. In various embodiments, the plunger head 3220 further includes one or more O-rings 3225 that surround a portion of the plunger barrel portion 3221.

The bubble trap portion 3212 of the reservoir 3210 is shaped so as to form a bubble trap region 3216 within an interior of the reservoir 3210, such that air bubbles in a fluidic medium may be trapped in the bubble trap region 3216 when the fluidic medium is expelled from the reservoir 3210 through the port 3217. In various embodiments, an interior surface of the bubble trap portion 3212 is angled at a substantially straight angle near the port 3217, so as to define the bubble trap region 3216. In some embodiments, the bubble trap portion 3212 extends from the barrel portion 3211 of the reservoir 3210 past a point 3218 of the reservoir 3210 where a fluidic medium from the barrel portion 3211 is able to move into an area of the reservoir 3210 that leads to the port 3217.

In various embodiments, the reservoir 3210 is shaped such that as the plunger head 3220 is depressed within the reservoir 3210, a fluidic medium is able to pass through the port 3217 while air bubbles in the reservoir 3210 collect in the bubble trap region 3216 defined by a substantially straight angled surface of the bubble trap portion 3212 of the reservoir 3210. Such a geometry of the reservoir 3210 allows for decreasing an amount of air bubbles that are delivered with a fluidic medium as compared with traditional reservoir geometries. In some embodiments, the bubble trap portion 3212 of the reservoir 3210 is angled outward from an interior region of the reservoir 3210 defined by the barrel portion 3211, and a fluidic medium is able to pass directly from the interior region of the reservoir 3210 defined by the barrel portion 3211 to the port 3217. In some embodiments, a surface 3215 of the bubble trap portion 3212 of the reservoir 3210 includes a surface finish or material such that air bubbles substantially do no stick to the surface 3215 and are shunted away from the port 3217 toward the bubble trap region 3216.

The plunger barrel portion 3221 is shaped such that a contour of an outer surface of the plunger barrel portion 3221 substantially matches or is substantially the same as a contour of an inner surface of the barrel portion 3211 of the reservoir 3210. In various embodiments, the plunger barrel portion 3221 has a diameter that is slightly smaller than a diameter of the inner surface of the barrel portion 3211 of the reservoir 3210, such that the plunger head 3220 is able to slide within the reservoir 3210. In some embodiments, an O-ring 3225 on the plunger barrel portion 3221 is in contact with the inner surface of the barrel portion 3211 of the reservoir 3210 when the plunger head 3220 is within the reservoir 3210.

In various embodiments, the plunger protruding portion 3222 is shaped such that a contour of an outer surface of the plunger protruding portion 3222 substantially matches or is substantially the same as a contour of an inner surface of the bubble trap portion 3212 of the reservoir 3210. In some embodiments, the plunger protruding portion 3222 is angled from the plunger barrel portion at a substantially straight angle and protrudes from the plunger barrel portion 3221. In various embodiments, the plunger protruding portion 3222 has a size that is slightly smaller than a region defined by the inner surface of the bubble trap portion 3212 of the reservoir 3210, such that the plunger protruding portion 3222 is able to slide within the bubble trap region 3216 of the reservoir 3210, and such that a space for a dead volume of air is left when the plunger head 3220 is fully depressed within the reservoir 3210. Thus, in various embodiments, the geometry of the reservoir 3210 and the plunger head 3220 allow for capturing air bubbles in a bubble trap region 3216 of the reservoir 3210 when a fluidic medium is being expelled from the port 3217 of the reservoir 3210.

Figure 77:
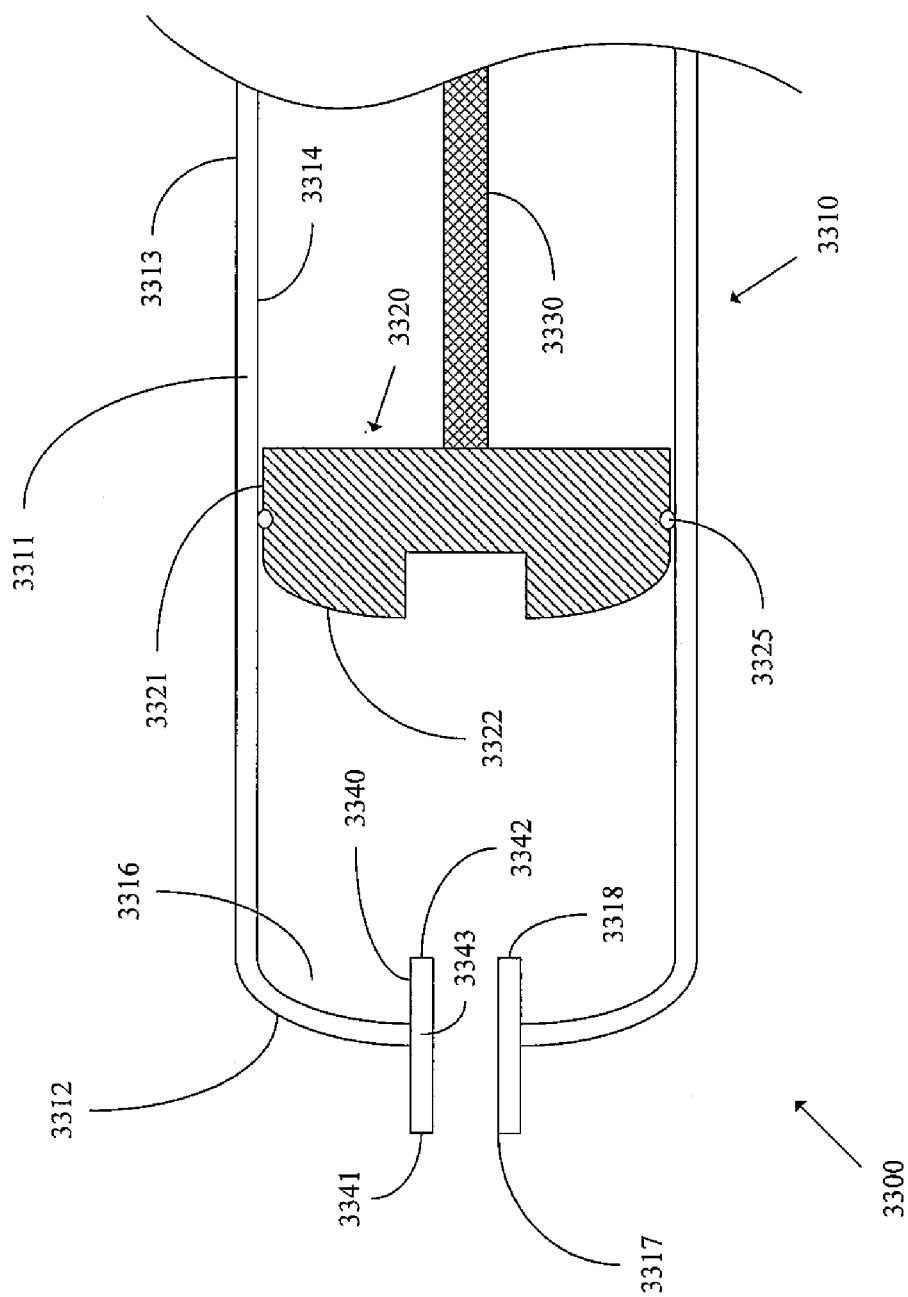
FIG. 77 illustrates a cross-sectional view of a system in accordance with an embodiment of the present invention.

FIG. 77 illustrates a cross-sectional view of a system 3300 in accordance with an embodiment of the present invention. The system 3300 includes a reservoir 3310, a plunger head 3320, and a plunger arm 3330. The reservoir 3310 includes a barrel portion 3311, a bubble trap portion 3312, a protruding portion 3340, and a port 3317. The reservoir 3310 has an outer surface 3313 and an inner surface 3314. The inner surface 3314 of the reservoir 3310 defines a hollow interior of the reservoir 3310, and the hollow interior of the reservoir 3310 is able to contain a fluidic medium. The port 3317 of the reservoir 3310 allows for the fluidic medium to be filled into or expelled from the hollow interior of the reservoir 3310. The protruding portion 3340 of the reservoir 3310 extends from the port 3317 toward the barrel portion 3311 of the reservoir 3310. The protruding portion 3340 has a first end 3341 and a second end 3342.

The plunger head 3320 is located within the reservoir 3310, and is moveable in an axial direction of the reservoir 3310, to expand or contract an interior volume of the reservoir 3310 in which a fluidic medium may be contained. The plunger head 3320 is connected to the plunger arm 3330, such that movement of the plunger arm 3330 in the axial direction of the reservoir 3310 causes movement of the plunger head 3320 in the axial direction of the reservoir 3310. The plunger head 3320 includes a plunger barrel portion 3321 and a plunger protruding portion 3322. In various embodiments, the plunger head 3320 further includes one or more O-rings 3325 that surround a portion of the plunger barrel portion 3321.

The bubble trap portion 3312 of the reservoir 3310 is shaped so as to form a bubble trap region 3316 within an interior of the reservoir 3310, such that air bubbles in a fluidic medium may be trapped in the bubble trap region 3316 when the fluidic medium is expelled from the reservoir 3310 through the port 3317. In various embodiments, a surface of the bubble trap portion 3312 extends from a point 3343 of the protruding portion 3340 of the reservoir 3310 that is between the first end 3341 and the second end 3342 of the protruding portion 3340, and the bubble trap portion 3312 is curved to connect to the barrel portion 3311, such that the bubble trap region 3316 is defined by a surface of the protruding portion 3340 between the point 3343 and the second end 3342 and by the curved surface of the bubble trap portion 3312. In some embodiments, the bubble trap portion 3312 extends from the barrel portion 3311 of the reservoir 3310 past a point 3318 of the reservoir 3310 where a fluidic medium from the barrel portion 3311 is able to move into an area of the reservoir 3310 that leads to the port 3317.

In various embodiments, the reservoir 3310 is shaped such that as the plunger head 3320 is depressed within the reservoir 3310, a fluidic medium is able to pass through the port 3317 while air bubbles in the reservoir 3310 collect in the bubble trap region 3316 of the reservoir 3310. Such a geometry of the reservoir 3310 allows for decreasing an amount of air bubbles that are delivered with a fluidic medium as compared with traditional reservoir geometries.

The plunger barrel portion 3321 is shaped such that a contour of an outer surface of the plunger barrel portion 3321 substantially matches or is substantially the same as a contour of an inner surface of the barrel portion 3311 of the reservoir 3310. In various embodiments, the plunger barrel portion 3321 has a diameter that is slightly smaller than a diameter of the inner surface of the barrel portion 3311 of the reservoir 3310, such that the plunger head 3320 is able to slide within the reservoir 3310. In some embodiments, an O-ring 3325 on the plunger barrel portion 3321 is in contact with the inner surface of the barrel portion 3311 of the reservoir 3310 when the plunger head 3320 is within the reservoir 3310.

In various embodiments, the plunger protruding portion 3322 is shaped such that a contour of an outer surface of the plunger protruding portion 3322 substantially matches or is substantially the same as a contour of an inner surface of the bubble trap portion 3312 of the reservoir 3310. In some embodiments, the plunger protruding portion 3322 has a surface that substantially matches a surface of the protruding portion 3340 between the point 3343 and the second end 3342 of the protruding portion 3340, such that when the plunger head 3320 is depressed within the reservoir 3310, the plunger head 3320 is able to pass along the protruding portion 3340. In various embodiments, the plunger protruding portion 3322 has a size that is slightly smaller than a region of the reservoir 3310 defined by the inner surface of the bubble trap portion 3312 and the protruding portion 3340, such that the plunger protruding portion 3322 is able to slide within the bubble trap region 3316 of the reservoir 3310, and such that a space for a dead volume of air is left when the plunger head 3320 is fully depressed within the reservoir 3310. Thus, in various embodiments, the geometry of the reservoir 3310 and the plunger head 3320 allow for capturing air bubbles in a bubble trap region 3316 of the reservoir 3310 when a fluidic medium is being expelled from the port 3317 of the reservoir 3310.

Figure 78A:
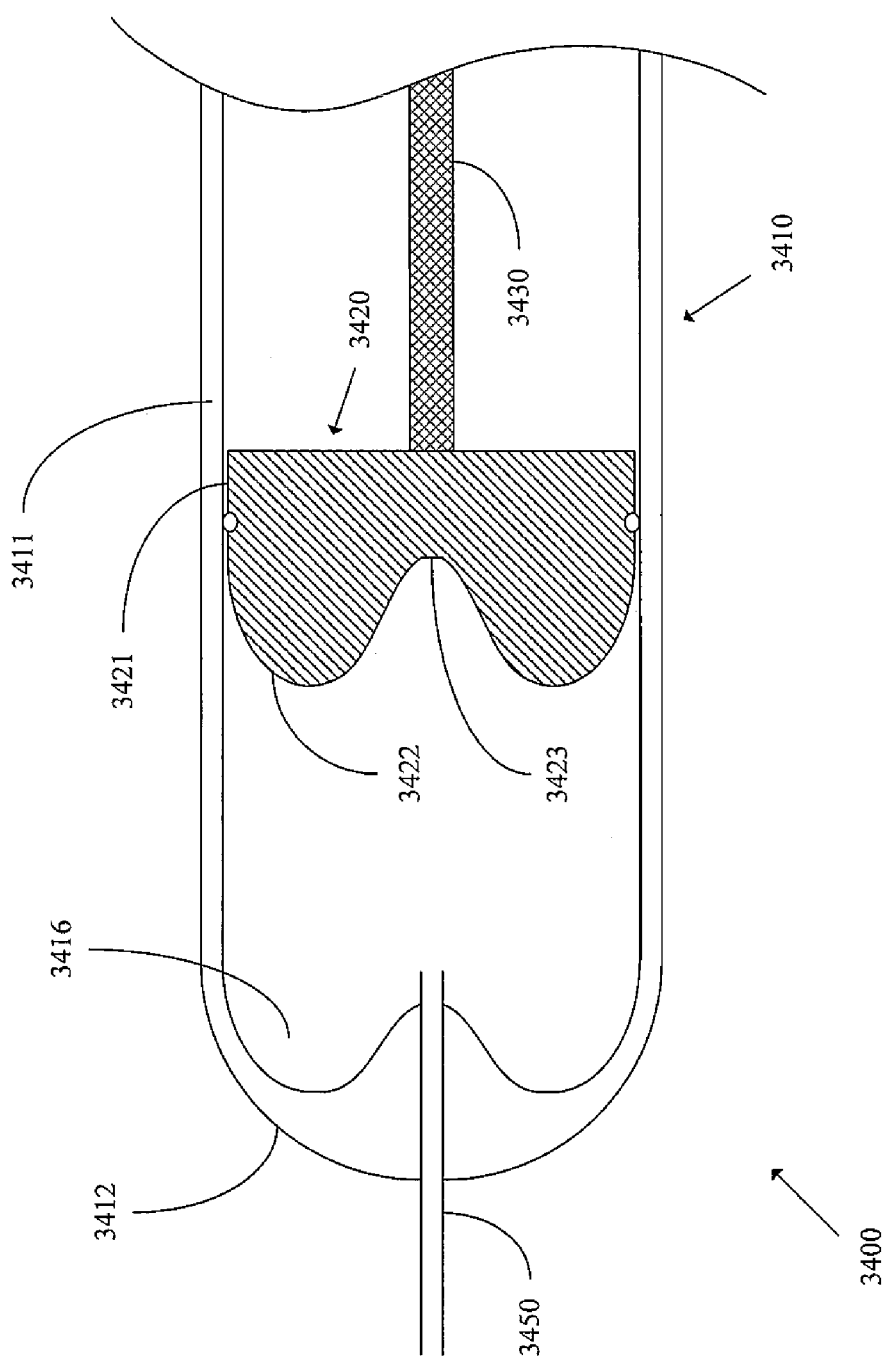
FIG. 78A illustrates a cross-sectional view of a system in accordance with an embodiment of the present invention.

FIG. 78A illustrates a cross-sectional view of a system 3400 in accordance with an embodiment of the present invention. The system 3400 includes a reservoir 3410, a plunger head 3420, and a plunger arm 3430. In various embodiments, the system 3400 further includes a needle 3450. The reservoir 3410 is similar to the reservoir 3110 of the system 3100 (refer to FIG. 75), and includes a barrel portion 3411 and a bubble trap portion 3412. The bubble trap portion 3412 defines a bubble trap region 3416. Thus, the reservoir 3410 has an air trap geometry that allows for capturing air bubbles.

The plunger head 3420 is similar to the plunger head 3120 of the system 3100 (refer to FIG. 75). The plunger head 3420 includes a plunger barrel portion 3421 and a plunger protruding portion 3422. The plunger head 3423 further includes a plunger depression portion 3423 for allowing the needle 3450 to be inserted into an interior of the reservoir 3410 when the plunger head 3420 is fully depressed within the reservoir 3410. In various embodiments, the reservoir 3410 is shaped to trap air bubbles. Also, in various embodiments, the reservoir 3410 and the plunger head 3420 are shaped so as to minimize a delivery of air bubbles when a fluidic medium is expelled from the reservoir 3410.

Figure 78B:
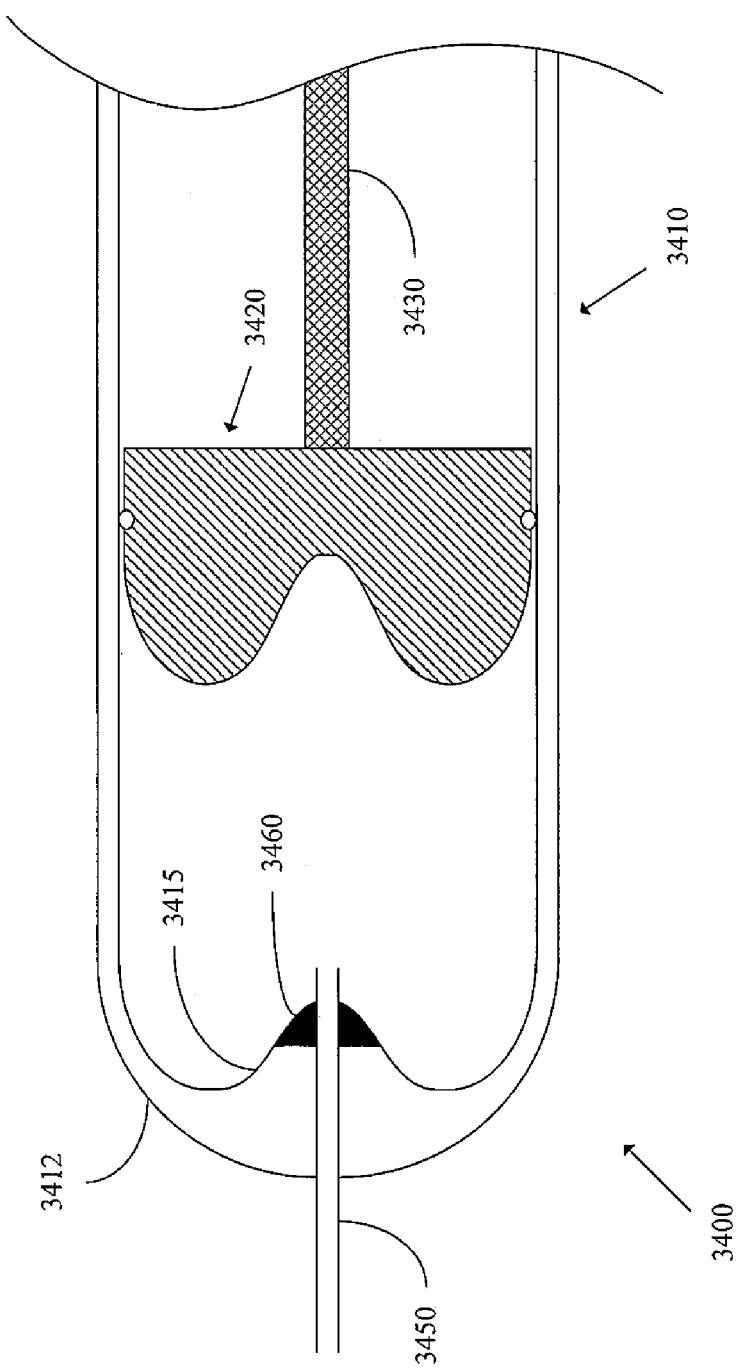
FIG. 78B illustrates a cross-sectional view of a system in accordance with an embodiment of the present invention.

FIG. 78B illustrates a cross-sectional view of the system 3400 of FIG. 78A in accordance with another embodiment of the present invention. In the embodiment illustrated in FIG. 78B, the system 3400 further includes a plug 3460. In various embodiments, the plug 3460 is located between an interior surface 3415 of the bubble trap portion 3412 of the reservoir 3410 and a location of the reservoir where a fluidic medium is able to be expelled from the reservoir. The plug 3460 may include, for example, a hydrophilic or a hydrophobic material, that will substantially keep air bubbles from being dispensed through an output port of the reservoir 3410. As a consequence, a delivery accuracy is able to be improved since a number of air bubbles expelled from the reservoir 3410 is further limited by the plug 3460.

Figure 79:
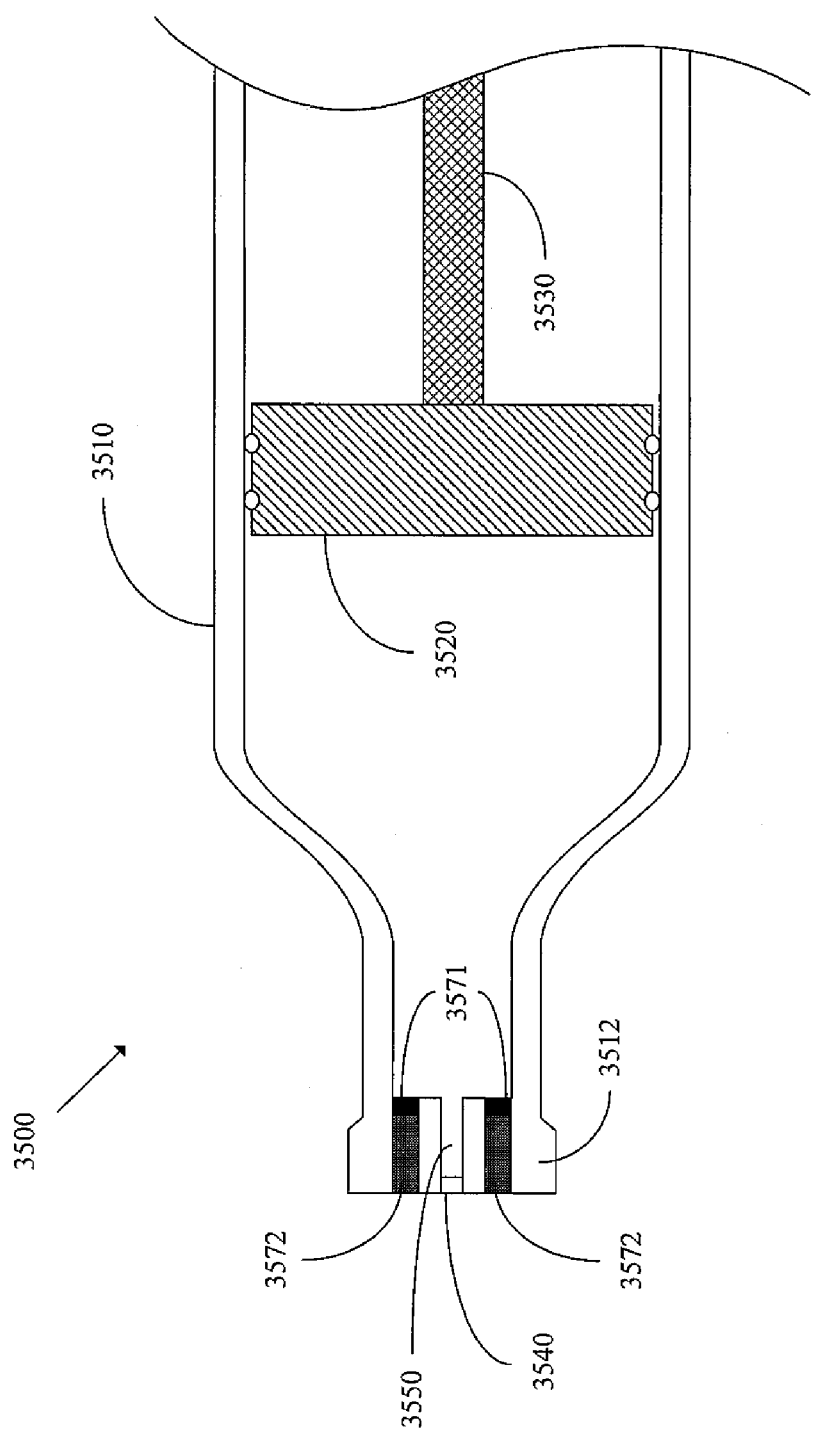
FIG. 79 illustrates a cross-sectional view of a system in accordance with an embodiment of the present invention.

FIG. 79 illustrates a cross-sectional view of a system 3500 in accordance with an embodiment of the present invention. The system 3500 includes a reservoir 3510, a plunger head 3520, a plunger arm 3530, a septum 3540, one or more hydrophobic filters 3571, and one or more air passages 3572. The reservoir 3510 has a hollow interior for containing a fluidic medium. The plunger head 3520 is located within the reservoir 3510 and is moveable in an axial direction of the reservoir 3510, to expand or contract an interior volume of the reservoir 3510. The reservoir includes a neck portion 3512. The septum 3540 is located at an end of the neck portion 3512 of the reservoir 3510, and a fluid channel 3550 is defined in the neck portion 3512 of the reservoir 3510 extending from the septum 3540.

The one or more air passages 3572 extend from within the reservoir 3510 to a same outer surface of the reservoir 3510 through which a fluidic medium is expelled from the reservoir 3510. In various embodiments, the one or more air passages 3572 surround the fluid channel 3550. The one or more hydrophobic filters 3571 are located at ends of the one or more air passages 3572 within the reservoir 3510. The hydrophobic filters 3571 include hydrophobic material that substantially prevents a fluidic medium in the reservoir 3510 from entering the one or more air passages 3572. The one or more air passages 3572 allow for air in the reservoir to pass through the one or more hydrophobic filters 3571 and to exit the reservoir 3510.

A method in accordance with the present invention allows for expelling a fluidic medium from the reservoir 3510. In a first step of the method, a fluid path is established through the septum 3540 to the fluid channel 3550. In a second step of the method, the plunger head 3520 is depressed within the reservoir 3510, such that the fluidic medium is expelled through the fluid channel 3550 and out of the reservoir 3510 through the septum 3540. When the fluidic medium is being expelled through the fluid channel 3550, air in the reservoir 3510 is able to pass through the one or more hydrophobic filters 3571 and out of the reservoir through the one or more air passages 3572. The fluidic medium is substantially prevented from entering the one or more air passages 3572 by the one or more hydrophobic filters 3571. Thus, in accordance with the method, the fluidic medium is able to be expelled from the reservoir 3510 while air in the reservoir 3510 is able to escape through the one or more air passages 3572 that exit the reservoir 3510 on a same side of the reservoir 3510 that the fluidic medium exits the reservoir 3510.

Figure 80A:
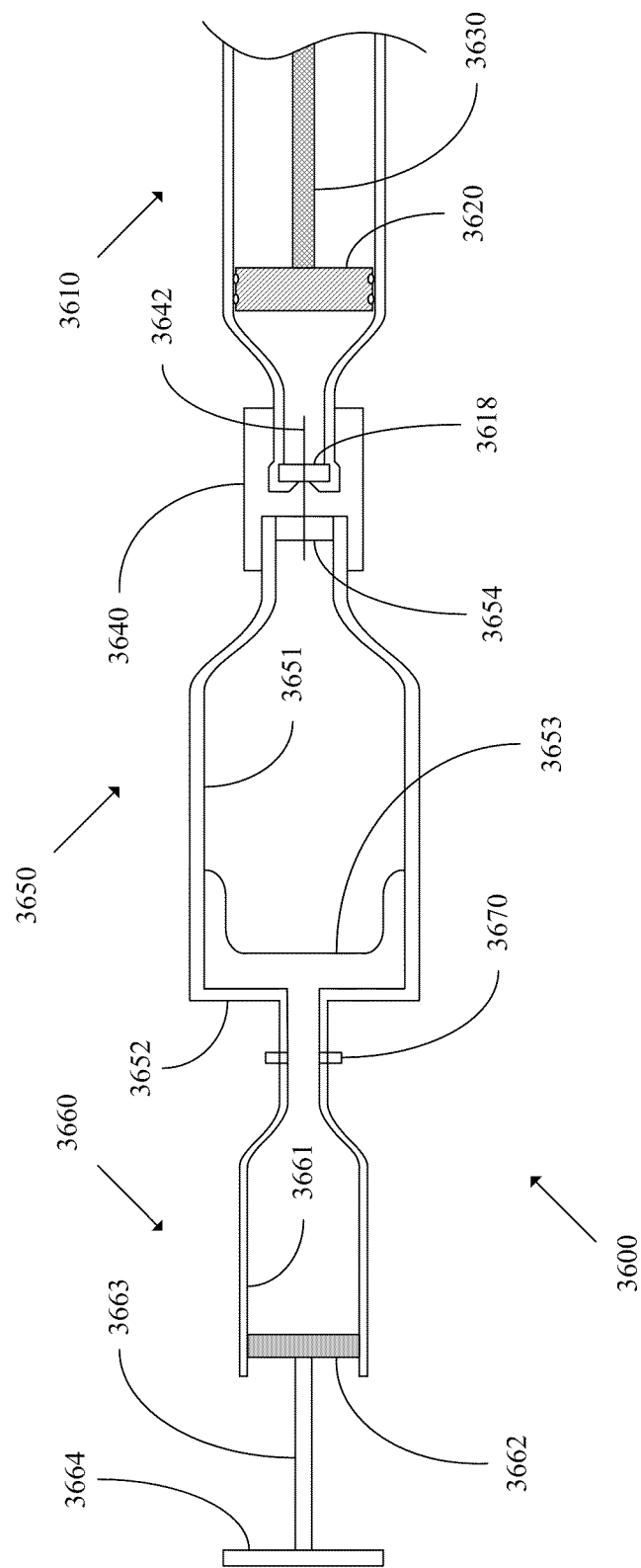
FIG. 80A illustrates a cross-sectional view of a system in accordance with an embodiment of the present invention.

FIG. 80A illustrates a cross-sectional view of a system 3600 in accordance with an embodiment of the present invention. The system 3600 includes a reservoir 3610, a plunger head 3620, a plunger arm 3630, a transfer guard 3640, a vial 3650, and a pressure providing device 3660. The reservoir 3610 has a hollow interior for containing a fluidic medium. The plunger head 3620 is located within the reservoir 3610 and is moveable in an axial direction of the reservoir 3610, to expand or contract an interior volume of the reservoir 3610. The plunger arm 3630 is connected to the plunger head 3620. In various embodiments, the reservoir 3610 includes a septum 3618 that is able to be pierced by a needle, such that the hollow interior of the reservoir 3610 is able to be filled with a fluidic medium that passes through the needle once the needle has pierced the septum 3618.

The vial 3650 includes a diaphragm 3653 that is connected to an inner surface 3651 of the vial 3650. The inner surface 3651 of the vial 3650 and an outer surface of the diaphragm 3653 define an interior volume of the vial 3650 that is able to contain a fluidic medium. In various embodiments, the diaphragm 3653 includes rubber, plastic, or the like, and is flexible. In some embodiments, the vial 3650 further includes a septum 3654 that is able to be pierced by a needle, such that a fluidic medium is able to be expelled from the vial 3650 through the needle once the needle has pierced the septum 3654. In various embodiments, the vial 3650 includes a bottom surface 3652 with an opening for allowing air or other motivation to enter into the vial 3650 on an opposite side of the diaphragm 3653 from a side of the diaphragm 3653 that is in contact with the fluidic medium in the vial 3650.

The transfer guard 3640 includes one or more needles 3642 for providing a fluid path from an interior volume of the vial 3650 to an interior volume of the reservoir 3610. In various embodiments, the transfer guard 3640 includes walls that help to shield the one or more needles 3642 from contact with a hand of a user when the user is connecting the vial 3650 and the reservoir 3610 with the transfer guard 3640. The one or more needles 3642 of the transfer guard 3640 are able to pierce the septum 3654 of the vial 3650 and the septum 3618 of the reservoir 3610, so as to provide a fluid path from the vial 3650 to the reservoir 3610. In various embodiments, a membrane may be incorporated into the fluid flow path in the transfer guard 3640 to trap air bubbles as a fluidic medium passes along the fluid flow path from the vial 3650 to the reservoir 3610.

The pressure providing device 3660 may include, for example, a syringe, or the like, for forcing air or other motivation, such as a fluid, through the opening in the bottom surface 3652 of the vial 3650. In various other embodiments, the pressure providing device 3660 may include, for example, a pump, or the like for providing pressure. The pressure providing device 3660 is connected to the vial 3650 at a connection point 3670 by, for example, an air tight connector, a screw connection, a clamp, or the like. In FIG. 80A, the pressure providing device 3660 is illustrated as a syringe having an inner surface 3661 defining a hollow interior, a plunger head 3662, a plunger arm 3663 connected to the plunger head 3662, and a handle 3664 connected to the plunger arm 3663. The syringe is configured such that air or other motivation is expelled from the syringe when the handle 3664 is pressed to cause the plunger head 3662 to advance within the interior of the syringe.

A method in accordance with an embodiment of the present invention allows for filling the reservoir 3610 in the system 3600. A first step in the method is to connect the pressure providing device 3660 to one end of the vial 3650 and connect another end of the vial 3650 to the reservoir 3610 using the transfer guard 3640. An example of such a connected structure is illustrated in FIG. 80A. A second step in the method is to use the pressure providing device 3660 to apply pressure to a side of the diaphragm 3653 in the vial 3650 that is opposite a side of diaphragm 3653 that is in contact with a fluidic medium. For example, in a case that the pressure providing device includes a syringe, the handle 3664 is pressed so as to advance the plunger head 3662 within the syringe and expel air or other motivation into the vial 3650 to thereby apply pressure to the diaphragm 3653.

Figure 80B:
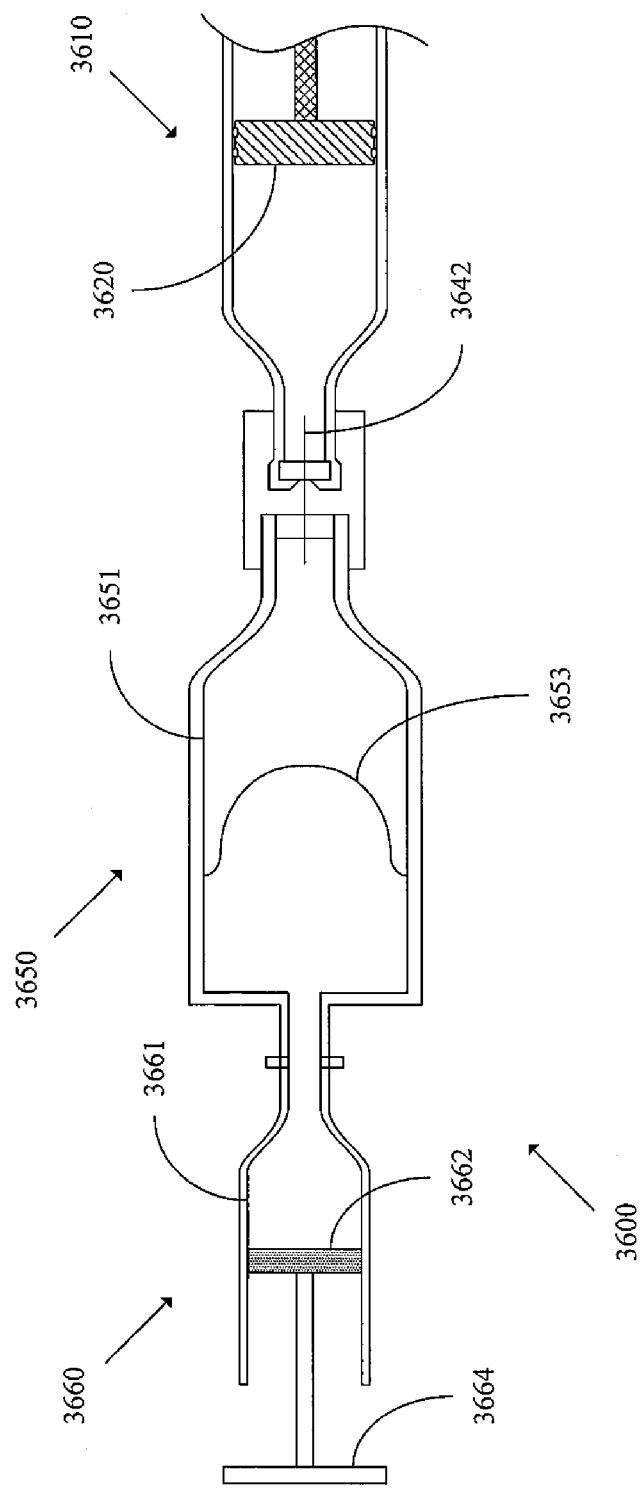
FIG. 80B illustrates a cross-sectional view of a system in accordance with an embodiment of the present invention.

The diaphragm 3653 within the vial 3650 is flexible, so the diaphragm 3653 expands when a pressure is applied to the diaphragm 3653 by the pressure providing device 3660. FIG. 80B illustrates a case in which the plunger head 3662 of the pressure providing device 3660 has been advanced so as to increase a pressure of a side of the diaphragm 3653 in the vial 3653 and, thus, cause the diaphragm 3653 to expand within the vial 3650. As the diaphragm 3653 expands due to the pressure from the pressure providing device 3660, an interior volume of the vial 3650 in which the fluidic medium is contained is reduced in size and, as a consequence, the fluidic medium is forced out of the vial 3650 through the fluid path to the interior volume of the reservoir 3610. The inflow of fluidic medium to the interior volume of the reservoir 3610 causes the plunger head 3620 to move backwards within the reservoir 3610. Increasing pressure may be applied from the pressure providing device 3660 to the diaphragm 3653 of the vial 3650 until a desired amount of fluidic medium has been filled into the reservoir 3610.

Thus, embodiments of the present invention provide a flexible diaphragm in a bottom of a vial and allow for external pressure to be applied to the flexible diaphragm so as to force a fluidic medium, such as insulin, or the like, into a reservoir. In various embodiments, a membrane is incorporated into the fluid flow path to trap air bubbles. In some embodiments of the method using the system 3600, an initial vacuum is applied to the vial 3650 to evacuate air in a dead space of the reservoir 3610 into the vial 3650 prior to filling the reservoir 3610.

Figure 81A:
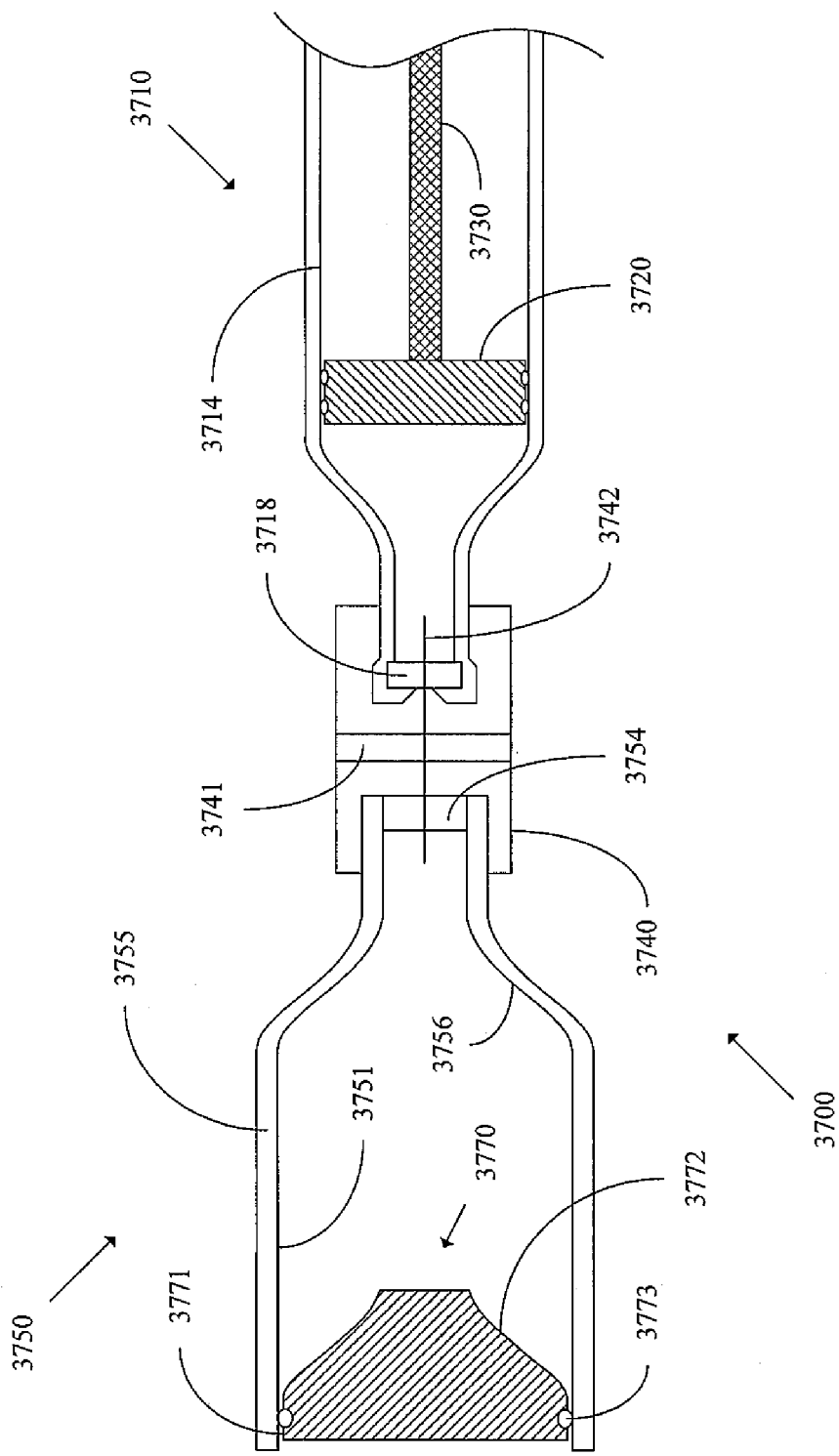
FIG. 81A illustrates a cross-sectional view of a system in accordance with an embodiment of the present invention.

FIG. 81A illustrates a cross-sectional view of a system 3700 in accordance with an embodiment of the present invention. The system 3700 includes a reservoir 3710, a plunger head 3720, a plunger arm 3750, a transfer guard 3740, a vial 3750, and a moveable element 3770. The reservoir 3710 has a hollow interior for containing a fluidic medium. The plunger head 3720 is located within the reservoir 3710 and is moveable in an axial direction of the reservoir 3710, to expand or contract an interior volume of the reservoir 3710. The plunger arm 3730 is connected to the plunger head 3720. In various embodiments, the reservoir 3710 includes a septum 3718 that is able to be pierced by a needle, such that the hollow interior of the reservoir 3710 is able to be filled with a fluidic medium that passes through the needle once the needle has pierced the septum 3718.

The moveable element 3770 is located within the vial 3750 and is moveable within the vial 3750 to expand or contract an interior volume of the vial 3750. The inner surface 3751 of the vial 3750 and a surface of the moveable element 3770 define an interior volume of the vial 3750 that is able to contain a fluidic medium. In various embodiments, the moveable element 3770 includes rubber, plastic, or the like. Also, in various embodiments, the moveable element 3770 includes a plunger, or the like. In some embodiments, the vial 3750 further includes a septum 3754 that is able to be pierced by a needle, such that a fluidic medium is able to be expelled from the vial 3750 through the needle once the needle has pierced the septum 3754.

The moveable element 3770 is able to move within the vial 3750 when a pressure is applied to the moveable element 3770. In various embodiments, the moveable element includes a barrel portion 3771 and a curved portion 3772, where a contour of an outer surface of the barrel portion 3771 is substantially the same as a contour of an inner surface 3751 of a barrel portion 3755 of the vial 3750, and where a contour of an outer surface of the curved portion 3772 is substantially the same as a contour of a curved portion 3756 of the vial 3750. Also, in various embodiments, the moveable element 3770 includes one or more O-rings 3773 that surround the barrel portion 3771 of the moveable element 3770 and that are in contact with the inner surface 3751 of the barrel portion 3755 of the vial 3750 when the moveable element 3770 is within the vial 3750.

The transfer guard 3740 includes one or more needles 3742 for providing a fluid path from an interior volume of the vial 3750 to an interior volume of the reservoir 3710. In various embodiments, the transfer guard 3740 includes walls that help to shield the one or more needles 3742 from contact with a hand of a user when the user is connecting the vial 3750 and the reservoir 3710 with the transfer guard 3740. The one or more needles 3742 of the transfer guard 3740 are able to pierce the septum 3754 of the vial 3750 and the septum 3718 of the reservoir 3710, so as to provide a fluid path from the vial 3750 to the reservoir 3710. In various embodiments, the transfer guard 3740 may include a membrane 3741 that is incorporated into the fluid flow path of the transfer guard 3740 to trap air bubbles as a fluidic medium passes along the fluid flow path from the vial 3750 to the reservoir 3710.

A method in accordance with an embodiment of the present invention allows for filling the reservoir 3710 in the system 3700. A first step in the method is to connect the vial 3750 to the reservoir 3710 using the transfer guard 3740. An example of such a connected structure is illustrated in FIG. 81A. A second step in the method is to apply pressure to a side of the moveable element 3770 in the vial 3750 that is opposite a side of moveable element 3770 that is in contact with a fluidic medium. For example, a user or a device may press on an external surface of the moveable element 3770 to advance the moveable element within the vial 3750. Thus, the moveable element 3770 acts as a moveable bottom of the storage vial 3750. In various embodiments, the moveable element 3770 may further include a handle (not shown) connected to the moveable element 3770 for applying pressure to the moveable element 3770.

Figure 81B:
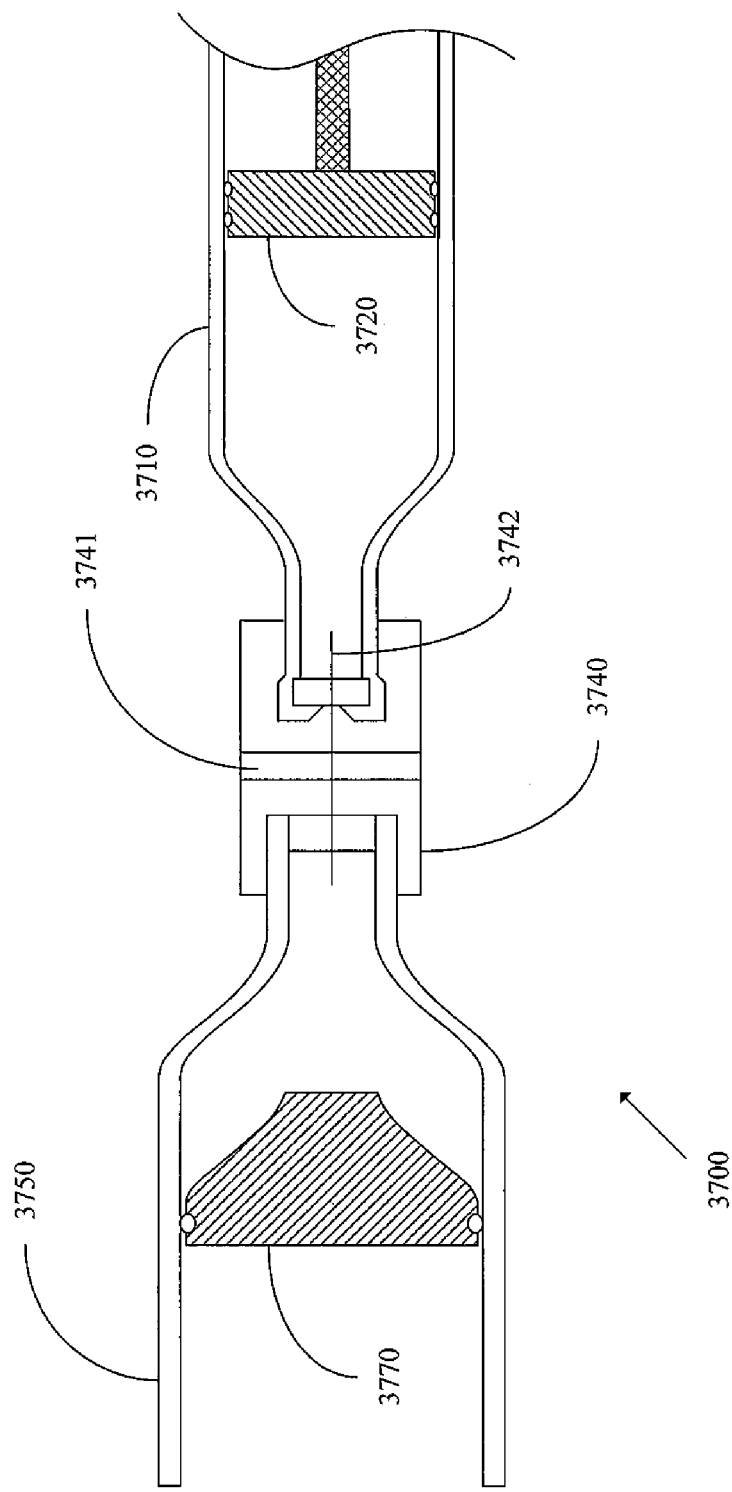
FIG. 81B illustrates a cross-sectional view of a system in accordance with an embodiment of the present invention.

When a pressure is applied to the moveable element 3770 to advance the moveable element 3770 within the vial 3750, the fluidic medium within the vial 3750 is forced through the needle 3742 and into the reservoir 3710. FIG. 81B illustrates a cross-sectional view of the system 3700 once the moveable element 3770 has been at least partially advanced within the vial 3750. When a force is applied to the moveable element 3770 to force fluidic medium from the vial 3750 to fill the reservoir 3710, the plunger head 3720 is forced backward within the reservoir 3710 by the force of the fluidic medium entering the reservoir 3710. Thus, embodiments of the present invention allow for a storage vial with a moveable bottom, and for applying a pressure to the moveable bottom of the storage vial to fill a reservoir. Also, when the fluidic medium passes from the vial 3750 to the reservoir 3710, the fluidic medium is passed through the membrane 3741 of the transfer guard 3740, which substantially removes air bubbles from the fluidic medium prior to the fluidic medium filling into the reservoir 3710.

Figure 82A:
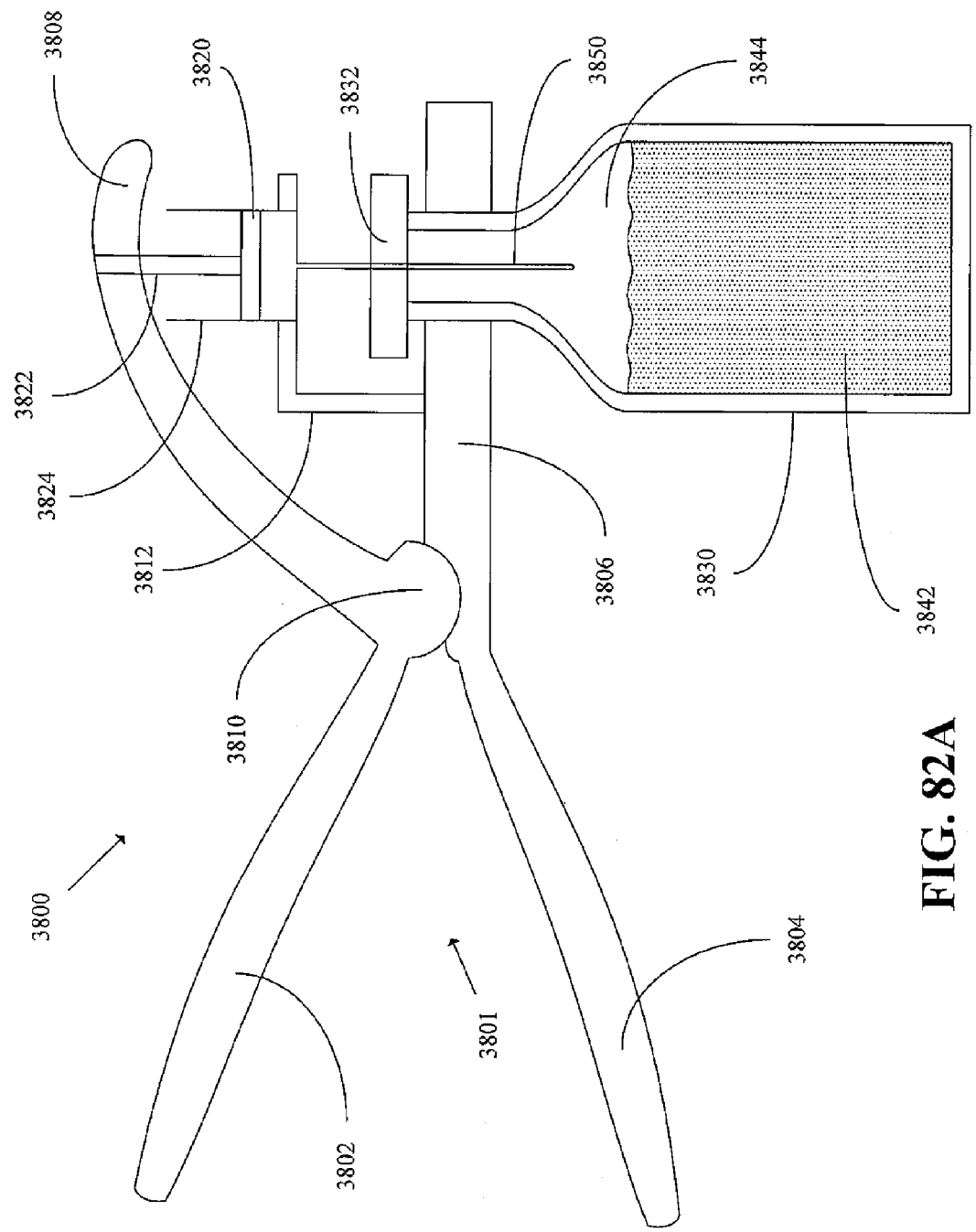
FIG. 82A illustrates a cross-sectional view of a system in accordance with an embodiment of the present invention.

FIG. 82A illustrates a cross-sectional view of a system 3800 in accordance with an embodiment of the present invention. The system 3800 includes a degassing tool 3801 and a vial 3830. The degassing tool 3801 includes a first handle 3802, a second handle 3804, a pivot member 3810, a first arm 3808, a second arm 3806, a holding arm 3812, a plunger housing 3824, a plunger head 3820, a plunger arm 3822, and an insertion member 3850. The vial 3830 contains a fluidic medium, such as insulin, or the like, up to a certain level within the vial 3830, and an area of the vial 3830 above the fluidic medium forms a headspace 3844 of the vial 3830. The vial includes a septum 3832 that may be pierced by the insertion member 3850 of the degassing tool 3801.

The first handle 3802, the second handle 3804, the first arm 3808, and the second arm 3806 are connected together by the pivot member 3810. In various embodiments, the first handle 3802, the pivot member 3810, and the first arm 3808 are formed as a single unit, and the second handle 3804 and the second arm 3806 are formed as a single unit. The first handle 3802 is able to pivot toward and away from the second handle 3804. The second arm 3806 may have a cavity for surrounding a neck of a vial. The holding arm 3812 extends from the second arm 3806 and holds the plunger housing 3824 between the first arm 3808 and the second arm 3806. The plunger head 3820 is connected to the plunger arm 3822 and the plunger head 3820 is able to slide within the plunger housing 3824. The insertion member 3850 may be, for example, a needle, and is connected to an output port of the plunger housing 3824. The plunger arm 3822 is connected to the first arm 3808.

The degassing tool 3801 is configured such that when the first handle 3802 is pivoted away from the second handle 3804, the first arm 3808 is pivoted such that the plunger arm 3822 causes the plunger head 3820 to advance within the plunger housing 3824 to reduce a volume in the plunger housing 3822 between the plunger head 3820 and the output port to the insertion member 3850. The degassing tool 3801 is also configured such that when the first handle 3802 is pivoted toward the second handle 3804, the first arm 3808 is pivoted such that the plunger arm 3822 causes the plunger head 3820 to retract within the plunger housing 3824 to increase a volume in the plunger housing 3822 between the plunger head 3824 and the output port to the insertion member 3850.

A method in accordance with the present invention allows for degassing the vial 3830 using the degassing tool 3801. In a first step, the first handle 3802 of the degassing tool 3801 is pivoted away from the second handle 3804, which causes the first arm 3808 to push on the plunger arm 3822 and, thus, advance the plunger head 3820 within the plunger housing 3824. In a second step, the insertion member 3850 is inserted through the septum 3832 of the vial 3830 and into the headspace 3844 of the vial 3830 above the fluidic medium 3842 within the vial 3830. An example of such a connection of the degassing tool 3801 and the vial 3830 is illustrated in FIG. 82A.

Figure 82B:
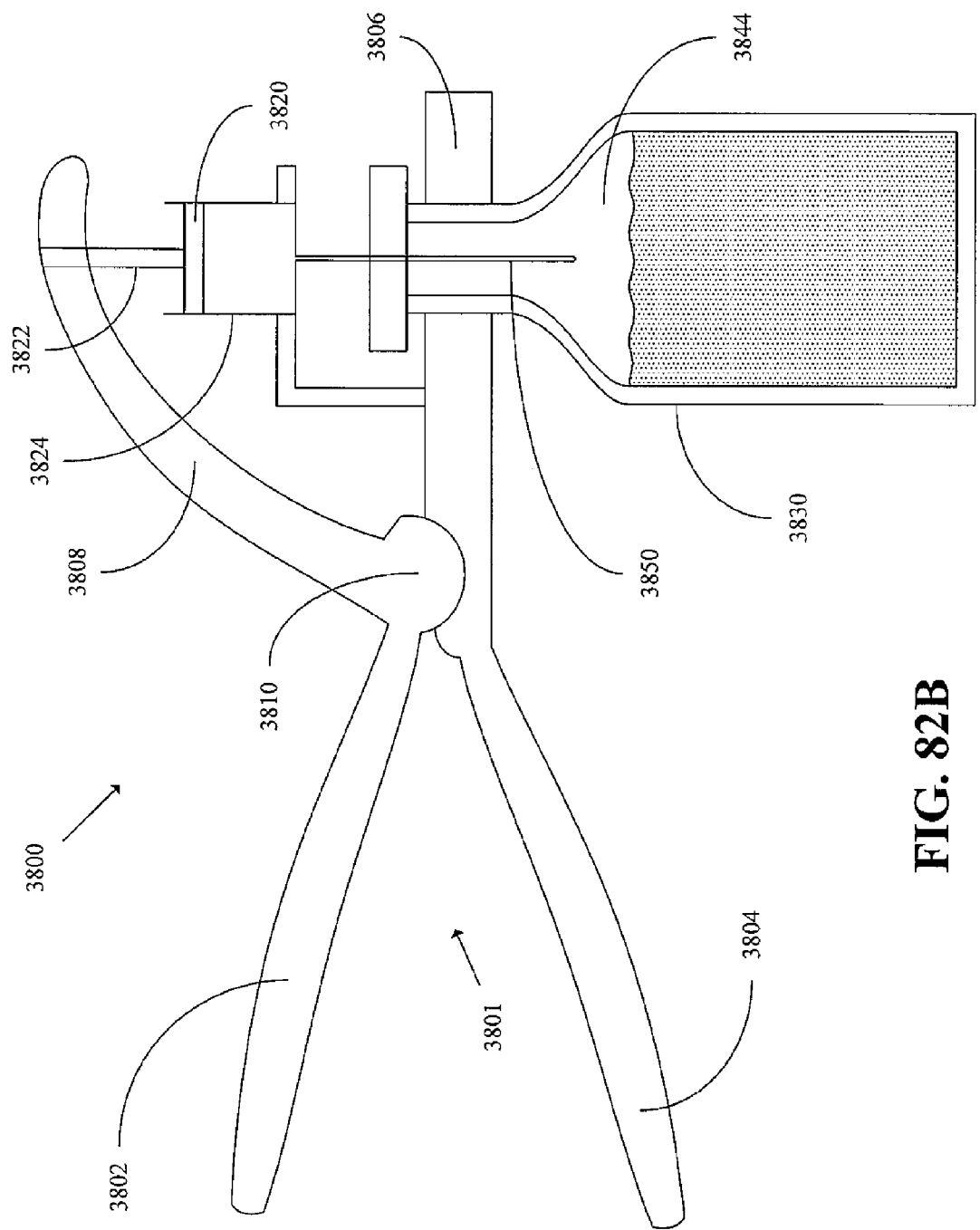
FIG. 82B illustrates a cross-sectional view of a system in accordance with an embodiment of the present invention.

In a third step, the first handle 3802 of the degassing tool 3801 is pivoted toward the second handle 3804, which causes the first arm 3808 to pull on the plunger arm 3822 and, thus, retract the plunger head 3820 within the plunger housing 3824. FIG. 82B illustrates a cross-section of the system 3800 in accordance with an embodiment of the present invention when the first handle 3802 has been pivoted toward the second handle 3804. When the plunger head 3820 retracts within the plunger housing 3824, air or gas in the headspace 3844 of the vial 3830 is drawn through the insertion member 3850 and into the plunger housing 3824. In various embodiments, the degassing tool 3801 is operated by a hand of a user. Once the gas has been drawn out of the headspace 3844 of the vial 3830, the vial 3830 is disconnected from the degassing tool 3801 and may be used to fill a reservoir. Thus, embodiments of the present invention provide for a hand powered purging device or degassing tool that can be connected to existing drug vials and, by performing a pumping action, can reduce a pressure inside of a vial by causing out-gassing to occur before using the vial to fill a reservoir.

Figure 83:
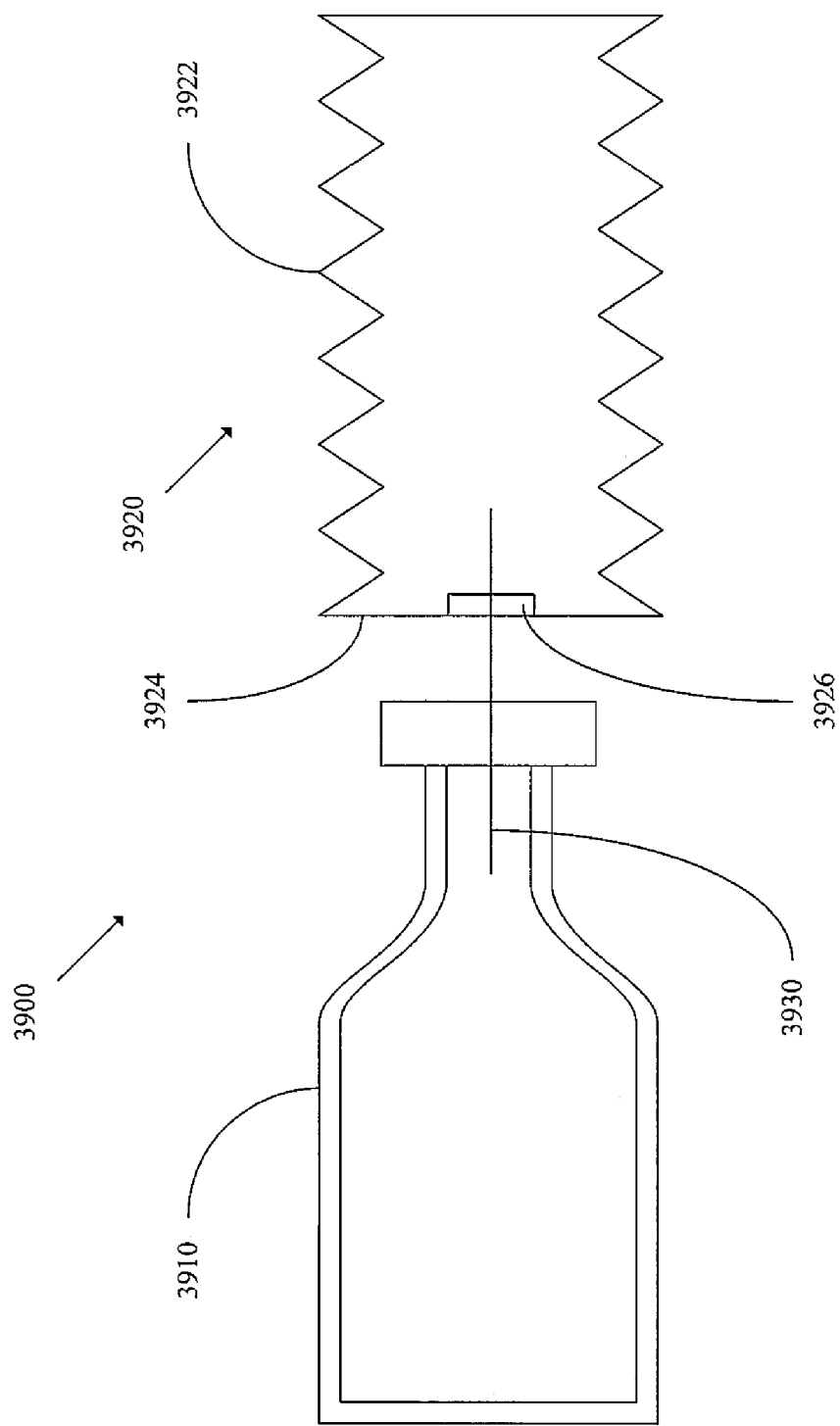
FIG. 83 illustrates a cross-sectional view of a system in accordance with an embodiment of the present invention.

FIG. 83 illustrates cross-sectional view of a system 3900 in accordance with an embodiment of the present invention. The system 3900 includes a reservoir 3920 and a vial 3910. The reservoir 3920 includes a front surface 3924, a bellows portion 3922 connected to the front surface, and a septum 3926. The bellows portion 3922 includes an accordion like structure, and is able to expand and contract to change an interior volume within the bellows portion 3922. Such a bellows portion 3922 allows for substantially eliminating a reservoir headspace when the bellows portion 3922 is fully contracted. In various embodiments, the system 3900 further includes a needle 3930 for providing a fluid path between the vial 3910 and the reservoir 3920. In some embodiments, a vacuum is applied to the reservoir 3920 such that the bellows portion 3922 is fully contracted prior to being filled, and then once the needle 3930 pierces the septum 3926 of the reservoir 3920, the bellows portion 3922 expands to fill with a fluidic medium transferred from the vial 3910 through the needle 3930.

Figure 84A:
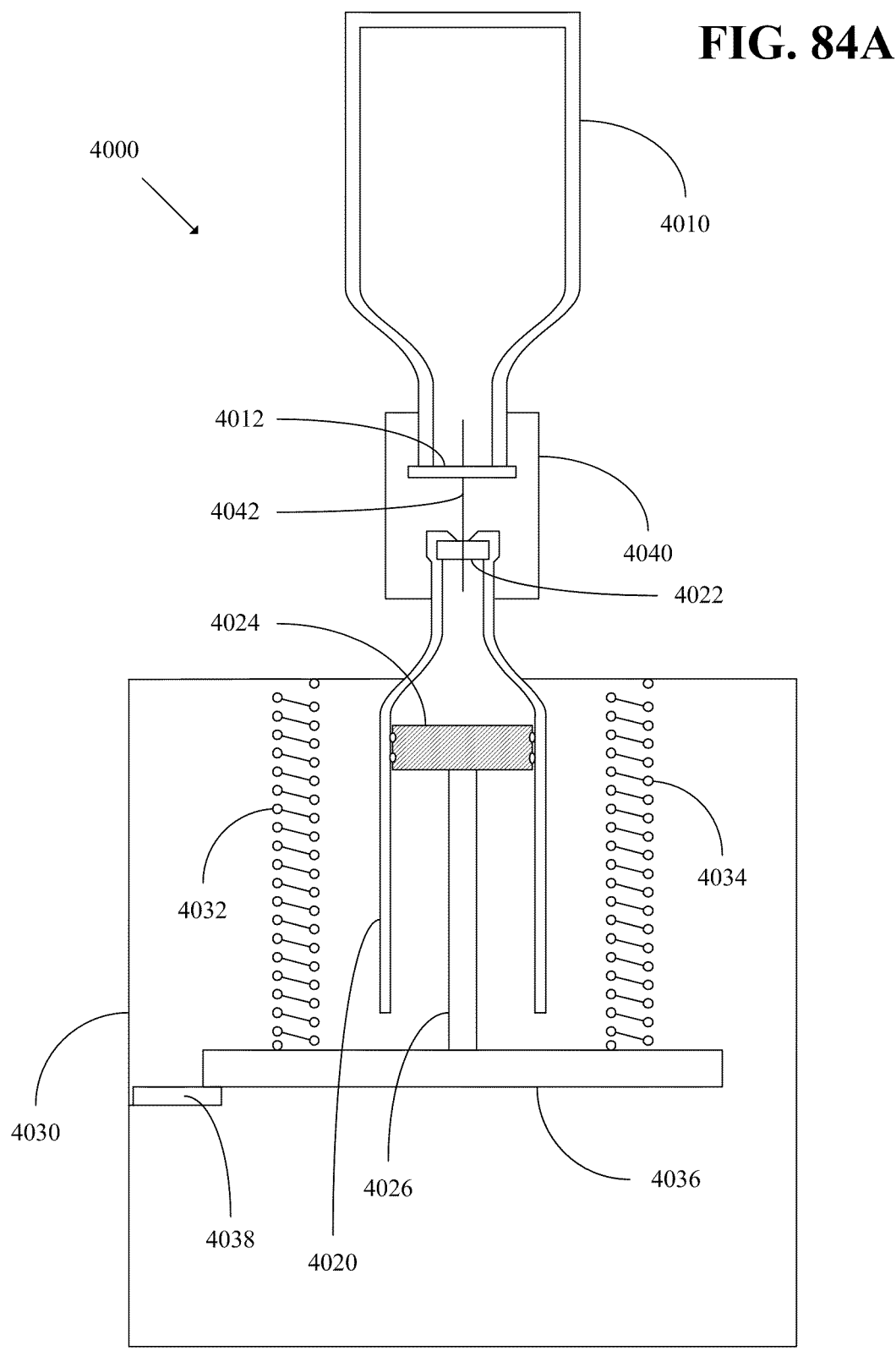
FIG. 84A illustrates a cross-sectional view of a system in accordance with an embodiment of the present invention.

FIG. 84A illustrates a cross-sectional view of a system 4000 in accordance with an embodiment of the present invention. The system 4000 includes a vial 4010, a reservoir 4020, a plunger head 4024, a plunger arm 4026, a transfer guard 4040, and an automated filling device 4030. The vial 4010 includes a septum 4012, and the vial 4010 allows for containing a fluidic medium. The reservoir 4020 has a hollow interior for containing a fluidic medium. The plunger head 4024 is located within the reservoir 4020 and is moveable within the reservoir 4020 to expand or contract an interior volume of the reservoir 4020. The plunger head 4024 is connected to the plunger arm 4026. The reservoir 4020 includes a septum 4022 at a port of the reservoir 4020. The transfer guard 4040 includes one or more needles 4042 for providing a fluid path from an interior volume of the vial 4010 to an interior volume of the reservoir 4020. The one or more needles 4042 of the transfer guard 4040 are able to pierce the septum 4012 of the vial 4010 and the septum 4022 of the reservoir 4020, so as to provide a fluid path from the vial 4010 to the reservoir 4020.

The automated filling device 4030 allows for automating a filling process of filling the reservoir 4020 with a fluidic medium from the vial 4010. The automated filling device 4030 includes a first spring 4032, a second spring 4034, a handle 4036. In various embodiments, the automated filling device 4030 further includes a latch 4038. In various embodiments, the plunger arm 4026 and the handle 4036 are configured such that the plunger arm 4026 is able to snap together with the handle 4036 to connect the plunger arm 4026 to the handle 4036. In various other embodiments, the plunger arm 4026 and the handle 4036 are configured to be connected in other ways, such as by screwing the plunger arm 4026 into the handle 4036. In some embodiments, the handle 4036 is part of the plunger arm 4026, and the handle 4036 is able to be connected to the first spring 4032 and the second spring 4034.

The first spring 4032 and the second spring 4034 are connected between a top surface of the automated filling device 4030 and the handle 4036. Both the first spring 4032 and the second spring 4034 are initially biased toward an expanded position, but are held compressed by the handle 4036, which may be held up by the latch 4038. The automated filling device 4030 allows for the reservoir 4020 to be snapped or otherwise connected in place within the automated filling device 4030, and then allows for filling the reservoir 4020 using a force applied by the first spring 4032 and the second spring 4034 on the handle 4036 when the latch 4038 is opened to allow the first spring 4032 and the second spring 4034 to push down on the handle 4036. In the system 4000, the handle 4036 is connected to the plunger arm 4026, and the plunger arm 4026 is connected to the plunger head 4024, such that a movement of the handle 4036 away from the reservoir 4020 causes the plunger head 4024 to retract within the reservoir 4020 to create a vacuum that enables a filling of the reservoir 4020.

A method in accordance with an embodiment of the present invention allows for using the automated filling device 4030 to fill the reservoir 4020 with a fluidic medium from the vial 4010. In a first step of the method, the first spring 4032 and the second spring 4034 are compressed by a force applied to the handle 4036, and the latch 4038 is engaged with the handle 4036 to hold the handle 4036 in place with the first spring 4032 and the second spring 4034 compressed. In a second step of the method, the reservoir 4020 and the plunger arm 4026 are connected to the automated filling device, such as by snapping the plunger arm 4026 to the handle 4036. In a third step of the method, a fluid path is established between the vial 4010 and the reservoir 4020 by using the needle 4042 of the transfer guard 4040 to pierce the septum 4012 of the vial 4010 and to pierce the septum 4022 of the reservoir 4020. In various embodiments, the vial 4010 is positioned in an inverted position when the fluid path is established with the reservoir 4020, such that a fluidic medium in the vial 4010 tends toward the septum 4012. An example of the system 4000 with such a connected structure is illustrated in FIG. 84A.

Figure 84B:
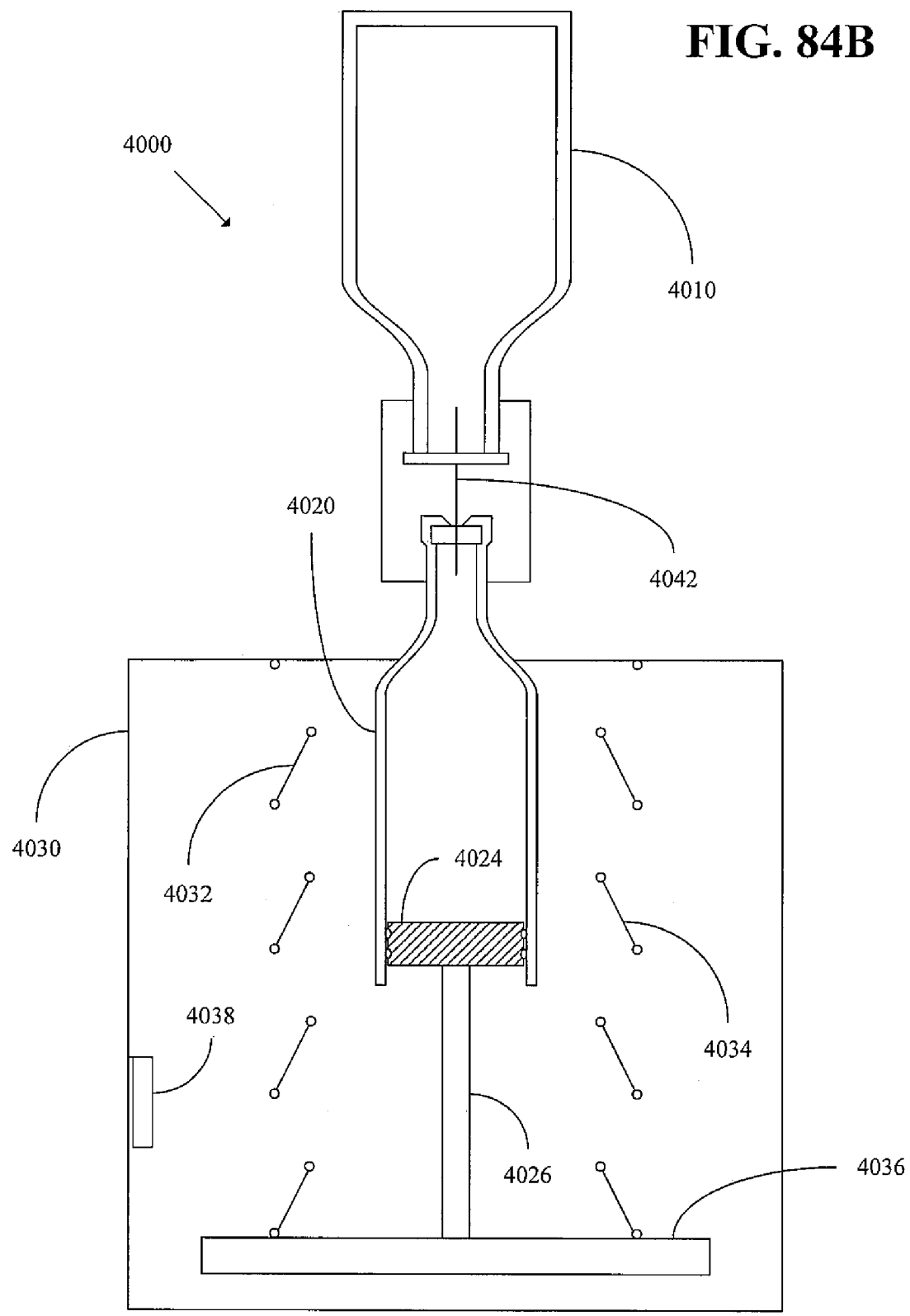
FIG. 84B illustrates a cross-sectional view of a system in accordance with an embodiment of the present invention.

In a fourth step of the method, the latch 4038 is released, such that the first spring 4032 and the second spring 4034 are able to expand and move the handle 4036 away from the reservoir 4020. FIG. 84B illustrates a cross-sectional view of the system 4000 after the first spring 4032 and the second spring 4034 have expanded to move the handle 4036. When the handle 4036 moves away from the reservoir 4020, the handle 4036 pulls the plunger arm 4026 to cause the plunger head 4024 to retract within the reservoir 4020. The retraction of the plunger head 4024 within the reservoir 4020 creates a vacuum that allows for the fluidic medium to be filled into the reservoir 4020 from the vial 4010. In various embodiments, the tension of the first spring 4032 and the second spring 4034 is selected so as to allow for the reservoir 4020 to fill slowly when the first spring 4032 and the second spring 4034 expand. Thus, various embodiments of the present invention allow for spring loaded automatic filling of a reservoir, and for slowly pulling a fluid or drug from an inverted vial into a reservoir. In some embodiments, a lead screw (not shown in FIG. 84B) may be used in place of the first spring 4032 and the second spring 4034 to move the plunger arm 4026 for an automated filling of the reservoir 4020.

Figure 85A:
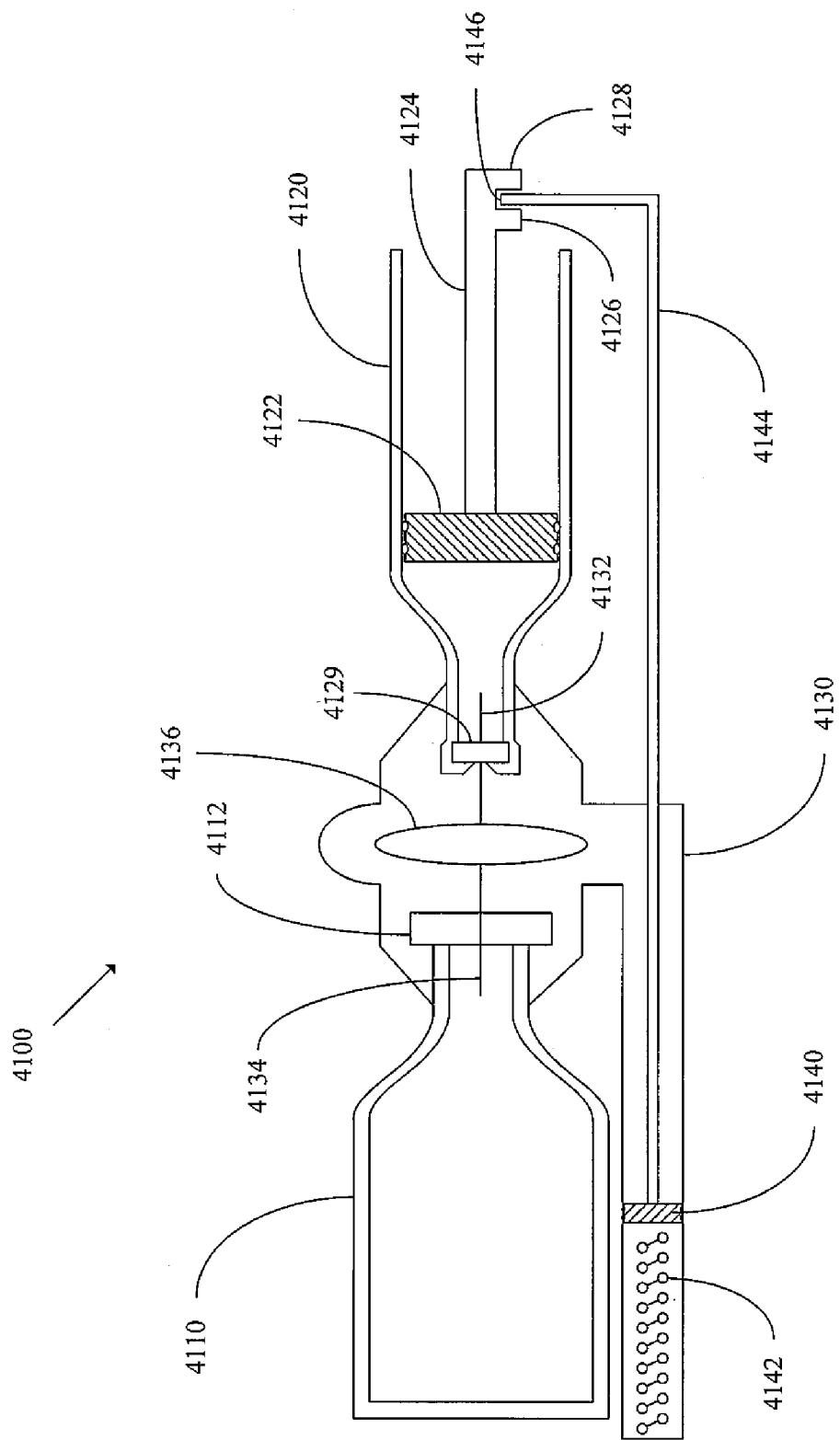
FIG. 85A illustrates a cross-sectional view of a system in accordance with an embodiment of the present invention.

FIG. 85A illustrates a cross-sectional side view of a system 4100 in accordance with an embodiment of the present invention. The system 4100 includes a vial 4110, a reservoir 4120, a plunger head 4122, a plunger arm 4124, and a stand 4130. The vial 4110 includes a septum 4112, and the vial allows for containing a fluidic medium. The reservoir 4120 has a hollow interior for containing a fluidic medium. The plunger head 4122 is located within the reservoir 4120 and is moveable within the reservoir 4120 to expand or contract an interior volume of the reservoir 4120. The plunger head 4122 is connected to the plunger arm 4124. The reservoir 4120 includes a septum 4129 at a port of the reservoir 4120.

The stand 4130 includes a connection structure, such as a transfer guard, or the like, for providing a fluid path from the vial 4110 to the reservoir 4120. The stand 4130 includes a first needle 4134, a second needle 4132, an air filter 4136, a plunger head 4140, a pressure providing device 4142, and a plunger arm 4144 connected to the plunger head 4140. The first needle 4134 may be used to pierce the septum 4112 of the vial 4110, and the second needle 4132 may be used to pierce the septum 4129 of the reservoir 4120, and the first needle 4134 may be connected to the second needle 4132 through the air filter 4136. The air filter allows for removing dissolved air from a fluidic medium being transferred from the vial 4110 to the reservoir 4120.

The plunger head 4140, the plunger arm 4144, and the pressure providing device 4142 allow for assisting with a filling of the reservoir 4120. In various embodiments, the pressure providing device 4142 includes a spring, or the like, that is biased toward an expanded position. In various other embodiments, the pressure providing device 4142 includes a canister with compressed air, where the compressed air may be released to provide a pressure. An end 4146 of the plunger arm 4144 of the stand 4130 may be inserted into a receptacle 4126 of the plunger arm 4124, such that a movement of the plunger head 4140 causes a movement of the plunger arm 4144 that leads to a movement of the plunger arm 4124 that causes a movement of the plunger head 4122 within the reservoir 4120.

A method in accordance with an embodiment of the present invention allows for using the stand 4130 to assist in filling the reservoir 4120 from the vial 4110. In a first step of the method, the vial 4110 and the reservoir 4120 are connected to the stand 4130. For example, the stand 4130 may include a nest for the vial 4110 and a nest for the reservoir 4120. When the reservoir 4120 is attached to the stand 4130, the end 4146 of the plunger arm 4144 of the stand 4130 is inserted into the receptacle 4126 of the plunger arm 4124. In a second step of the method, the pressure providing device 4142 is caused to provide a pressure to the plunger head 4140 so as to move the plunger head 4140 to cause the plunger arm 4144 to move, which causes the plunger arm 4124 to move and, thus, causes the plunger head 4122 to retract within the reservoir 4120. FIG. 85B illustrates a cross-sectional side view of the system 4100 when the pressure providing device 4142 has caused a movement of the plunger head 4140 which has caused a movement of the plunger head 4122 within the reservoir 4120. When the plunger head 4122 is retracted within the reservoir 4122, a fluidic medium passes from the vial 4110 through the air filter 4136 and fills into the reservoir 4120. The air filter 4136 removes dissolved air from the fluidic medium.

Figure 85C:
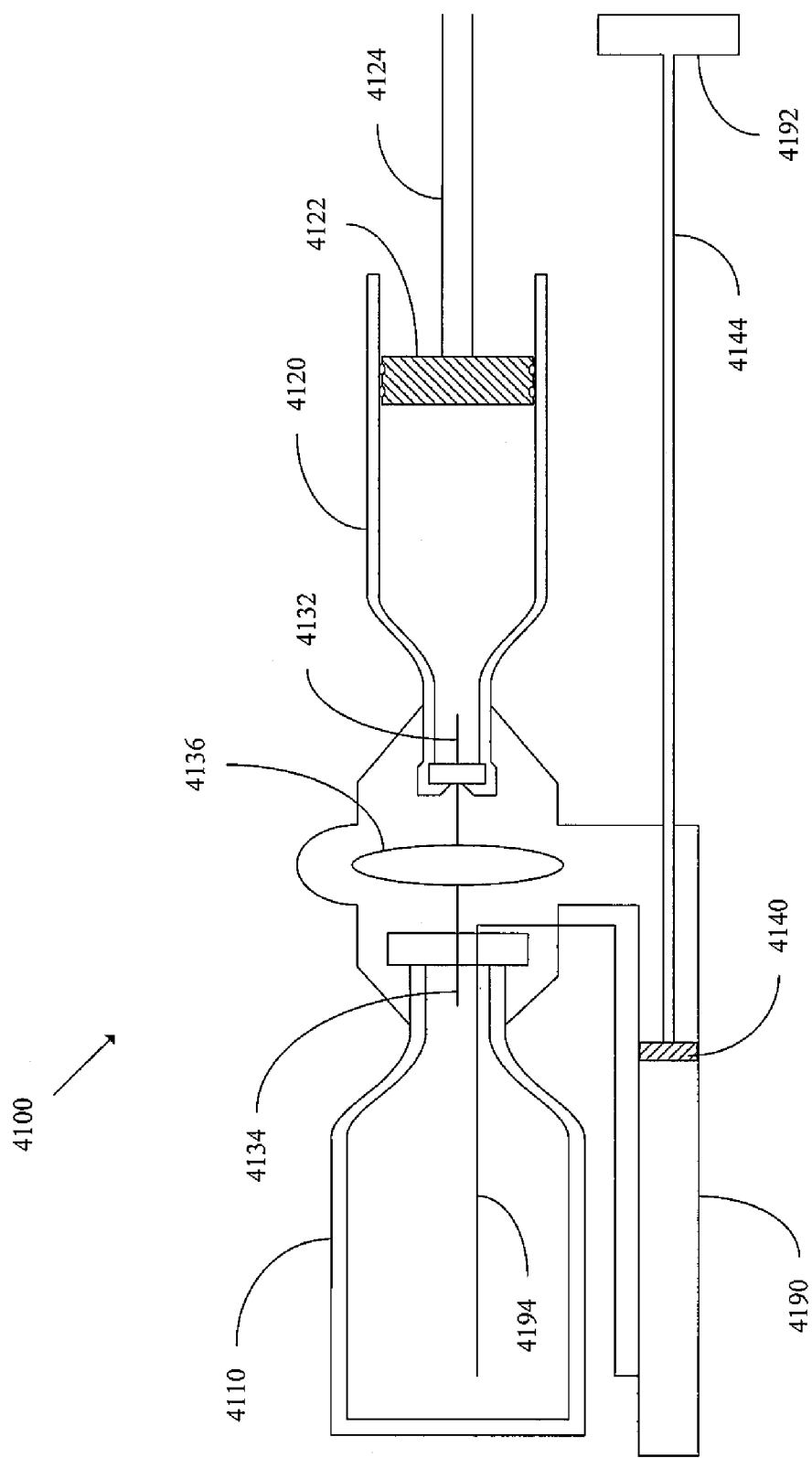
FIG. 85C illustrates a cross-sectional view of a system in accordance with an embodiment of the present invention.

FIG. 85C illustrates a cross-sectional side view of the system 4100 in accordance with another embodiment of the present invention. In the embodiment of FIG. 85C, the plunger arm 4144 includes a handle 4192 at an end of the plunger arm 4144. Also, in the embodiment of FIG. 85C, the system 4100 includes a pressure channel 4190 and an air path 4194. In the embodiment of FIG. 85C, the handle 4192 may be pressed to move the plunger head 4140 and create a pressure within the pressure channel 4190, which then pushes air through the air path 4194 to increase a pressure within the vial 4110 and, as a consequence, forces a fluidic medium from the vial 4110 to the reservoir 4120.

Figure 85D:
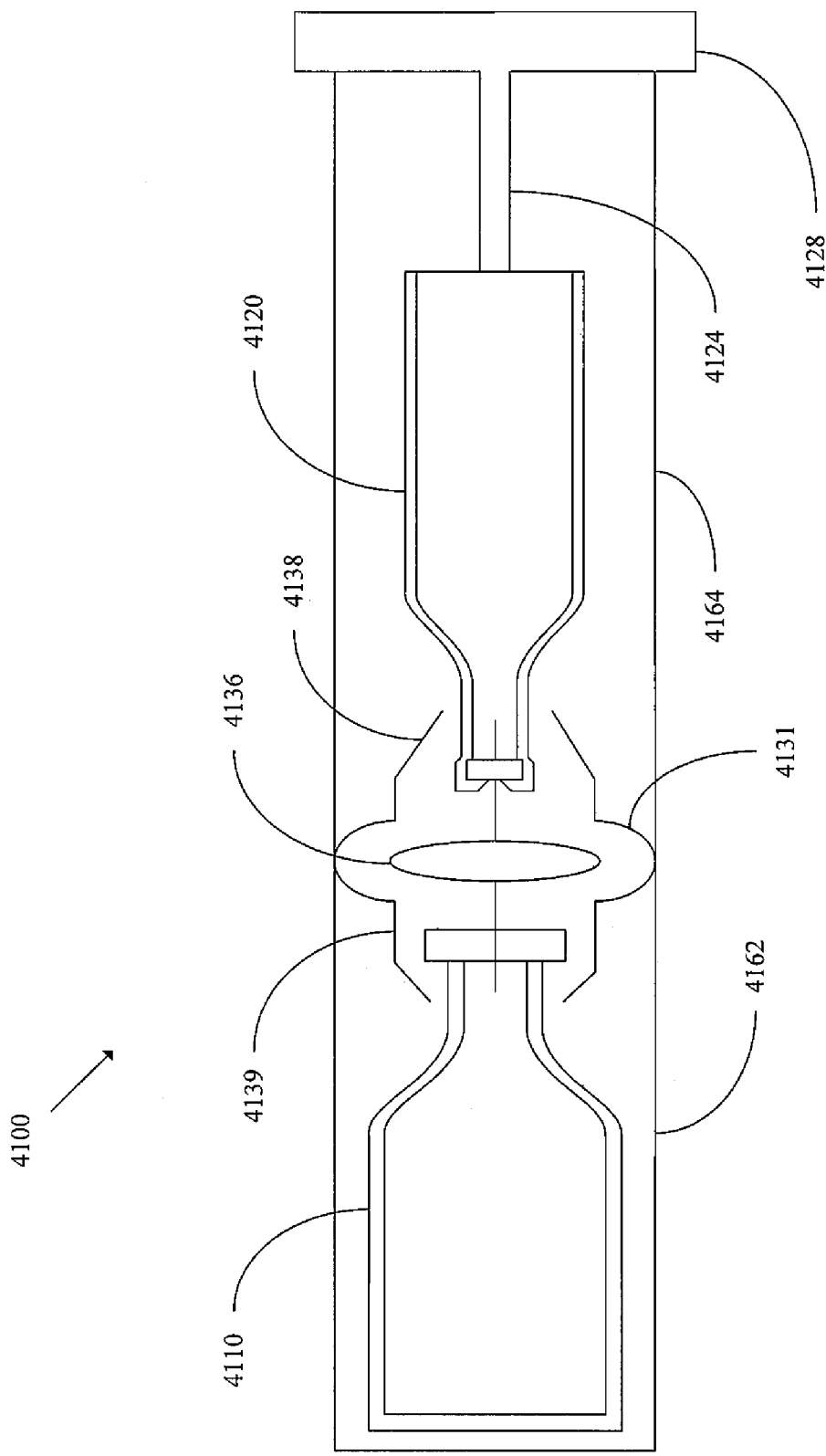
FIG. 85D illustrates a cross-sectional top view of a system in accordance with an embodiment of the present invention.
Figure 85E:
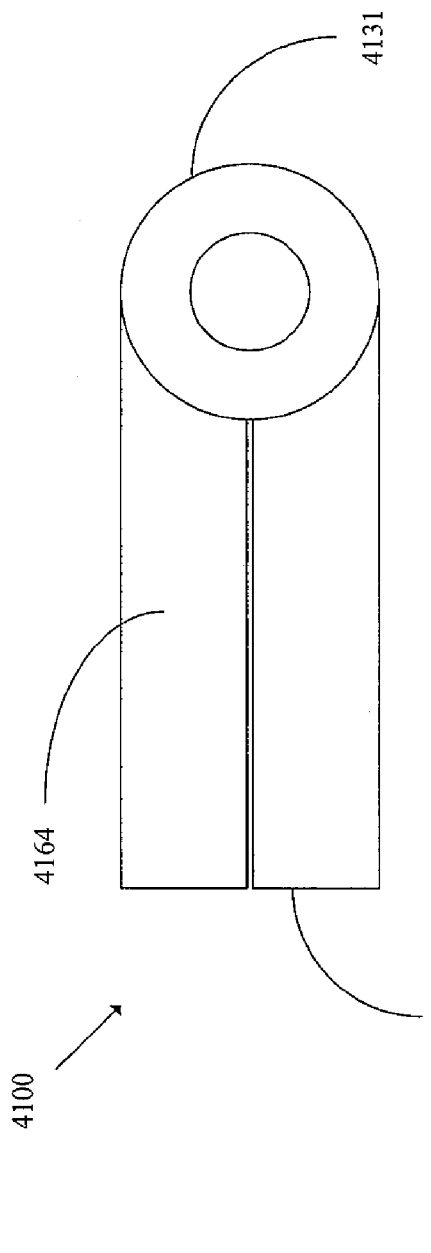
FIG. 85E illustrates a cross-sectional view of a system in accordance with an embodiment of the present invention.
Figure 85F:
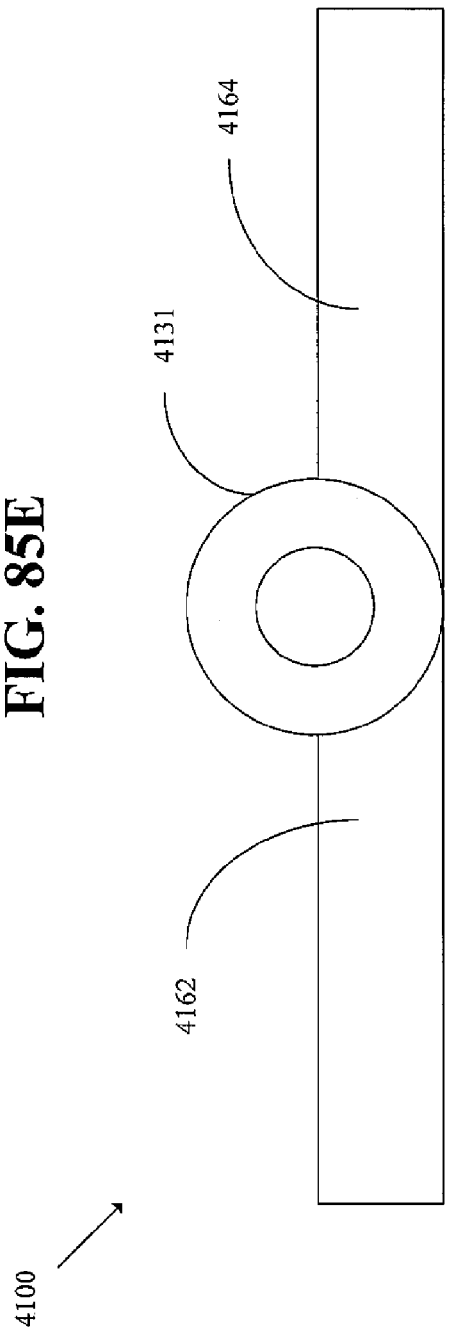
FIG. 85F illustrates a cross-sectional view of a system in accordance with an embodiment of the present invention.

FIG. 85D illustrates a cross-sectional top view of the system 4100 in accordance with an embodiment of the present invention. The system 4100 includes a first holding member 4162 for holding the vial 4110, and a second holding member 4164 for holding the reservoir 4120. A transfer guard 4131 that is part of the stand 4130 (refer to FIG. 85A) includes a first nest 4139 for holding the vial 4110 and a second nest 4138 for holding the reservoir 4120. FIG. 85E illustrates a cross-sectional side view of the system 4100 in accordance with an embodiment of the present invention in which the first holding member 4162 and the second holding member 4164 may be folded together around the transfer guard 4131. FIG. 85F illustrates a cross-sectional side view of the system 4100 of FIG. 85E in which the first holding member 4162 and the second holding member 4164 have been unfolded.

Figure 86A:
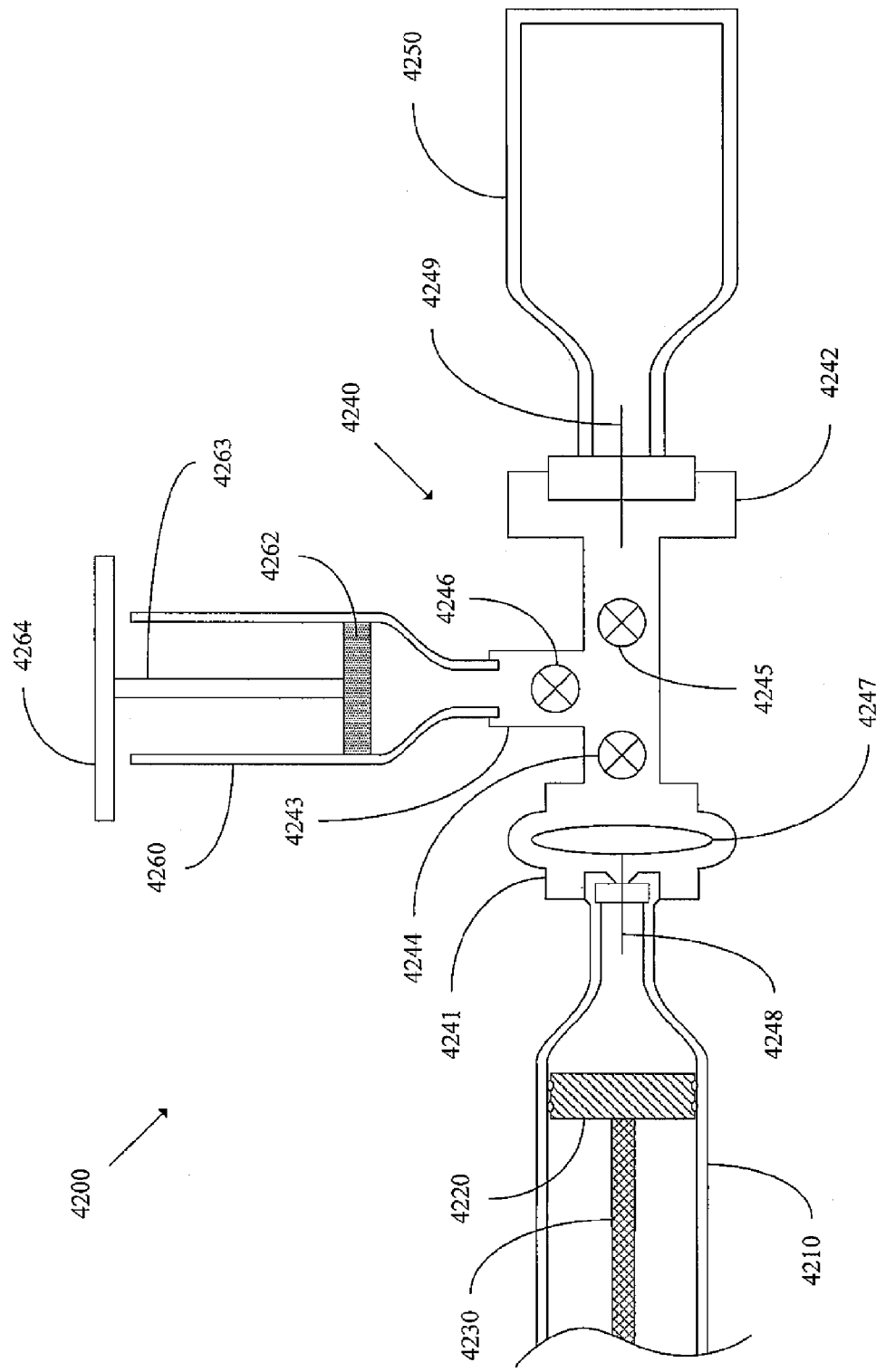
FIG. 86A illustrates a cross-sectional view of a system in accordance with an embodiment of the present invention.

FIG. 86A illustrates a cross-sectional view of a system 4200 in accordance with an embodiment of the present invention. The system 4200 includes a reservoir 4210, a plunger head 4220, a plunger arm 4230, a transfer guard 4240, a vial 4250, and a vacuum plunger 4260. The vial 4250 has a hollow interior for containing a fluidic medium. The reservoir 4210 has a hollow interior for containing a fluidic medium. The plunger head 4220 is located within the reservoir 4210 and is moveable within the reservoir 4210 to expand or contract an interior volume of the reservoir 4210. The plunger head 4220 is connected to the plunger arm 4230. The vacuum plunger 4260 includes a plunger head 4262, a plunger arm 4263 connected to the plunger head 4262, and a handle 4264 connected to the plunger arm 4263. The plunger head 4262 is moveable within a housing of the vacuum plunger to expand or contract an interior volume of the vacuum plunger 4260.

The transfer guard 4240 includes a reservoir nest 4241, a vial nest 4242, a vacuum plunger nest 4243, a first valve 4244, a second valve 4245, a third valve 4246, a filter 4247, a first needle 4248, and a second needle 4249. The reservoir nest 4241 is configured to be connected to the reservoir 4210, such that the first needle 4248 is inserted into the interior volume of the reservoir 4210. The vial nest 4242 is configured to be connected to the vial 4250, such that the second needle 4250 is inserted into an interior volume of the vial 4250. The vacuum plunger nest 4243 is configured to be connected to the vacuum plunger 4260. The first valve 4244 allows for a fluidic medium to flow into the reservoir 4210 when the first valve 4244 is open, and prevents a fluidic medium from flowing into the reservoir 4210 when the first valve 4244 is closed. The second valve 4245 allows for a fluidic medium to flow out of the vial 4250 when the second valve 4245 is open, and prevents a fluidic medium from flowing out of the vial 4250 when the second valve 4245 is closed. The third valve 4246 allows for a fluidic medium to flow into and out of the vacuum plunger 4260 when the third valve 4246 is open, and prevents a fluidic medium from flowing into or out of the vacuum plunger 4260 when the third valve is closed. The filter 4247 allows for filtering air from a fluidic medium.

A method in accordance with the present invention allows for filling the reservoir 4210 using the transfer guard 4240. In a first step of the method, the reservoir nest 4241 is connected to the reservoir 4210, the vial nest 4242 is connected to the vial 4250, and the vacuum plunger nest 4243 is connected to the vacuum plunger 4260. Also, in an initial position, the plunger head 4262 is depressed within the vacuum plunger 4260, and the plunger head 4220 is depressed within the reservoir 4210. Moreover, in an initial state, the first valve 4244, the second valve 4245, and the third valve 4246 are all closed. An example of the system 4200 in such a state is illustrated in FIG. 86A.

In a second step of the method, the second valve 4245 and the third valve 4246 are opened, and the handle 4264 is pulled to cause the plunger head 4262 to retract within a housing of the vacuum plunger 4260. FIG. 86B illustrates a cross-sectional view of the system 4200 in accordance with an embodiment of the present invention when the plunger head 4262 has been retracted within a housing of the vacuum plunger 4260. By retracting the plunger head 4262 within the housing of the vacuum plunger 4260 when the second valve 4245 and the third valve 4246 are open, a fluidic medium is caused to flow from the vial 4250 into an interior volume of the vacuum plunger 4260.

Figure 86C:
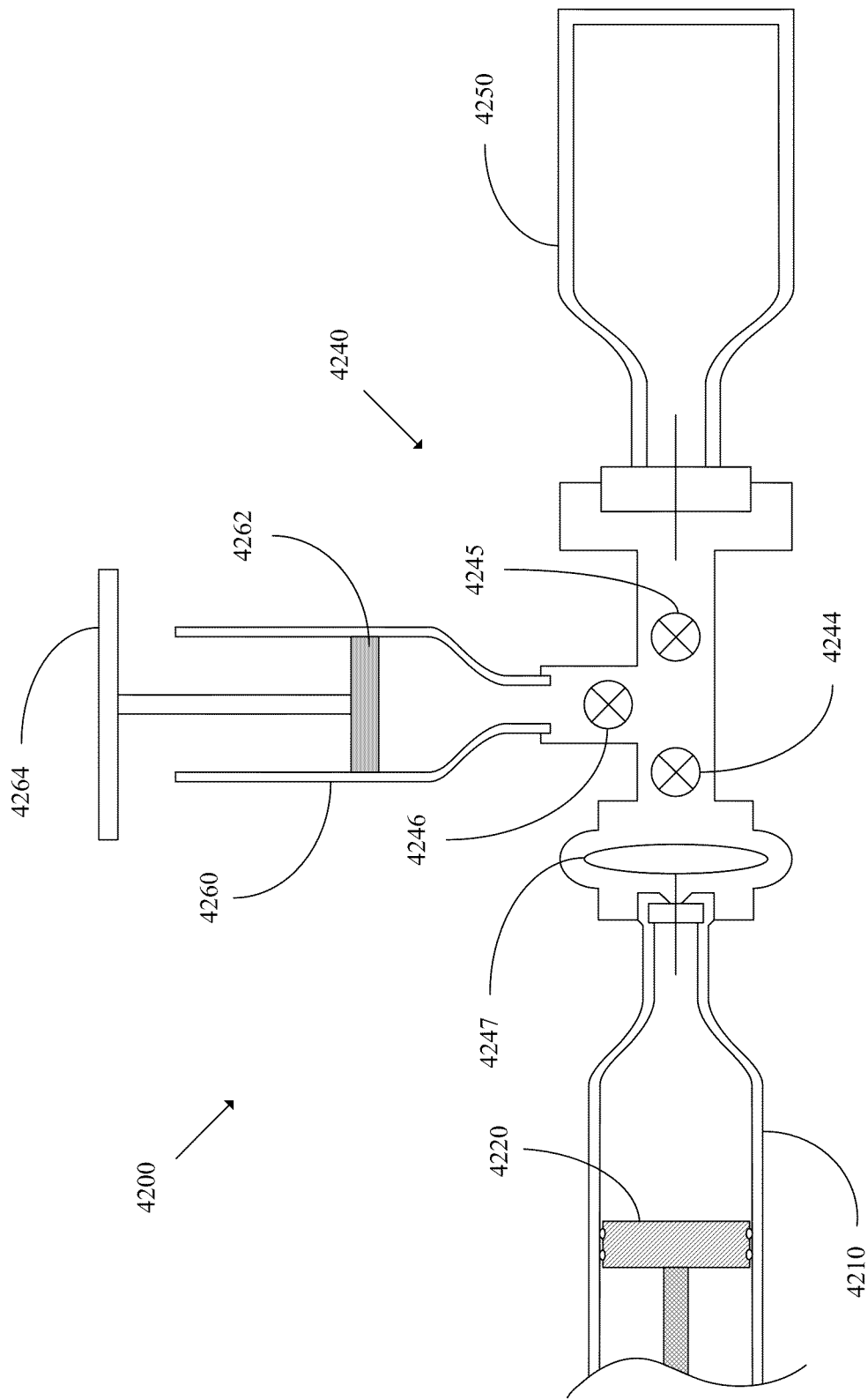
FIG. 86C illustrates a cross-sectional view of a system in accordance with an embodiment of the present invention.

In a third step of the method, the second valve 4245 is closed and the first valve 4244 is opened, and the handle 4264 is pushed to cause the plunger head 4262 to advance within the housing of the vacuum plunger 4260. FIG. 86C illustrates a cross-sectional view of the system 4200 in accordance with an embodiment of the present invention when the plunger head 4262 has been advanced within the housing of the vacuum plunger 4260. By advancing the plunger head 4262 within the housing of the vacuum plunger 4260 when the third valve 4246 and the first valve 4244 are open, a fluidic medium is caused to flow from the vacuum plunger 4260 into the interior volume of the reservoir 4210 while forcing the plunger head 4220 to retract within the reservoir 4210. The filter 4247 filters air bubbles out of the fluidic medium as the fluidic medium passes from the vacuum plunger 4260 to the reservoir 4210.

Therefore, embodiments of the present invention allow for incorporating a series of valves into a transfer guard and for using a hand operated vacuum plunger and a filter or membrane to filter out air bubbles. Moreover, embodiments of the present invention allow for a two step degassing process in which a first step involves vacuum aspiration and a second step involves pushing a fluidic medium across a filter. Thus, embodiments of the present invention allow for filling a reservoir by pushing a fluidic medium across a filter and into the reservoir. In some embodiments, cavitation is used to degas a fluidic medium.

Figure 87A:
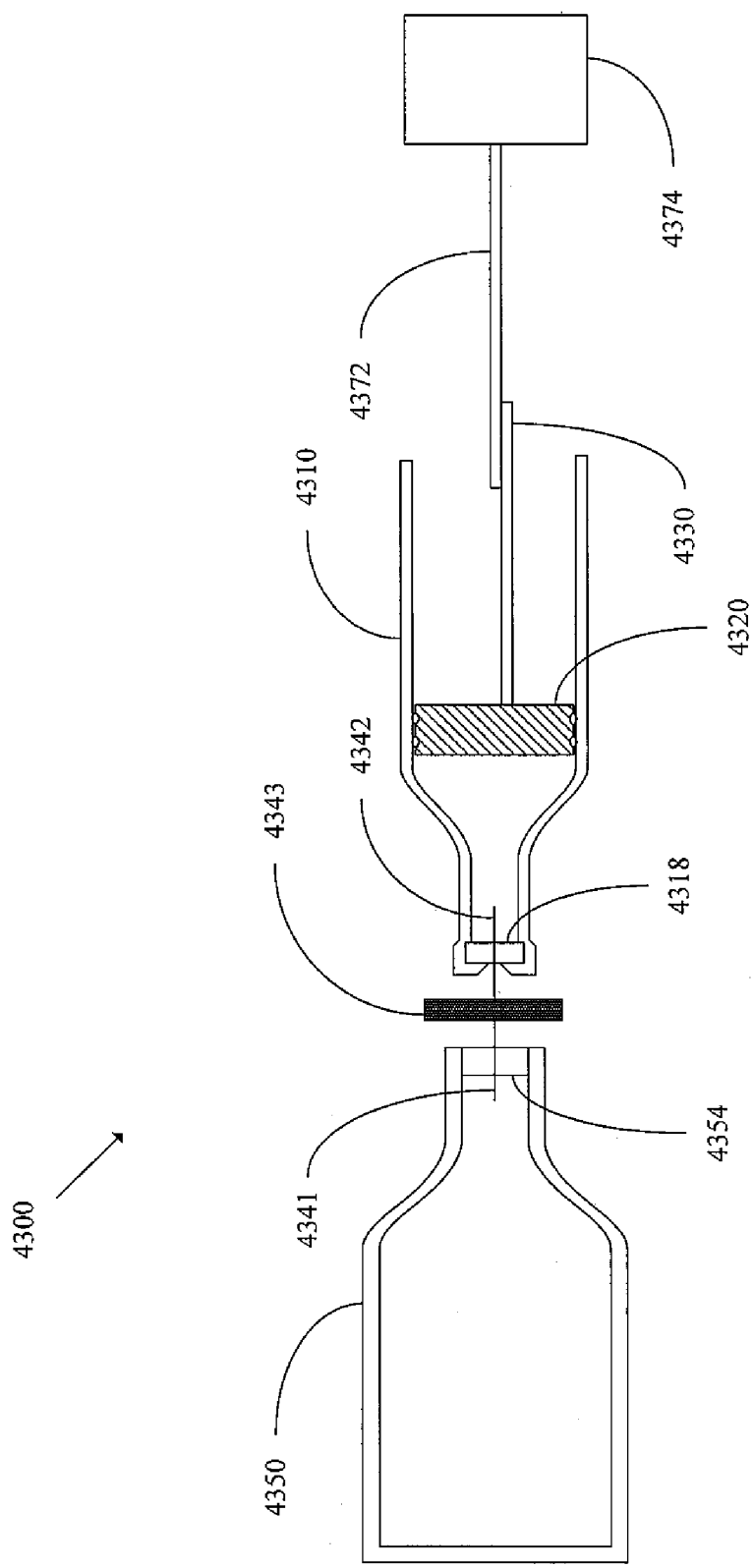
FIG. 87A illustrates a cross-sectional view of a system in accordance with an embodiment of the present invention.

FIG. 87A illustrates a cross-sectional view of a system 4300 in accordance with an embodiment of the present invention. The system 4300 includes a reservoir 4310, a plunger head 4320, a plunger arm 4330, a vial 4350, a first needle 4341, a second needle 4342, a filter 4343, a driving shaft 4372, and a motor 4374. The vial 4350 has a hollow interior for containing a fluidic medium, and the vial 4350 includes a septum 4354. The reservoir 4310 has a hollow interior for containing a fluidic medium, and the reservoir 4310 includes a septum 4318. The plunger head 4320 is located within the reservoir 4310 and is moveable within the reservoir 4310 to expand or contract an interior volume of the reservoir 4310. The plunger head 4320 is connected to the plunger arm 4330. The plunger arm 4330 may include, for example, a half-nut, a quarter nut, a U-shaped nut, or the like, that is able to engage with the drive shaft 4372. The drive shaft 4372 may be, for example, a partial screw or the like. The drive shaft 4372 is connected to the motor 4374, and the motor 4374 is able to be controlled to turn the drive shaft 4372 in a clockwise manner and in a counter-clockwise manner.

When the reservoir 4310 is connected to a fluid path for providing a fluidic medium to a body of a user, the motor 4374 may be controlled to turn the drive shaft 4372 in a certain direction to move the plunger arm 4330 and advance the plunger head 4320 within the reservoir 4310. During a filling process, the motor 4374 may be controlled to turn the drive shaft 4372 in a reverse direction from the certain direction so as to move the plunger arm 4330 and retract the plunger head 4320 within the reservoir 4310. The first needle 4341 is able to pierce the septum 4354 of the vial 4350 and the second needle 4342 is able to pierce the septum 4318 of the reservoir 4310, such that a fluid path may be established from the vial 4350 to the reservoir 4310 through the filter 4343. The filter 4343 allows for substantially removing air bubbles from a fluidic medium that passes from the vial 4350 to the reservoir 4310.

Figure 87B:
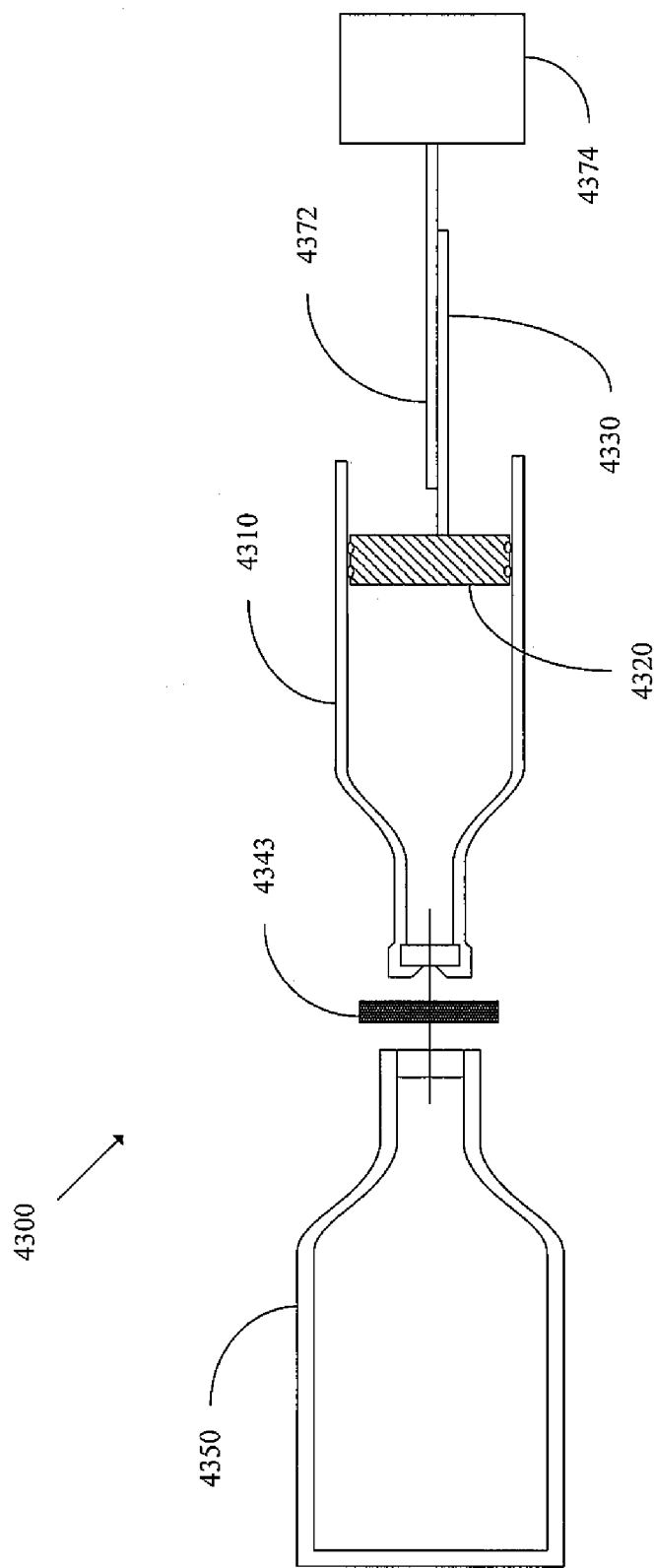
FIG. 87B illustrates a cross-sectional view of a system in accordance with an embodiment of the present invention.

Thus, by turning the drive shaft 4372 in a specified direction, the plunger head 4320 is able to be retracted within the reservoir 4310 and, thus, a fluidic medium may be drawn from the vial 4350 into the reservoir 4310 by turning the drive shaft 4372 in the specified direction. In various embodiments, the same motor 4374 and drive shaft 4372 are used for both filling the reservoir 4310 and expelling a fluidic medium from the reservoir 4310 to a user. FIG. 87B illustrates a cross-sectional view of the system 4300 in accordance with an embodiment of the present invention in which the drive shaft 4372 has been turned by the motor 4374 to cause the plunger head 4320 to retract within the reservoir 4310. In various embodiments, the plunger arm 4330 is configured to provide a positive engagement with the drive shaft 4372 regardless of a direction of turning of the drive shaft 4372. Also, in various embodiments, more energy is provided to the motor 4374 when turning the drive shaft 4372 to retract the plunger head 4320 than when turning the drive shaft 4372 to advance the plunger head 4320, so as to allow for a faster retraction motion to fill the reservoir 4310.

Figure 88:
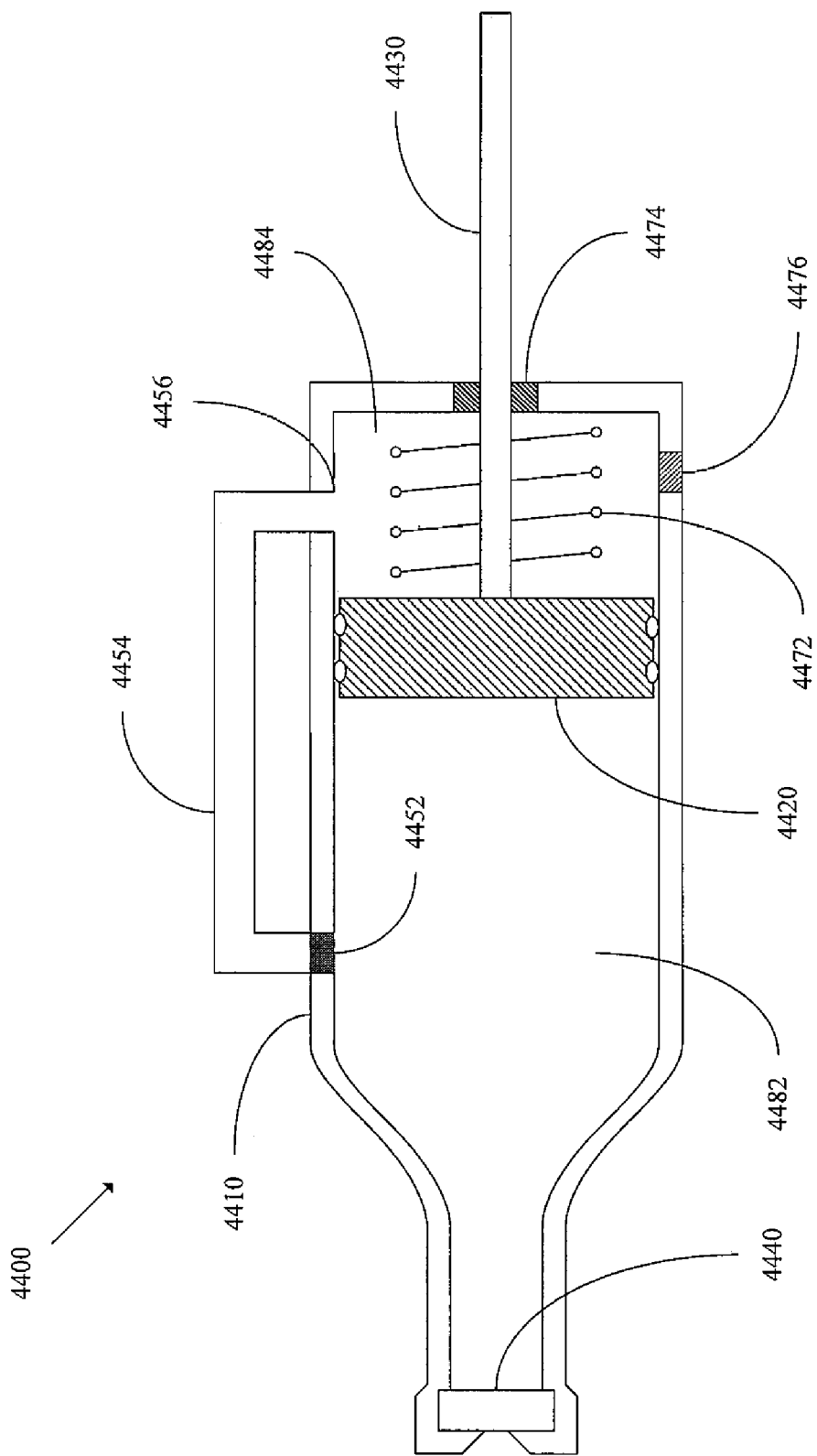
FIG. 88 illustrates a cross-sectional view of a system in accordance with an embodiment of the present invention.

FIG. 88 illustrates a cross-sectional view of a system 4400 in accordance with an embodiment of the present invention. The system 4400 includes a reservoir 4410, a plunger head 4420, a plunger arm 4430, a septum 4440, a membrane 4452, a channel 4454, a spring 4472, a seal 4474, and a valve 4476. The reservoir 4410 has a interior volume 4482 for containing a fluidic medium between the plunger head 4420 and the septum 4440. The reservoir 4410 also has a chamber 4484 on an opposite side of the plunger head 4420 from the interior volume 4482. The plunger head 4420 may be advanced within the reservoir 4410 to expel a fluidic medium from the reservoir 4410. The spring 4472 is connected between a surface of the reservoir 4410 and the plunger head 4420 in the chamber 4484. The seal 4474 creates a substantially air-tight seal around the plunger arm 4430 in a location where the plunger arm 4430 exits the chamber 4484. The valve 4476 allows for a vacuum to be applied to the chamber 4484. The membrane 4452 is located in an opening in a wall of the reservoir 4410 and air is able to pass from the interior volume 4482 through the membrane 4452 and through the channel 4454 into the chamber 4484. The membrane 4452 may include, for example, a hydrophobic material, or the like.

In some embodiments, a vacuum is applied to the chamber 4484 through the valve 4476 to create a vacuum in the chamber 4484, and then the valve 4476 is closed. The membrane 4452 and the channel 4454 allow for a transfer of air bubbles from a fluidic medium side of the plunger head 4420 to a back side of the plunger head 4420. The membrane 4452 substantially prevents a loss of fluid through the channel 4454. A slight vacuum in the chamber 4484 and a backing of the plunger head 4420 by the spring 4472 promote the migration of air bubbles from the interior volume 4482 to the chamber 4484 through the channel 4454 without greatly affecting operational forces. Thus, embodiments of the present invention allow for a vacuum pull in a chamber behind a plunger head to pull air out of an interior volume of a reservoir through a channel from the interior volume to the chamber. Such embodiments may allow for continuous degassing of a fluid in the interior volume of the reservoir.

Figure 89:
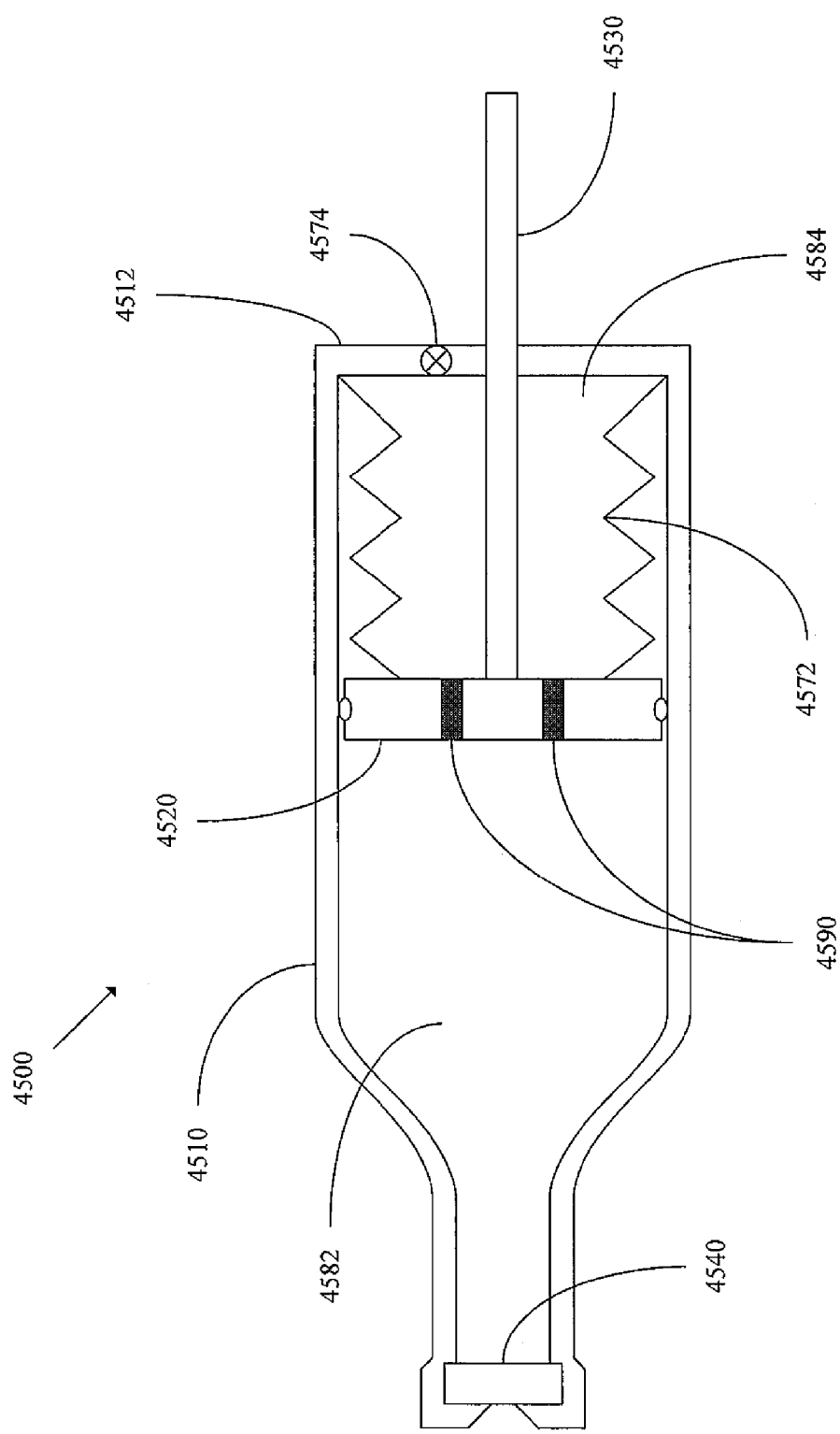
FIG. 89 illustrates a cross-sectional view of a system in accordance with an embodiment of the present invention.

FIG. 89 illustrates a cross-sectional view of a system 4500 in accordance with an embodiment of the present invention. The system 4500 includes a reservoir 4510, a plunger head 4520, a plunger arm 4530, a septum 4540, a bellows member 4572, a one-way valve 4574, and one or more membranes 4590. The plunger head 4520 is connected to the plunger arm 4530, and the plunger head 4520 may slide within the reservoir 4510. The reservoir 4510 has an interior volume 4582 for containing a fluidic medium between the plunger head 4520 and the septum 4540, where the septum 4540 is located at an exit port of the reservoir 4510. The bellows member 4572 is connected between a back surface 4512 of the reservoir 4510 and the plunger head 4520. The bellows member 4572 is connected to a backside of plunger head 4520 that is opposite a side of the plunger head 4520 that contacts a fluidic medium. The bellows member 4572 is sealed to the plunger head 4520. The one or more membranes 4590 are located on a face of the plunger head 4520 that comes in contact with a fluidic medium, and the one or more membranes 4590 lead to channels through the plunger head 4520 that extend from the face of the plunger head 4520 to the backside of the plunger head 4520.

The one or more membranes 4590 include, for example, a hydrophobic material, or the like, that allows for air to pass through, but substantially prevents a passage of a fluid. Thus, air is able to pass from the interior volume 4582 of the reservoir 4510 through the one or more membranes 4590 and through the plunger head 4520 into an area 4584 within the bellows member 4572. The bellows member 4572 is able to expand or contract with a movement of the plunger head 4520. As the plunger head 4520 is moved forward to deliver a fluidic medium, a vacuum is generated in the bellows member 4572 and, thus, air bubbles or vapor are drawn through the one or more membranes 4590 and into the area 4584 within the bellows member 4572. When the reservoir 4510 is completely filled, the bellows member 4572 is fully compressed, and the air in the bellows member 4572 is forced through the one-way valve 4574.

Figure 90:
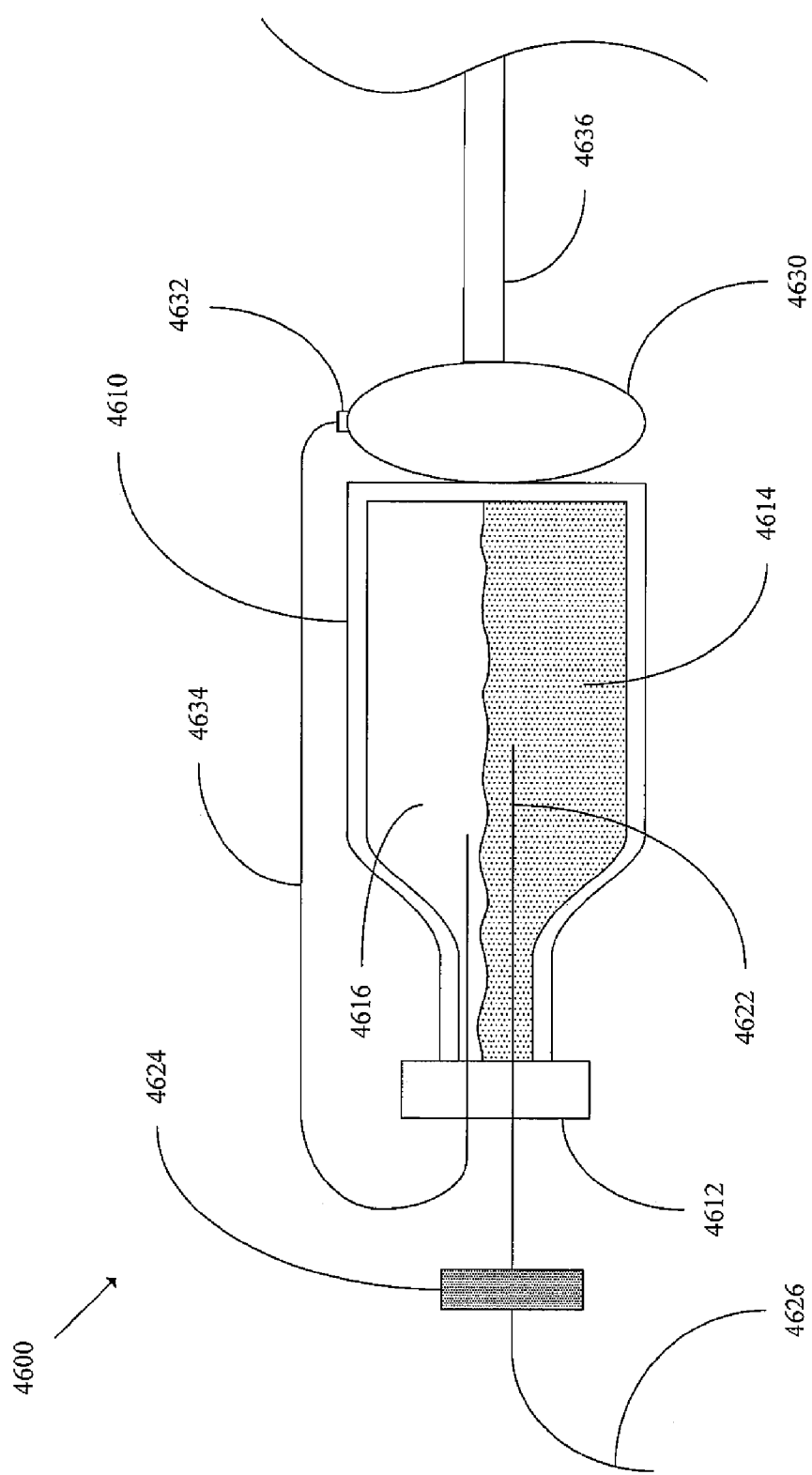
FIG. 90 illustrates a cross-sectional view of a system in accordance with an embodiment of the present invention.

FIG. 90 illustrates a cross-sectional view of a system 4600 in accordance with an embodiment of the present invention. The system 4600 includes a vial 4610, an air sack 4630, a one-way valve 4632, an air line 4634, a drive shaft 4636, a fluid line 4622, a filter 4624, and an insertion line 4626. The vial 4610 contains a fluidic medium 4614 within a housing of the vial 4610. An air space is provided in the vial 4610 in an area 4616 above the fluidic medium 4614. The fluid line 4622 may be inserted into the vial 4610 through a septum 4612 of the vial 4610. One end of the air line 4634 is connected to the one-way valve, and another end of the air line 4634 is inserted into the area 4616 of the vial 4634 above the fluidic medium 4614. The one-way valve allows for air to be pushed out of the air sack 4630 and through the air line 4634 into the area 4616 in the vial 4610.

The drive shaft 4636 allows for compressing the air sack 4630 so as to cause air to be pushed through the one-way valve 4632 and through the air line 4634. One end of the fluid line 4622 is positioned within the fluidic medium 4614 in the vial 4610, and another end of the fluid line 4622 is connected to the filter 4624. The filter 4624 allows for filtering air bubbles out of a fluidic medium that passes from the fluid line 4622 to the insertion line 4626 through the filter 4624. During operation, the drive shaft 4636 compresses the bulb or air sack 4630 to force air into the vial 4610 through the air line 4634. The air that exits the air line 4634 in the vial 4610 is provided into the area 4616 that is above the fluidic medium 4614, so the air from the air line 4634 is provided into the vial 4610 without percolating through the fluidic medium 4614. An increase in pressure caused by air from the air line 4634 forces the fluidic medium 4614 through the fluid line 4622 to the filter 4624 and on to the insertion line 4626. In various embodiments, the insertion line 4626 is inserted into a reservoir (not shown in FIG. 90), such that the reservoir is able to be filled from the vial 4610. Also, in various alternate embodiments, the fluidic medium 4614 may be delivered directly through the fluid line 4622 without passing through the filter 4624.

Figure 91:
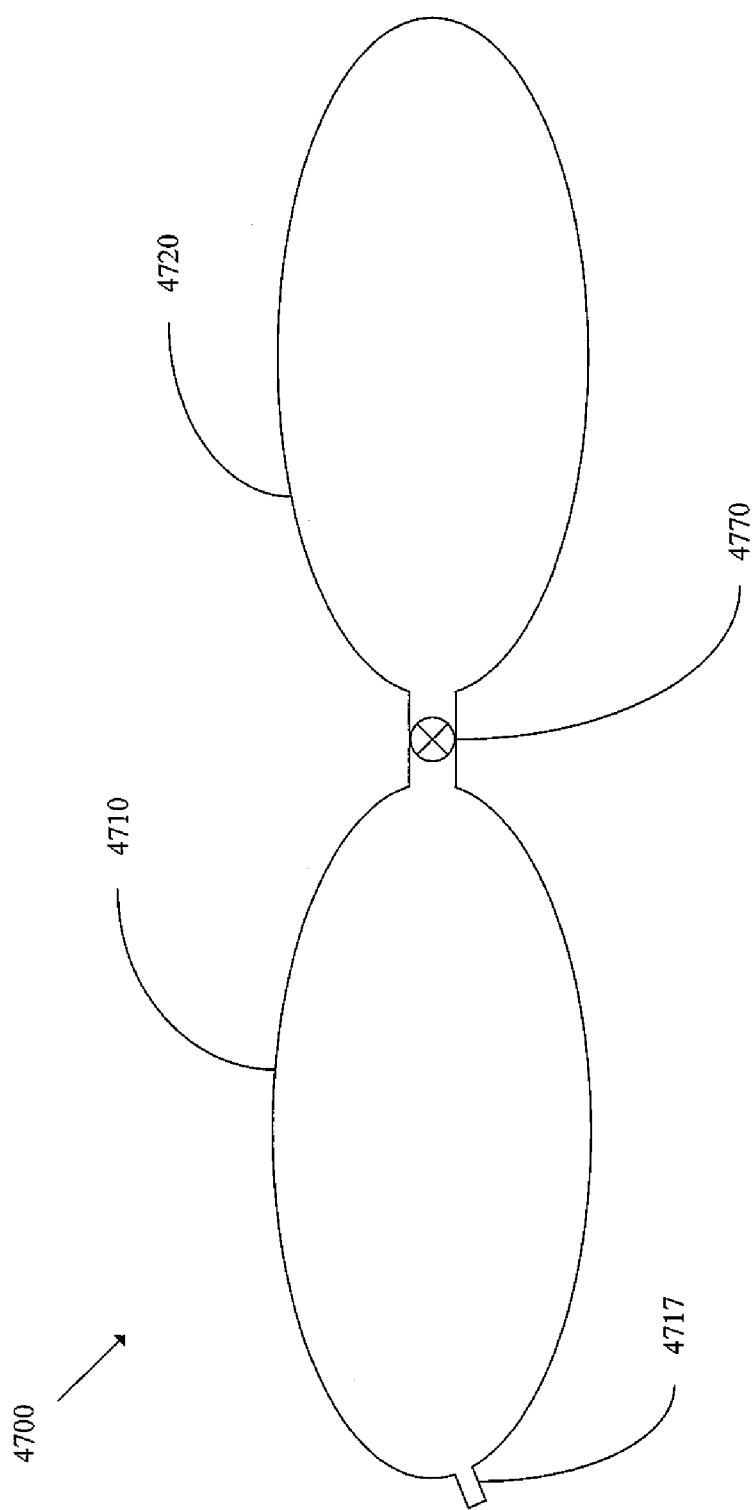
FIG. 91 illustrates a cross-sectional view of a system in accordance with an embodiment of the present invention.

FIG. 91 illustrates a system 4700 in accordance with an embodiment of the present invention. The system 4700 includes a pressure sack 4720, a one-way valve 4770, a reservoir sack 4710, and an outlet path 4717. The system 4700 is configured such that when the reservoir sack 4710 contains a fluidic medium, the pressure sack 4720 may be used to force air through the one-way valve 4770 and, thus, cause the fluidic medium to be expelled from the reservoir sack 4710 through the outlet path 4717.

Figure 92:
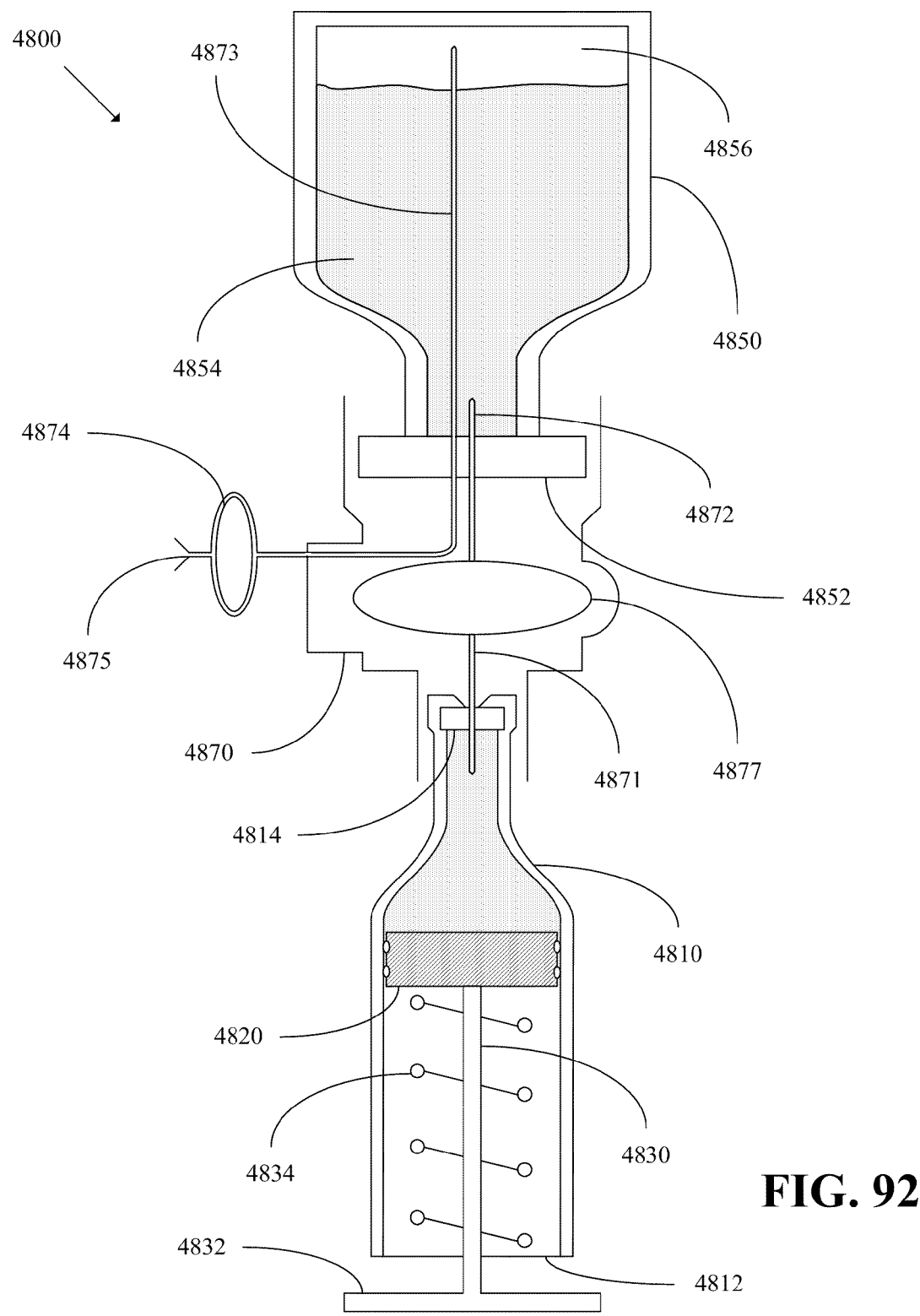
FIG. 92 illustrates a cross-sectional view of a system in accordance with an embodiment of the present invention.

FIG. 92 illustrates a cross-sectional view of a system 4800 in accordance with an embodiment of the present invention. The system 4800 includes a reservoir 4810, a plunger head 4820, a plunger arm 4830, a handle 4832, a spring 4834, a septum 4814, a first needle 4871, a second needle 4872, a long needle 4873, a hydrophobic membrane 4874, an air inlet 4875, a vial 4850, a septum 4852, a transfer guard 4870, and a filter 4877. The system 4800 is configured such that when the vial 4850 is inverted and the long needle 4873 is inserted into the vial 4850, the long needle 4873 vents to atmosphere from the air inlet 4875 to a headspace 4856 in the vial 4850 above an area 4854 of the vial 4850 that contains the fluidic medium. Thus, by using the long needle 4873 to vent the headspace 4856 of the vial 4850 to atmosphere, there is no percolation of air through the fluidic medium in the vial 4850.

The hydrophobic membrane 4874 substantially reduces an addition of water vapor through the long needle 4873 to the vial 4850. The system 4800 is configured such that as a fluidic medium is drawn into the reservoir 4810, it passes through the filter 4877, which may include a membrane, to filter out air bubbles and/or degas the fluidic medium. The venting with the long needle 4873 eases filling and may eliminate a need for a current first step in a filling processes that requires forcing air into the vial 4850. Thus, the long needle 4873 in the vial 4850 provides for atmospheric pressure in the headspace 4856 of the vial 4850. Also, water vapor is restricted from entering the vial 4850 through the long needle 4873 by the hydrophobic membrane 4874. Equalizing a pressure of the vial 4850 with an atmospheric pressure helps to prime the vial 4850. The spring 4834 provides a retaining force behind the plunger head 4820 in the reservoir 4810. Thus, the system 4800 provides for a vial pressure equalizer using the long needle 4873, with a spring 4834 to assist movement of the plunger head 4820, and a filter 4877 to filter air bubbles out of a fluidic medium as the fluidic medium is filled into the reservoir 4810.

Figure 93:
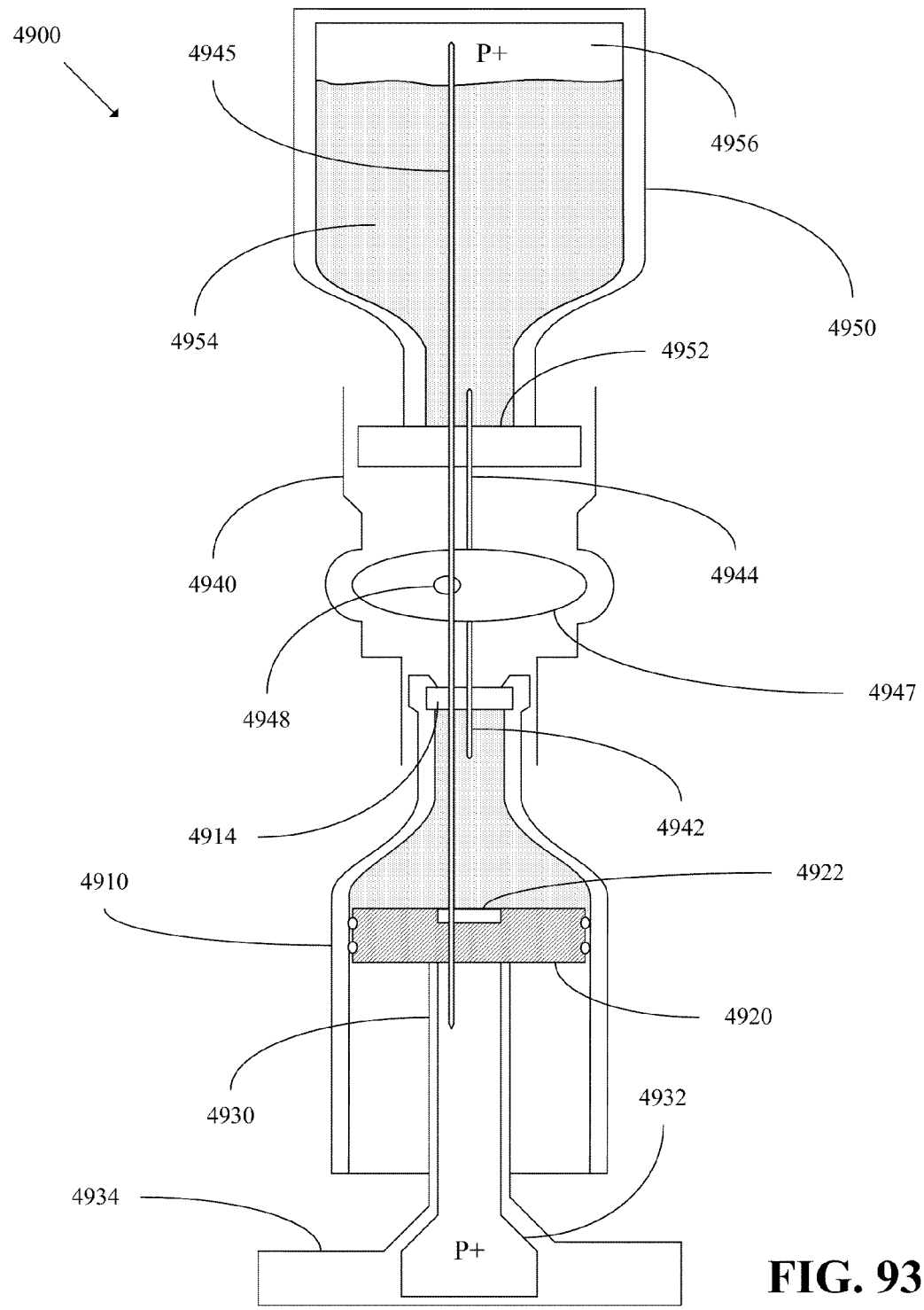
FIG. 93 illustrates a cross-sectional view of a system in accordance with an embodiment of the present invention.

FIG. 93 illustrates a cross-sectional view of a system 4900 in accordance with an embodiment of the present invention. The system 4900 includes a reservoir 4910, a plunger head 4920, a plunger head septum 4922, a plunger rod 4930, a handle 4934, a pressurized vessel 4932, a reservoir septum 4914, a first short needle 4942, a second short needle 4944, an air filter 4947, a hydrophobic membrane 4948, a transfer guard 4940, a vial 4950, a vial septum 4952, and a long needle 4945. The vial 4950 has a headspace 4956 that is above a fluidic medium 4954 within the vial 4950.

The pressurized vessel 4932 contains air under pressure and is located within the plunger rod 4930 and the handle 4934. The long needle 4945 penetrates the plunger head septum 4922, the reservoir septum 4914, and the vial septum 4952 to provide an air path between the pressurized vessel 4932 and the headspace 4956 in the vial 4950. The hydrophobic membrane 4948 restricts fluid and vapor from passing through the long needle 4945. The first short needle 4942, the filter 4947, and the second short needle 4944 provide a fluid path from the vial 4950 to the reservoir 4910. Thus, air passes through the long needle 4945 from the pressurized vessel 4932 to the headspace 4956 in the vial 4950, and the fluidic medium 4954 in the vial 4950 is forced out of the vial 4950 due to the pressure from the pressurized vessel 4932, and the fluidic medium 4954 flows from the vial 4950 through the second short needle 4944, the filter 4947, and the first short needle 4942 to the reservoir 4910. The filter 4947 allows for filtering air bubbles from the fluidic medium as the fluidic medium passes from the vial 4950 to the reservoir 4910. In various embodiments, the pressurized vessel 4932 is contained entirely within the plunger rod 4930.

Figure 94:
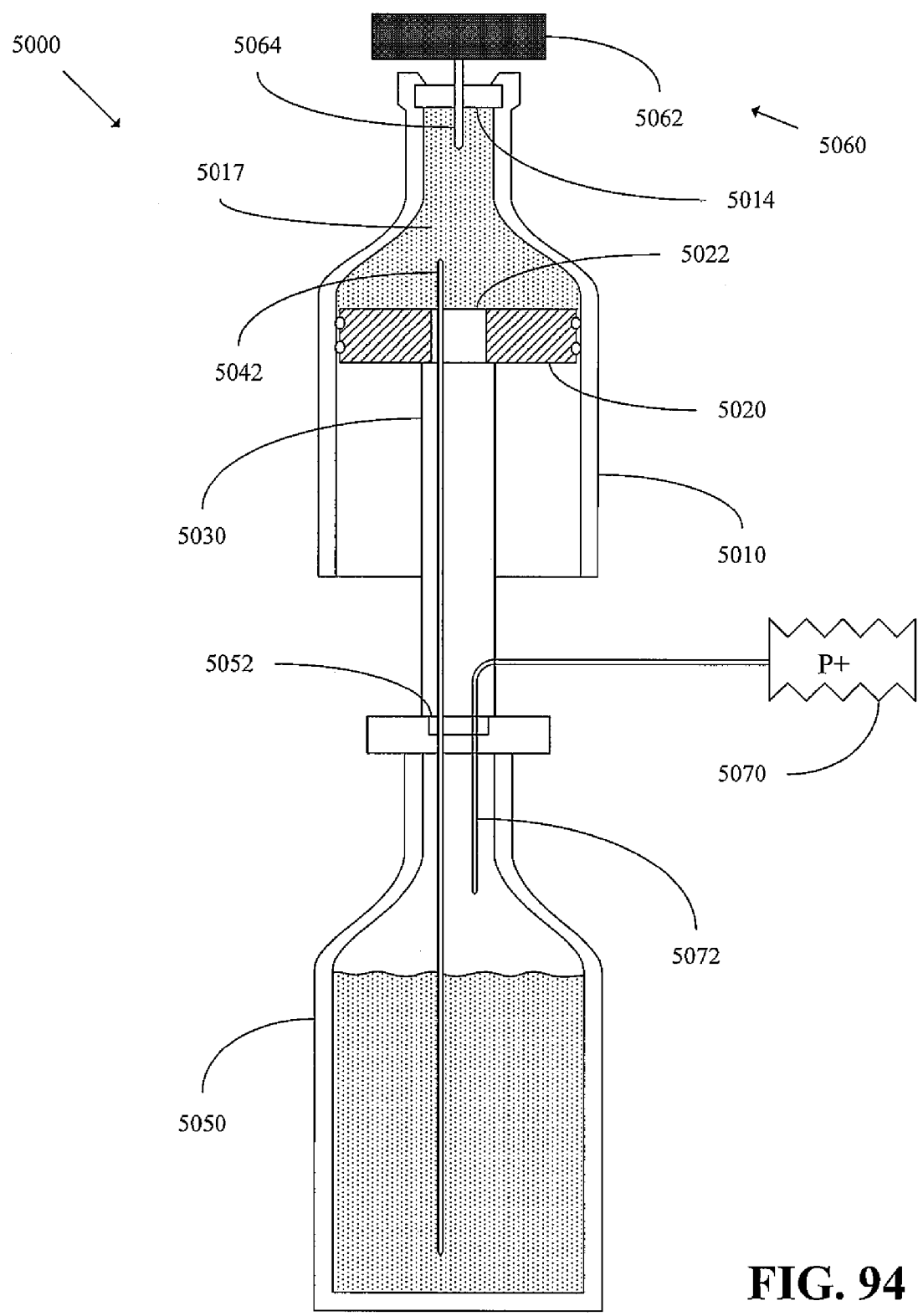
FIG. 94 illustrates a cross-sectional view of a system in accordance with an embodiment of the present invention.

FIG. 94 illustrates a cross-sectional view of a system 5000 in accordance with an embodiment of the present invention. The system 5000 includes a reservoir 5010, a plunger head 5020, a plunger head septum 5022, a reservoir septum 5014, a short needle 5064, a hydrophobic filter 5062, a plunger arm 5030, a vial 5050, a vial septum 5052, a bellows 5070, a needle 5072, and a long needle 5042. The reservoir 5010 has an interior volume 5017 for holding a fluidic medium between the plunger head 5020 and the septum 5014. The plunger head 5020 is moveable within the reservoir 5010. One end of the short needle 5064 is inserted through the reservoir septum 5014, and another end of the short needle 5064 is connected to the hydrophobic membrane 5062.

The vial 5050 is able to remain upright during a filling processes when a fluidic medium is transferred from the vial 5050 to the reservoir 5010. One end of the needle 5072 is connected to the bellows 5070, and another end of the needle 5072 pierces the vial septum and is positioned in a headspace within the vial 5050. The long needle 5042 is positioned to run from a lower region of the vial 5050 through the vial septum 5052 and through the plunger arm 5030, and through the plunger head septum 5022 into the interior volume 5017 of the reservoir 5010. In various embodiments, the plunger head septum 5022 may be at an end of a channel through a center of the plunger head 5020. Thus, the long needle 5042 is able to pass from a backside of the plunger head 5020 and into the interior volume 5017 of the reservoir 5010. The short needle 5064 allows for venting air through the hydrophobic membrane 5062, and the hydrophobic membrane substantially prevents a loss of a fluidic medium through the short needle 5064 during a filling process.

During a filling process, the bellows 5070 is compressed to force air through the needle 5072 and into the vial 5050. An increase pressure in the vial 5050 due to the air from the bellows 5070 forces a fluidic medium from the vial 5050 up the long needle 5042 and into the interior volume 5017 of the reservoir 5010. In various embodiments, during the filling processes, the plunger head 5020 is held stationary, but the reservoir 5010 is allowed to move upward with respect to the plunger head 5020 so as to increase a volume of the interior volume 5017 and allow for a fluidic medium to flow into the interior volume 5017 from the vial 5050 when the bellows 5070 is compressed.

Figure 95:
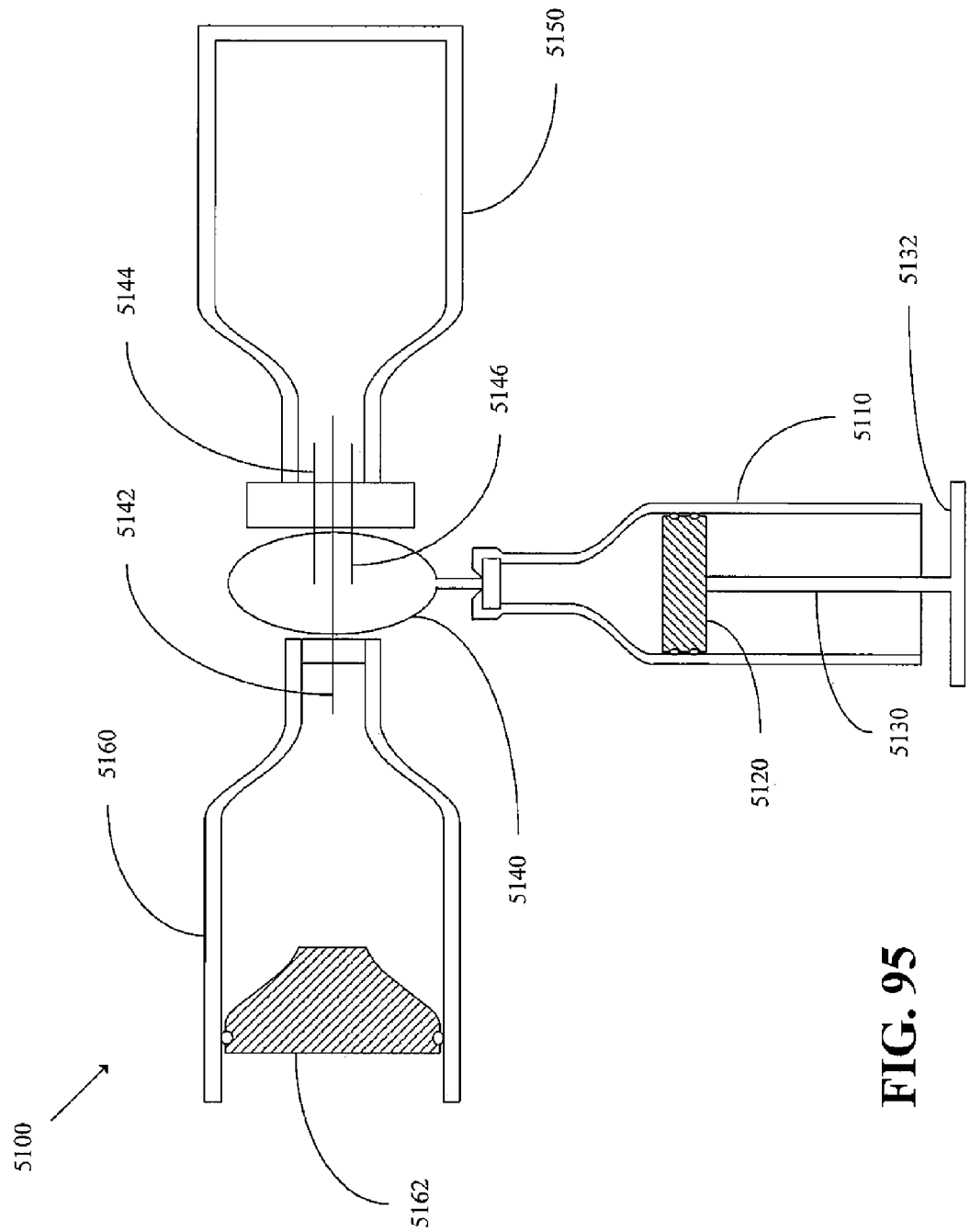
FIG. 95 illustrates a cross-sectional view of a system in accordance with an embodiment of the present invention.

FIG. 95 illustrates a cross-sectional view of a system 5100 in accordance with an embodiment of the present invention. The system 5100 includes a reservoir 5110, a plunger head 5120, a plunger arm 5130, a handle 5132, a vial 5150, a pressure source 5160, a piston 5162, an air needle 5142, a first fluid needle 5144, a second fluid needle 5146, and a filter 5140. The piston 5162 is moveable within the pressure source 5160 to generate pressure. The air needle 5142 provides a path for air to pass from the pressure source 5160 to an interior of the vial 5150. The vial 5150 contains a fluidic medium. The vial 5150 is connected to the filter 5140 by the first fluid needle 5144 and the second fluid needle 5146. The filter is connected to a port of the reservoir 5110. The reservoir 5110 has an interior volume for holding a fluidic medium. The plunger head 5120 is able to slide within the reservoir 5110.

During a filling operation with the system 5100, the piston 5162 is advanced within the pressure source 5160 to force air through the air needle 5142 and into the vial 5150. The increased pressure in the vial 5150 due to the pressure from the pressure source causes a fluidic medium in the vial 5150 to be expelled through the first fluid needle 5144 and the second fluid needle 5146 to the filter 5140. The filter 5140 filters air bubbles out of the fluidic medium, and then the fluidic medium fills into the interior volume of the reservoir 5110. Thus, in various embodiments, a fluidic medium or solution, such as insulin, is forced across a filter during filling, and the fluidic medium is pushed into a reservoir rather than being pulled into the reservoir. Also, while the system 5100 is illustrated as a multiple needle design with a first fluid needle 5144 and a second fluid needle 5146, it should be appreciated that, in various embodiments, more than two fluid needles may be used between the vial 5150 and the filter 5140 and that, in various other embodiments, a single fluid needle may be used between the vial 5150 and the filter 5140.

Figure 96:
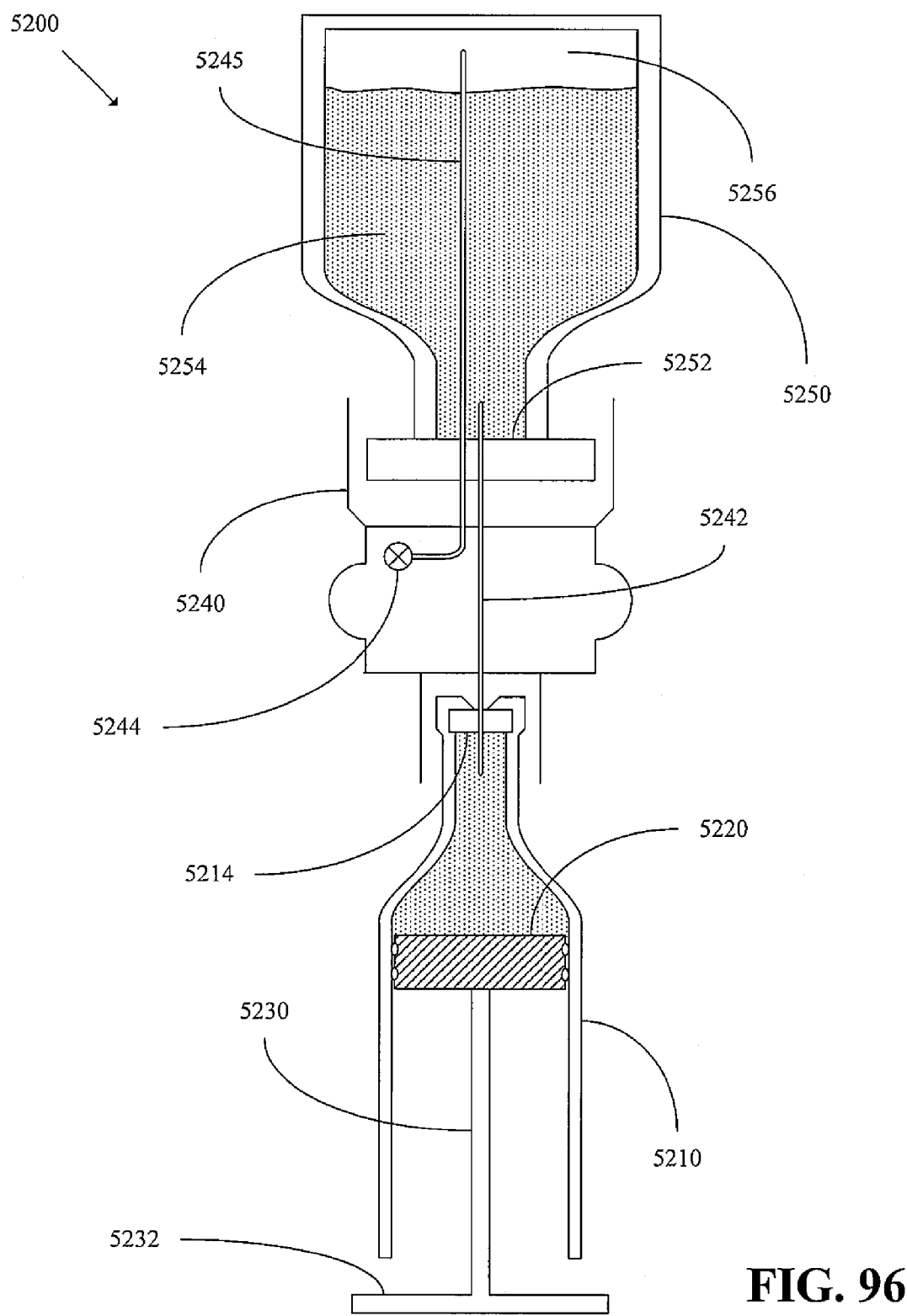
FIG. 96 illustrates a cross-sectional view of a system in accordance with an embodiment of the present invention.

FIG. 96 illustrates a cross-sectional view of a system 5200 in accordance with an embodiment of the present invention. The system 5200 includes a reservoir 5210, a plunger head 5220, a plunger arm 5230, a handle 5232, a vial 5250, and a transfer guard 5240. The transfer guard 5240 includes a first needle 5242, a second needle 5245, and a pressure valve 5244. The vial 5250 contains a fluidic medium 5254. The reservoir 5210 is able to contain a fluidic medium within an interior volume of the reservoir 5210. The plunger head 5220 is able to slide within the reservoir 5210.

The transfer guard 5240 is configured such that when the vial 5250 is attached to the transfer guard 5240, the first needle 5242 and the second needle 5245 pierce a septum 5252 of the vial 5250. The transfer guard 5240 is further configured such that when the reservoir 5210 is attached to the transfer guard 5240, the first needle 5242 pierces a septum 5214 of the reservoir 5210. Thus, the transfer guard 5240 allows for establishing a fluid transfer path from the vial 5250 to the reservoir 5210 through the first needle 5242.

One end of the second needle 5245 is located within a headspace 5256 of the vial 5250 above the fluidic medium 5254 when the transfer guard 5240 is connected to the vial 5250. Another end of the second needle 5245 is connected to the one-way valve 5244. The one-way valve 5244 allows for air to enter the headspace 5256 of the vial 5250 through the second needle 5245, but substantially prevents liquid from coming out of the vial 5250 through the second needle 5245. In various embodiments, the second needle 5245 allows for venting the headspace 5256 of the vial 5250 to atmosphere and, thus, the handle 5232 can be used to pull the plunger head 5220 back to draw a fluidic medium out of the vial 5250 and into the reservoir 5210 without first having to pump air into the vial 5250 from the reservoir 5210.

Figure 97:
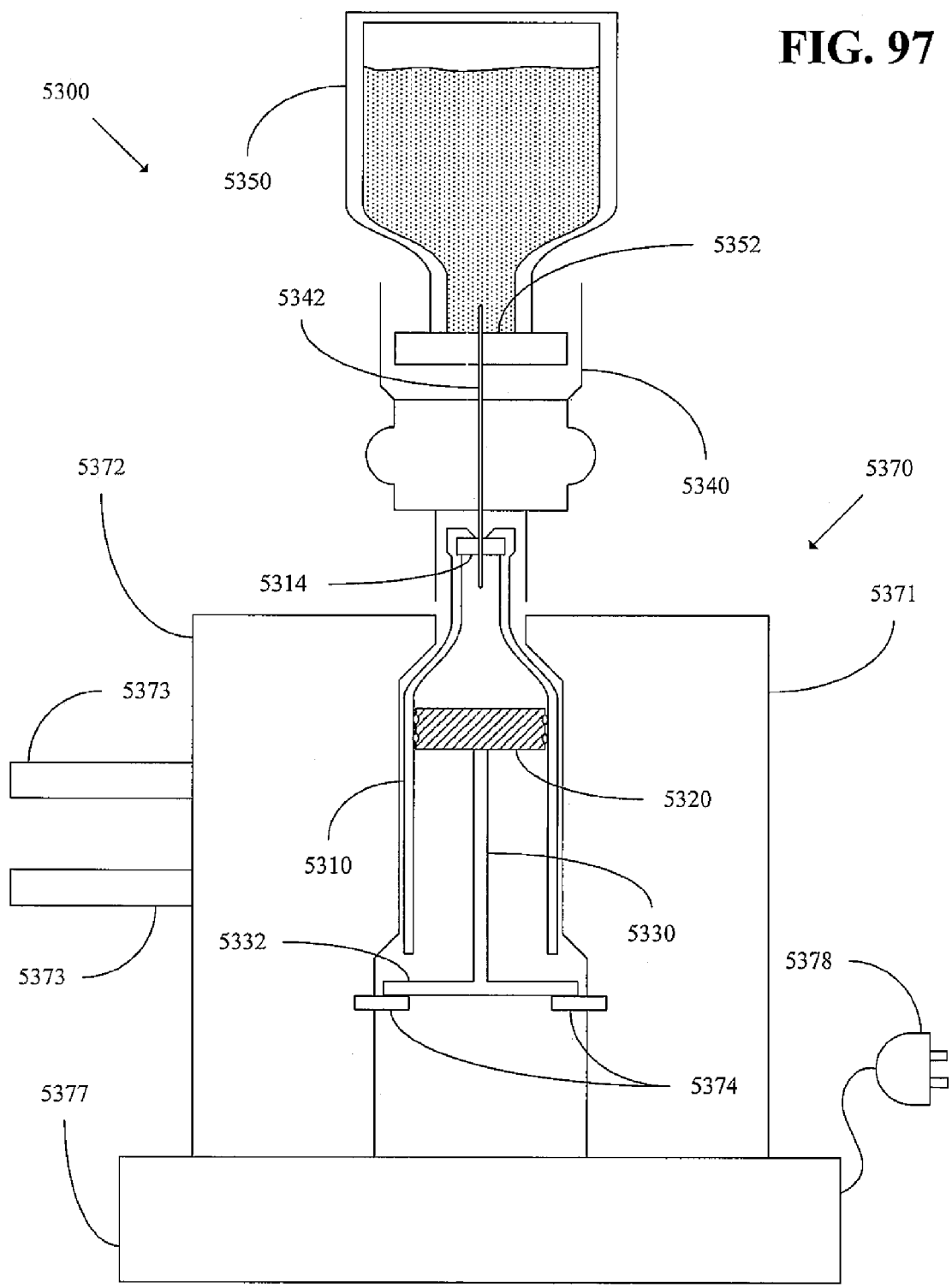
FIG. 97 illustrates a cross-sectional view of a system in accordance with an embodiment of the present invention.

FIG. 97 illustrates a cross-sectional view of a system 5300 in accordance with an embodiment of the present invention. The system 5300 includes a reservoir 5310, a plunger head 5320, a plunger arm 5330, a transfer guard 5340, a vial 5350, and a vibrating apparatus 5370. The vial 5350 includes a vial septum 5352. The transfer guard 5340 includes a needle 5342. The reservoir 5310 includes a septum 5314. The vibrating apparatus 5370 includes a first holder 5371 and a second holder 5372 for holding the reservoir 5310, one or more supports 5373, one or more latches 5374, a vibrator 5377, and a power source 5378. The power source 5378 may include, for example, a plug for plugging in the vibrator 5377, a battery for powering the vibrator 5377, or the like.

During a filling process, the needle 5342 of the transfer guard 5340 establishes a fluid path between the vial 5350 and the reservoir 5310. The one or more latches 5374 are released to allow fluid to flow into the reservoir 5310. While the reservoir 5310 is filling with a fluidic medium, the vibrator 5377 vibrates the reservoir 5310 such that air bubbles in the fluidic medium travel upwards within the reservoir 5310. Thus, the vibrator 5377 allows for shaking the reservoir 5310 so as to shake bubbles free in a fluidic medium being filled into the reservoir 5310. In various embodiments, once the filling process has completed in the system 5300, the vial 5350 is disconnected from the transfer guard 5340, and air in the reservoir 5310 is pushed out by pressing on the handle 5332.

Figure 103:
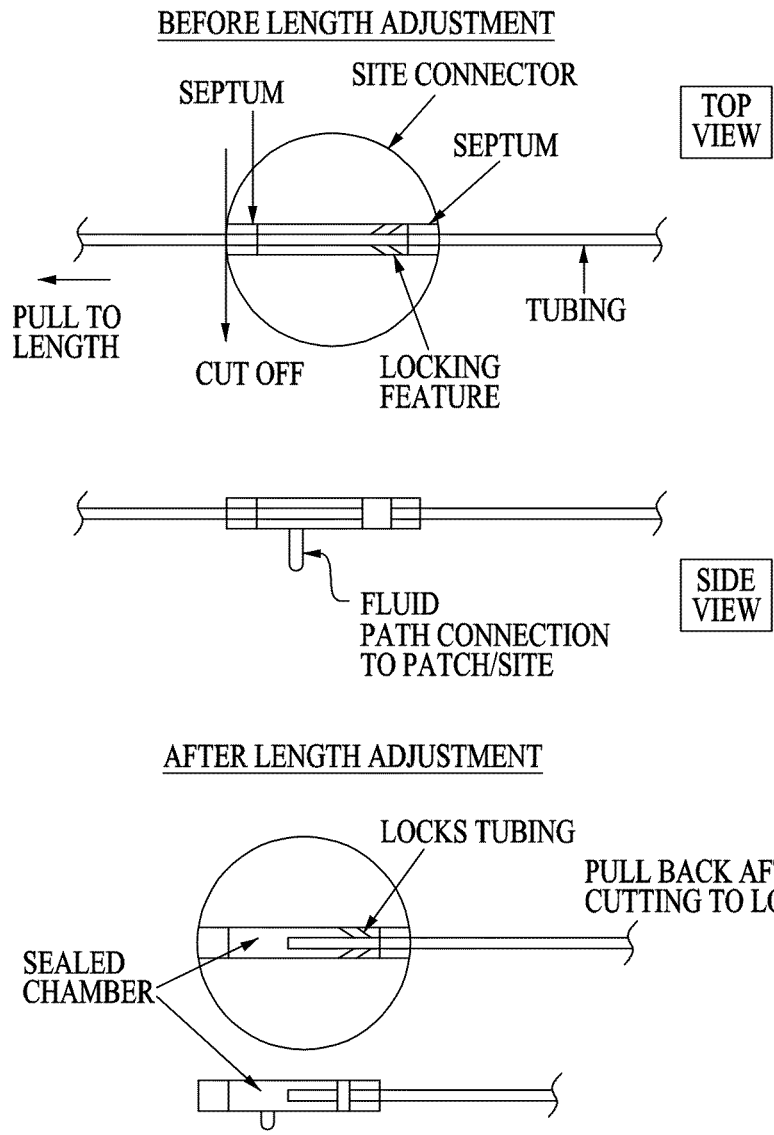

An embodiment of a coupling device for coupling fluid flow tubing ends together is shown in FIGS. 99-102. An embodiment of an adjustable length tubing for an infusion set is shown in FIG. 103. Such embodiments may be employed with infusion delivery devices and needle inserting devices as described herein or in other suitable systems.

While various embodiments of the present invention may be used with in an insulin delivery system for treating diabetes, other embodiments of the invention may be employed for delivering other infusion media to a patient-user for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like. Also, while embodiments of the present invention are described herein for delivering or infusing an infusion medium to a patient-user, other embodiments may be configured to draw a medium from a patient-user.

Figure 98A:
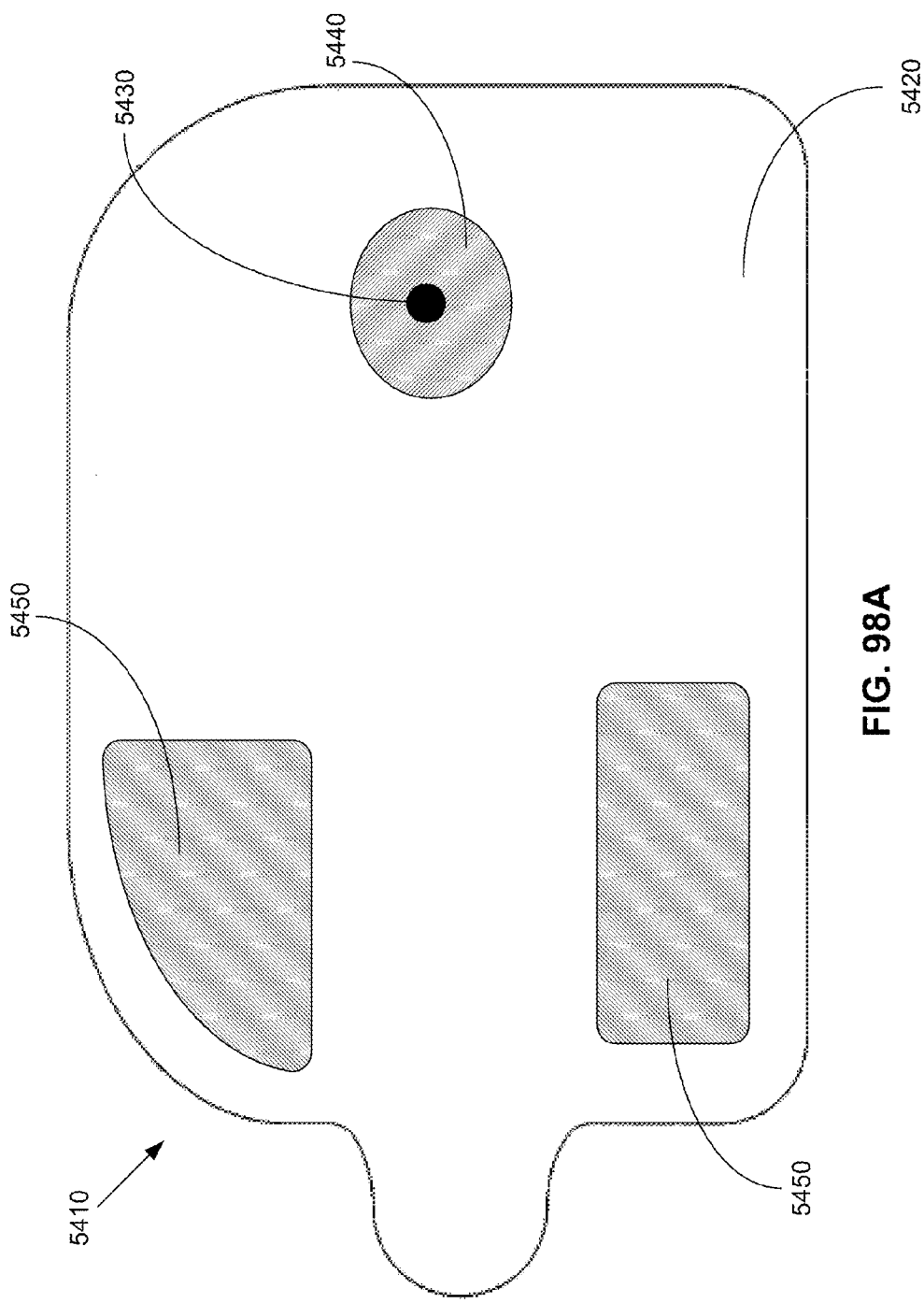
FIG. 98A illustrates an adhesive patch in accordance with an embodiment of the present invention.
Figure 99:
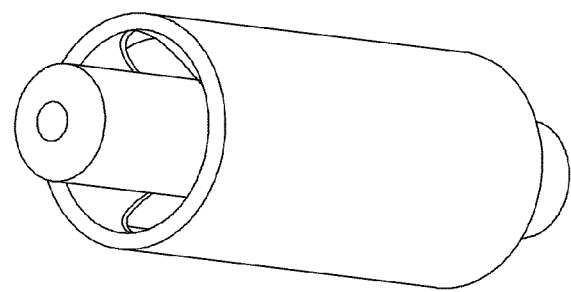
FIGS. 99-103 illustrate various tubing connector arrangements.
Figure 100:
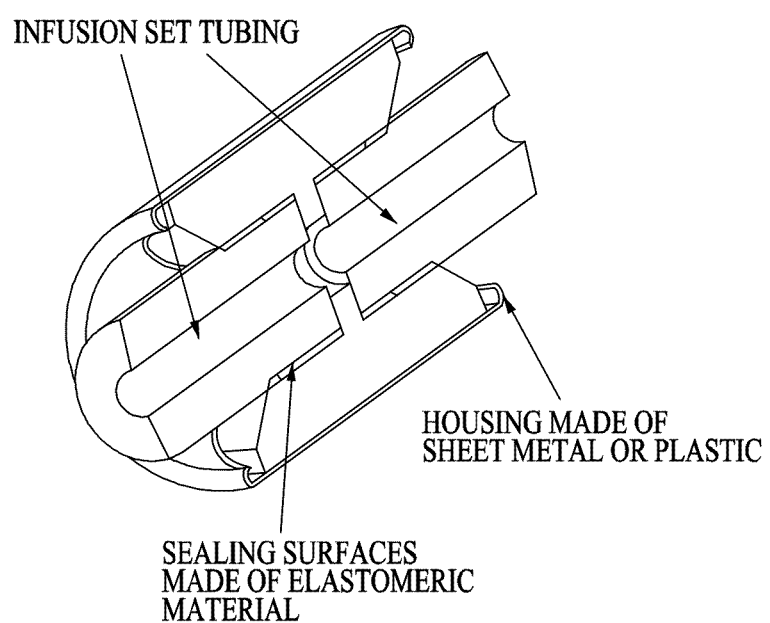
Figure 101:
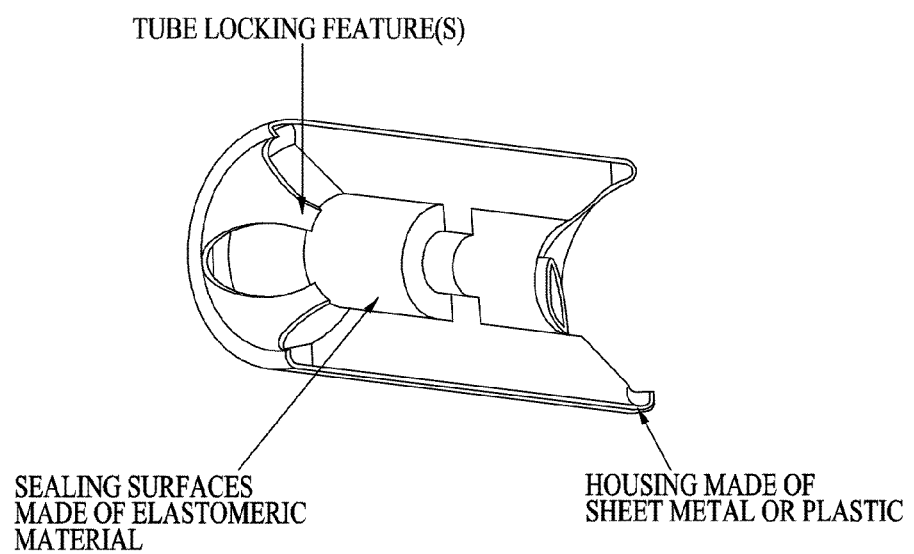
Figure 102:
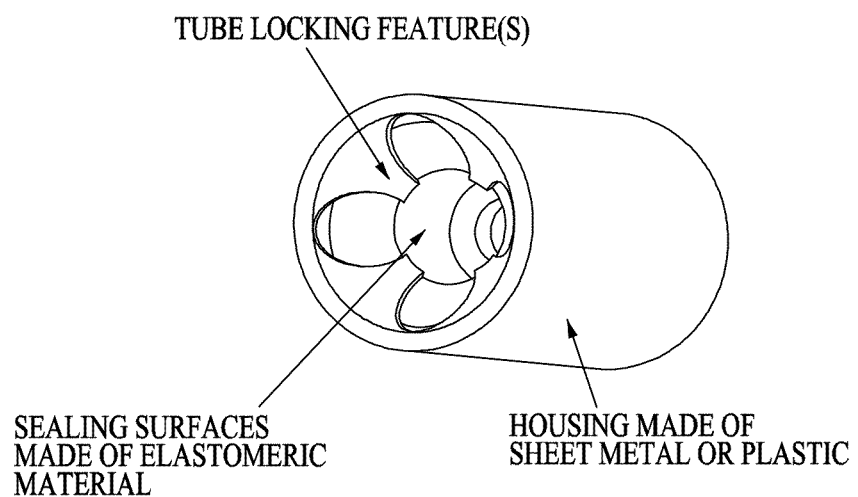

FIG. 98A illustrates an adhesive patch in accordance with an embodiment of the present invention. The adhesive patch may include, but is not limited to, a medical device (such as 5505 in FIG. 104A), a base 5410 of the medical device, and an adhesive material. The medical device may be configured to monitor or treat a user-patient during operation of the medical device. The medical device may be, for example, an external patch pump, a catheter, sensor, or the like. The base 5410 of the medical device may be for securing the medical device to the user-patient during operation of the medical device. The base 5410 of the medical device may have at least a first area 5440 and a second area 5420 that contact the user-patient upon the base 5410 of the medical device being secured to the user-patient. In some embodiments, the base 5410 of the medical device may be attached to the skin of the user-patient. In further embodiments, the surface area of the second area 5420 of the base 5410 may be greater than the surface area of the first area 5440 of the base 5410.

Due to variations in disposable medical devices, skin types, and skin sensitivity levels, sometimes large quantities of adhesive tapes and patches are used to affix a device to the skin, which may lead to excess perspiration, skin irritation, itching, discomfort, and possibly infection. This is especially true of patients with auto-immune deficiencies due to disease states or the administration of certain drug therapies. A medical adhesive with a high adhesion rate proximal to an infusion site, an insertion site, a wound site, or the like, and more breath-ability in areas more distant from such a site, would require a smaller contact area and, thus, may reduce skin irritation, perspiration, and a chance of infection. Such a medical adhesive may also promote device efficacy.

In some embodiments, the adhesive material may be provided on at least the first area 5440 of the base 5410 and the second area 5420 of the base 5410. The adhesive material may have a different adhesion strength on the first area 5440 of the base 5410 than the second area 5420 of the base 5410. In some embodiments, the adhesive material may have a greater adhesion strength on the first area 5440 of the base 5410 than on the second area 5420 of the base 5410. As a result, the adhesion strength between the user-patient and the base 5410 of the medical device may be strongest at the first area 5440. In various embodiments, the adhesive material may adhere to human skin.

In some embodiments, the medical device may include at least one of a needle (not shown) and a cannula (not shown). The at least one of the needle and the cannula may be for inserting into the skin of the user-patient during operation of the medical device. The at least one of the needle and the cannula may be arranged in the first area 5440 of the base 5410. In various embodiments, the base 5410 of the medical device may have an opening 5430 through which the at least one of the needle and the cannula may extend during operation of the medical device. In some embodiments, the first area 5440 of the base 5410 with the adhesive material having a greater adhesion strength than the second area 5420 of the base 5410 may be adjacent the opening 5430 of the base 5410. In further embodiments, the first area 5440 with the adhesive material having a greater adhesion strength than the second area 5420 may at least partially surround or encircle the opening 5430 of the base 5410. Thus, in some embodiments, a base 5410 of a medical device may feature a first area 5440 with an adhesive material having a greater adhesion strength than a second area 5420 around an opening 5430 of the base 5410, such that the base 5410 may be held most securely against the skin of the user-patient at and/or around the opening 5430 of the base 5410.

In some embodiments, the opening 5430 of the base 5410 may correspond to a wound site on the skin of the user-patient. Accordingly, the base 5410 of the medical device could be placed on the skin of the user-patient such that the first area 5440 of the base 5410 with the adhesive material having a greater adhesion strength than the second area 5420 of the base 5410 may be near the wound site, for example partially surrounding or encircling the wound site As such, the base 5410 may be held most securely against the skin of the user-patient at and/or near the wound site of the user-patient. In various embodiments, the first area 5440 of the base 5410 may be adjacent to at least one edge of the base 5410 of the medical device. As such, the base 5410 of the medical device may be held most securely against the skin of the user-patient at and/or near at least one edge of the base 5410.

In some embodiments, the base 5410 of the medical device may include a third area 5450 that contacts the user-patient upon the base 5410 of the medical device being secured to the user-patient. The adhesive material provided on the third area 5450 of the base 5410 may be for securing the base 5410 of the medical device to the user-patient. The adhesive material may have a greater adhesion strength on the third area 5450 of the base 5410 than on the second area 5420 of the base 5410. In some embodiments, the third area 5450 may be located away from the first area 5440 and/or the opening 5430 of the base 5410, such as near an edge of the base 5410 of the medical device. As such, the base 5410 of the medical device can be securely attached to the user-patient with less adhesive material since adhesives may lead to excess perspiration, skin irritation, itching, discomfort, and possibly infection. In further embodiments, the adhesive material on the first area 5440 of the base 5410 may be equal to or stronger than the adhesive material on the third area 5450 of the base 5410. Therefore in such embodiments, the adhesion strength between the base 5410 of the medical device and the user-patient may be strongest at or near the opening 5430 of the base 5410, while the adhesion strength between the base 5410 and the user-patient may be stronger at the third area 5450 of the base 5410, for example near the edge of the base 5410, than the second area 5420 of the base 5410.

The areas 5420, 5440, and 5450 of the base 5410 are merely illustrative of an example of a configuration of the adhesive patch system with areas of varying adhesion strengths. It should be understood that embodiments of the adhesive patch system are not limited to such an arrangement of the areas 5420, 5440, and 5450, but that the areas 5420, 5440, 5450 may be positioned in any arrangement on the base 5410 of the medical device. Furthermore, it should be understood that embodiments of the adhesive patch system are not limited in number to areas 5420, 5440, and 5450. Additional areas of varying adhesion strengths may also be used.

Embodiments of the present invention allow for an adhesive patch, or adhesive tape, featuring areas with increased adhesion strength that ensure that a catheter, a sensor, or other device introduced through the skin of a user-patient will remain in place. Such adhesive patches may allow for reducing an amount of skin coverage of the adhesive patch as compared with an adhesive patch that has only a uniform adhesion capability across the adhesive patch. Thereby, skin irritation and perspiration may be reduced with an adhesive patch having varying levels of adhesion capability in different areas on the adhesive patch, and comfort and wearability of a medical device that uses such an adhesive patch may be increased.

An adhesive patch having selective areas of increased adhesion strength may reduce a failure rate of infusion sets by providing increased adhesion strengths around an insertion site of a catheter and, thus, helping to prevent the catheter from being partially pulled out and then kinked. Also, such adhesive patches with variable adhesion strength may allow for greater securing of a patch delivery system and minimize the patch footprint on the skin of the patient. Adhesive patches with variable adhesion strength may also allow for greater securing of glucose sensor products to a patient without increasing a patch size. Embodiments of the present invention allow for selective use of augmented adhesives on an adhesive patch.

In other embodiments, such as the embodiment exemplified in FIG. 98B, the adhesive material may have a lesser adhesion strength on the first area 5440' of the base 5410 than on the second area 5420 of the base 5410. As a result, the adhesion strength between the user-patient and the base 5410 of the medical device may be weakest at the first area 5440' of the base. Such an embodiment may allow for ease of removal of the base 5410 and the medical device by the user-patient. For example, the user-patient may be able to insert his or her fingers between the base 5410 and his or her skin at the first area 5440' and then detach or otherwise unsecure the base 5410 and the medical device off his or her skin.

FIGS. 104 and 105 illustrate an adhesive patch system 5500 in accordance with an embodiment of the present invention. The adhesive patch system 5500 may include, but is not limited to, a medical device 5505, a base 5510 of the medical device 5505, and an adhesive material 5540. The medical device 5505 may be configured to monitor or treat a user-patient during operation of the medical device 5505. The medical device 5505 may be, for example, an external patch pump, a catheter, sensor, or the like. The base 5510 of the medical device 5505 may be for securing the medical device 5505 to the user-patient during operation of the medical device 5505. The base may have an area 5520 that contacts the user-patient upon the base 5510 being secured to the user-patient. In some embodiments, the base 5510 of the medical device 5505 may be attached to the skin 5580 of the user-patient.

In some embodiments, the adhesive material 5540 may be provided on at least a portion of the area 5520 of the base 5510. The adhesive material 5540 may be configured to react with a catalyst 5545 for activating the adhesive material 5540. The adhesive material 5540 may have a different adhesion strength upon activation of the adhesive material 5540 by the catalyst 5545 than before activation of the adhesive material 5540. In various embodiments, the adhesive material 5540 may adhere to human skin.

In various embodiments, the catalyst 5545 may be deliverable or otherwise introducible to the adhesive material 5540. The catalyst 5545 may be configured to react with the adhesive material 5540 to increase or decrease the adhesion strength of the adhesive material 5540. In various embodiments, the catalyst 5545 may activate some or substantially all of the adhesive material 5540 to change the adhesion strength of the adhesive material 5540. In some embodiments, the adhesive material 5540 may be configured to react with the catalyst 5545 when the catalyst 5545 is applied to the adhesive material 5540. As such, the adhesion strength of the adhesive material 5540 may increase once the catalyst 5545 is delivered to the adhesive material 5540. In some embodiments, the adhesive material 5540 may be configured to react with the catalyst 5545 a period of time, such as 15 to 30 seconds, or longer, after the catalyst 5545 is delivered to the adhesive material 5540. Accordingly, a change in the adhesion strength of the adhesive material 5540 may be delayed a short time after the catalyst 5545 is delivered to the adhesive material 5540. Such an embodiment may allow the user-patient to rearrange the base 5510 and/or the medical device 5505 after securing the medical device 5505 to his or her skin in a case, for example, where the placement of the medical device 5505 was incorrect or uncomfortable to the user-patient.

In some embodiments, the adhesive material 5540 may have a greater adhesion strength upon activation of the adhesive material 5540 by the catalyst 5545 than before activation of the adhesive material 5540. As a result, the adhesion strength between the user-patient and the base 5510 of the medical device 5505 may be strongest where the adhesive material 5540 is activated.

According to some embodiments, the base 5510 of the medical device 5505 may be placed on the skin 5580 of the user-patient before the adhesive material 5540 is activated by the catalyst 5545 to change the adhesion strength of the adhesive material 5540. In some embodiments, the adhesion strength of the adhesive material 5540 may be sufficient to affix the base 5510 of the medical device 5505 to the skin 5580 of the user-patient before the catalyst 5545 activates the adhesive material 5540. Once the base 5510 of the medical device 5505 is placed on the skin 5580 of the user-patient, the catalyst 5545 may be then delivered to the adhesive material 5540 to increase the adhesion strength of the adhesive material 5540 such that the base 5510 of the medical device 5505 may have a stronger bond between the adhesive material 5540 and the skin 5580 of the user-patient. In other embodiments, the catalyst 5545 may be delivered to the adhesive material 5540 to activate the adhesive material 5540, and therefore increase the adhesion strength of the adhesive material 5540, before the base 5510 and the adhesive material 5540 is applied to the skin 5580 of the user-patient.

In some embodiments, the adhesive material 5540 may have a lesser adhesion strength upon activation of the adhesive material 5540 by the catalyst 5545 than before activation of the adhesive material 5540. As a result, the adhesion strength between the user-patient and the base 5510 of the medical device 5505 may be weakest where the adhesive material 5540 is activated. According to such embodiments, the base 5510 may be placed on the skin 5580 of the user-patient before the adhesive material 5540 is activated by the catalyst 5545 to decrease the adhesion strength of the adhesive material 5540. When the user-patient wishes to remove or rearrange the medical device

5505, the catalyst 5545 may be delivered to the adhesive material 5540 to decrease partially or substantially all of the adhesion strength of the adhesive material 5540. As such, the base 5510 of the medical device 5505 may have a weaker bond or no bond at all between the area on the base 5510 of the medical device 5505 with the activated adhesive material 5540 and the skin 5580 of the user-patient.

In other embodiments, the catalyst 5545 may be delivered to the adhesive material 5540 to activate the adhesive material 5540, and therefore decrease the adhesion strength of the adhesive material 5540, before the base 5510 of the medical device 5505 and the adhesive material 5540 is applied to the skin 5580 of the user-patient. For example, a user-patient sensitive to an adhesive material with a strong adhesion strength may wish to reduce the adhesion strength of the adhesive material 5540, and thus decrease the strength of the bond between the base 5510 of the medical device 5505 and the skin 5580 of the user-patient, before affixing the medical device 5505 to his or her skin 5580.

In various embodiments, the catalyst 5545 may comprise a temperature source. For example, the catalyst may be a heat source that could be introduced to the adhesive material 5540 to heat the adhesive material 5540. In such an example, the heating of the adhesive material 5540 may increase the adhesion strength of the adhesive material 5540. Similarly, the catalyst 5545 may be a cooling source that may be used to cool the adhesive material 5540 to increase the adhesion strength of the adhesive material 5540. In addition to or alternative to, the temperature source may be introduced to or otherwise applied to the adhesive material 5540 to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select a temperature source and/or an adhesive material 5540 to react together to activate the adhesive material 5540 to increase or decrease the adhesion strength of the adhesive material 5540.

In various embodiments, the catalyst 5545 may comprise a moisture source, such as water, perspiration, or the like. Many active user-patients have difficulty keeping a medical device secured to their skin while exercising due to excess perspiration weakening the adhesive bond between the medical device and the skin of the user-patient. Similarly, user-patients who swim face a similar problem due to water weakening the adhesive bond between the medical device and the skin of the user-patient. Thus in some embodiments, the moisture source and/or the adhesive material 5540 may be selected and/or configured to react together to activate the adhesive material 5540 so as to increase the adhesion strength of the adhesive material 5540. Such embodiments may be beneficial to such user-patients. Additionally, a catalyst 5545, such as water, may be inexpensive and easily accessible to all types of user-patients to change the adhesion strength of the adhesive material 5540. In some embodiments, the moisture source and/or the adhesive material 5540 may be selected and/or configured to deactivate the adhesive material 5540 when the moisture source evaporates or otherwise dries, so as to decrease the adhesion strength of the adhesive material 5540. For example, according to such an embodiment, a catalyst 5545 comprising water may be used to activate the adhesive material 5540. When the water evaporates, the adhesive material 5545 may return to its original adhesion strength so that the medical device 5505 can be easily detached from the skin 5580 of the user-patient.

In addition or in the alternative, the moisture source and/or the adhesive material 5540 may be selected and/or configured to react together to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select a moisture source and/or an adhesive material 5540 to react together to activate the adhesive material 5540 to increase or decrease the adhesion strength of the adhesive material 5540.

In various embodiments, the catalyst 5545 may comprise a fluid source, such as a liquid or a gas. Similar to the embodiments above, the fluid source and/or the adhesive material 5540 may be selected and/or configured to react together to activate the adhesive material 5540 so as to increase the adhesion strength of the adhesive material 5540. In addition or in the alternative, the fluid source and the adhesive material 5540 may be selected and/or configured to react together to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select a fluid source and/or an adhesive material 5540 to react together to activate the adhesive material 5540 to increase or decrease the adhesion strength of the adhesive material 5540.

In various embodiments, the catalyst 5545 may comprise a light source. Similar to the embodiments above, the light source and/or the adhesive material 5540 may be selected and/or configured to react together to activate the adhesive material 5540 so as to increase the adhesion strength of the adhesive material 5540. In addition or in the alternative, the light source and the adhesive material 5540 may be selected and/or configured to react together to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select a light source and/or an adhesive material 5540 to react together to activate the adhesive material 5540 to increase or decrease the adhesion strength of the adhesive material 5540.

In various embodiments, the catalyst 5545 may comprise an electromagnetic source. Similar to the embodiments above, the electromagnetic source and/or the adhesive material 5540 may be selected and/or configured to react together to activate the adhesive material 5540 so as to increase the adhesion strength of the adhesive material 5540. In addition or in the alternative, the electromagnetic source and the adhesive material 5540 may be selected and/or configured to react together to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select an electromagnetic source and/or an adhesive material 5540 to react together to activate the adhesive material 5540 to increase or decrease the adhesion strength of the adhesive material 5540.

In various embodiments, the catalyst 5545 may comprise an infrared source. Similar to the embodiments above, the infrared source and/or the adhesive material 5540 may be selected and/or configured to react together to activate the adhesive material 5540 so as to increase the adhesion strength of the adhesive material 5540. In addition or in the alternative, the infrared source and the adhesive material 5540 may be selected and/or configured to react together to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select an infrared source and/or an adhesive material 5540 to react together to activate the adhesive material 5540 to increase or decrease the adhesion strength of the adhesive material 5540.

In various embodiments, the catalyst 5545 may comprise a frequency source. Similar to the embodiments above, the frequency source and/or the adhesive material 5540 may be selected and/or configured to react together to activate the adhesive material 5540 so as to increase the adhesion strength of the adhesive material 5540. In addition or in the alternative, the frequency source and the adhesive material 5540 may be selected and/or configured to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select a frequency source and/or an adhesive material 5540 to react together to activate the adhesive material 5540 to increase or decrease the adhesion strength of the adhesive material 5540.

In various embodiments, the catalyst 5545 may comprise a high frequency vibration source. Similar to the embodiments above, the high frequency vibration source and/or the adhesive material 5540 may be selected and/or configured to react together to activate the adhesive material 5540 so as to increase the adhesion strength of the adhesive material 5540. In addition or in the alternative, the high frequency vibration and the adhesive material 5540 may be selected and/or configured to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select a high frequency vibration source and/or an adhesive material 5540 to react together to activate the adhesive material 5540 to increase or decrease the adhesion strength of the adhesive material 5540.

In various embodiments, the catalyst 5545 may comprise a chemical agent. Similar to the embodiments above, the chemical agent and/or the adhesive material 5540 may be selected and/or configured to react together to activate the adhesive material 5540 so as to increase the adhesion strength of the adhesive material 5540. In addition or in the alternative, the chemical agent and the adhesive material 5540 may be selected and/or configured to react together to weaken or destroy the adhesion strength of the adhesive material 5540 so that the base 5510 and the medical device 5505 can be more easily removed from the skin 5580 of the user-patient. It should be understood that a person of ordinary skill in the art should know how to configure or select a chemical agent and/or an adhesive material 5540 to react together to activate the adhesive material 5540 to increase or decrease the adhesion strength of the adhesive material 5540.

In some embodiments, the catalyst 5545 and/or the adhesive material 5540 may be selected and/or configured to deactivate the adhesive material a period of time after activation of the adhesive material 5540. In further embodiments, the catalyst 5545 and/or the adhesive material 5540 may be selected and/or configured to react together to temporarily activate the adhesive material 5540 for a period of time, such as one hour, twelve hours, or any amount of time that may be required by the user-patient. For example, according to such an embodiment, a catalyst 5545 comprising water may be used to activate the adhesive material 5540. When the water evaporates, the adhesive material 5545 may return to its original adhesion strength so that the medical device 5505 can be easily detached from the skin 5580 of the user-patient. It should be understood that a person of ordinary skill in the art should know how to configure or select a catalyst and/or an adhesive material 5540 to deactivate the adhesive material a period of time after activation of the adhesive material 5540. It should be further understood that a person of ordinary skill in the art should know how to configure or select a catalyst and/or an adhesive material 5540 to react together to temporarily activate the adhesive material 5540 for a period of time.

In some embodiments, the adhesive patch system 5500 may include a delivery device 5525 for introducing, applying, or otherwise delivering the catalyst 5545 to the adhesive material 5540 to activate the adhesive material 5540 to change the adhesion strength of the adhesive material 5540. In various embodiments, the base 5510 of the medical device 5505 may be affixed to the skin 5580 of the user-patient before the delivery device 5525 delivers the catalyst 5545. Once the base 5510 of the medical device 5505 is affixed to the skin 5580 of the user-patient, the catalyst 5545 may be delivered to or otherwise applied to the adhesive material 5540 by the delivery device 5525 to activate the adhesive material 5540 to increase (or decrease) the adhesion strength between the base 5510 of the medical device 5505 and the skin 5580 of the user-patient. In other embodiments, the catalyst 5545 may be deliverable by the delivery device 5525 to activate the adhesive material 5540 to increase the adhesion strength of the adhesive material 5540 before the base 5510 of the medical device 5505 is affixed to the skin 5580 of the user-patient. According to such embodiments, for example, once the base 5510 of the medical device 5505 is secured to the skin 5580 of the user-patient no further activation may be necessary to increase the adhesion strength of the adhesive material 5540.

In addition or in the alternative, the delivery device 5525 may deliver the catalyst 5545 to the adhesive material 5540 in a case where the base 5510 of the medical device 5505 is affixed to the skin 5580 of the user-patient and the user-patient wishes to reduce the adhesion strength of the adhesive material 5540, for example, to remove or rearrange the position of the medical device 5505. In further embodiments, the catalyst 5545 may be deliverable by the delivery device 5525 to activate the adhesive material 5540 to weaken the adhesion strength of the adhesive material 5540 before the base 5510 of the medical device 5505 is affixed to the skin 5580 of the user-patient, for example, to accommodate user-patients sensitive to adhesive materials with strong adhesion strengths.

In some embodiments, the delivery device 5525 may be connected to or connectable to the medical device 5505 to deliver the catalyst 5545 to the adhesive material 5540. In various embodiments, the delivery device 5525 may be placed on or proximate to the medical device 5505 to deliver the catalyst 5545 to the adhesive material 5540 to activate the adhesive material 5540 to increase (or decrease) the adhesion strength of the adhesive material 5540. For example, a user-patient may place a delivery device 5525 containing a light source as the catalyst 5545 near the adhesive material 5540 to transmit light to the adhesive material 5540 to activate the adhesive material 5540 to increase (or decrease) the adhesion strength of the adhesive material 5540. As a further example, a user-patient may place a delivery device 5525 containing a heat source as the catalyst 5545 near the medical device 5505 while the base 5510 of the medical device 5505 is affixed to the skin 5580 of the user-patient to heat the adhesive material 5540 so as to activate the adhesive material 5540 to increase (or decrease) the adhesion strength of the adhesive material 5540 while the adhesive material 5540 is on the skin 5580 of the user-patient. As a further example, the delivery device 5525 may contain a reservoir (not shown) of a chemical agent, which serves as the catalyst 5545. The user-patient may spray, pour, or otherwise apply the chemical agent on the adhesive material 5540 to activate the adhesive material 5540.

In some embodiments, the delivery device 5525 may comprise a layer (not shown), such as an adhesive sticker, a patch, a film, or the like. The layer may contain the catalyst 5545 for activating the adhesive material 5540. The layer may be configured to be placeable by the user-patient on a selective area of the bottom surface of the base 5510 of the medical device 5505, such that the adhesive material 5540 is activated at the selective area, for example to increase (or decrease) the adhesion strength of the adhesive material 5540. Additional layers can be applied to the bottom surface of the base 5510 of the medical device 5505 at other selective areas as needed by the user-patient. In some embodiments, additional layers can be applied to a previously placed layer to further increase (or decrease) the adhesion strength of the adhesive material 5540 at that location.

Figure 104A:
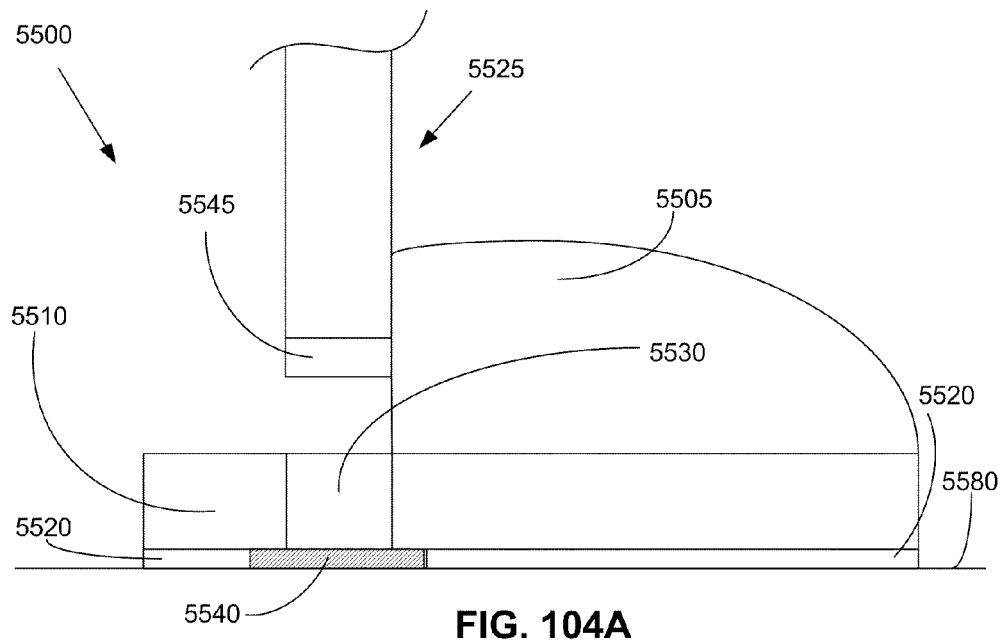
FIGS. 104A and 104B illustrate a medical device in accordance with an embodiment of the present invention.
Figure 104B:
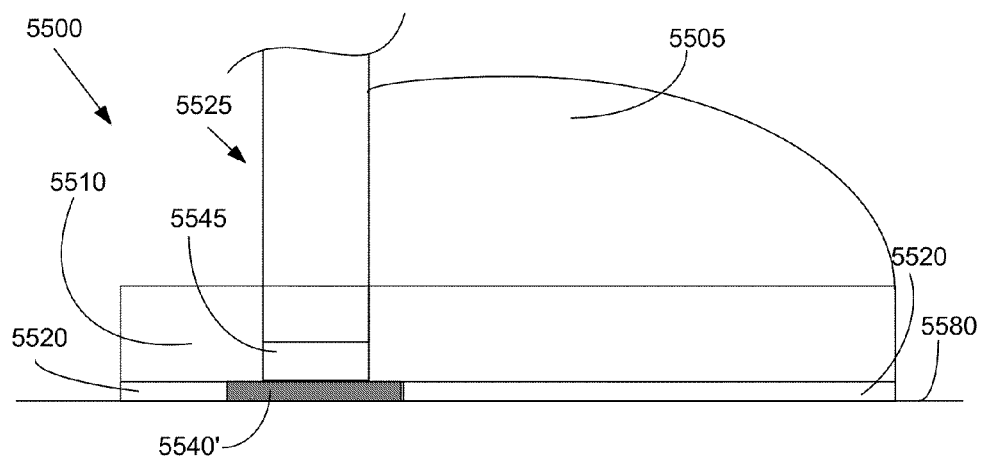
Figure 104C:
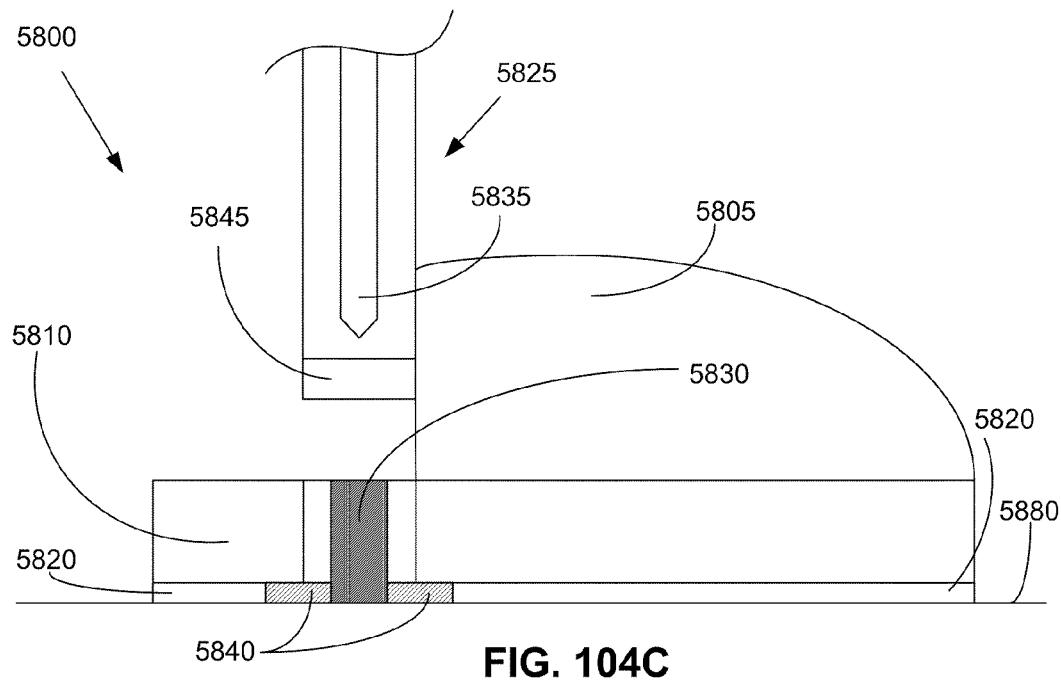
FIGS. 104C and 104D illustrate a medical device in accordance with an embodiment of the present invention.
Figure 104D:
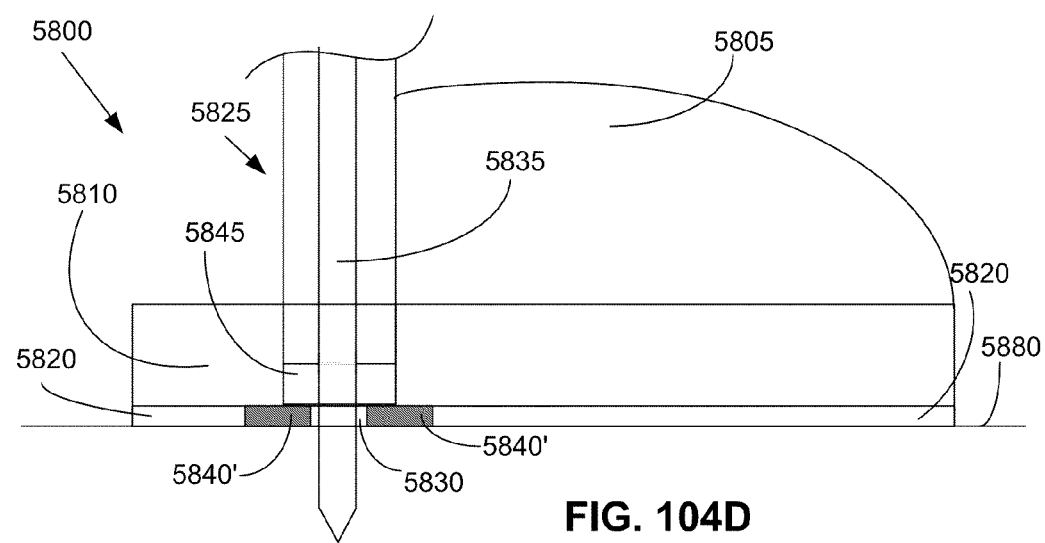

In further embodiments, such as the embodiments shown in FIGS. 104C and 104D, an adhesive patch system 5800, which may be similar to the adhesive patch system 5500 described with respect to FIGS. 104A and 104B, may further include an inserter 5825 for the base 5810 or an infusion set, such as, but is not limited to, one of the inserters described in the background section of the patent application titled Insertion Device for an Insertion Set and Method of Using the Same, filed on Feb. 20, 2003, Ser. No. 10/370,436, the contents of which are herein incorporated by reference. The inserter 5825 may include a cannula (not shown) and/or an insertion needle 5835 for piercing the skin 5880 of the user-patient. In some embodiments, the delivery device (for example 5845) may be operatively connected to an end of the inserter 5825 such that the catalyst 5845 is deliverable to the adhesive material 5840 to activate the adhesive material 5840 to increase (or decrease) the adhesion strength of the adhesive material 5840 when the cannula and/or the insertion needle 5835 pierce the skin 5880 of the user-patient.

In some embodiments, the inserter 5825 may be configured to operatively engage the medical device 5805 to deliver the catalyst 5845 to the adhesive material 5840 to activate the adhesive material 5840 to increase (or decrease) the adhesion strength of the adhesive material 5840. For example, the medical device 5805 may have an aperture 5830 for inserting the inserter 5825 to allow the inserter 5825 to pass through the base 5810 and/or the medical device 5805 and pierce the skin 5880 of the user-patient with the insertion needle 5835 and/or the cannula. In this example, the inserter 5825 may include a heated end 5845, or an end containing any of the catalysts described above. Therefore, in a case where the medical device 5805 is secured to the skin 5880 of the user-patient and the inserter 5825 is inserted into or placed near the aperture 5830 to pierce the skin 5880 of the user-patient, the heated end 5845 may react with the adhesive material 5840 to activate the adhesive material 5840 to increase the adhesion strength of the adhesive material 5840.

With reference to FIGS. 104A and 104B, in some embodiments, the delivery device 5525 may be used to weaken the adhesion strength between the base 5510 of the medical device 5505 and the skin 5580 of the user-patient and/or detach the base 5510 of the medical device 5505 partially or completely from the skin 5580 of the user-patient. In some embodiments, such as the embodiments exemplified in FIGS. 105A through 105C, an adhesive patch system 5900, which may be similar to the adhesive patch systems 5500 and 5800 described with respect to FIGS. 104A-104B and 104C-104D, may include a delivery device 5925 configured and/or shaped to fit around, support, receive, or otherwise engage the medical device 5905. For example, the delivery device may include a contoured end 5925a configured to complement a contoured surface 5905a of the medical device 5905. Before or while the medical device 5505 is fit into the countered end 5925a of the delivery device 5925, the delivery device 5925 may delivery the catalyst (not shown) to the adhesive material 5940 to activate the adhesive material 5940' to decrease or destroy the adhesion strength of the adhesive material 5940. The user-patient may then withdraw the delivery device 5925, which may be supporting the medical device 5905, away from the skin 5980 of the user-patient to remove the medical device 5905 from his or her skin.

With reference to FIGS. 104A and 104B, in various embodiments, the delivery device 5525 may be insertable between the skin 5580 of the user-patient and the adhesive patch 5500. In such embodiments, the delivery device may be a scraping device (not shown), or the like, that may be pryable or otherwise insertable between the skin 5580 of the user-patient and the base 5510 of the medical device 5505. Once the delivery device 5525 is inserted between the skin 5580 of the user-patient and the base 5510 of the medical device 5505, the catalyst 5545 may be delivered to the adhesive material 5540 to activate the adhesive material 5540 to reduce or destroy the adhesion strength of the adhesive material 5540. In some embodiments, the catalyst 5545 may be air, such that in a case where the delivery device 5525 is inserted between the skin 5580 of the user-patient and the base 5510 of the medical device 5505, and the adhesive material 5540 is exposed to air the adhesive material 5540 may be activated to decrease the adhesion strength of the adhesive material 5540.

FIGS. 106A through 106E illustrate a delivery patch system 5600 in accordance with an embodiment of the present invention. The delivery patch system 5600 may include, but is not limited to, a medical device (not shown) having a base 5610, and a pierceable membrane 5640. The medical device may be configured to monitor or treat the user during operation of the medical device. The medical device may be, for example, an external patch pump, a catheter, sensor, or the like. The medical device may be operable with an insertion needle 5635, such as one of the insertion needles previously described. For example, the insertion needle 5635 may be the inserter for the base 5610 or an infusion set as described above. The base 5610 may be adapted to be secured to the user-patient during operation of the medical device. The pierceable membrane 5640 may contain an agent 5650, such as an anti-inflammatory, an antiseptic, or analgesic. The pierceable membrane 5640 may be positioned to be pierced by the insertion needle 5635 during operation of the medical device.

In some embodiments, the pierceable membrane 5640 containing the agent 5650 may be a pierceable layer, bubble, or the like, at least partially surrounding the agent 5650 to contain the agent 5650 between the pierceable membrane 5640 and the base 5610 of the medical device. In other embodiments, the pierceable membrane 5640 maybe a pierceable layer, bubble, or the like, at least substantially or completely surrounding the agent 5650 to contain the agent 5640 within the pierceable membrane 5640. In further embodiments, the pierceable membrane 5640 containing the agent may be the exterior surface of the agent 5650. For example, the agent 5650 may be a gel, which may be applied to the base 5610 of the medical device or directly to the skin 5680 of the user-patient. In such an example, the exterior surface of the gel may be pierced by the insertion needle 5635 during operation of the medical device.

In addition, the pierceable membrane 5640 may allow the insertion needle 5635 to cause some of the agent 5650' to be carried from the pierceable membrane 5640 to the user-patient. In some embodiments, the insertion needle 5635 may pierce the pierceable membrane 5640 and carry some of the agent 5650' from the pierceable membrane 5640 to the user-patient. In other embodiments, the insertion needle 5635 may pierce or breach the pierceable membrane 5640 to allow at least some of the agent 5650' to flow from the pierceable membrane 5740 to the user-patient.

In some embodiments, the pierceable membrane 5640 may be located on a bottom surface of the base 5610 of the medical device. Thus, in a case where the medical device is secured to the user-patient the pierceable membrane 5640 may be positioned between the user-patient and the bottom surface of the base 5610 of the medical device.

To use the delivery patch system 5600, the user-patient may secure the base 5610 of the medical device to himself or herself, such as upon the skin 5680 of the user-patient, such that the pierceable membrane 5640 is positioned between the skin 5680 of the user-patient and the base 5610 of the medical device. The user-patient may then pierce the pierceable membrane 5640 with the insertion needle 5635. As the insertion needle 5635 pierces the pierceable membrane 5640 containing the agent 5650, the needle 5610 may collect some of the agent 5650' and carry it to a location 5690 underneath the skin 5680 of the user-patient once the insertion needle 5635 pierces the skin 5680 of the user-patient. In other embodiments, the insertion needle 5635 may pierce or breach the pierceable membrane 5640 to allow at least some of the agent 5650' to flow out of the pierceable membrane 5640 to the skin 5680 of the user-patient.

In some embodiments, the delivery patch system 5600 may further include a removable layer (not shown) at least partially covering the pierceable membrane 5640 containing the agent 5650. The user-patient may remove the layer to expose the pierceable membrane 5640 and/or the agent 5650 and then apply the base 5610 to the user-patient as described above. In some embodiments, the pierceable membrane 5640 and/or the agent 5650 may be configured to react with air, such that in a case where the layer is removed and the pierceable membrane 5640 and/or the agent 5650 is exposed to air, the reacted agent 5650 may be applied to the skin 5680 of the user-patient. For example, the agent 5650 may be configured to react with air so as to provide a cold source that when applied to the skin 5680 of the user-patient may provide an analgesic effect, for example by numbing the skin 5680 of the user-patient, to mitigate discomfort as the insertion needle 5635 pierces the skin 5680 of the user-patient.

In other embodiments, the pierceable membrane 5640 may be located on a top surface of the base 5610 of the medical device. Thus, in a case where the medical device is secured to the user-patient, the base 5610 of the medical device may be positioned between the user-patient and the pierceable membrane 5640. In such embodiments, the user-patient may secure the base 5610 of the medical device to himself or herself, such as upon the skin 5680 of the user-patient, such that the base 5610 of the medical device is positioned between the skin 5680 of the user-patient and the pierceable membrane 5640. The user-patient may then pierce the pierceable membrane 5640 with the insertion needle 5635 before passing through the base 5610 of the medical device. As the insertion needle 5635 pierces the pierceable membrane 5640 containing the agent 5650, the insertion needle 5635 may collect some of the agent 5650' and carry it to a location 5690 underneath the skin 5680 of the user-patient once the insertion needle 5635 pierces the skin 5680 of the user-patient.

FIGS. 107A through 107C illustrate a delivery patch system 5700 in accordance with an embodiment of the present invention. The delivery patch system 5700 may include, but is not limited to, a medical device (not shown) having a base 5710, and a pierceable membrane 5740. The medical device may be configured to monitor or treat the user during operation of the medical device. The medical device may be, for example, an external patch pump, a catheter, sensor, or the like. The medical device may be operable with an insertion needle 5735, as previously described. For example, the insertion needle 5735 may be the inserter for the base 5710 or an infusion set as described above. The base 5710 of the medical device may be adapted to be secured to the user-patient during operation of the medical device. The pierceable membrane 5740 may contain an agent 5750, such as an anti-inflammatory, an antiseptic, or analgesic. The pierceable membrane 5740 may be positioned to be pierced by the insertion needle 5735 during operation of the medical device.

In some embodiments, the pierceable membrane 5740 containing the agent 5750 may be a pierceable layer, bubble, or the like, at least partially surrounding the agent 5750 to contain the agent 5750 between the pierceable membrane 5740 and the skin of the user-patient 5780. In other embodiments, the pierceable membrane 5740 maybe a pierceable layer, bubble, or the like, at least substantially or completely surrounding the agent 5750 to contain the agent 5740 within the pierceable membrane 5740. In further embodiments, the pierceable membrane 5740 containing the agent may be the exterior surface of the agent 5750. For example, the agent 5750 may be a gel, which may be applied to the base 5710 of the medical device or directly to the skin 5780 of the user-patient. In such an example, the exterior surface of the gel may be pierced by the insertion needle 5735 during operation of the medical device.

In addition, the pierceable membrane 5740 may allow the insertion needle 5735 to cause some of the agent 5750' to be carried from the pierceable membrane 5740 to the user-patient. In some embodiments, the insertion needle 5735 may pierce the pierceable membrane 5740 and carry some of the agent 5750' from the pierceable membrane 5740 to the user-patient. In other embodiments, the insertion needle 5735 may pierce or breach the pierceable membrane 5740 to allow at least some of the agent 5750 to flow from the pierceable membrane 5740 to the user-patient.

The pierceable membrane 5740 may be applied to the skin 5780 of the user-patient in preparation for placement of base 5710 of the medical device on the skin 5780 of the user-patient, such that in case where the pierceable membrane 5740 is applied to the skin 5780 of the user-patient and the base 5710 of the medical device is placed on the skin 5780 of the user-patient the pierceable membrane 5740 is positioned between the skin 5780 and a bottom surface of the base 5710 of the medical device.

To use the delivery patch system 5700, the user-patient may apply the pierceable membrane 5740 containing the agent 5750 upon the skin 5780 of the user-patient. Then the user-patient may secure the base 5710 of the medical device to himself or herself such that the pierceable membrane 5740 is positioned between the skin 5780 of the user-patient and the base 5710 of the medical device. The user-patient may then insert or pierce the insertion needle 5735 into the medical device so as to pass through the medical device and pierce the pierceable membrane 5740 and the skin 5780 of the user-patient. As the insertion needle 5735 pierces the pierceable membrane 5740 containing the agent 5750, the insertion needle 5735 may collect some of the agent 5750' and deliver it to a location 5790 underneath the skin 5780 of the user-patient once the insertion needle 5735 pierces the skin 5780 of the user-patient. In other embodiments, the insertion needle 5735 may pierce or breach the pierceable membrane 5740 to allow at least some of the agent 5750' to flow out of the pierceable membrane 5740 to the skin 5780 of the user-patient.

In some embodiments, the insertion needle 5735 may pierce the skin 5780 of the user-patient while the base 5710 of the medical device is secured to the user-patient. In some embodiments, at least one of the pierceable membrane 5740 and the agent 5750 may be configured to allow the agent 5750 to react with the skin 5780 of the user-patient before the pierceable membrane 5740 is pierced by the insertion needle 5735. For example, the user-patient may allow the agent 5750, such as an analgesic that numbs the skin 5780 of the user-patient, to react with the skin 5780 of the user-patient for a period of time, such as 15 to 30 seconds, or longer, before securing the base 5710 of the medical device to the user-patient or otherwise piercing the pierceable membrane 5740 and skin 5780 of the user-patient.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A medical device comprising:
   a medical monitoring device comprising a sensor configured to detect a biological parameter on a patient or a treatment device comprising an electronic infusion pump configured to deliver an infusion medium to a patient, the medical monitoring or treatment device including and operable with an insertion needle positioned to be inserted into the patient to insert a cannula into the patient, the insertion needle configured to extend through the cannula when the insertion needle is inserted into a patient to insert the cannula into the patient, the insertion needle configured to be withdrawn from the cannula to leave the cannula at least partially in the patient after the cannula is inserted into the patient, the cannula having an interior channel for conveying fluid to or from the medical monitoring or treatment device after the insertion needle is withdrawn from the cannula and during operation of the medical monitoring or treatment device;
   a pierceable membrane defining an interior volume containing an agent, the pierceable membrane positioned to be pierced by the insertion needle to allow the insertion needle to cause at least some of the agent contained in the interior volume of the pierceable membrane to be communicated from the interior volume of the pierceable membrane, outside the cannula, to the patient as the insertion needle is moved to an insertion position to be inserted into the patient with the cannula; and
   a base adapted to be secured to the patient during operation of the medical monitoring or treatment device, the base having a bottom surface that is arranged to contact a portion of the skin of the patient when the base is secured to the patient;
   wherein the pierceable membrane is arranged on and attached to the bottom surface of the base such that the insertion needle is external to the internal volume of the pierceable membrane when the needle begins to move toward the insertion position, and such that the insertion needle passes through the pierceable membrane on the bottom surface of the base as the insertion needle continues to move to the insertion position; and
   wherein the pierceable membrane is positioned between a portion of the bottom surface of the base and the skin of the patient in a case where the base is secured to the patient during operation of the medical monitoring or treatment device.

2. The medical device according to claim 1,
   wherein the insertion needle carries the at least some of the agent from the interior volume of the pierceable membrane to the patient.

3. The medical device according to claim 1,
   wherein the insertion needle pierces the pierceable membrane to allow the at least some of the agent to flow from the interior volume of the pierceable membrane to the patient.

4. The medical device according to claim 1, the base adapted to be secured to the skin of the patient.

5. The medical device according to claim 4, at least one of the pierceable membrane and the agent configured to allow at least some of the agent to react with the skin of the patient before the pierceable membrane is pierced by the insertion needle.

6. The medical device according to claim 1,
   wherein the agent comprises an antiseptic.

7. The medical device according to claim 1, the device further comprising:
   a removable layer at least partially covering the pierceable membrane.

8. The medical device according to claim 7,
   wherein the pierceable membrane is reactable with air upon the removable layer being at least partially removed from the pierceable membrane.

9. The medical device according to claim 1,
   the insertion needle having an outer surface;
   wherein at least some of the agent collects on the outer surface of the insertion needle upon the insertion needle piercing the pierceable membrane;
   wherein the at least some of the agent is carried on the outer surface of the insertion needle as the insertion needle moves to the patient.

10. The medical device according to claim 1, wherein the insertion needle is supported at least partially within the cannula for movement with the cannula relative to the pierceable membrane and the patient.

11. The medical device according to claim 1:
wherein the base is adapted to be secured to the skin of the patient during operation of the medical monitoring or treatment device, the base supporting the pierceable membrane;
wherein the insertion needle is supported at least partially within the cannula for movement with the cannula relative to the pierceable membrane and the base.

12. The medical device according to claim 11, wherein the insertion needle is supported for movement relative to the base.

13. The medical device according to claim 1, wherein the insertion needle is supported for movement with the cannula to pierce the pierceable membrane and then pierce the patient after piercing the pierceable membrane.

14. The medical device according to claim 1, wherein the base is adapted to be secured to the skin of the patient during operation of the medical monitoring or treatment device, the base supporting the insertion needle for movement with the cannula relative to the base to pierce the pierceable membrane and then pierce the skin of the patient after piercing the pierceable membrane in a case where the base is secured to the skin of the patient.

15. The medical device according to claim 1, wherein, in one motion, the insertion needle penetrates a first side of the pierceable membrane, then the agent, then a second side of the pieceable membrane, then the patient.

16. The medical device according to claim 1, wherein a sharp end of the needle is external to the internal volume of the pierceable membrane after the insertion needle passes through the pierceable membrane.

17. The medical device according to claim 1, wherein the medical monitoring or treatment device comprises a treatment device comprising an electronic infusion pump, said treatment device further comprising:
a first member having a reservoir for containing an infusion medium; and
a second member having an injection site structure through which the insertion needle is inserted as the insertion needle moves to the insertion position;
wherein the first member is separate from but selectively connectable to the second member, such that when connected, there is a fluid flow connection between the reservoir and the insertion needle when the insertion needle is in the insertion position.

18. The medical device according to claim 1, wherein the medical monitoring or treatment device comprises a medical monitoring device comprising a sensor, said medical monitoring device further comprising:
a first member of the medical device having said sensor; and
a second member having an injection site structure through which the insertion needle is inserted as the insertion needle moves to the insertion position;
wherein the first member is separate from but selectively connectable to the second member, such that when connected, there is a fluid flow connection between the first member and the insertion needle when the insertion needle is in the insertion position.

19. The medical device according to claim 1, wherein the bottom surface of the base has a generally flat section that contacts the portion of the skin of the patient when the base is secured to the patient, wherein the pierceable membrane is attached to a portion of the generally flat section of the base.

20. The medical device according to claim 19, wherein the portion of the generally flat section to which the pierceable membrane is attached is flat and contiguous with the generally flat section that contact the portion of the skin of the patient when the base is secured to the patient.

21. A delivery method comprising:
providing a medical monitoring device comprising a sensor configured to detect a biological parameter on a patient through a cannula or a treatment device comprising an electronic infusion pump configured to deliver an infusion medium to a patient through a cannula, the medical monitoring or treatment device operable with an insertion needle for inserting the cannula into the patient;
extending the insertion needle through the cannula and supporting the insertion needle and the cannula in a position for insertion of the insertion needle and cannula into the patient, the insertion needle configured to be withdrawn from the cannula to leave the cannula at least partially in the patient after the cannula is inserted into the patient, the cannula having an interior channel for conveying fluid to or from the medical monitoring or treatment device after the insertion needle is withdrawn from the cannula and during operation of the medical monitoring or treatment device;
positioning a pierceable membrane to define an interior volume containing an agent to be pierced by the insertion needle during operation of the medical monitoring or treatment device and to allow the insertion needle to cause at least some of the agent contained in the interior volume of the pierceable membrane to be communicated from the interior volume of the pierceable membrane, outside the cannula, to the patient as the insertion needle is moved to an insertion position to be inserted with the cannula into the patient; and
providing a base adapted to be secured to the skin of the patient during operation of the medical monitoring or treatment device, the base having a bottom surface that is arranged to contact a portion of the skin of the patient when the base is secured to the patient;
wherein the pierceable membrane is arranged on and attached to the bottom surface of the base such that the insertion needle is external to the internal volume of the pierceable membrane when the needle begins to move toward the insertion position, and such that the insertion needle passes through the pierceable membrane on the bottom surface of the base as the insertion needle continues to move to the insertion position; and
wherein the pierceable membrane is positioned between a portion of the bottom surface of the base and the skin of the patient in a case where the base is secured to the patient during operation of the medical monitoring or treatment device.

22. The method according to claim 21, the method further comprising:
moving the insertion needle relative to the pierceable membrane to pierce the pierceable membrane;
collecting at least some of the agent on an outer surface of the insertion needle upon the insertion needle piercing the pierceable membrane; and
carrying the at least some of the agent on the outer surface of the insertion needle to the skin of the patient.

23. The method according to claim 22, the method further comprising:
supporting the pierceable membrane on the base in a position such that a portion of the agent flows to the skin of the patient in a case where the base is secured to the skin of the patient and the insertion needle pierces the pierceable membrane.

24. The method according to claim 21, the method further comprising:
supporting the insertion needle at least partially within the cannula for movement with the cannula relative to the base to pierce the pierceable membrane and then pierce the skin of the patient after piercing the pierceable membrane in a case where the base is secured to the skin of the patient.

25. The method according to claim 21, further comprising:
penetrating with the insertion needle, in one motion, a first side of the pierceable membrane, then the agent, then a second side of the pieceable membrane, then the patient.

26. The method according to claim 21, wherein a sharp end of the needle is external to the internal volume of the pierceable membrane after the insertion needle passes through the pierceable membrane.

27. The method according to claim 21,
wherein the medical monitoring or treatment device comprises a treatment device comprising an electronic infusion pump, said treatment device further comprising:
a first member having a reservoir for containing an infusion medium; and
a second member having an injection site structure through which the insertion needle is inserted as the insertion needle moves to the insertion position;
wherein the first member is separate from but selectively connectable to the second member, such that when connected, there is a fluid flow connection between the reservoir and the insertion needle when the insertion needle is in the insertion position.

28. The method according to claim 21,
wherein the medical monitoring or treatment device comprises a medical monitoring device comprising a sensor, said medical monitoring device further comprising:
a first member of the medical device having said sensor; and
a second member having an injection site structure through which the insertion needle is inserted as the insertion needle moves to the insertion position;
wherein the first member is separate from but selectively connectable to the second member, such that when connected, there is a fluid flow connection between the first member and the insertion needle when the insertion needle is in the insertion position.

29. The method of claim 21, wherein the bottom surface of the base has a generally flat section that contacts the portion of the skin of the patient when the base is secured to the patient, wherein the pierceable membrane is attached to a portion of the generally flat section of the base.

30. The method of claim 29, wherein the portion of the generally flat section to which the piercable membrane is attached is flat and contiguous with the generally flat section that contact the portion of the skin of the patient when the base is secured to the patient.

* * * * *